United States Patent
Arora et al.

(10) Patent No.: US 10,023,589 B2
(45) Date of Patent: *Jul. 17, 2018

(54) PYRAZOLO[1,5A]PYRIMIDINE DERIVATIVES AS IRAK4 MODULATORS

(71) Applicants: Hoffmann-La Roche Inc., Nutley, NJ (US); Roche Palo Alto LLC, Palo Alto, CA (US)

(72) Inventors: Nidhi Arora, Cupertino, CA (US); Shaoqing Chen, Bridgewater, NJ (US); Johannes Cornelius Hermann, Jersey City, NJ (US); Andreas Kuglstatter, Montclair, NJ (US); Sharada Shenvi Labadie, Sunnyvale, CA (US); Clara Jeou Jen Lin, Palo Alto, CA (US); Matthew C. Lucas, Lexington, MA (US); Amy Geraldine Moore, Mountain View, CA (US); Eva Papp, Palo Alto, CA (US); Francisco Xavier Talamas, Livingston, NJ (US); Jutta Wanner, Montclair, NJ (US); Yansheng Zhai, Nutley, NJ (US)

(73) Assignees: Hoffmann-La Roche Inc., Nutley, NJ (US); Roche Palo Alto LLC, Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/975,004

(22) Filed: Dec. 18, 2015

(65) Prior Publication Data
US 2016/0207936 A1    Jul. 21, 2016

Related U.S. Application Data

(60) Division of application No. 14/243,074, filed on Apr. 2, 2014, now Pat. No. 9,255,110, which is a continuation of application No. 13/180,589, filed on Jul. 12, 2011, now abandoned.

(60) Provisional application No. 61/363,855, filed on Jul. 13, 2010, provisional application No. 61/485,145, filed on May 12, 2011.

(51) Int. Cl.
*C07D 495/04*    (2006.01)
*C07D 487/04*    (2006.01)

(52) U.S. Cl.
CPC ......... *C07D 495/04* (2013.01); *C07D 487/04* (2013.01)

(58) Field of Classification Search
CPC .............................. C07D 495/04; C07D 487/04
See application file for complete search history.

(56) References Cited

U.S. PATENT DOCUMENTS

| 9,255,110 | B2 * | 2/2016 | Arora | C07D 495/04 |
| 2012/0190665 | A1 | 7/2012 | Gibbons et al. | 514/210.18 |
| 2012/0302567 | A1 * | 11/2012 | Jung | C07D 495/04 |
| | | | | 514/234.2 |

FOREIGN PATENT DOCUMENTS

| CN | 101537007 | 9/2009 |
| JP | 2008013527 A | 1/2008 |
| WO | 2005/004810 | 1/2005 |
| WO | 2005002552 | 1/2005 |
| WO | WO 2010/051549 A1 | 5/2010 |
| WO | 2011025940 A1 | 3/2011 |
| WO | 2011093672 A2 | 8/2011 |
| WO | 2011093684 A2 | 8/2011 |
| WO | 2012007375 A1 | 1/2012 |

OTHER PUBLICATIONS

STN Registry No. 908229-74-3, Caplus Chemcat, entered STN: Sep. 22, 2006.
STN Registry No. 312919-78-1, Caplus Chemcat, entered STN: Jan. 5, 2001.
John Huppatz, "Systemic Fungicides. The Synthesis of Pyrazolo[1,5-a]pyrimidine Analogues of Carboxin," Australian Journal of Chemistry 38(1), 221-230, 1985.
STN Registry No. 725696-66-2, Caplus Chemcat, entered STN: Aug. 12, 2004.
STN Registry No. 717874-08-3, Caplus Chemcat, entered STN: Jul. 28, 2004.
STN Registry No. 957364-18-0, Caplus Chemcat, entered STN: Dec. 11, 2007.
STN Registry No. 908228-92-2, Caplus Chemcat, entered STN: Sep. 22, 2006.

(Continued)

*Primary Examiner* — Jennifer M Kim

(57) ABSTRACT

Compounds of the formula I or II:

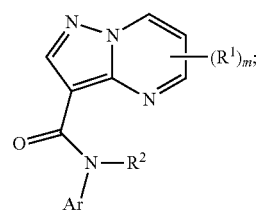

I

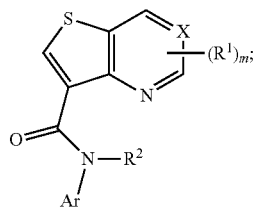

II wherein X, m, Ar, $R^1$ and $R^2$ are as defined herein. The subject compounds are useful for treatment of IRAK-mediated conditions.

19 Claims, No Drawings

(56) References Cited

OTHER PUBLICATIONS

STN Registry No. 717829-94-2, Caplus Chemcat, entered STN: Jul. 28, 2004.
STN Registry No. 361469-85-4, Caplus Chemcat, entered STN: Oct. 11, 2001.
STN Registry No. 908230-21-7, Caplus Chemcat, entered STN: Sep. 22, 2006.
The English translation of the Japanese Office Action, dated May 22, 2015, in the corresponding Japanese Application No. 2013-519044.
STN Registry No. 310488-52-3, Caplus Chemcat, entered STN: Dec. 21, 2000.
STN Registry No. 717828-52-9, Caplus Chemcat, entered STN: Jul. 28, 2004.
STN Registry No. 310448-40-9, Caplus Chemcat, entered STN: Dec. 21, 2000.
STN Registry No. 957299-82-0, Caplus Chemcat, entered STN: Dec. 10, 2007.
STN Registry No. 725696-69-5, Caplus Chemcat, entered STN: Aug. 12, 2004.
The English translation of the Chinese Office Action, dated Apr. 1, 2017, in the related Chinese Application No. 201510559974.8.
Shallow et al., "Development and Implementation of a Miniaturized High-Throughput Time-Resolved Fluorescence Energy Transfer Assay to Identify Small Molecule Inhibitors of Polo-Like Kinase 1", Assay and Drug Development Technologies, vol. 5, No. 6, pp. 723-735, Dec. 31, 2007.
The English translation of the Japanese Office Action, dated Jul. 26, 2017, in the related Japanese Application No. 2016-151041.
STN Registry No. 310448-55-6, Caplus Chemeat, entered STN: Dec. 21, 2000.
STN Registry No. 310448-34-1, Caplus Chemeat, entered STN: Dec. 21, 2000.
STN Registry No. 310448-32-9, Caplus Chemeat, entered STN: Dec. 21, 2000.
The English translation of the Mexican Office Action, dated Jun. 16, 2014, in the corresponding Mexican Application No. MA/a/2013/000390.
The English translation of the Chinese Office Action, dated Feb. 23, 2018, in the related Chinese Application No. 201510559974.8.
STN Registry No. 1258715-05-7, entered STN: Jan. 7, 2011.

\* cited by examiner

PYRAZOLO[1,5A]PYRIMIDINE DERIVATIVES AS IRAK4 MODULATORS

CROSS-REFERENCE TO RELATED APPLICATIONS

This application is a Divisional of U.S. patent application Ser. No. 14/243,074, filed on Apr. 2, 2014, now U.S. Pat. No. 9,255,110, which is a Continuation of U.S. patent application Ser. No. 13/180,589, filed on Jul. 12, 2011, now abandoned, which claims priority from U.S. Provisional Patent Application No. 61/363,855, filed on Jul. 13, 2010, and U.S. Provisional Patent Application No. 61/485,145 filed on May 12, 2011. Each of the prior mentioned applications is hereby incorporated by reference herein in its entirety.

FIELD OF THE INVENTION

This invention pertains to compounds useful for treatment of autoimmune and inflammatory diseases associated with Interleukin-1 Receptor Associated Kinase (IRAK), and more particularly compounds that modulate the function of IRAK-1 and/or IRAK-4.

BACKGROUND OF THE INVENTION

TIR-domain containing cell surface receptors such as the Toll-like receptors and the IL-1 and IL-18 receptors play critical roles in innate immunity and have been implicated in the pathogenesis of autoimmunity. TLRs, for example, recognize pathogenic or endogenous ligands and provide a requisite signal for dendritic cell maturation and antigen presentation to T cells (13). Similarly, the proteins that mediate signaling from these receptors have also been shown to play important roles in the pathogenesis of autoimmune disorders. For example mice deficient in MyD88, an adaptor protein that directly interacts with the TIR domain are more susceptible to bacterial, fungal and parasitic infections. In addition, MyD88 deficient mice are resistant to experimental autoimmune encephalomyelitis (EAE) and streptococcal cell wall-induced arthritis (7, 11, 18).

The Interleukin-1 Receptor Associated Kinase (IRAK) family is comprised of four family members IRAK-1, IRAK-2, IRAK-3/M, and IRAK-4. These proteins are characterized by a typical N-terminal death domain that mediates interaction with MyD88-family adaptor proteins and a centrally located kinase domain. Whereas IRAK-1 and IRAK-4 have kinase activity, IRAK-2 and IRAK-3/M are catalytically inactive. Upon activation of their upstream cognate receptors, IRAK-4 is thought to phosphorylate IRAK-1 resulting in the activation and autophosphorylation of IRAK-1 and subsequent phosphorylation of downstream substrates. The hyperphosphorylation of IRAK-1 directs its dissociation from the receptor complex and its eventual ubiquitylation and proteasomal degradation. Phosphorylation of downstream substrates such as Pellino-2 ultimately leads to the activation of the MAPKs such as p38 and c-Jun N-terminal kinase (JNK) and NF-kB followed by production of pro-inflammatory cytokines, chemokines, and destructive enzymes (8, 10, 22).

The role of IRAK-1 and IRAK-4 in innate immunity and in the pathogenesis of autoimmune diseases is emerging. Patients with destabilizing or null mutations in IRAK-4 demonstrate defects in TLR signaling and the production of pro-inflammatory cytokines such as IL-1 and TNF (2, 3, 5, 17), as well as antiviral cytokines such as IFNα and IFNβ (27). These patients demonstrate an increased susceptibility to gram-positive bacterial infections although they are generally resistant to gram-negative bacterial, viral, and fungal infections. Similarly, IRAK-4 deficient mice have defects in TLR- and IL-1-mediated cytokine production and increased susceptibility to infection. IRAK-1 deficient mice demonstrated a loss of responsiveness to lipopolysaccharides (LPS), IL-1, IL-18 as well as impaired Th1 development (9). These mice were resistant to experimental autoimmune encephalomyelitis, exhibiting little or no CNS inflammation.

Accordingly, compounds that modulate the function of IRAK-1 and/or IRAK-4 represent an attractive approach to the development of therapeutic agents for the treatment of inflammatory, cell proliferative and immune-related conditions and diseases associated with IRAK-mediated signal transduction, such as rheumatoid arthritis, inflammatory bowel disease, multiple sclerosis, diabetes, obesity, allergic disease, psoriasis, asthma, graft rejection, cancer and sepsis.

Activation of SYK tyrosine kinase is an important in the signally pathways following the activation of mast cells (J. A. Taylor et al., Molec. and Cell Biol., 1995, 15, 4149). SYK kinase activation and activity is considered for Fc epsilon RI (high-affinity IgE receptor)-mediated release of mediators from mast cells. Inhibitors of SYK kinase can thus block the release of allergic and pro-inflammatory mediators and cytokines, and are potentially useful for treatment of inflammatory and allergic disorders such as asthma, chronic obstructive pulmonary disease (COPD), adult respiratory distress syndrome (ARDS), ulcerative colitis, Crohn's disease, bronchitis, conjunctivitis, psoriasis, scleroderma, urticaria, dermatitis and allergic rhinitis.

SUMMARY OF THE INVENTION

The invention provides compounds of the formula I or formula II:

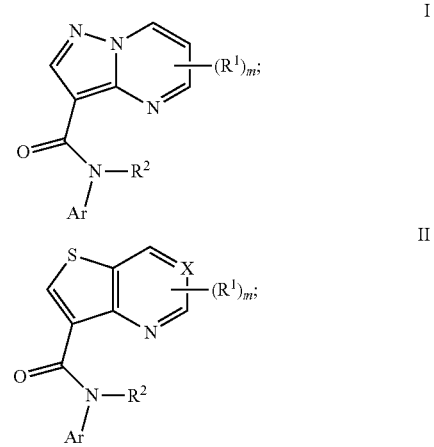

or a pharmaceutically acceptable salt thereof,
wherein:
X is N or CH
m is 1 or 2;
Ar is:
optionally substituted aryl; or
optionally substituted heteroaryl;

$R^1$ is:
hydrogen;
$C_{1-6}$alkyl;
$C_{1-6}$alkoxy;
hydroxy;
hydroxy-$C_{1-6}$alkyl;
$C_{1-6}$alkyl-amino;
amino-$C_{1-6}$alkyl;
amino-$C_{1-6}$alkyl-amino;
hydroxy-$C_{1-6}$alkylamino
$C_{3-6}$cycloalkylamino;
amino-$C_{3-6}$cycloalkylamino;
amino-$C_{3-6}$heterocycloalkylamino;
aminocarbonyl;
halo;
hydroxy-$C_{1-6}$alkyl; or
hydroxy-$C_{1-6}$alkoxy; and
$R^2$ is:
hydrogen; or
$C_{1-6}$alkyl.

The invention also provides and pharmaceutical compositions comprising the compounds, methods of using the compounds, and methods of preparing the compounds.

DETAILED DESCRIPTION OF THE INVENTION

Definitions

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

"Alkyl" means the monovalent linear or branched saturated hydrocarbon moiety, consisting solely of carbon and hydrogen atoms, having from one to twelve carbon atoms. "Lower alkyl" refers to an alkyl group of one to six carbon atoms, i.e. $C_1$-$C_6$alkyl. Examples of alkyl groups include, but are not limited to, methyl, ethyl, propyl, isopropyl, isobutyl, sec-butyl, tert-butyl, pentyl, n-hexyl, octyl, dodecyl, and the like.

"Alkenyl" means a linear monovalent hydrocarbon radical of two to six carbon atoms or a branched monovalent hydrocarbon radical of three to six carbon atoms, containing at least one double bond, e.g., ethenyl, propenyl, and the like.

"Alkynyl" means a linear monovalent hydrocarbon radical of two to six carbon atoms or a branched monovalent hydrocarbon radical of three to six carbon atoms, containing at least one triple bond, e.g., ethynyl, propynyl, and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkoxy" and "alkyloxy", which may be used interchangeably, mean a moiety of the formula —OR, wherein R is an alkyl moiety as defined herein. Examples of alkoxy moieties include, but are not limited to, methoxy, ethoxy, isopropoxy, and the like.

"Alkoxyalkyl" means a moiety of the formula $R^a$—O—$R^b$—, where $R^a$ is alkyl and $R^b$ is alkylene as defined herein. Exemplary alkoxyalkyl groups include, by way of example, 2-methoxyethyl, 3-methoxypropyl, 1-methyl-2-methoxyethyl, 1-(2-methoxyethyl)-3-methoxypropyl, and 1-(2-methoxyethyl)-3-methoxypropyl.

"Alkoxyalkoxy" means a group of the formula —O—R—R' wherein R is alkylene and R' is alkoxy as defined herein.

"Alkylcarbonyl" means a moiety of the formula —C(O)—R, wherein R is alkyl as defined herein.

"Alkoxycarbonyl" means a group of the formula —C(O)—R wherein R is alkoxy as defined herein.

"Alkylcarbonylalkyl" means a group of the formula —R—C(O)—R wherein R is alkylene and R' is alkyl as defined herein.

"Alkoxycarbonylalkyl" means a group of the formula —R—C(O)—R wherein R is alkylene and R' is alkoxy as defined herein.

"Alkoxycarbonylalkoxy" means a group of the formula —O—R—C(O)—R' wherein R is alkylene and R' is alkoxy as defined herein.

"Alkylcarbonylamino" means a group of the formula —NRR'—C(O)—R" wherein R is hydrogen or alkyl, R' is alkylene and R" is alkyl as defined herein.

"Hydroxycarbonylalkoxy" means a group of the formula —O—R—C(O)—OH wherein R is alkylene as defined herein.

"Alkylaminocarbonylalkoxy" means a group of the formula —O—R—C(O)—NHR' wherein R is alkylene and R' is alkyl as defined herein.

"Dialkylaminocarbonylalkoxy" means a group of the formula —O—R—C(O)—NR'R" wherein R is alkylene and R' and R" are alkyl as defined herein.

"Alkylaminoalkoxy" means a group of the formula —O—R—NHR' wherein R is alkylene and R' is alkyl as defined herein.

"Dialkylaminoalkoxy" means a group of the formula —O—R—NR'R' wherein R is alkylene and R' and R" are alkyl as defined herein.

"Alkylsulfonyl" means a moiety of the formula —$SO_2$—R, wherein R is alkyl as defined herein.

"Alkylsulfonylalkyl" means a moiety of the formula —R'—$SO_2$—R" where R' is alkylene and R" is alkyl as defined herein.

"Alkylsulfonylalkoxy" means a group of the formula —O—R—$SO_2$—R' wherein R is alkylene and R' is alkyl as defined herein.

"Amino" means a moiety of the formula —NRR' wherein R and R' each independently is hydrogen or alkyl as defined herein. "Amino" thus includes "alkylamino" (where one of R and R' is alkyl and the other is hydrogen) and "dialkylamino" (where R and R' are both alkyl).

"Hydroxyalkylamino" means a moiety of the formula —NRR' wherein R and R' is hydrogen or alkyl and R' is hydroxyalkyl as defined herein.

"Aminocarbonyl" means a group of the formula —C(O)—R wherein R is amino as defined herein.

"Alkoxyamino" means a moiety of the formula —NR—OR' wherein R is hydrogen or alkyl and R' is alkyl as defined herein.

"Alkylsulfanyl" means a moiety of the formula —SR wherein R is alkyl as defined herein.

"Aminoalkyl" means a group —R—R' wherein R' is amino and R is alkylene as defined herein. "Aminoalkyl" includes aminomethyl, aminoethyl, 1-aminopropyl, 2-aminopropyl, and the like. The amino moiety of "aminoalkyl" may be substituted once or twice with alkyl to provide "alkylaminoalkyl" and "dialkylaminoalkyl" respectively. "Alkylaminoalkyl" includes methylaminomethyl, methylaminoethyl, methylaminopropyl, ethylaminoethyl and the like. "Dialkylaminoalkyl" includes dimethylaminomethyl, dimethylaminoethyl, dimethylaminopropyl, N-methyl-N-ethylaminoethyl, and the like.

"Aminoalkoxy" means a group —OR—R' wherein R' is amino and R is alkylene as defined herein.

"Alkylsulfonylamido" means a moiety of the formula —NR'SO$_2$—R wherein R is alkyl and R' is hydrogen or alkyl.

"Aminocarbonyloxyalkyl" or "carbamylalkyl" means a group of the formula —R—O—C(O)—NR'R" wherein R is alkylene and R', R" each independently is hydrogen or alkyl as defined herein.

"Alkynylalkoxy" means a group of the formula —O—R—R' wherein R is alkylene and R' is alkynyl as defined herein.

"Aryl" means a monovalent cyclic aromatic hydrocarbon moiety consisting of a mono-, bi- or tricyclic aromatic ring. The aryl group can be optionally substituted as defined herein.

Examples of aryl moieties include, but are not limited to, phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, including partially hydrogenated derivatives thereof, each being optionally substituted.

"Arylalkyl" and "Aralkyl", which may be used interchangeably, mean a radical-R$^a$R$^b$ where R$^a$ is an alkylene group and R$^b$ is an aryl group as defined herein; e.g., phenylalkyls such as benzyl, phenylethyl, 3-(3-chlorophenyl)-2-methylpentyl, and the like are examples of arylalkyl.

"Arylsulfonyl" means a group of the formula —SO$_2$—R wherein R is aryl as defined herein.

"Aryloxy" means a group of the formula —O—R wherein R is aryl as defined herein.

"Aralkyloxy" means a group of the formula —O—R—R" wherein R is alkylene and R' is aryl as defined herein.

"Carboxy" or "hydroxycarbonyl", which may be used interchangeably, means a group of the formula —C(O)—OH.

"Cyanoalkyl" means a moiety of the formula —R'—R", where R' is alkylene as defined herein and R" is cyano or nitrile.

"Cycloalkyl" means a monovalent saturated carbocyclic moiety consisting of mono- or bicyclic rings. Preferred cycloalkyl are unsubstituted or substituted with alkyl. Cycloalkyl can optionally be substituted with one or more substituents, wherein each substituent is independently hydroxy, alkyl, alkoxy, halo, haloalkyl, amino, monoalkylamino, or dialkylamino, unless otherwise specifically indicated. Examples of cycloalkyl moieties include, but are not limited to, cyclopropyl, cyclobutyl, cyclopentyl, cyclohexyl, cycloheptyl, and the like, including partially unsaturated (cycloalkenyl) derivatives thereof.

"Cycloalkylalkyl" means a moiety of the formula —R'—R", where R' is alkylene and R" is cycloalkyl as defined herein.

"Cycloalkylalkoxy" means a group of the formula —O—R—R' wherein R is alkylene and R' is cycloalkyl as defined herein.

"Heteroalkyl" means an alkyl radical as defined herein wherein one, two or three hydrogen atoms have been replaced with a substituent independently selected from the group consisting of —OR$^a$, —NR$^b$R$^C$, and —S(O)$_n$R$^d$ (where n is an integer from 0 to 2), with the understanding that the point of attachment of the heteroalkyl radical is through a carbon atom, wherein R$^a$ is hydrogen, acyl, alkyl, cycloalkyl, or cycloalkylalkyl; R$^b$ and R$^c$ are independently of each other hydrogen, acyl, alkyl, cycloalkyl, or cycloalkylalkyl; and when n is 0, R$^d$ is hydrogen, alkyl, cycloalkyl, or cycloalkylalkyl, and when n is 1 or 2, R$^d$ is alkyl, cycloalkyl, cycloalkylalkyl, amino, acylamino, monoalkylamino, or dialkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like.

"Heteroaryl" means a monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring may be optionally substituted as defined herein. Examples of heteroaryl moieties include, but are not limited to, optionally substituted imidazolyl, oxazolyl, isoxazolyl, thiazolyl, isothiazolyl, oxadiazolyl, thiadiazolyl, pyrazinyl, thienyl, benzothienyl, thiophenyl, furanyl, pyranyl, pyridyl, pyrrolyl, pyrazolyl, pyrimidyl, quinolinyl, isoquinolinyl, benzofuryl, benzothiophenyl, benzothiopyranyl, benzimidazolyl, benzooxazolyl, benzooxadiazolyl, benzothiazolyl, benzothiadiazolyl, benzopyranyl, indolyl, isoindolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, including partially hydrogenated derivatives thereof, each optionally substituted.

"Heteroarylalkyl" or "heteroaralkyl" means a group of the formula —R—R' wherein R is alkylene and R' is heteroaryl as defined herein.

"Heteroarylsulfonyl" means a group of the formula —SO$_2$—R wherein R is heteroaryl as defined herein.

"Heteroaryloxy" means a group of the formula —O—R wherein R is heteroaryl as defined herein.

"Heteroaralkyloxy" means a group of the formula —O—R—R" wherein R is alkylene and R' is heteroaryl as defined herein.

The terms "halo", "halogen" and "halide", which may be used interchangeably, refer to a substituent fluoro, chloro, bromo, or iodo.

"Haloalkyl" means alkyl as defined herein in which one or more hydrogen has been replaced with same or different halogen. Exemplary haloalkyls include —CH$_2$Cl, —CH$_2$CF$_3$, —CH$_2$CCl$_3$, perfluoroalkyl (e.g., —CF$_3$), and the like.

"Haloalkoxy" means a moiety of the formula —OR, wherein R is a haloalkyl moiety as defined herein. An exemplary haloalkoxy is difluoromethoxy.

"Heterocycloamino" means a saturated ring wherein at least one ring atom is N, NH or N-alkyl and the remaining ring atoms form an alkylene group.

"Heterocyclyl" means a monovalent saturated moiety, consisting of one to three rings, incorporating one, two, or three or four heteroatoms (chosen from nitrogen, oxygen or sulfur).

The heterocyclyl ring may be optionally substituted as defined herein. Examples of heterocyclyl moieties include, but are not limited to, optionally substituted piperidinyl, piperazinyl, homopiperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, quinuclidinyl, quinolinyl, isoquinolinyl, benzimidazolyl, thiadiazolylidinyl, benzothiazolidinyl, benzoazolylidinyl, dihydrofuryl, tetrahydrofuryl, dihydropyranyl, tetrahydropyranyl, thiamorpholinyl, thiamorpholinylsulfoxide, thiamorpholinylsulfone, dihydroquinolinyl, dihydrisoquinolinyl, tetrahydroquinolinyl, tetrahydrisoquinolinyl, and the like.

"Heterocyclylalkyl" means a moiety of the formula —R—R' wherein R is alkylene and R' is heterocyclyl as defined herein.

"Heterocyclyloxy" means a moiety of the formula —OR wherein R is heterocyclyl as defined herein.

"Heterocyclylalkoxy" means a moiety of the formula —OR—R' wherein R is alkylene and R' is heterocyclyl as defined herein.

"Hydroxyalkoxy" means a moiety of the formula —OR wherein R is hydroxyalkyl as defined herein.

"Hydroxyalkenyl" means a moiety of the formula —R—OH wherein R is alkenyl as defined herein.

"Hydroxyalkylamino" means a moiety of the formula —NR—R' wherein R is hydrogen or alkyl and R' is hydroxyalkyl as defined herein.

"Hydroxyalkylaminocarbonyl" means a moiety of the formula —C(O)NR—R' wherein R is hydrogen or alkyl and R' is hydroxyalkyl as defined herein.

"Hydroxyalkylaminoalkyl" means a moiety of the formula —R—NR'—R" wherein R is alkylene, R' is hydrogen or alkyl, and R" is hydroxyalkyl as defined herein.

"Hydroxycarbonylalkyl" or "carboxyalkyl" means a group of the formula —R—(CO)—OH where R is alkylene as defined herein.

"Hydroxycarbonylalkoxy" means a group of the formula —O—R—C(O)—OH wherein R is alkylene as defined herein.

"Hydroxyalkyloxycarbonylalkyl" or "hydroxyalkoxycarbonylalkyl" means a group of the formula —R—C(O)—O—R—OH wherein each R is alkylene and may be the same or different.

"Hydroxyalkyl" means an alkyl moiety as defined herein, substituted with one or more, such as one, two or three hydroxy groups, provided that the same carbon atom does not carry more than one hydroxy group. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl "Hydroxycycloalkyl" means a cycloalkyl moiety as defined herein wherein one, two or three hydrogen atoms in the cycloalkyl radical have been replaced with a hydroxy substituent. Representative examples include, but are not limited to, 2-, 3-, or 4-hydroxycyclohexyl, and the like.

"Alkoxy hydroxyalkyl" and "hydroxy alkoxyalkyl", which may be used interchangeably, means an alkyl as defined herein that is substituted at least once with hydroxy and at least once with alkoxy. "Alkoxy hydroxyalkyl" and "hydroxy alkoxyalkyl" thus encompass, for example, 2-hydroxy-3-methoxy-propan-1-yl and the like.

"Phenylaminocarbonyl" means a group of the formula —C(O)—NR—R' wherein R is hydrogen or alkyl as defined herein and R' is phenyl.

"Urea" or "ureido" means a group of the formula —NR'—C(O)—NR"R'" wherein R', R" and R'" each independently is hydrogen or alkyl.

"Carbamate" means a group of the formula —O—C(O)—NR'R" wherein R' and R" each independently is hydrogen or alkyl.

"Carboxy" means a group of the formula —O—C(O)—OH.

"Sulfonamido" means a group of the formula —SO$_2$—NR'R" wherein R', R" and R'" each independently is hydrogen or alkyl.

"Optionally substituted", when used in association with "aryl", phenyl", "heteroaryl", "cycloalkyl" or "heterocyclyl" means an aryl, phenyl, heteroaryl, cycloalkyl or heterocyclyl which is optionally substituted independently with one to four substituents, preferably one or two substituents selected from alkyl, cycloalkyl, cycloalkylalkyl, heteroalkyl, hydroxyalkyl, halo, nitro, cyano, hydroxy, alkoxy, amino, acylamino, mono-alkylamino, di-alkylamino, haloalkyl, haloalkoxy, heteroalkyl, —COR, —SO$_2$R (where R is hydrogen, alkyl, phenyl or phenylalkyl), —(CR'R")$_n$—COOR (where n is an integer from 0 to 5, R' and R" are independently hydrogen or alkyl, and R is hydrogen, alkyl, cycloalkyl, cycloalkylalkyl, phenyl or phenylalkyl), or —(CR'R")$_n$—CONR$^a$R$^b$ (where n is an integer from 0 to 5, R' and R" are independently hydrogen or alkyl, and R$^a$ and R$^b$ are, independently of each other, hydrogen, alkyl, cycloalkyl, cycloalkylalkyl, phenyl or phenylalkyl). Certain preferred optional substituents for "aryl", phenyl", "heteroaryl", "cycloalkyl" or "heterocyclyl" include alkyl, halo, haloalkyl, alkoxy, cyano, amino and alkylsulfonyl. More preferred substituents are methyl, fluoro, chloro, trifluoromethyl, methoxy, amino and methanesulfonyl.

"Leaving group" means the group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Modulator" means a molecule that interacts with a target. The interactions include, but are not limited to, agonist, antagonist, and the like, as defined herein.

"Optional" or "optionally" means that the subsequently described event or circumstance may but need not occur, and that the description includes instances where the event or circumstance occurs and instances in which it does not.

"Disease" and "Disease state" means any disease, condition, symptom, disorder or indication.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound. Such salts include:

acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like; or salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

The preferred pharmaceutically acceptable salts are the salts formed from acetic acid, hydrochloric acid, sulphuric acid, methanesulfonic acid, maleic acid, phosphoric acid, tartaric acid, citric acid, sodium, potassium, calcium, zinc, and magnesium.

It should be understood that all references to pharmaceutically acceptable salts include solvent addition forms (solvates) or crystal forms (polymorphs) as defined herein, of the same acid addition salt.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive nitrogen and/or oxygen atoms present in the reactants. For example, the terms "amino-protecting group" and "nitrogen protecting group" are used interchangeably herein and refer to those organic groups intended to protect the nitrogen atom against undesirable reactions during synthetic procedures. Exemplary nitrogen protecting groups include, but are not limited to, trifluoroacetyl, acetamido, benzyl (Bn), benzyloxycarbonyl (carbobenzyloxy, CBZ), p-methoxybenzyloxycarbonyl, p-nitrobenzyloxycarbonyl, tert-butoxycarbonyl (BOC), and the like. The artisan in the art will know how to chose a group for the ease of removal and for the ability to withstand the following reactions.

"Solvates" means solvent additions forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Subject" means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Inflammatory disease" means disease states or indications that are accompanied by inflammatory, allergic, and/or proliferative processes and can include:

(i) Lung diseases: chronic, obstructive lung diseases of any genesis, particularly bronchial asthma and chronic obstructive pulmonary disease (COPD); adult respiratory distress syndrome (ARDS); bronchiectasis; bronchitis of various genesis; all forms of restrictive lung diseases, particularly allergic alveolitis; all forms of lung edema, particularly toxic lung edema; all forms of interstitial lung diseases of any genesis, e.g., radiation pneumonitis; and sarcoidosis and granulomatoses, particularly Boeck disease.

(ii) Rheumatic diseases or autoimmune diseases or joint diseases: all forms of rheumatic diseases, especially rheumatoid arthritis, acute rheumatic fever, and polymyalgia rheumatica; reactive arthritis; rheumatic soft tissue diseases; inflammatory soft tissue diseases of other genesis; arthritic symptoms in degenerative joint diseases (arthroses); traumatic arthritis; collagenoses of any genesis, e. g., systemic lupus erythematosus, scleroderma, polymyositis, dermatomyositis, Sjögren syndrome, Still disease, and Felty syndrome;

(iii) Allergic diseases: all forms of allergic reactions, e.g., angioneurotic edema, hay fever, insect bites, allergic reactions to drugs, blood derivatives, contrast agents, etc., anaphylactic shock (anaphylaxis), urticaria, angioneurotic edema, and contact dermatitis;

(iv) Vasculitis diseases: panarteritis nodosa, polyarteritis nodosa, arteritis temporalis, Wegner granulomatosis, giant cell arthritis, and erythema nodosum;

(v) Dermatological diseases: atopic dermatitis, particularly in children; psoriasis; pityriasis rubra pilaris; erythematous diseases triggered by various noxa, e.g., rays, chemicals, burns, etc.; bullous dermatoses; diseases of the lichenoid complex; pruritus (e.g., of allergic genesis); seborrheic dermatitis; rosacea; pemphigus vulgaris; erythema multiforme exudativum; balanitis; vulvitis; hair loss, such as occurs in alopecia areata; and cutaneous T cell lymphomas;

(vi) Renal diseases: nephrotic syndrome; and all types of nephritis, e.g., glomerulonephritis;

(vii) Hepatic diseases: acute liver cell disintegration; acute hepatitis of various genesis, e.g., viral, toxic, drug-induced; and chronically aggressive and/or chronically intermittent hepatitis; (viii) Gastrointestinal diseases: inflammatory bowel diseases, e.g., regional enteritis (Crohn disease), colitis ulcerosa; gastritis; peptic esophagitis (refluxoesophagitis); and gastroenteritis of other genesis, e.g., nontropical sprue;

(ix) Proctological diseases: anal eczema; fissures; hemorrhoids; and idiopathic proctitis;

(x) Eye diseases: allergic keratitis, uveitis, or iritis; conjunctivitis; blepharitis; neuritis nervi optici; choroiditis; and sympathetic ophthalmia;

(xi) Diseases of the ear, nose, and throat (ENT) area: allergic rhinitis or hay fever; otitis externa, e.g., caused by contact eczema, infection, etc.; and otitis media;

(xii) Neurological diseases: brain edema, particularly tumor-related brain edema; multiple sclerosis; acute encephalomyelitis; meningitis; acute spinal cord injury; stroke; and various forms of seizures, e.g., nodding spasms;

(xiii) Blood diseases: acquired hemolytic anemia; and idiopathic thrombocytopenia;

(xiv) Tumor diseases: acute lymphatic leukemia; malignant lymphoma; lymphogranulomatoses; lymphosarcoma; extensive metastases, particularly in mammary, bronchial, and prostatic carcinoma;
(xv) Endocrine diseases: endocrine ophthalmopathy; endocrine orbitopathia; thyrotoxic crisis; Thyroiditis de Quervain; Hashimoto thyroiditis; Morbus Basedow; granulomatous thyroiditis; struma lymphomatosa; and Grave disease;
(xvi) Organ and tissue transplantations and graft-versus-host diseases;
(xvii) Severe states of shock, e.g., septic shock, anaphylactic shock, and systemic inflammatory response syndrome (SIRS);
(xviii) Substitution therapy in: congenital primary adrenal insufficiency, e.g., adrenogenital syndrome; acquired primary adrenal insufficiency, e.g., Addison disease, autoimmune adrenalitis, post-infection, tumors, metastases, etc.; congenital secondary adrenal insufficiency, e.g., congenital hypopituitarism; and acquired secondary adrenal insufficiency, e.g., post-infection, tumors, metastases, etc.;
(xix) Pain of inflammatory genesis, e.g., lumbago; and
(xx) Various other disease-states or conditions including type I diabetes (insulin-dependent diabetes), osteoarthritis, Guillain-Barre syndrome, restenosis following percutaneous transluminal coronary angioplasty, Alzheimer disease, acute and chronic pain, atherosclerosis, reperfusion injury, bone resorption diseases, congestive heart failure, myocardial infarction, thermal injury, multiple organ injury secondary to trauma, acute purulent meningitis, necrotizing enterocolitis and syndromes associated with hemodialysis, leukopheresis, and granulocyte transfusion.

"Arthritis" means diseases or conditions damage to joints of the body and pain associated with such joint damage. Arthritis includes rheumatoid arthritis, osteoarthritis, psoriatic arthritis, septic arthritis and gouty arthritis.

"Pain" includes, without limitation, inflammatory pain; surgical pain; visceral pain; dental pain; premenstrual pain; central pain; pain due to burns; migraine or cluster headaches; nerve injury; neuritis; neuralgias; poisoning; ischemic injury; interstitial cystitis; cancer pain; viral, parasitic or bacterial infection; post-traumatic injury; or pain associated with irritable bowel syndrome.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The terms "those defined above" and "those defined herein" when referring to a variable incorporates by reference the broad definition of the variable as well as preferred, more preferred and most preferred definitions, if any.

"Treating" or "treatment" of a disease state includes, inter alia, inhibiting the disease state, i.e., arresting the development of the disease state or its clinical symptoms, and/or relieving the disease state, i.e., causing temporary or permanent regression of the disease state or its clinical symptoms.

The terms "treating", "contacting", and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Nomenclature and Structures

In general, the nomenclature used in this Application is based on AUTONOM™ v.4.0, a Beilstein Institute computerized system for the generation of IUPAC systematic nomenclature. Chemical structures shown herein were prepared using ISIS® version 2.2. Any open valency appearing on a carbon, oxygen sulfur or nitrogen atom in the structures herein indicates the presence of a hydrogen atom unless indicated otherwise. Where a nitrogen-containing heteroaryl ring is shown with an open valency on a nitrogen atom, and variables such as $R^a$, $R^b$ or $R^c$ are shown on the heteroaryl ring, such variables may be bound or joined to the open valency nitrogen. Where a chiral center exists in a structure but no specific stereochemistry is shown for the chiral center, both enantiomers associated with the chiral center are encompassed by the structure. Where a structure shown herein may exist in multiple tautomeric forms, all such tautomers are encompassed by the structure. The atoms represented in the structures herein are intended to encompass all naturally occurring isotopes of such atoms. Thus, for example, the hydrogen atoms represented herein are meant to include deuterium and tritium, and the carbon atoms are meant to include $C^{13}$ and $C^{14}$ isotopes.

All patents and publications identified herein are incorporated herein by reference in their entirety.

Compounds of the Invention

The invention provides compounds of the formula I or formula II:

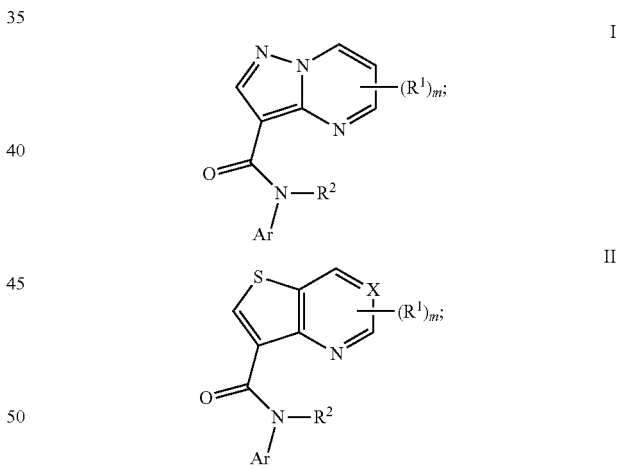

or a pharmaceutically acceptable salt thereof, wherein:
X is N or CH
m is 1 or 2;
Ar is:
optionally substituted aryl; or
optionally substituted heteroaryl;
$R^1$ is:
hydrogen;
$C_{1-6}$alkyl;
$C_{1-6}$alkoxy;
hydroxy;
hydroxy-$C_{1-6}$alkyl;
$C_{1-6}$alkyl-amino;

amino-$C_{1-6}$alkyl;
amino-$C_{1-6}$alkyl-amino;
hydroxy-$C_{1-6}$alkylamino
$C_{3-6}$cycloalkylamino;
amino-$C_{3-6}$cycloalkylamino;
amino-$C_{3-6}$heterocycloalkylamino;
aminocarbonyl;
halo;
hydroxy-$C_{1-6}$alkyl; or
hydroxy-$C_{1-6}$alkoxy; and
$R^2$ is:
hydrogen; or
$C_{1-6}$alkyl.

In certain embodiments the compounds of the invention are of formula I.

In certain embodiments the compounds of the invention are of formula II.

In certain embodiments of formula II, X is N.

In certain embodiments of formula II, X is CH.

In certain embodiments of formula I or formula II, $R^2$ is hydrogen.

In certain embodiments of formula I or formula II, m is 1.

In certain embodiments of formula I or formula II, m is 2.

In certain embodiments of formula I or formula II, Ar is optionally substituted aryl.

In certain embodiments of formula I or formula II, Ar is optionally substituted phenyl or optionally substituted naphthyl.

In certain embodiments of formula I or formula II, Ar is substituted phenyl.

In certain embodiments of formula I or formula II, Ar is substituted naphthyl.

In certain embodiments of formula I or formula II, Ar is phenyl substituted one, two or three times with a group or groups independently selected from: halo; $C_{1-6}$alkyl; halo-$C_{1-6}$alkyl; $C_{1-6}$alkenyl; $C_{1-6}$alkoxy; halo-$C_{1-6}$alkoxy; hydroxy-$C_{1-6}$alkyl; hydroxy-$C_{1-6}$alkylamino; $C_{1-6}$alkyl-amino; hydroxy; amino; amino-$C_{1-6}$alkyl; aminocarbonyl; hydroxy-$C_{1-6}$alkoxy; hydroxy-$C_{1-6}$alkenyl; $C_{1-6}$alkoxy-$C_{1-6}$alkoxy; $C_{1-6}$alkylsulfonyl; $C_{1-6}$alkylsulfanyl; piperidinyl wherein the piperidinyl moiety is optionally substituted with hydroxy, amino, amino-$C_{1-6}$alkyl, hydroxy-$C_{1-6}$alkyl or aminocarbonyl; phenylaminocarbonyl; hydroxy-$C_{1-6}$alkylamino; cyclohexyloxy wherein the cyclohexyl moiety thereof is optionally substituted with hydroxy, amino, amino-$C_{1-6}$alkyl or hydroxy-$C_{1-6}$alkyl; cyclopentyloxy wherein the cyclopentyl moiety thereof is optionally substituted with hydroxy, amino, amino-$C_{1-6}$alkyl or hydroxy-$C_{1-6}$alkyl; piperidinyloxy wherein the piperidinyl moiety thereof is optionally substituted with hydroxy, amino, amino-$C_{1-6}$alkyl, hydroxy-$C_{1-6}$alkyl or aminocarbonyl; phenyl wherein the phenyl moiety is optionally substituted with amino, hydroxy, amino-$C_{1-6}$alkyl, hydroxy-$C_{1-6}$alkyl or aminocarbonyl; pyrrolidinyl wherein the pyrrolidinyl moiety is optionally substituted with hydroxy, amino, amino-$C_{1-6}$alkyl, hydroxy-$C_{1-6}$alkyl or aminocarbonyl; pyrrolidinyloxy wherein the pyrrolidinyl moiety is optionally substituted with hydroxy, amino, amino-$C_{1-6}$alkyl, hydroxy-$C_{1-6}$alkyl or aminocarbonyl; piperazinyl wherein the piperazinyl moiety is optionally substituted with $C_{1-6}$alkyl; oxazol-$C_{1-6}$alkoxy wherein the oxazol moiety thereof is optionally substituted with $C_{1-6}$alkyl; morpholinyl; hydroxy-$C_{1-6}$alkylaminocarbonyl; $C_{3-6}$cycloalkyl; azepanyl wherein the azepanyl moiety is optionally substituted with hydroxy, amino, amino-$C_{1-6}$alkyl, hydroxy-$C_{1-6}$alkyl or aminocarbonyl; benzyl wherein the phenyl moiety thereof is optionally substituted with amino, hydroxy, amino-$C_{1-6}$alkyl, hydroxy-$C_{1-6}$alkyl or aminocarbonyl; $C_{1-6}$alkoxycarbonyl-$C_{1-6}$alkoxy; and $C_{1-6}$alkylcarbonylamino.

In certain embodiments of formula I or formula II, Ar is phenyl substituted once or twice with a group or groups independently selected from: halo; $C_{1-6}$alkyl; halo-$C_{1-6}$alkyl; $C_{1-6}$alkenyl; $C_{1-6}$alkoxy; halo-$C_{1-6}$alkoxy; hydroxy-$C_{1-6}$alkyl; hydroxy-$C_{1-6}$alkylamino; $C_{1-6}$alkyl-amino; hydroxy; amino; amino-$C_{1-6}$alkyl; aminocarbonyl; hydroxy-$C_{1-6}$alkoxy; hydroxy-$C_{1-6}$alkenyl; $C_{1-6}$alkoxy-$C_{1-6}$alkoxy; $C_{1-6}$alkylsulfonyl; $C_{1-6}$alkylsulfanyl; piperidinyl wherein the piperidinyl moiety is optionally substituted with hydroxy, amino, amino-$C_{1-6}$alkyl, hydroxy-$C_{1-6}$alkyl or aminocarbonyl; phenylaminocarbonyl; hydroxy-$C_{1-6}$alkylamino; cyclohexyloxy wherein the cyclohexyl moiety thereof is optionally substituted with hydroxy, amino, amino-$C_{1-6}$alkyl or hydroxy-$C_{1-6}$alkyl; cyclopentyloxy wherein the cyclopentyl moiety thereof is optionally substituted with hydroxy, amino, amino-$C_{1-6}$alkyl or hydroxy-$C_{1-6}$alkyl; piperidinyloxy wherein the piperidinyl moiety thereof is optionally substituted with hydroxy, amino, amino-$C_{1-6}$alkyl, hydroxy-$C_{1-6}$alkyl or aminocarbonyl; phenyl wherein the phenyl moiety is optionally substituted with amino, hydroxy, amino-$C_{1-6}$alkyl, hydroxy-$C_{1-6}$alkyl or aminocarbonyl; pyrrolidinyl wherein the pyrrolidinyl moiety is optionally substituted with hydroxy, amino, amino-$C_{1-6}$alkyl, hydroxy-$C_{1-6}$alkyl or aminocarbonyl; pyrrolidinyloxy wherein the pyrrolidinyl moiety is optionally substituted with hydroxy, amino, amino-$C_{1-6}$alkyl, hydroxy-$C_{1-6}$alkyl or aminocarbonyl; piperazinyl wherein the piperazinyl moiety is optionally substituted with $C_{1-6}$alkyl; oxazol-$C_{1-6}$alkoxy wherein the oxazol moiety thereof is optionally substituted with $C_{1-6}$alkyl; morpholinyl; hydroxy-$C_{1-6}$alkylaminocarbonyl; $C_{3-6}$cycloalkyl; azepanyl wherein the azepanyl moiety is optionally substituted with hydroxy, amino, amino-$C_{1-6}$alkyl, hydroxy-$C_{1-6}$alkyl or aminocarbonyl; benzyl wherein the phenyl moiety thereof is optionally substituted with amino, hydroxy, amino-$C_{1-6}$alkyl, hydroxy-$C_{1-6}$alkyl or aminocarbonyl; $C_{1-6}$alkoxycarbonyl-$C_{1-6}$alkoxy; and $C_{1-6}$alkylcarbonylamino.

In certain embodiments of formula I or formula II, Ar is phenyl substituted once with halo and once with a group selected from: halo; $C_{1-6}$alkyl; halo-$C_{1-6}$alkyl; $C_{1-6}$alkenyl; $C_{1-6}$alkoxy; halo-$C_{1-6}$alkoxy; hydroxy-$C_{1-6}$alkyl; hydroxy-$C_{1-6}$alkylamino; $C_{1-6}$alkyl-amino; hydroxy; amino; amino-$C_{1-6}$alkyl; aminocarbonyl; hydroxy-$C_{1-6}$alkoxy; hydroxy-$C_{1-6}$alkenyl; $C_{1-6}$alkoxy-$C_{1-6}$alkoxy; $C_{1-6}$alkylsulfonyl; $C_{1-6}$alkylsulfanyl; piperidinyl wherein the piperidinyl moiety is optionally substituted with hydroxy, amino, amino-$C_{1-6}$alkyl, hydroxy-$C_{1-6}$alkyl or aminocarbonyl; phenylaminocarbonyl; hydroxy-$C_{1-6}$alkylamino; cyclohexyloxy wherein the cyclohexyl moiety thereof is optionally substituted with hydroxy, amino, amino-$C_{1-6}$alkyl or hydroxy-$C_{1-6}$alkyl; cyclopentyloxy wherein the cyclopentyl moiety thereof is optionally substituted with hydroxy, amino, amino-$C_{1-6}$alkyl or hydroxy-$C_{1-6}$alkyl; piperidinyloxy wherein the piperidinyl moiety thereof is optionally substituted with hydroxy, amino, amino-$C_{1-6}$alkyl, hydroxy-$C_{1-6}$alkyl or aminocarbonyl; phenyl wherein the phenyl moiety is optionally substituted with amino, hydroxy, amino-$C_{1-6}$alkyl, hydroxy-$C_{1-6}$alkyl or aminocarbonyl; pyrrolidinyl wherein the pyrrolidinyl moiety is optionally substituted with hydroxy, amino, amino-$C_{1-6}$alkyl, hydroxy-$C_{1-6}$alkyl or aminocarbonyl; pyrrolidinyloxy wherein the pyrrolidinyl moiety is optionally substituted with hydroxy, amino, amino-$C_{1-6}$alkyl, hydroxy-$C_{1-6}$alkyl or aminocarbonyl; piperazinyl wherein the piperazinyl moiety is optionally substituted with $C_{1-6}$alkyl; oxazol-$C_{1-6}$alkoxy wherein the oxazol moiety thereof is optionally substituted with $C_{1-6}$alkyl; morpholinyl; hydroxy-$C_{1-6}$alkylaminocarbonyl; $C_{3-6}$cycloalkyl; azepanyl wherein the azepanyl moiety is optionally substituted with hydroxy, amino, amino-$C_{1-6}$alkyl, hydroxy-$C_{1-6}$alkyl or aminocarbonyl; benzyl wherein the phenyl moiety thereof is optionally substituted with amino, hydroxy, amino-$C_{1-6}$alkyl, hydroxy-$C_{1-6}$alkyl or aminocarbonyl; $C_{1-6}$alkoxycarbonyl-$C_{1-6}$alkoxy; and $C_{1-6}$alkylcarbonylamino.

In certain embodiments of formula I or formula II, Ar is substituted aryl selected from: 2-(4-aminomethyl-piperidin-1-yl)-5-chloro-phenyl; 2-(4-aminomethyl-piperidin-1-yl)-4-phenylcarbamoyl-phenyl; 5-chloro-2-[4-(1-hydroxy-ethyl)-piperidin-1-yl]-phenyl; 5-chloro-2-(4-hydroxymethyl-piperidin-1-yl)-phenyl; 5-chloro-2-(4-hydroxy-cyclohexyloxy)-phenyl; 5-chloro-2-piperidin-1-yl-phenyl; 2-(4-aminomethyl-piperidin-1-yl)-5-chloro-phenyl; 2-[4-(1-amino-ethyl)-piperidin-1-yl]-5-chloro-phenyl; 2-(4-carbamoyl-piperidin-1-yl)-5-chloro-phenyl; 5-chloro-2-[3-(1-hydroxy-ethyl)-pyrrolidin-1-yl]-phenyl; 4'-aminomethyl-4-chloro-biphenyl-2-yl; 5-chloro-2-methoxy-phenyl; 3-amino-2-(4-aminomethyl-piperidin-1-yl)-phenyl; 3-amino-2-piperidin-1-yl-phenyl; 5-hydroxymethyl-2-piperidin-1-yl-phenyl; 4-chloro-4'-hydroxymethyl-biphenyl-2-yl; 5-chloro-2-isopropoxy-phenyl; 5-chloro-2-(3-hydroxymethyl-cyclopentyloxy)-phenyl; 5-chloro-2-pyrrolidin-1-yl-phenyl; 5-chloro-2-(3-hydroxy-cyclopentyloxy)-phenyl; 5-chloro-2-(3-hydroxy-propoxy)-phenyl; 5-chloro-2-(4-hydroxy-butoxy; 2-methoxy-4-phenylcarbamoyl-phenyl; 5-chloro-2-(3-hydroxy-piperidin-1-yl)-phenyl; 5-chloro-2-(piperidin-4-yloxy)-phenyl; 4-chloro-4'-hydroxy-biphenyl-2-yl; 5-chloro-2-(3-hydroxy-pyrrolidin-1-yl)-phenyl; 5-chloro-2-(3,4-dihydroxy-butoxy; 5-chloro-2-(4-methyl-piperazin-1-yl)-phenyl; 5-chloro-2-(oxazol-5-ylmethoxy)-phenyl; 5-chloro-2-morpholin-4-yl-phenyl; 4-chloro-biphenyl-2-yl; 2-(3-aminomethyl-pyrrolidin-1-yl)-5-chloro-phenyl; 5-chloro-2-(3-hydroxy-cyclohexyloxy)-phenyl; 4-(3-hydroxy-propylcarbamoyl)-2-methoxy-phenyl; 5-chloro-2-(3-hydroxymethyl-pyrrolidin-1-yl)-phenyl; 5-chloro-2-difluoromethoxy-phenyl; 5-chloro-2-dimethylamino-phenyl; 2-(3-amino-pyrrolidin-1-yl)-5-chloro-phenyl; 5-chloro-2-methylsulfanyl-phenyl; 5-chloro-2-cyclohexyl-phenyl; 3-(2-hydroxy-ethylamino)-2-piperidin-1-yl-phenyl; 5-chloro-2-(4-methyl-oxazol-5-ylmethoxy)-phenyl; biphenyl-2-yl; 5-chloro-2-(3-hydroxy-1,1-dimethyl-propoxy)-phenyl; 2-(4-amino-cyclohexyloxy)-5-chloro-phenyl; 2-azepan-1-yl-5-chloro-phenyl; 4-(2-hydroxy-ethylcarbamoyl)-2-methoxy-phenyl; 4-hydroxy-cyclohexyloxy)-phenyl; 5-chloro-2-(2-methoxy-ethoxy)-phenyl; 4-chloro-3'-hydroxy-biphenyl-2-yl; 5-bromo-2-methoxy-phenyl; 5-chloro-2-[(2-hydroxy-ethyl)-methyl-amino]-phenyl; 5-chloro-2-(4-hydroxy-phenoxy)-phenyl; 4-carbamoyl-2-methoxy-phenyl; 5-chloro-2-isobutoxy-phenyl; 5-chloro-2-(2,3-dihydroxy-propoxy)-phenyl; 5-chloro-2-(3-methoxy-propoxy)-phenyl; 5-chloro-2-(3-hydroxymethyl-piperidin-1-yl)-phenyl; 5-chloro-2-(3-hydroxy-benzyloxy; 5-chloro-2,4-dimethoxy-phenyl; 2-methoxy-5-vinyl-phenyl; 3-(3-hydroxy-propylamino)-2-piperidin-1-yl-phenyl5-chloro-2-(4-hydroxy-butyl)-phenyl; 2-[3-(1-amino-ethyl)-pyrrolidin-1-yl]-5-chloro-phenyl; 5-chloro-2-[(3-hydroxy-propyl)-methyl-amino]-phenyl; 5-chloro-2-(4-methylaminomethyl-piperidin-1-yl)-phenyl; 5-(3-hydroxy-propenyl)-2-methoxy-phenyl; 5-chloro-2-ethyl-phenyl; 4-methanesulfonyl-2-methoxy-phenyl; 5-chloro-2-(3-hydroxy-phenoxy)-phenyl; 2,4-dimethoxy-phenyl; 5-fluoro-2-methoxy-phenyl; 5-chloro-2-phenoxy-phenyl; 5-(3-hydroxy-propyl)-2-methoxy-phenyl5-chloro-2-(2-hydroxymethyl-piperidin-1-yl)-phenyl; 5-chloro-2-(4-dimethylaminomethyl-piperidin-1-yl)-phenyl; 3-methoxy-biphenyl-4-yl; 5-ethyl-2-methoxy-phenyl; 5-methoxy-2-methyl-biphenyl-4-yl; 2-methoxy-3,5-dimethyl-phenyl; 4-dimethylcarbamoyl-2-methoxy-pheny; 5-acetylamino-2-methoxy-phenyl; 5-chloro-2-methoxy-4-phenylcarbamoyl-phenyl; and 4-hydroxymethyl-2-methoxy-phenyl; 3-(3-hydroxy-cyclopentyloxy)-naphthalen-2-yl; 3-(3-hydroxy-propoxy)-naphthalen-2-yl; 7-hydroxymethyl-3-methoxy-naphthalen-2-yl; 3-(4-hydroxy-cyclohexyloxy)-naphthalen-2-yl; and 3-methoxy-naphthalen-2-yl.

In certain embodiments of formula I or formula II, Ar is substituted phenyl selected from: 2-(4-aminomethyl-piperidin-1-yl)-5-chloro-phenyl; 2-(4-aminomethyl-piperidin-1-yl)-4-phenylcarbamoyl-phenyl; 5-chloro-2-[4-(1-hydroxy-ethyl)-piperidin-1-yl]-phenyl; 5-chloro-2-(4-hydroxymethyl-piperidin-1-yl)-phenyl; 5-chloro-2-(4-hydroxy-cyclohexyloxy)-phenyl; 5-chloro-2-piperidin-1-yl-phenyl; 2-(4-aminomethyl-piperidin-1-yl)-5-chloro-phenyl; 2-[4-(1-amino-ethyl)-piperidin-1-yl]-5-chloro-phenyl; 2-(4-carbamoyl-piperidin-1-yl)-5-chloro-phenyl; 5-chloro-2-[3-(1-hydroxy-ethyl)-pyrrolidin-1-yl]-phenyl; 4'-aminomethyl-4-chloro-biphenyl-2-yl; 5-chloro-2-methoxy-phenyl; 3-amino-2-(4-aminomethyl-piperidin-1-yl)-phenyl; 3-amino-2-piperidin-1-yl-phenyl; 5-hydroxymethyl-2-piperidin-1-yl-phenyl; 4-chloro-4'-hydroxymethyl-biphenyl-2-yl; 5-chloro-2-isopropoxy-phenyl; 5-chloro-2-(3-hydroxymethyl-cyclopentyloxy)-phenyl; 5-chloro-2-pyrrolidin-1-yl-phenyl; 5-chloro-2-(3-hydroxy-cyclopentyloxy)-phenyl; 5-chloro-2-(3-hydroxy-propoxy)-phenyl; 5-chloro-2-(4-hydroxy-butoxy; 2-methoxy-4-phenylcarbamoyl-phenyl; 5-chloro-2-(3-hydroxy-piperidin-1-yl)-phenyl; 5-chloro-2-(piperidin-4-yloxy)-phenyl; 4-chloro-4'-hydroxy-biphenyl-2-yl; 5-chloro-2-(3-hydroxy-pyrrolidin-1-yl)-phenyl; 5-chloro-2-(3,4-dihydroxy-butoxy; 5-chloro-2-(4-methyl-piperazin-1-yl)-phenyl; 5-chloro-2-(oxazol-5-ylmethoxy)-phenyl; 5-chloro-2-morpholin-4-yl-phenyl; 4-chloro-biphenyl-2-yl; 2-(3-aminomethyl-pyrrolidin-1-yl)-5-chloro-phenyl; 5-chloro-2-(3-hydroxy-cyclohexyloxy)-phenyl; 4-(3-hydroxy-propylcarbamoyl)-2-methoxy-phenyl; 5-chloro-2-(3-hydroxymethyl-pyrrolidin-1-yl)-phenyl; 5-chloro-2-difluoromethoxy-phenyl; 5-chloro-2-dimethylamino-phenyl; 2-(3-amino-pyrrolidin-1-yl)-5-chloro-phenyl; 5-chloro-2-methylsulfanyl-phenyl; 5-chloro-2-cyclohexyl-phenyl; 3-(2-hydroxy-ethylamino)-2-piperidin-1-yl-phenyl; 5-chloro-2-(4-methyl-oxazol-5-ylmethoxy)-phenyl; biphenyl-2-yl; 5-chloro-2-(3-hydroxy-1,1-dimethyl-propoxy)-phenyl; 2-(4-amino-cyclohexyloxy)-5-chloro-phenyl; 2-azepan-1-yl-5-chloro-phenyl; 4-(2-hydroxy-ethylcarbamoyl)-2-methoxy-phenyl; 4-hydroxy-cyclohexyloxy)-phenyl; 5-chloro-2-(2-methoxy-ethoxy)-phenyl; 4-chloro-3'-hydroxy-biphenyl-2-yl; 5-bromo-2-methoxy-phenyl; 5-chloro-2-[(2-hydroxy-ethyl)-methyl-amino]-phenyl; 5-chloro-2-(4-hydroxy-phenoxy)-phenyl; 4-carbamoyl-2-methoxy-phenyl; 5-chloro-2-isobutoxy-phenyl; 5-chloro-2-(2,3-dihydroxy-propoxy)-phenyl; 5-chloro-2-(3-methoxy-propoxy)-phenyl; 5-chloro-2-(3-hydroxymethyl-piperidin-1-yl)-phenyl; 5-chloro-2-(3-hydroxy-benzyloxy; 5-chloro-2,4-dimethoxy-phenyl; 2-methoxy-5-vinyl-phenyl; 3-(3-hydroxy-propylamino)-2-piperidin-1-yl-phenyl5-chloro-2-(4-hydroxy-butyl)-phenyl; 2-[3-(1-amino-ethyl)-pyrrolidin-1-yl]-5-chloro-phenyl; 5-chloro-2-[(3-hydroxy-propyl)-methyl-amino]-phenyl; 5-chloro-2-(4-methylaminomethyl-piperidin-1-yl)-phenyl; 5-(3-hydroxy-propenyl)-2-methoxy-phenyl; 5-chloro-2-ethyl-phenyl; 4-methanesulfonyl-2-methoxy-phenyl; 5-chloro-2-(3-hydroxy-phenoxy)-phenyl; 2,4-dimethoxy-phenyl; 5-fluoro-2-methoxy-phenyl;

5-chloro-2-phenoxy-phenyl; 5-(3-hydroxy-propyl)-2-methoxy-phenyl5-chloro-2-(2-hydroxymethyl-piperidin-1-yl)-phenyl; and 5-chloro-2-(4-dimethylaminomethyl-piperidin-1-yl)-phenyl.

In certain embodiments of formula I or formula II, Ar is substituted naphthyl selected from: 3-(3-hydroxy-cyclopentyloxy)-naphthalen-2-yl; 3-(3-hydroxy-propoxy)-naphthalen-2-yl; 7-hydroxymethyl-3-methoxy-naphthalen-2-yl; 3-(4-hydroxy-cyclohexyloxy)-naphthalen-2-yl; and 3-methoxy-naphthalen-2-yl.

In certain embodiments of formula I or formula II, Ar is 2-(4-aminomethyl-piperidin-1-yl)-5-chloro-phenyl.

In certain embodiments of formula I or formula II, Ar is 2-(4-aminomethyl-piperidin-1-yl)-4-phenylcarbamoyl-phenyl.

In certain embodiments of formula I or formula II, Ar is 5-chloro-2-[4-(1-hydroxy-ethyl)-piperidin-1-yl]-phenyl.

In certain embodiments of formula I or formula II, Ar is 5-chloro-2-(4-hydroxymethyl-piperidin-1-yl)-phenyl.

In certain embodiments of formula I or formula II, Ar is 5-chloro-2-(4-hydroxy-cyclohexyloxy)-phenyl.

In certain embodiments of formula I or formula II, Ar is 5-chloro-2-piperidin-1-yl-phenyl.

In certain embodiments of formula I or formula II, Ar is 2-(4-aminomethyl-piperidin-1-yl)-5-chloro-phenyl.

In certain embodiments of formula I or formula II, Ar is 2-[4-(1-amino-ethyl)-piperidin-1-yl]-5-chloro-phenyl.

In certain embodiments of formula I or formula II, Ar is 2-(4-carbamoyl-piperidin-1-yl)-5-chloro-phenyl.

In certain embodiments of formula I or formula II, Ar is 5-chloro-2-[3-(1-hydroxy-ethyl)-pyrrolidin-1-yl]-phenyl.

In certain embodiments of formula I or formula II, Ar is 4'-aminomethyl-4-chloro-biphenyl-2-yl.

In certain embodiments of formula I or formula II, Ar is 5-chloro-2-methoxy-phenyl.

In certain embodiments of formula I or formula II, Ar is 3-amino-2-(4-aminomethyl-piperidin-1-yl)-phenyl.

In certain embodiments of formula I or formula II, Ar is 3-amino-2-piperidin-1-yl-phenyl.

In certain embodiments of formula I or formula II, Ar is 5-hydroxymethyl-2-piperidin-1-yl-phenyl.

In certain embodiments of formula I or formula II, Ar is 3-(3-hydroxy-cyclopentyloxy)-naphthalen-2-yl.

In certain embodiments of formula I or formula II, Ar is 4-chloro-4'-hydroxymethyl-biphenyl-2-yl.

In certain embodiments of formula I or formula II, Ar is 5-chloro-2-isopropoxy-phenyl.

In certain embodiments of formula I or formula II, Ar is 5-chloro-2-(3-hydroxymethyl-cyclopentyloxy)-phenyl.

In certain embodiments of formula I or formula II, Ar is 5-chloro-2-pyrrolidin-1-yl-phenyl.

In certain embodiments of formula I or formula II, Ar is 3-(3-hydroxy-propoxy)-naphthalen-2-yl.

In certain embodiments of formula I or formula II, Ar is 7-hydroxymethyl-3-methoxy-naphthalen-2-yl.

In certain embodiments of formula I or formula II, Ar is 5-chloro-2-(3-hydroxy-cyclopentyloxy)-phenyl.

In certain embodiments of formula I or formula II, Ar is 5-chloro-2-(3-hydroxy-propoxy)-phenyl.

In certain embodiments of formula I or formula II, Ar is 3-(4-hydroxy-cyclohexyloxy)-naphthalen-2-yl.

In certain embodiments of formula I or formula II, Ar is 5-chloro-2-(4-hydroxy-butoxy.

In certain embodiments of formula I or formula II, Ar is 2-methoxy-4-phenylcarbamoyl-phenyl.

In certain embodiments of formula I or formula II, Ar is 5-chloro-2-(3-hydroxy-piperidin-1-yl)-phenyl.

In certain embodiments of formula I or formula II, Ar is 5-chloro-2-(piperidin-4-yloxy)-phenyl.

In certain embodiments of formula I or formula II, Ar is 4-chloro-4'-hydroxy-biphenyl-2-yl.

In certain embodiments of formula I or formula II, Ar is 5-chloro-2-(3-hydroxy-pyrrolidin-1-yl)-phenyl.

In certain embodiments of formula I or formula II, Ar is 5-chloro-2-(3,4-dihydroxy-butoxy.

In certain embodiments of formula I or formula II, Ar is 5-chloro-2-(4-methyl-piperazin-1-yl)-phenyl.

In certain embodiments of formula I or formula II, Ar is 5-chloro-2-(oxazol-5-ylmethoxy)-phenyl.

In certain embodiments of formula I or formula II, Ar is 5-chloro-2-morpholin-4-yl-phenyl.

In certain embodiments of formula I or formula II, Ar is 4-chloro-biphenyl-2-yl.

In certain embodiments of formula I or formula II, Ar is 2-(3-aminomethyl-pyrrolidin-1-yl)-5-chloro-phenyl.

In certain embodiments of formula I or formula II, Ar is 5-chloro-2-(3-hydroxy-cyclohexyloxy)-phenyl.

In certain embodiments of formula I or formula II, Ar is 3-methoxy-naphthalen-2-yl.

In certain embodiments of formula I or formula II, Ar is 4-(3-hydroxy-propylcarbamoyl)-2-methoxy-phenyl.

In certain embodiments of formula I or formula II, Ar is 5-chloro-2-(3-hydroxymethyl-pyrrolidin-1-yl)-phenyl.

In certain embodiments of formula I or formula II, Ar is 5-chloro-2-difluoromethoxy-phenyl.

In certain embodiments of formula I or formula II, Ar is 5-chloro-2-dimethylamino-phenyl.

In certain embodiments of formula I or formula II, Ar is 2-(3-amino-pyrrolidin-1-yl)-5-chloro-phenyl.

In certain embodiments of formula I or formula II, Ar is 5-chloro-2-methylsulfanyl-phenyl.

In certain embodiments of formula I or formula II, Ar is 5-chloro-2-cyclohexyl-phenyl. In certain embodiments of formula I or formula II, Ar is 3-(2-hydroxy-ethylamino)-2-piperidin-1-yl-phenyl.

In certain embodiments of formula I or formula II, Ar is 5-chloro-2-(4-methyl-oxazol-5-ylmethoxy)-phenyl.

In certain embodiments of formula I or formula II, Ar is biphenyl-2-yl.

In certain embodiments of formula I or formula II, Ar is 5-chloro-2-(3-hydroxy-1,1-dimethyl-propoxy)-phenyl.

In certain embodiments of formula I or formula II, Ar is 2-(4-amino-cyclohexyloxy)-5-chloro-phenyl.

In certain embodiments of formula I or formula II, Ar is 2-azepan-1-yl-5-chloro-phenyl.

In certain embodiments of formula I or formula II, Ar is 4-(2-hydroxy-ethylcarbamoyl)-2-methoxy-phenyl.

In certain embodiments of formula I or formula II, Ar is 4-hydroxy-cyclohexyloxy)-phenyl.

In certain embodiments of formula I or formula II, Ar is 5-chloro-2-(2-methoxy-ethoxy)-phenyl.

In certain embodiments of formula I or formula II, Ar is 4-chloro-3'-hydroxy-biphenyl-2-yl.

In certain embodiments of formula I or formula II, Ar is 5-bromo-2-methoxy-phenyl.

In certain embodiments of formula I or formula II, Ar is 5-chloro-2-[(2-hydroxy-ethyl)-methyl-amino]-phenyl.

In certain embodiments of formula I or formula II, Ar is 5-chloro-2-(4-hydroxy-phenoxy)-phenyl.

In certain embodiments of formula I or formula II, Ar is 4-carbamoyl-2-methoxy-phenyl.

In certain embodiments of formula I or formula II, Ar is 5-chloro-2-isobutoxy-phenyl.

In certain embodiments of formula I or formula II, Ar is 5-chloro-2-(2,3-dihydroxy-propoxy)-phenyl.

In certain embodiments of formula I or formula II, Ar is 5-chloro-2-(3-methoxy-propoxy)-phenyl.

In certain embodiments of formula I or formula II, Ar is 5-chloro-2-(3-hydroxymethyl-piperidin-1-yl)-phenyl.

In certain embodiments of formula I or formula II, Ar is 5-chloro-2-(3-hydroxy-benzyloxy.

In certain embodiments of formula I or formula II, Ar is 5-chloro-2,4-dimethoxy-phenyl.

In certain embodiments of formula I or formula II, Ar is 2-methoxy-5-vinyl-phenyl.

In certain embodiments of formula I or formula II, Ar is 3-(3-hydroxy-propylamino)-2-piperidin-1-yl-phenyl.

In certain embodiments of formula I or formula II, Ar is 5-chloro-2-(4-hydroxy-butyl)-phenyl.

In certain embodiments of formula I or formula II, Ar is 2-[3-(1-amino-ethyl)-pyrrolidin-1-yl]-5-chloro-phenyl.

In certain embodiments of formula I or formula II, Ar is 5-chloro-2-[(3-hydroxy-propyl)-methyl-amino]-phenyl.

In certain embodiments of formula I or formula II, Ar is 5-chloro-2-(4-methylaminomethyl-piperidin-1-yl)-phenyl.

In certain embodiments of formula I or formula II, Ar is 5-(3-hydroxy-propenyl)-2-methoxy-phenyl.

In certain embodiments of formula I or formula II, Ar is 5-chloro-2-ethyl-phenyl.

In certain embodiments of formula I or formula II, Ar is 4-methanesulfonyl-2-methoxy-phenyl.

In certain embodiments of formula I or formula II, Ar is 5-chloro-2-(3-hydroxy-phenoxy)-phenyl.

In certain embodiments of formula I or formula II, Ar is 2,4-dimethoxy-phenyl.

In certain embodiments of formula I or formula II, Ar is 5-fluoro-2-methoxy-phenyl.

In certain embodiments of formula I or formula II, Ar is 5-chloro-2-phenoxy-phenyl.

In certain embodiments of formula I or formula II, Ar is 5-(3-hydroxy-propyl)-2-methoxy-phenyl.

In certain embodiments of formula I or formula II, Ar is 5-chloro-2-(2-hydroxymethyl-piperidin-1-yl)-phenyl.

In certain embodiments of formula I or formula II, Ar is 5-chloro-2-(4-dimethylaminomethyl-piperidin-1-yl)-phenyl.

In certain embodiments of formula I or formula II, Ar is 3-methoxy-biphenyl-4-yl.

In certain embodiments of formula I or formula II, Ar is 5-ethyl-2-methoxy-phenyl.

In certain embodiments of formula I or formula II, Ar is 5-methoxy-2-methyl-biphenyl-4-yl.

In certain embodiments of formula I or formula II, Ar is 2-methoxy-3,5-dimethyl-phenyl.

In certain embodiments of formula I or formula II, Ar is 4-dimethylcarbamoyl-2-methoxy-phenyl.

In certain embodiments of formula I or formula II, Ar is 5-acetylamino-2-methoxy-phenyl.

In certain embodiments of formula I or formula II, Ar is 5-chloro-2-methoxy-4-phenylcarbamoyl-phenyl.

In certain embodiments of formula I or formula II, Ar is 4-hydroxymethyl-2-methoxy-phenyl.

In certain embodiments of formula I or formula II, Ar is optionally substituted heteroaryl.

In certain embodiments of formula I or formula II, Ar heteroaryl selected from: pyridinyl; benzo[1,3]dioxolyl; quinolinyl; 2-oxo-2,3-dihydro-indolyl; indolyl; benzimidazolyl; or indazolyl; each optionally substituted once or twice with a group or groups independently selected from: halo; $C_{1-6}$alkyl; halo-$C_{1-6}$alkyl; $C_{1-6}$alkenyl; $C_{1-6}$alkoxy; halo-$C_{1-6}$alkoxy; hydroxy-$C_{1-6}$alkyl; hydroxy-$C_{1-6}$alkylamino; $C_{1-6}$alkyl-amino; hydroxy; amino; amino-$C_{1-6}$alkyl; aminocarbonyl; hydroxy-$C_{1-6}$alkoxy; hydroxy-$C_{1-6}$alkenyl; $C_{1-6}$alkoxy-$C_{1-6}$alkoxy; $C_{1-6}$alkylsulfonyl; $C_{1-6}$alkylsulfanyl; piperidinyl wherein the piperidinyl moiety is optionally substituted with hydroxy, amino, amino-$C_{1-6}$alkyl, hydroxy-$C_{1-6}$alkyl or aminocarbonyl; phenylaminocarbonyl; hydroxy-$C_{1-6}$alkylamino; cyclohexyloxy wherein the cyclohexyl moiety thereof is optionally substituted with hydroxy, amino, amino-$C_{1-6}$alkyl or hydroxy-$C_{1-6}$alkyl; cyclopentyloxy wherein the cyclopentyl moiety thereof is optionally substituted with hydroxy, amino, amino-$C_{1-6}$alkyl or hydroxy-$C_{1-6}$alkyl; piperidinyloxy wherein the piperidinyl moiety thereof is optionally substituted with hydroxy, amino, amino-$C_{1-6}$alkyl, hydroxy-$C_{1-6}$alkyl or aminocarbonyl; phenyl wherein the phenyl moiety is optionally substituted with amino, hydroxy, amino-$C_{1-6}$alkyl, hydroxy-$C_{1-6}$alkyl or aminocarbonyl; pyrrolidinyl wherein the pyrrolidinyl moiety is optionally substituted with hydroxy, amino, amino-$C_{1-6}$alkyl, hydroxy-$C_{1-6}$alkyl or aminocarbonyl; pyrrolidinyloxy wherein the pyrrolidinyl moiety is optionally substituted with hydroxy, amino, amino-$C_{1-6}$ alkyl, hydroxy-$C_{1-6}$alkyl or aminocarbonyl; piperazinyl wherein the piperazinyl moiety is optionally substituted with $C_{1-6}$alkyl; oxazol-$C_{1-6}$alkoxy wherein the oxazol moiety thereof is optionally substituted with $C_{1-6}$alkyl; morpholinyl; hydroxy-$C_{1-6}$alkylaminocarbonyl; $C_{3-6}$cycloalkyl; azepanyl wherein the azepanyl moiety is optionally substituted with hydroxy, amino, amino-$C_{1-6}$alkyl, hydroxy-$C_{1-6}$ alkyl or aminocarbonyl; benzyl wherein the phenyl moiety thereof is optionally substituted with amino, hydroxy, amino-$C_{1-6}$alkyl, hydroxy-$C_{1-6}$alkyl or aminocarbonyl; $C_{1-6}$alkoxycarbonyl-$C_{1-6}$alkoxy; and $C_{1-6}$alkylcarbonylamino.

In certain embodiments of formula I or formula II, Ar is heteroaryl selected from: quinolinyl; 2-oxo-2,3-dihydro-indolyl; indolyl; benzimidazolyl; or indazolyl; each optionally substituted once or twice with a group or groups independently selected from: halo; $C_{1-6}$alkyl; halo-$C_{1-6}$alkyl; $C_{1-6}$alkenyl; $C_{1-6}$alkoxy; halo-$C_{1-6}$alkoxy; hydroxy-$C_{1-6}$ alkyl; hydroxy-$C_{1-6}$alkylamino; $C_{1-6}$alkyl-amino; hydroxy; amino; amino-$C_{1-6}$alkyl; aminocarbonyl; hydroxy-$C_{1-6}$ alkoxy; hydroxy-$C_{1-6}$alkenyl; $C_{1-6}$alkoxy-$C_{1-6}$alkoxy; $C_{1-6}$alkylsulfonyl; $C_{1-6}$alkylsulfanyl; piperidinyl wherein the piperidinyl moiety is optionally substituted with hydroxy, amino, amino-$C_{1-6}$alkyl, hydroxy-$C_{1-6}$alkyl or aminocarbonyl; phenylaminocarbonyl; hydroxy-$C_{1-6}$alkylamino; cyclohexyloxy wherein the cyclohexyl moiety thereof is optionally substituted with hydroxy, amino, amino-$C_{1-6}$alkyl or hydroxy-$C_{1-6}$alkyl; cyclopentyloxy wherein the cyclopentyl moiety thereof is optionally substituted with hydroxy, amino, amino-$C_{1-6}$alkyl or hydroxy-$C_{1-6}$ alkyl; piperidinyloxy wherein the piperidinyl moiety thereof is optionally substituted with hydroxy, amino, amino-$C_{1-6}$ alkyl, hydroxy-$C_{1-6}$alkyl or aminocarbonyl; phenyl wherein the phenyl moiety is optionally substituted with amino, hydroxy, amino-$C_{1-6}$alkyl, hydroxy-$C_{1-6}$alkyl or aminocarbonyl; pyrrolidinyl wherein the pyrrolidinyl moiety is optionally substituted with hydroxy, amino, amino-$C_{1-6}$ alkyl, hydroxy-$C_{1-6}$alkyl or aminocarbonyl; pyrrolidinyloxy wherein the pyrrolidinyl moiety is optionally substituted with hydroxy, amino, amino-$C_{1-6}$alkyl, hydroxy-$C_{1-6}$alkyl or aminocarbonyl; piperazinyl wherein the piperazinyl moiety is optionally substituted with $C_{1-6}$alkyl; oxazol-$C_{1-6}$ alkoxy wherein the oxazol moiety thereof is optionally substituted with $C_{1-6}$alkyl; morpholinyl; hydroxy-$C_{1-6}$alkylaminocarbonyl; $C_{3-6}$cycloalkyl; azepanyl wherein the azepanyl moiety is optionally substituted with hydroxy, amino, amino-$C_{1-6}$alkyl, hydroxy-$C_{1-6}$alkyl or aminocarbonyl; benzyl wherein the phenyl moiety thereof is optionally substituted with amino, hydroxy, amino-$C_{1-6}$alkyl, hydroxy-$C_{1-6}$alkyl or aminocarbonyl; $C_{1-6}$alkoxycarbonyl-$C_{1-6}$alkoxy; and $C_{1-6}$alkylcarbonylamino.

In certain embodiments of formula I or formula II, Ar is heteroaryl selected from: quinolinyl; 2-oxo-2,3-dihydro-indolyl; indolyl; benzimidazolyl; or indazolyl; each optionally substituted once or twice with a group or groups independently selected from: $C_{1-6}$alkyl; $C_{1-6}$alkoxy; hydroxy-$C_{1-6}$alkoxy; hydroxy-$C_{1-6}$alkylamino; amino-$C_{1-6}$alkoxy; cyclohexyloxy wherein the cyclohexyl moiety thereof is optionally substituted with hydroxy, amino, amino-$C_{1-6}$alkyl or hydroxy-$C_{1-6}$alkyl; piperidinyl wherein the piperidinyl moiety is optionally substituted with hydroxy, amino, amino-$C_{1-6}$alkyl, hydroxy-$C_{1-6}$alkyl or aminocarbonyl; piperidinyloxy wherein the piperidinyl moiety thereof is optionally substituted with hydroxy, amino, amino-$C_{1-6}$alkyl, hydroxy-$C_{1-6}$alkyl or aminocarbonyl; cyclopentyloxy wherein the cyclopentyl moiety thereof is optionally substituted with hydroxy, amino, amino-$C_{1-6}$alkyl or hydroxy-$C_{1-6}$alkyl; and pyrrolidinyloxy wherein the pyrrolidinyl moiety is optionally substituted with hydroxy, amino, amino-$C_{1-6}$alkyl, hydroxy-$C_{1-6}$alkyl or aminocarbonyl.

In certain embodiments of formula I or formula II, Ar is heteroaryl selected from: quinolinyl; 2-oxo-2,3-dihydro-indolyl; indolyl; benzimidazolyl; or indazolyl, each substituted once or twice with a group or groups independently selected from: $C_{1-6}$alkyl; $C_{1-6}$alkoxy; hydroxy-$C_{1-6}$alkoxy; hydroxy-$C_{1-6}$alkylamino; amino-$C_{1-6}$alkoxy; cyclohexyloxy wherein the cyclohexyl moiety thereof is optionally substituted with hydroxy, amino, amino-$C_{1-6}$alkyl or hydroxy-$C_{1-6}$alkyl; piperidinyl wherein the piperidinyl moiety is optionally substituted with hydroxy, amino, amino-$C_{1-6}$alkyl, hydroxy-$C_{1-6}$alkyl or aminocarbonyl; piperidinyloxy wherein the piperidinyl moiety thereof is optionally substituted with hydroxy, amino, amino-$C_{1-6}$alkyl, hydroxy-$C_{1-6}$alkyl or aminocarbonyl; cyclopentyloxy wherein the cyclopentyl moiety thereof is optionally substituted with hydroxy, amino, amino-$C_{1-6}$alkyl or hydroxy-$C_{1-6}$alkyl; and pyrrolidinyloxy wherein the pyrrolidinyl moiety is optionally substituted with hydroxy, amino, amino-$C_{1-6}$alkyl, hydroxy-$C_{1-6}$alkyl or aminocarbonyl.

In certain embodiments of formula I or formula II, Ar is quinolinyl optionally substituted once or twice with a group or groups independently selected from: $C_{1-6}$alkyl; $C_{1-6}$alkoxy; hydroxy-$C_{1-6}$alkoxy; hydroxy-$C_{1-6}$alkylamino; amino-$C_{1-6}$alkoxy; cyclohexyloxy wherein the cyclohexyl moiety thereof is optionally substituted with hydroxy, amino, amino-$C_{1-6}$alkyl or hydroxy-$C_{1-6}$alkyl; piperidinyl wherein the piperidinyl moiety is optionally substituted with hydroxy, amino, amino-$C_{1-6}$alkyl, hydroxy-$C_{1-6}$alkyl or aminocarbonyl; piperidinyloxy wherein the piperidinyl moiety thereof is optionally substituted with hydroxy, amino, amino-$C_{1-6}$alkyl, hydroxy-$C_{1-6}$alkyl or aminocarbonyl; cyclopentyloxy wherein the cyclopentyl moiety thereof is optionally substituted with hydroxy, amino, amino-$C_{1-6}$alkyl or hydroxy-$C_{1-6}$alkyl; and pyrrolidinyloxy wherein the pyrrolidinyl moiety is optionally substituted with hydroxy, amino, amino-$C_{1-6}$alkyl, hydroxy-$C_{1-6}$alkyl or aminocarbonyl.

In certain embodiments of formula I or formula II, Ar is 2-oxo-2,3-dihydro-indolyl optionally substituted once or twice with a group or groups independently selected from: $C_{1-6}$alkyl; $C_{1-6}$alkoxy; hydroxy-$C_{1-6}$alkoxy; hydroxy-$C_{1-6}$alkylamino; amino-$C_{1-6}$alkoxy; cyclohexyloxy wherein the cyclohexyl moiety thereof is optionally substituted with hydroxy, amino, amino-$C_{1-6}$alkyl or hydroxy-$C_{1-6}$alkyl; piperidinyl wherein the piperidinyl moiety is optionally substituted with hydroxy, amino, amino-$C_{1-6}$alkyl, hydroxy-$C_{1-6}$alkyl or aminocarbonyl; piperidinyloxy wherein the piperidinyl moiety thereof is optionally substituted with hydroxy, amino, amino-$C_{1-6}$alkyl, hydroxy-$C_{1-6}$alkyl or aminocarbonyl; cyclopentyloxy wherein the cyclopentyl moiety thereof is optionally substituted with hydroxy, amino, amino-$C_{1-6}$alkyl or hydroxy-$C_{1-6}$alkyl; and pyrrolidinyloxy wherein the pyrrolidinyl moiety is optionally substituted with hydroxy, amino, amino-$C_{1-6}$alkyl, hydroxy-$C_{1-6}$alkyl or aminocarbonyl.

In certain embodiments of formula I or formula II, Ar is indolyl optionally substituted once or twice with a group or groups independently selected from: $C_{1-6}$alkyl; $C_{1-6}$alkoxy; hydroxy-$C_{1-6}$alkoxy; hydroxy-$C_{1-6}$alkylamino; amino-$C_{1-6}$alkoxy; cyclohexyloxy wherein the cyclohexyl moiety thereof is optionally substituted with hydroxy, amino, amino-$C_{1-6}$alkyl or hydroxy-$C_{1-6}$alkyl; piperidinyl wherein the piperidinyl moiety is optionally substituted with hydroxy, amino, amino-$C_{1-6}$alkyl, hydroxy-$C_{1-6}$alkyl or aminocarbonyl; piperidinyloxy wherein the piperidinyl moiety thereof is optionally substituted with hydroxy, amino, amino-$C_{1-6}$alkyl, hydroxy-$C_{1-6}$alkyl or aminocarbonyl; cyclopentyloxy wherein the cyclopentyl moiety thereof is optionally substituted with hydroxy, amino, amino-$C_{1-6}$alkyl or hydroxy-$C_{1-6}$alkyl; and pyrrolidinyloxy wherein the pyrrolidinyl moiety is optionally substituted with hydroxy, amino, amino-$C_{1-6}$alkyl, hydroxy-$C_{1-6}$alkyl or aminocarbonyl.

In certain embodiments of formula I or formula II, Ar is indazolyl optionally substituted once or twice with a group or groups independently selected from: $C_{1-6}$alkyl; $C_{1-6}$alkoxy; hydroxy-$C_{1-6}$alkoxy; hydroxy-$C_{1-6}$alkylamino; amino-$C_{1-6}$alkoxy; cyclohexyloxy wherein the cyclohexyl moiety thereof is optionally substituted with hydroxy, amino, amino-$C_{1-6}$alkyl or hydroxy-$C_{1-6}$alkyl; piperidinyl wherein the piperidinyl moiety is optionally substituted with hydroxy, amino, amino-$C_{1-6}$alkyl, hydroxy-$C_{1-6}$alkyl or aminocarbonyl; piperidinyloxy wherein the piperidinyl moiety thereof is optionally substituted with hydroxy, amino, amino-$C_{1-6}$alkyl, hydroxy-$C_{1-6}$alkyl or aminocarbonyl; cyclopentyloxy wherein the cyclopentyl moiety thereof is optionally substituted with hydroxy, amino, amino-$C_{1-6}$alkyl or hydroxy-$C_{1-6}$alkyl; and pyrrolidinyloxy wherein the pyrrolidinyl moiety is optionally substituted with hydroxy, amino, amino-$C_{1-6}$alkyl, hydroxy-$C_{1-6}$alkyl or aminocarbonyl.

In certain embodiments of formula I or formula II, Ar is benzimidazolyl optionally substituted once or twice with a group or groups independently selected from: $C_{1-6}$alkyl; $C_{1-6}$alkoxy; hydroxy-$C_{1-6}$alkoxy; hydroxy-$C_{1-6}$alkylamino; amino-$C_{1-6}$alkoxy; cyclohexyloxy wherein the cyclohexyl moiety thereof is optionally substituted with hydroxy, amino, amino-$C_{1-6}$alkyl or hydroxy-$C_{1-6}$alkyl; piperidinyl wherein the piperidinyl moiety is optionally substituted with hydroxy, amino, amino-$C_{1-6}$alkyl, hydroxy-$C_{1-6}$alkyl or aminocarbonyl; piperidinyloxy wherein the piperidinyl moiety thereof is optionally substituted with hydroxy, amino, amino-$C_{1-6}$alkyl, hydroxy-$C_{1-6}$alkyl or aminocarbonyl; cyclopentyloxy wherein the cyclopentyl moiety thereof is optionally substituted with hydroxy, amino, amino-$C_{1-6}$alkyl or hydroxy-$C_{1-6}$alkyl; and pyrrolidinyloxy wherein the pyrrolidinyl moiety is optionally substituted with hydroxy, amino, amino-$C_{1-6}$alkyl, hydroxy-$C_{1-6}$alkyl or aminocarbonyl.

In certain embodiments of formula I or formula II, Ar is quinolin-6-yl substituted once or twice with a group or groups independently selected from: $C_{1-6}$alkyl; $C_{1-6}$alkoxy; hydroxy-$C_{1-6}$alkoxy; hydroxy-$C_{1-6}$alkylamino; amino-$C_{1-6}$alkoxy; cyclohexyloxy wherein the cyclohexyl moiety thereof is optionally substituted with hydroxy, amino, amino-$C_{1-6}$alkyl or hydroxy-$C_{1-6}$alkyl; piperidinyl wherein the piperidinyl moiety is optionally substituted with hydroxy, amino, amino-$C_{1-6}$alkyl, hydroxy-$C_{1-6}$alkyl or aminocarbonyl; piperidinyloxy wherein the piperidinyl moiety thereof is optionally substituted with hydroxy, amino, amino-$C_{1-6}$alkyl, hydroxy-$C_{1-6}$alkyl or aminocarbonyl; cyclopentyloxy wherein the cyclopentyl moiety thereof is optionally substituted with hydroxy, amino, amino-$C_{1-6}$alkyl or hydroxy-$C_{1-6}$alkyl; and pyrrolidinyloxy wherein the pyrrolidinyl moiety is optionally substituted with hydroxy, amino, amino-$C_{1-6}$alkyl, hydroxy-$C_{1-6}$alkyl or aminocarbonyl.

In certain embodiments of formula I or formula II, Ar is quinolin-6-yl substituted at the 7-position, and optionally substituted at the 2-position, with a group or groups independently selected from: $C_{1-6}$alkyl; $C_{1-6}$alkoxy; hydroxy-$C_{1-6}$alkoxy; hydroxy-$C_{1-6}$alkylamino; amino-$C_{1-6}$alkoxy; cyclohexyloxy wherein the cyclohexyl moiety thereof is optionally substituted with hydroxy, amino, amino-$C_{1-6}$alkyl or hydroxy-$C_{1-6}$alkyl; piperidinyl wherein the piperidinyl moiety is optionally substituted with hydroxy, amino, amino-$C_{1-6}$alkyl, hydroxy-$C_{1-6}$alkyl or aminocarbonyl; piperidinyloxy wherein the piperidinyl moiety thereof is optionally substituted with hydroxy, amino, amino-$C_{1-6}$alkyl, hydroxy-$C_{1-6}$alkyl or aminocarbonyl; cyclopentyloxy wherein the cyclopentyl moiety thereof is optionally substituted with hydroxy, amino, amino-$C_{1-6}$alkyl or hydroxy-$C_{1-6}$alkyl; and pyrrolidinyloxy wherein the pyrrolidinyl moiety is optionally substituted with hydroxy, amino, amino-$C_{1-6}$alkyl, hydroxy-$C_{1-6}$alkyl or aminocarbonyl.

In certain embodiments of formula I or formula II, Ar is heteroaryl selected from: 7-(4-aminomethyl-piperidin-1-yl)-quinolin-6-yl; 2-(2-hydroxy-ethylamino)-7-methoxy-quinolin-6-yl; 7-(4-hydroxy-cyclohexyloxy)-quinolin-6-yl; 7-methoxy-quinolin-6-yl; 7-piperidin-1-yl-quinolin-6-yl; 7-(3-hydroxy-cyclopentyloxy)-quinolin-6-yl; 7-(3-hydroxy-1-methyl-butoxy)-quinolin-6-yl; 7-(3-hydroxy-butoxy)-quinolin-6-yl; 7-(piperidin-4-yloxy)-quinolin-6-yl; 7-(3-hydroxy-1,1-dimethyl-propoxy)-quinolin-6-yl; 7-(3-amino-propoxy)-quinolin-6-yl; 7-(3-hydroxy-cyclopentyloxy)-quinolin-6-yl; 7-(piperidin-4-yloxy)-quinolin-6-yl; 7-(3-hydroxy-propoxy)-quinolin-6-yl; 7-(pyrrolidin-3-yloxy)-quinolin-6-yl; 7-(4-hydroxymethyl-piperidin-1-yl)-quinolin-6-yl; 7-(4-aminomethyl-piperidin-1-yl)-quinolin-6-yl; quinolin-6-yl; 5-(4-hydroxymethyl-piperidin-1-yl)-2-oxo-2,3-dihydro-1H-indol-6-yl; 5-(4-hydroxymethyl-phenyl)-2-methyl-1H-indol-6-yl; 2-oxo-5-piperidin-1-yl-2,3-dihydro-1H-indol-6-yl; 6-methoxy-1H-indazol-5-yl; 5-methoxy-2-methyl-1H-indol-6-yl; 5-methoxy-1H-indol-6-yl; or 1-(3-hydroxy-propyl)-1H-benzoimidazol-2-yl.

In certain embodiments of formula I or formula II, Ar is heteroaryl selected from: 7-(4-aminomethyl-piperidin-1-yl)-quinolin-6-yl; 2-(2-hydroxy-ethylamino)-7-methoxy-quinolin-6-yl; 7-(4-hydroxy-cyclohexyloxy)-quinolin-6-yl; 7-methoxy-quinolin-6-yl; 7-piperidin-1-yl-quinolin-6-yl; 7-(3-hydroxy-cyclopentyloxy)-quinolin-6-yl; 7-(3-hydroxy-1-methyl-butoxy)-quinolin-6-yl; 7-(3-hydroxy-butoxy)-quinolin-6-yl; 7-(piperidin-4-yloxy)-quinolin-6-yl; 7-(3-hydroxy-1,1-dimethyl-propoxy)-quinolin-6-yl; 7-(3-amino-propoxy)-quinolin-6-yl; 7-(3-hydroxy-cyclopentyloxy)-quinolin-6-yl; 7-(piperidin-4-yloxy)-quinolin-6-yl; 7-(3-hydroxy-propoxy)-quinolin-6-yl; 7-(pyrrolidin-3-yloxy)-quinolin-6-yl; 7-(4-hydroxymethyl-piperidin-1-yl)-quinolin-6-yl; 7-(4-aminomethyl-piperidin-1-yl)-quinolin-6-yl; and quinolin-6-yl.

In certain embodiments of formula I or formula II, Ar is quinolinyl selected from: 7-(4-aminomethyl-piperidin-1-yl)-quinolin-6-yl; 2-(2-hydroxy-ethylamino)-7-methoxy-quinolin-6-yl; 7-(4-hydroxy-cyclohexyloxy)-quinolin-6-yl; 7-methoxy-quinolin-6-yl; 7-piperidin-1-yl-quinolin-6-yl; 7-(3-hydroxy-cyclopentyloxy)-quinolin-6-yl; 7-(3-hydroxy-1-methyl-butoxy)-quinolin-6-yl; 7-(3-hydroxy-butoxy)-quinolin-6-yl; 7-(piperidin-4-yloxy)-quinolin-6-yl; 7-(3-hydroxy-1,1-dimethyl-propoxy)-quinolin-6-yl; 7-(3-amino-propoxy)-quinolin-6-yl; 7-(3-hydroxy-cyclopentyloxy)-quinolin-6-yl; 7-(piperidin-4-yloxy)-quinolin-6-yl; 7-(3-hydroxy-propoxy)-quinolin-6-yl; 7-(pyrrolidin-3-yloxy)-quinolin-6-yl; 7-(4-hydroxymethyl-piperidin-1-yl)-quinolin-6-yl; 7-(4-aminomethyl-piperidin-1-yl)-quinolin-6-yl; and quinolin-6-yl.

In certain embodiments of formula I or formula II, Ar is quinolinyl selected from: 7-(4-aminomethyl-piperidin-1-yl)-quinolin-6-yl; 2-(2-hydroxy-ethylamino)-7-methoxy-quinolin-6-yl; 7-(4-hydroxy-cyclohexyloxy)-quinolin-6-yl; 7-methoxy-quinolin-6-yl; 7-piperidin-1-yl-quinolin-6-yl; 7-(3-hydroxy-cyclopentyloxy)-quinolin-6-yl; 7-(3-hydroxy-1-methyl-butoxy)-quinolin-6-yl; 7-(3-hydroxy-butoxy)-quinolin-6-yl; 7-(piperidin-4-yloxy)-quinolin-6-yl; 7-(3-hydroxy-1,1-dimethyl-propoxy)-quinolin-6-yl; 7-(3-amino-propoxy)-quinolin-6-yl; 7-(3-hydroxy-cyclopentyloxy)-quinolin-6-yl; 7-(piperidin-4-yloxy)-quinolin-6-yl; 7-(3-hydroxy-propoxy)-quinolin-6-yl; 7-(pyrrolidin-3-yloxy)-quinolin-6-yl; 7-(4-hydroxymethyl-piperidin-1-yl)-quinolin-6-yl; and 7-(4-aminomethyl-piperidin-1-yl)-quinolin-6-yl.

In certain embodiments of formula I or formula II, each $R^1$ is independently: hydrogen; $C_{1-6}$alkyl; $C_{1-6}$alkoxy; hydroxy; hydroxy-$C_{1-6}$alkyl; $C_{1-6}$alkyl-amino; amino-$C_{1-6}$alkyl; amino-$C_{1-6}$alkyl-amino; hydroxy-$C_{1-6}$alkylamino; $C_{3-6}$cycloalkylamino; halo; or aminocarbonyl.

In certain embodiments of formula I or formula II, $R^1$ is hydrogen.

In certain embodiments of formula I or formula II, $R^1$ is $C_{1-6}$alkyl.

In certain embodiments of formula I or formula II, $R^1$ is $C_{1-6}$alkoxy.

In certain embodiments of formula I or formula II, $R^1$ is hydroxy.

In certain embodiments of formula I or formula II, $R^1$ is hydroxy-$C_{1-6}$alkyl.

In certain embodiments of formula I or formula II, $R^1$ is $C_{1-6}$alkyl-amino.

In certain embodiments of formula I or formula II, $R^1$ is amino-$C_{1-6}$alkyl.

In certain embodiments of formula I or formula II, $R^1$ is amino-$C_{1-6}$alkyl-amino.

In certain embodiments of formula I or formula II, $R^1$ is hydroxy-$C_{1-6}$alkylamino.

In certain embodiments of formula I or formula II, $R^1$ is $C_{3-6}$cycloalkylamino.

In certain embodiments of formula I or formula II, $R^1$ is aminocarbonyl.

In certain embodiments of formula I or formula II, $R^1$ is halo.

In certain embodiments of formula I or formula II, $R^1$ is hydroxy-$C_{1-6}$alkyl.

In certain embodiments of formula I or formula II, $R^1$ is hydroxy-$C_{1-6}$alkoxy.

In certain embodiments of formula I or formula II, $R^1$ is: hydrogen; hydroxy; 2-amino-ethyl)-methyl-amino; 2-amino-ethylamino; methy; methoxy; 2-hydroxy-ethyl)-methyl-amino; hydroxymethyl; 2-hydroxy-1-methyl-ethyl-amino; 2-cyclopropylamino; 2-hydroxy-ethylamino; 2,3-di-hydroxy-propylamino; 3-amino-propylamino; aminocarbonyl; 2-hydroxy-ethyl)-isopropyl-amino; bromo; isobutylamino; isopropyl-methyl-amino; 3-hydroxy-propylamino; 1-hydroxymethyl-propylamino; 2-hydroxy-ethyl; 2-acetylamino-ethylamino; 3-hydroxy-propyl; or isopropyl-amino.

In certain embodiments of formula I or formula II, $R^1$ is hydroxy.

In certain embodiments of formula I or formula II, $R^1$ is 2-amino-ethyl)-methyl-amino.

In certain embodiments of formula I or formula II, $R^1$ is 2-amino-ethylamino.

In certain embodiments of formula I or formula II, $R^1$ is methyl.

In certain embodiments of formula I or formula II, $R^1$ is methoxy.

In certain embodiments of formula I or formula II, $R^1$ is 2-hydroxy-ethyl)-methyl-amino.

In certain embodiments of formula I or formula II, $R^1$ is hydroxymethyl.

In certain embodiments of formula I or formula II, $R^1$ is 2-hydroxy-1-methyl-ethylamino.

In certain embodiments of formula I or formula II, $R^1$ is 2-cyclopropylamino.

In certain embodiments of formula I or formula II, $R^1$ is 2-hydroxy-ethylamino.

In certain embodiments of formula I or formula II, $R^1$ is 2,3-dihydroxy-propylamino.

In certain embodiments of formula I or formula II, $R^1$ is 3-amino-propylamino.

In certain embodiments of formula I or formula II, $R^1$ is aminocarbonyl.

In certain embodiments of formula I or formula II, $R^1$ is 2-hydroxy-ethyl)-isopropyl-amino.

In certain embodiments of formula I or formula II, $R^1$ is bromo.

In certain embodiments of formula I or formula II, $R^1$ is isobutylamino.

In certain embodiments of formula I or formula II, $R^1$ is isopropyl-methyl-amino.

In certain embodiments of formula I or formula II, $R^1$ is 3-hydroxy-propylamino.

In certain embodiments of formula I or formula II, $R^1$ is 1-hydroxymethyl-propylamino.

In certain embodiments of formula I or formula II, $R^1$ is 2-hydroxy-ethyl.

In certain embodiments of formula I or formula II, $R^1$ is 2-acetylamino-ethylamino.

In certain embodiments of formula I or formula II, $R^1$ is 3-hydroxy-propyl.

In certain embodiments of formula I or formula II, $R^1$ is isopropyl-amino.

In certain embodiments, the compounds of formula I and II may respectively be of formulas Ia or IIa:

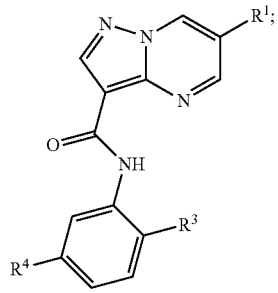

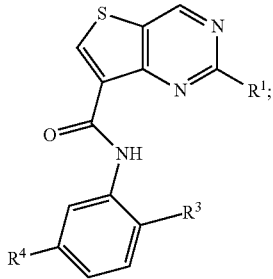

wherein:

$R^3$ and $R^4$ each independently is: halo; $C_{1-6}$alkyl; halo-$C_{1-6}$alkyl; $C_{1-6}$alkenyl; $C_{1-6}$alkoxy; halo-$C_{1-6}$alkoxy; hydroxy-$C_{1-6}$alkyl; hydroxy-$C_{1-6}$alkylamino; $C_{1-6}$alkylamino; hydroxy; amino; amino-$C_{1-6}$alkyl; aminocarbonyl; hydroxy-$C_{1-6}$alkoxy; hydroxy-$C_{1-6}$alkenyl; $C_{1-6}$alkoxy-$C_{1-6}$alkoxy; $C_{1-6}$alkylsulfonyl; $C_{1-6}$alkylsulfanyl; piperidinyl wherein the piperidinyl moiety is optionally substituted with hydroxy, amino, amino-$C_{1-6}$alkyl, hydroxy-$C_{1-6}$alkyl or aminocarbonyl; phenylaminocarbonyl; hydroxy-$C_{1-6}$alkylamino; cyclohexyloxy wherein the cyclohexyl moiety thereof is optionally substituted with hydroxy, amino, amino-$C_{1-6}$alkyl or hydroxy-$C_{1-6}$alkyl; cyclopentyloxy wherein the cyclopentyl moiety thereof is optionally substituted with hydroxy, amino, amino-$C_{1-6}$alkyl or hydroxy-$C_{1-6}$alkyl; piperidinyloxy wherein the piperidinyl moiety thereof is optionally substituted with hydroxy, amino, amino-$C_{1-6}$alkyl, hydroxy-$C_{1-6}$alkyl or aminocarbonyl; phenyl wherein the phenyl moiety is optionally substituted with amino, hydroxy, amino-$C_{1-6}$alkyl, hydroxy-$C_{1-6}$alkyl or aminocarbonyl; pyrrolidinyl wherein the pyrrolidinyl moiety is optionally substituted with hydroxy, amino, amino-$C_{1-6}$alkyl, hydroxy-$C_{1-6}$alkyl or aminocarbonyl; pyrrolidinyloxy wherein the pyrrolidinyl moiety is optionally substituted with hydroxy, amino, amino-$C_{1-6}$alkyl, hydroxy-$C_{1-6}$alkyl or aminocarbonyl; piperazinyl wherein the piperazinyl moiety is optionally substituted with $C_{1-6}$alkyl; oxazol-$C_{1-6}$alkoxy wherein the oxazol moiety thereof is optionally substituted with $C_{1-6}$alkyl; morpholinyl; hydroxy-$C_{1-6}$alkylaminocarbonyl; $C_{3-6}$cycloalkyl; azepanyl wherein the azepanyl moiety is optionally substituted with hydroxy, amino, amino-$C_{1-6}$alkyl, hydroxy-$C_{1-6}$alkyl or aminocarbonyl; benzyl wherein the phenyl moiety thereof is optionally substituted with amino, hydroxy, amino-$C_{1-6}$alkyl, hydroxy-$C_{1-6}$alkyl or aminocarbonyl; $C_{1-6}$alkoxycarbonyl-$C_{1-6}$alkoxy; or $C_{1-6}$alkylcarbonylamino; and $R^1$ is as defined herein.

In certain embodiments of formula Ia or formula IIa, $R^4$ is halo.

In certain embodiments of formula Ia or formula IIa, $R^4$ is chloro.

In certain embodiments of formula Ia or formula IIa, $R^3$ is halo.

In certain embodiments of formula Ia or formula IIa, $R^3$ is $C_{1-6}$alkyl.

In certain embodiments of formula Ia or formula IIa, $R^3$ is halo-$C_{1-6}$alkyl.

In certain embodiments of formula Ia or formula IIa, $R^3$ is $C_{1-6}$alkenyl.

In certain embodiments of formula Ia or formula IIa, $R^3$ is $C_{1-6}$alkoxy.

In certain embodiments of formula Ia or formula IIa, $R^3$ is halo-$C_{1-6}$alkoxy.

In certain embodiments of formula Ia or formula IIa, $R^3$ is hydroxy-$C_{1-6}$alkyl.

In certain embodiments of formula Ia or formula IIa, $R^3$ is hydroxy-$C_{1-6}$alkylamino.

In certain embodiments of formula Ia or formula IIa, $R^3$ is $C_{1-6}$alkyl-amino.

In certain embodiments of formula Ia or formula IIa, $R^3$ is hydroxy; amino.

In certain embodiments of formula Ia or formula IIa, $R^3$ is amino-$C_{1-6}$alkyl.

In certain embodiments of formula Ia or formula IIa, $R^3$ is aminocarbonyl.

In certain embodiments of formula Ia or formula IIa, $R^3$ is hydroxy-$C_{1-6}$alkoxy.

In certain embodiments of formula Ia or formula IIa, $R^3$ is hydroxy-$C_{1-6}$alkenyl.

In certain embodiments of formula Ia or formula IIa, $R^3$ is $C_{1-6}$alkoxy-$C_{1-6}$alkoxy.

In certain embodiments of formula Ia or formula IIa, $R^3$ is $C_{1-6}$alkylsulfonyl.

In certain embodiments of formula Ia or formula IIa, $R^3$ is $C_{1-6}$alkylsulfanyl.

In certain embodiments of formula Ia or formula IIa, $R^3$ is piperidinyl wherein the piperidinyl moiety is optionally substituted with hydroxy, amino, amino-$C_{1-6}$alkyl, hydroxy-$C_{1-6}$alkyl or aminocarbonyl.

In certain embodiments of formula Ia or formula IIa, $R^3$ is phenylaminocarbonyl.

In certain embodiments of formula Ia or formula IIa, $R^3$ is hydroxy-$C_{1-6}$alkylamino.

In certain embodiments of formula Ia or formula IIa, $R^3$ is cyclohexyloxy wherein the cyclohexyl moiety thereof is optionally substituted with hydroxy, amino, amino-$C_{1-6}$alkyl or hydroxy-$C_{1-6}$alkyl.

In certain embodiments of formula Ia or formula IIa, $R^3$ is cyclopentyloxy wherein the cyclopentyl moiety thereof is optionally substituted with hydroxy, amino, amino-$C_{1-6}$alkyl or hydroxy-$C_{1-6}$alkyl.

In certain embodiments of formula Ia or formula IIa, $R^3$ is piperidinyloxy wherein the piperidinyl moiety thereof is optionally substituted with hydroxy, amino, amino-$C_{1-6}$alkyl, hydroxy-$C_{1-6}$alkyl or aminocarbonyl.

In certain embodiments of formula Ia or formula IIa, $R^3$ is phenyl wherein the phenyl moiety is optionally substituted with amino, hydroxy, amino-$C_{1-6}$alkyl, hydroxy-$C_{1-6}$alkyl or aminocarbonyl.

In certain embodiments of formula Ia or formula IIa, $R^3$ is pyrrolidinyl wherein the pyrrolidinyl moiety is optionally substituted with hydroxy, amino, amino-$C_{1-6}$alkyl, hydroxy-$C_{1-6}$alkyl or aminocarbonyl.

In certain embodiments of formula Ia or formula IIa, $R^3$ is pyrrolidinyloxy wherein the pyrrolidinyl moiety is optionally substituted with hydroxy, amino, amino-$C_{1-6}$alkyl, hydroxy-$C_{1-6}$alkyl or aminocarbonyl.

In certain embodiments of formula Ia or formula IIa, $R^3$ is piperazinyl wherein the piperazinyl moiety is optionally substituted with $C_{1-6}$alkyl.

In certain embodiments of formula Ia or formula IIa, $R^3$ is oxazol-$C_{1-6}$alkoxy wherein the oxazol moiety thereof is optionally substituted with $C_{1-6}$alkyl.

In certain embodiments of formula Ia or formula IIa, $R^3$ is morpholinyl.

In certain embodiments of formula Ia or formula IIa, $R^3$ is hydroxy-$C_{1-6}$alkylaminocarbonyl.

In certain embodiments of formula Ia or formula IIa, $R^3$ is $C_{3-6}$cycloalkyl.

In certain embodiments of formula Ia or formula IIa, $R^3$ is azepanyl wherein the azepanyl moiety is optionally substituted with hydroxy, amino, amino-$C_{1-6}$alkyl, hydroxy-$C_{1-6}$alkyl or aminocarbonyl.

In certain embodiments of formula Ia or formula IIa, $R^3$ is benzyl wherein the phenyl moiety thereof is optionally substituted with amino, hydroxy, amino-$C_{1-6}$alkyl, hydroxy-$C_{1-6}$alkyl or aminocarbonyl.

In certain embodiments of formula Ia or formula IIa, $R^3$ is $C_{1-6}$alkoxycarbonyl-$C_{1-6}$alkoxy.

In certain embodiments of formula Ia or formula IIa, $R^3$ is $C_{1-6}$alkylcarbonylamino.

In certain embodiments, the compounds of formula I and II may respectively be of formulas Ib or IIb:

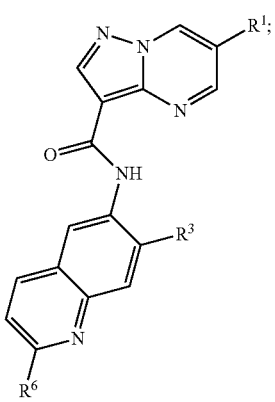

Ia

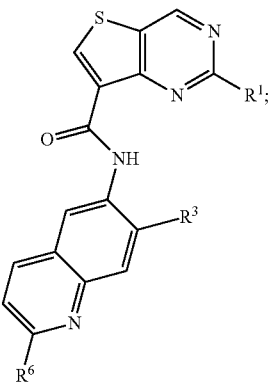

IIa wherein:

$R^5$ and $R^6$ each independently is: hydrogen; halo; $C_{1-6}$alkyl; halo-$C_{1-6}$alkyl; $C_{1-6}$alkenyl; $C_{1-6}$alkoxy; halo-$C_{1-6}$ alkoxy; hydroxy-$C_{1-6}$alkyl; hydroxy-$C_{1-6}$alkylamino; $C_{1-6}$alkyl-amino; hydroxy; amino; amino-$C_{1-6}$alkyl; aminocarbonyl; hydroxy-$C_{1-6}$alkoxy; hydroxy-$C_{1-6}$alkenyl; $C_{1-6}$alkoxy-$C_{1-6}$alkoxy; $C_{1-6}$alkylsulfonyl; $C_{1-6}$alkylsulfanyl; piperidinyl wherein the piperidinyl moiety is optionally substituted with hydroxy, amino, amino-$C_{1-6}$alkyl, hydroxy-$C_{1-6}$alkyl or aminocarbonyl; phenylaminocarbonyl; hydroxy-$C_{1-6}$alkylamino; cyclohexyloxy wherein the cyclohexyl moiety thereof is optionally substituted with hydroxy, amino, amino-$C_{1-6}$alkyl or hydroxy-$C_{1-6}$alkyl; cyclopentyloxy wherein the cyclopentyl moiety thereof is optionally substituted with hydroxy, amino, amino-$C_{1-6}$alkyl or hydroxy-$C_{1-6}$alkyl; piperidinyloxy wherein the piperidinyl moiety thereof is optionally substituted with hydroxy, amino, amino-$C_{1-6}$alkyl, hydroxy-$C_{1-6}$alkyl or aminocarbonyl; phenyl wherein the phenyl moiety is optionally substituted with amino, hydroxy, amino-$C_{1-6}$alkyl, hydroxy-$C_{1-6}$alkyl or aminocarbonyl; pyrrolidinyl wherein the pyrrolidinyl moiety is optionally substituted with hydroxy, amino, amino-$C_{1-6}$alkyl, hydroxy-$C_{1-6}$alkyl or aminocarbonyl; pyrrolidinyloxy wherein the pyrrolidinyl moiety is optionally substituted with hydroxy, amino, amino-$C_{1-6}$alkyl, hydroxy-$C_{1-6}$alkyl or aminocarbonyl; piperazinyl wherein the piperazinyl moiety is optionally substituted with $C_{1-6}$alkyl; oxazol-$C_{1-6}$alkoxy wherein the oxazol moiety thereof is optionally substituted with $C_{1-6}$alkyl; morpholinyl; hydroxy-$C_{1-6}$alkylaminocarbonyl; $C_{3-6}$cycloalkyl; azepanyl wherein the azepanyl moiety is optionally substituted with hydroxy, amino, amino-$C_{1-6}$alkyl, hydroxy-$C_{1-6}$alkyl or aminocarbonyl; benzyl wherein the phenyl moiety thereof is optionally substituted with amino, hydroxy, amino-$C_{1-6}$alkyl, hydroxy-$C_{1-6}$alkyl or aminocarbonyl; $C_{1-6}$alkoxycarbonyl-$C_{1-6}$alkoxy; or $C_{1-6}$alkylcarbonylamino; and $R^1$ is as defined herein.

In certain embodiments of formula Ib or formula IIb, $R^5$ and $R^6$ each independently is: halo; $C_{1-6}$alkyl; halo-$C_{1-6}$alkyl; $C_{1-6}$alkenyl; $C_{1-6}$alkoxy; halo-$C_{1-6}$alkoxy; hydroxy-$C_{1-6}$alkyl; hydroxy-$C_{1-6}$alkylamino; $C_{1-6}$alkyl-amino; hydroxy; amino; amino-$C_{1-6}$alkyl; aminocarbonyl; hydroxy-$C_{1-6}$alkoxy; hydroxy-$C_{1-6}$alkenyl; $C_{1-6}$alkoxy-$C_{1-6}$alkoxy; $C_{1-6}$alkylsulfonyl; $C_{1-6}$alkylsulfanyl; piperidinyl wherein the piperidinyl moiety is optionally substituted with hydroxy, amino, amino-$C_{1-6}$alkyl, hydroxy-$C_{1-6}$alkyl or aminocarbonyl; phenylaminocarbonyl; hydroxy-$C_{1-6}$alkylamino; cyclohexyloxy wherein the cyclohexyl moiety thereof is optionally substituted with hydroxy, amino, amino-$C_{1-6}$alkyl or hydroxy-$C_{1-6}$alkyl; cyclopentyloxy wherein the cyclopentyl moiety thereof is optionally substituted with hydroxy, amino, amino-$C_{1-6}$alkyl or hydroxy-$C_{1-6}$alkyl; piperidinyloxy wherein the piperidinyl moiety thereof is optionally substituted with hydroxy, amino, amino-$C_{1-6}$alkyl, hydroxy-$C_{1-6}$alkyl or aminocarbonyl; phenyl wherein the phenyl moiety is optionally substituted with amino, hydroxy, amino-$C_{1-6}$alkyl, hydroxy-$C_{1-6}$alkyl or aminocarbonyl; pyrrolidinyl wherein the pyrrolidinyl moiety is optionally substituted with hydroxy, amino, amino-$C_{1-6}$alkyl, hydroxy-$C_{1-6}$alkyl or aminocarbonyl; pyrrolidinyloxy wherein the pyrrolidinyl moiety is optionally substituted with hydroxy, amino, amino-$C_{1-6}$alkyl, hydroxy-$C_{1-6}$alkyl or aminocarbonyl; piperazinyl wherein the piperazinyl moiety is optionally substituted with $C_{1-6}$alkyl; oxazol-$C_{1-6}$alkoxy wherein the oxazol moiety thereof is optionally substituted with $C_{1-6}$alkyl; morpholinyl; hydroxy-$C_{1-6}$alkylaminocarbonyl; $C_{3-6}$cycloalkyl; azepanyl wherein the azepanyl moiety is optionally substituted with hydroxy, amino, amino-$C_{1-6}$alkyl, hydroxy-$C_{1-6}$alkyl or aminocarbonyl; benzyl wherein the phenyl moiety thereof is optionally substituted with amino, hydroxy, amino-$C_{1-6}$alkyl, hydroxy-$C_{1-6}$alkyl or aminocarbonyl; $C_{1-6}$alkoxycarbonyl-$C_{1-6}$alkoxy; or $C_{1-6}$alkylcarbonylamino.

In certain embodiments of formula Ib or formula IIb, $R^5$ is hydrogen.

In certain embodiments of formula Ia or formula IIa, $R^5$ is halo.

In certain embodiments of formula Ia or formula IIa, $R^5$ is $C_{1-6}$alkyl.

In certain embodiments of formula Ia or formula IIa, $R^5$ is halo-$C_{1-6}$alkyl.

In certain embodiments of formula Ia or formula IIa, $R^5$ is $C_{1-6}$alkenyl.

In certain embodiments of formula Ia or formula IIa, $R^5$ is $C_{1-6}$alkoxy.

In certain embodiments of formula Ia or formula IIa, $R^5$ is halo-$C_{1-6}$alkoxy.

In certain embodiments of formula Ia or formula IIa, $R^5$ is hydroxy-$C_{1-6}$alkyl.

In certain embodiments of formula Ia or formula IIa, $R^5$ is hydroxy-$C_{1-6}$alkylamino.

In certain embodiments of formula Ia or formula IIa, $R^5$ is $C_{1-6}$alkyl-amino.

In certain embodiments of formula Ia or formula IIa, $R^5$ is hydroxy; amino.

In certain embodiments of formula Ia or formula IIa, $R^5$ is amino-$C_{1-6}$alkyl.

In certain embodiments of formula Ia or formula IIa, $R^5$ is aminocarbonyl.

In certain embodiments of formula Ia or formula IIa, $R^5$ is hydroxy-$C_{1-6}$alkoxy.

In certain embodiments of formula Ia or formula IIa, $R^5$ is hydroxy-$C_{1-6}$alkenyl.

In certain embodiments of formula Ia or formula IIa, $R^5$ is $C_{1-6}$alkoxy-$C_{1-6}$alkoxy.

In certain embodiments of formula Ia or formula IIa, $R^5$ is $C_{1-6}$alkylsulfonyl.

In certain embodiments of formula Ia or formula IIa, $R^5$ is $C_{1-6}$alkylsulfanyl.

In certain embodiments of formula Ia or formula IIa, $R^5$ is piperidinyl wherein the piperidinyl moiety is optionally substituted with hydroxy, amino, amino-$C_{1-6}$alkyl, hydroxy-$C_{1-6}$alkyl or aminocarbonyl.

In certain embodiments of formula Ia or formula IIa, $R^5$ is phenylaminocarbonyl.

In certain embodiments of formula Ia or formula IIa, $R^5$ is hydroxy-$C_{1-6}$alkylamino.

In certain embodiments of formula Ia or formula IIa, $R^5$ is cyclohexyloxy wherein the cyclohexyl moiety thereof is optionally substituted with hydroxy, amino, amino-$C_{1-6}$alkyl or hydroxy-$C_{1-6}$alkyl.

In certain embodiments of formula Ia or formula IIa, $R^5$ is cyclopentyloxy wherein the cyclopentyl moiety thereof is optionally substituted with hydroxy, amino, amino-$C_{1-6}$alkyl or hydroxy-$C_{1-6}$alkyl.

In certain embodiments of formula Ia or formula IIa, $R^5$ is piperidinyloxy wherein the piperidinyl moiety thereof is optionally substituted with hydroxy, amino, amino-$C_{1-6}$alkyl, hydroxy-$C_{1-6}$alkyl or aminocarbonyl.

In certain embodiments of formula Ia or formula IIa, $R^5$ is phenyl wherein the phenyl moiety is optionally substituted with amino, hydroxy, amino-$C_{1-6}$alkyl, hydroxy-$C_{1-6}$alkyl or aminocarbonyl.

In certain embodiments of formula Ia or formula IIa, $R^5$ is pyrrolidinyl wherein the pyrrolidinyl moiety is optionally substituted with hydroxy, amino, amino-$C_{1-6}$alkyl, hydroxy-$C_{1-6}$alkyl or aminocarbonyl.

In certain embodiments of formula Ia or formula IIa, $R^5$ is pyrrolidinyloxy wherein the pyrrolidinyl moiety is optionally substituted with hydroxy, amino, amino-$C_{1-6}$alkyl, hydroxy-$C_{1-6}$alkyl or aminocarbonyl.

In certain embodiments of formula Ia or formula IIa, $R^5$ is piperazinyl wherein the piperazinyl moiety is optionally substituted with $C_{1-6}$alkyl.

In certain embodiments of formula Ia or formula IIa, $R^5$ is oxazol-$C_{1-6}$alkoxy wherein the oxazol moiety thereof is optionally substituted with $C_{1-6}$alkyl.

In certain embodiments of formula Ia or formula IIa, $R^5$ is morpholinyl.

In certain embodiments of formula Ia or formula IIa, $R^5$ is hydroxy-$C_{1-6}$alkylaminocarbonyl.

In certain embodiments of formula Ia or formula IIa, $R^5$ is $C_{3-6}$cycloalkyl.

In certain embodiments of formula Ia or formula IIa, $R^5$ is azepanyl wherein the azepanyl moiety is optionally substituted with hydroxy, amino, amino-$C_{1-6}$alkyl, hydroxy-$C_{1-6}$alkyl or aminocarbonyl.

In certain embodiments of formula Ia or formula IIa, $R^5$ is benzyl wherein the phenyl moiety thereof is optionally substituted with amino, hydroxy, amino-$C_{1-6}$alkyl, hydroxy-$C_{1-6}$alkyl or aminocarbonyl.

In certain embodiments of formula Ia or formula IIa, $R^5$ is $C_{1-6}$alkoxycarbonyl-$C_{1-6}$alkoxy.

In certain embodiments of formula Ia or formula IIa, $R^5$ is $C_{1-6}$alkylcarbonylamino.

In certain embodiments of formula Ib or formula IIb, $R^6$ is hydrogen.

In certain embodiments of formula Ia or formula IIa, $R^6$ is halo.

In certain embodiments of formula Ia or formula IIa, $R^6$ is $C_{1-6}$alkyl.

In certain embodiments of formula Ia or formula IIa, $R^6$ is halo-$C_{1-6}$alkyl.

In certain embodiments of formula Ia or formula IIa, $R^6$ is $C_{1-6}$alkenyl.

In certain embodiments of formula Ia or formula IIa, $R^6$ is $C_{1-6}$alkoxy.

In certain embodiments of formula Ia or formula IIa, $R^6$ is halo-$C_{1-6}$alkoxy.

In certain embodiments of formula Ia or formula IIa, $R^6$ is hydroxy-$C_{1-6}$alkyl.

In certain embodiments of formula Ia or formula IIa, $R^6$ is hydroxy-$C_{1-6}$alkylamino.

In certain embodiments of formula Ia or formula IIa, $R^6$ is $C_{1-6}$alkyl-amino.

In certain embodiments of formula Ia or formula IIa, $R^6$ is hydroxy; amino.

In certain embodiments of formula Ia or formula IIa, $R^6$ is amino-$C_{1-6}$alkyl.

In certain embodiments of formula Ia or formula IIa, $R^6$ is aminocarbonyl.

In certain embodiments of formula Ia or formula IIa, $R^6$ is hydroxy-$C_{1-6}$alkoxy.

In certain embodiments of formula Ia or formula IIa, $R^6$ is hydroxy-$C_{1-6}$alkenyl.

In certain embodiments of formula Ia or formula IIa, $R^6$ is $C_{1-6}$alkoxy-$C_{1-6}$alkoxy.

In certain embodiments of formula Ia or formula IIa, $R^6$ is $C_{1-6}$alkylsulfonyl.

In certain embodiments of formula Ia or formula IIa, $R^6$ is $C_{1-6}$alkylsulfanyl.

In certain embodiments of formula Ia or formula IIa, $R^6$ is piperidinyl wherein the piperidinyl moiety is optionally substituted with hydroxy, amino, amino-$C_{1-6}$alkyl, hydroxy-$C_{1-6}$alkyl or aminocarbonyl.

In certain embodiments of formula Ia or formula IIa, $R^6$ is phenylaminocarbonyl.

In certain embodiments of formula Ia or formula IIa, $R^6$ is hydroxy-$C_{1-6}$alkylamino.

In certain embodiments of formula Ia or formula IIa, $R^6$ is cyclohexyloxy wherein the cyclohexyl moiety thereof is optionally substituted with hydroxy, amino, amino-$C_{1-6}$alkyl or hydroxy-$C_{1-6}$alkyl.

In certain embodiments of formula Ia or formula IIa, $R^6$ is cyclopentyloxy wherein the cyclopentyl moiety thereof is optionally substituted with hydroxy, amino, amino-$C_{1-6}$alkyl or hydroxy-$C_{1-6}$alkyl.

In certain embodiments of formula Ia or formula IIa, $R^6$ is piperidinyloxy wherein the piperidinyl moiety thereof is optionally substituted with hydroxy, amino, amino-$C_{1-6}$alkyl, hydroxy-$C_{1-6}$alkyl or aminocarbonyl.

In certain embodiments of formula Ia or formula IIa, $R^6$ is phenyl wherein the phenyl moiety is optionally substituted with amino, hydroxy, amino-$C_{1-6}$alkyl, hydroxy-$C_{1-6}$alkyl or aminocarbonyl.

In certain embodiments of formula Ia or formula IIa, $R^6$ is pyrrolidinyl wherein the pyrrolidinyl moiety is optionally substituted with hydroxy, amino, amino-$C_{1-6}$alkyl, hydroxy-$C_{1-6}$alkyl or aminocarbonyl.

In certain embodiments of formula Ia or formula IIa, $R^6$ is pyrrolidinyloxy wherein the pyrrolidinyl moiety is optionally substituted with hydroxy, amino, amino-$C_{1-6}$alkyl, hydroxy-$C_{1-6}$alkyl or aminocarbonyl.

In certain embodiments of formula Ia or formula IIa, $R^6$ is piperazinyl wherein the piperazinyl moiety is optionally substituted with $C_{1-6}$alkyl.

In certain embodiments of formula Ia or formula IIa, $R^6$ is oxazol-$C_{1-6}$alkoxy wherein the oxazol moiety thereof is optionally substituted with $C_{1-6}$alkyl.

In certain embodiments of formula Ia or formula IIa, $R^6$ is morpholinyl.

In certain embodiments of formula Ia or formula IIa, $R^6$ is hydroxy-$C_{1-6}$alkylaminocarbonyl.

In certain embodiments of formula Ia or formula IIa, $R^6$ is $C_{3-6}$cycloalkyl.

In certain embodiments of formula Ia or formula IIa, $R^6$ is azepanyl wherein the azepanyl moiety is optionally substituted with hydroxy, amino, amino-$C_{1-6}$alkyl, hydroxy-$C_{1-6}$alkyl or aminocarbonyl.

In certain embodiments of formula Ia or formula IIa, $R^6$ is benzyl wherein the phenyl moiety thereof is optionally substituted with amino, hydroxy, amino-$C_{1-6}$alkyl, hydroxy-$C_{1-6}$alkyl or aminocarbonyl.

In certain embodiments of formula Ia or formula IIa, $R^6$ is $C_{1-6}$alkoxycarbonyl-$C_{1-6}$alkoxy.

In certain embodiments of formula Ia or formula IIa, $R^6$ is $C_{1-6}$alkylcarbonylamino.

Where any of $R^1$, $R^2$, $R^3$, $R^4$, $R^5$ and $R^6$ is alkyl or contains an alkyl moiety, such alkyl is preferably lower alkyl, i.e. $C_1$-$C_6$alkyl, and in many embodiments is $C_1$-$C_4$alkyl.

The invention provides compounds of the formula I' or formula II':

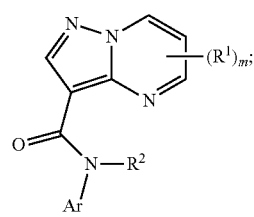

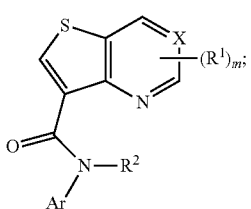

or pharmaceutically acceptable salts thereof,
wherein:
X is N or CH
m is 1 or 2;
Ar is:
optionally substituted aryl; or
optionally substituted heteroaryl;
$R^1$ is:
hydrogen;
$C_{1-6}$alkyl;
$C_{1-6}$alkoxy;
hydroxy;
hydroxy-$C_{1-6}$alkyl;
$C_{1-6}$alkyl-amino;
amino-$C_{1-6}$alkyl;
amino-$C_{1-6}$alkyl-amino;
hydroxy-$C_{1-6}$alkylamino
$C_{3-6}$cycloalkylamino;
aminocarbonyl;
halo;
hydroxy-$C_{1-6}$alkyl; or
hydroxy-$C_{1-6}$alkoxy; and
$R^2$ is:
hydrogen; or
$C_{1-6}$alkyl.

The invention also provides methods for treating a disease or condition mediated by or otherwise associated with an IRAK receptor, the method comprising administering to a subject in need thereof an effective amount of a compound of the invention.

The invention also provides methods for treating a disease or condition mediated by or otherwise associated with an SYK receptor, the method comprising administering to a subject in need thereof an effective amount of a compound of the invention.

The disease may be an inflammatory disease such as arthritis, and more particularly rheumatoid arthritis, osteoarthritis, psoriasis, allergic dermatitis, asthma, chronic obstructive pulmonary disease, airways hyper-responsiveness, septic shock, glomerulonephritis, irritable bowel disease, and Crohn's disease.

The disease may be a pain condition, such as inflammatory pain; surgical pain; visceral pain; dental pain; premenstrual pain; central pain; pain due to burns; migraine or cluster headaches; nerve injury; neuritis; neuralgias; poisoning; ischemic injury; interstitial cystitis; cancer pain; viral, parasitic or bacterial infection; post-traumatic injury; or pain associated with irritable bowel syndrome.

The disease may be a respiratory disorder, such as chronic obstructive pulmonary disorder (COPD), asthma, or bronchospasm, or a gastrointestinal (GI) disorder such as Irritable Bowel Syndrome (IBS), Inflammatory Bowel Disease (IBD), biliary colic and other biliary disorders, renal colic, diarrhea-dominant IBS, pain associated with GI distension.

Representative compounds in accordance with the methods of the invention are shown in Table 1 with reference to the experimental examples below, together with $IC_{50}$ values (micromolar) for IRAK1, IRAK4 and SYK for selected compounds.

TABLE 1

| # | Structure | Chemical Name | IRAK 4 | IRAK 1 | SYK | Ex. |
|---|-----------|---------------|--------|--------|-----|-----|
| 1 | 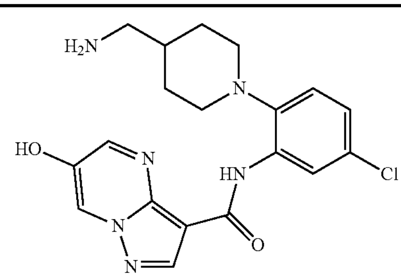 | 6-Hydroxy-pyrazolo[1,5-alpha]pyrimidine-3-carboxylic acid[2-(4-aminomethyl-piperidin-1-yl)-5-chloro-phenyl]-amide | 0.001 | 0.055 | | 14 |
| 2 | 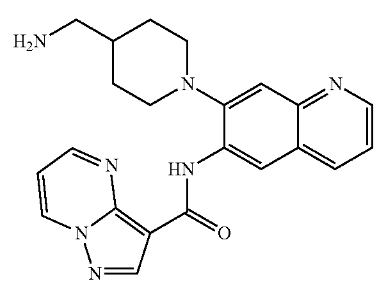 [SMILES: NCC1CCN(c2cc3ncccc3cc2NC(=O)c2cnn3cccnc23)CC1] | Pyrazolo[1,5-alpha]pyrimidine-3-carboxylic acid[7-(4-aminomethyl-piperidin-1-yl)-quinolin-6-yl]-amide | 0.002 | | | 15 |

TABLE 1-continued

| # | Structure | Chemical Name | IRAK 4 | IRAK 1 | SYK | Ex. |
|---|---|---|---|---|---|---|
| 3 | 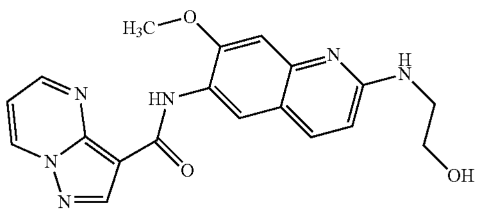 [SMILES: COc1cc2nc(NCCO)ccc2cc1NC(=O)c1cnn2cccnc12] | Pyrazolo[1,5-alpha]pyrimidine-3-carboxylic acid[2-(2-hydroxy-ethylamino)-7-methoxy-quinolin-6-yl]-amide | 0.003 | | | 1 |
| 4 | 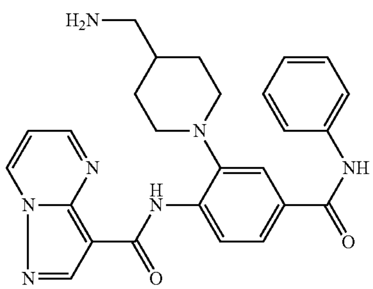 [SMILES: NCC1CCN(c2cc(C(=O)Nc3ccccc3)ccc2NC(=O)c2cnn3cccnc23)CC1] | Pyrazolo[1,5-alpha]pyrimidine-3-carboxylic acid[2-(4-aminomethyl-piperidin-1-yl)-4-phenylcarbamoyl-phenyl]-amide | 0.004 | 0.45 | | 15 |
| 5 | 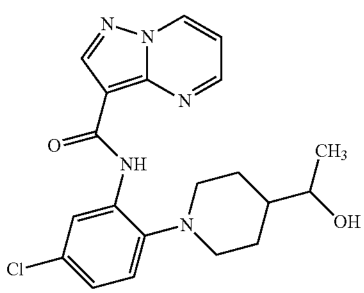 [SMILES: CC(O)C1CCN(c2ccc(Cl)cc2NC(=O)c2cnn3cccnc23)CC1] | Pyrazolo[1,5-alpha]pyrimidine-3-carboxylic acid{5-chloro-2-[4-(1-hydroxy-ethyl)-piperidin-1-yl]-phenyl}-amide | 0.005 | 0.97 | | 5 |
| 6 | 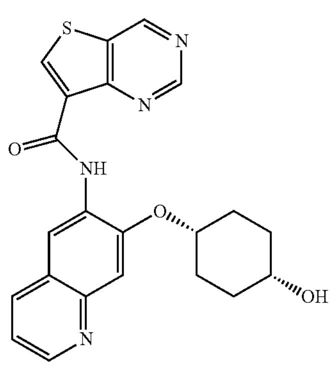 [SMILES: O=C(Nc1cc2cccnc2cc1O[C@H]1CC[C@@H](O)CC1)c1csc2cncnc12] | Thieno[3,2-d]pyrimidine-7-carboxylic acid[7-(4-hydroxy-cyclohexyloxy)-quinolin-6-yl]-amide | 0.007 | 0.07 | | 5 |
| 7 | 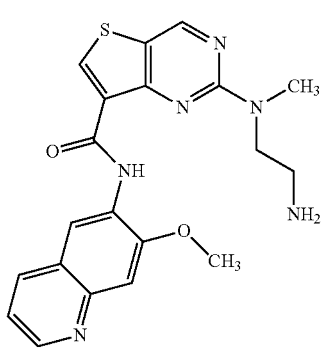 [SMILES: COc1cc2ncccc2cc1NC(=O)c1csc2cnc(N(C)CCN)nc12] | 2-[(2-Amino-ethyl)-methyl-amino]-thieno[3,2-d]pyrimidine-7-carboxylic acid(7-methoxy-quinolin-6-yl)-amide | 0.008 | 0.9825 | 0.41 | 12 |

TABLE 1-continued

| # | Structure | Chemical Name | IRAK 4 | IRAK 1 | SYK | Ex. |
|---|---|---|---|---|---|---|
| 8 | 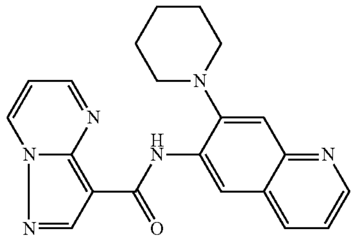 [SMILES: O=C(Nc1cc2cccnc2cc1N1CCCCC1)c1cnn2cccnc12] | Pyrazolo[1,5-alpha]pyrimidine-3-carboxylic acid(7-piperidin-1-yl-quinolin-6-yl)-amide | 0.008 | | | 1 |
| 9 | 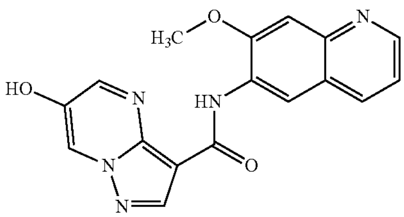 [SMILES: COc1cc2ncccc2cc1NC(=O)c1cnn2cc(O)cnc12] | 6-Hydroxy-pyrazolo[1,5-alpha]pyrimidine-3-carboxylic acid(7-methoxy-quinolin-6-yl)-amide | 0.009 | 0.20 | | 14 |
| 10 | 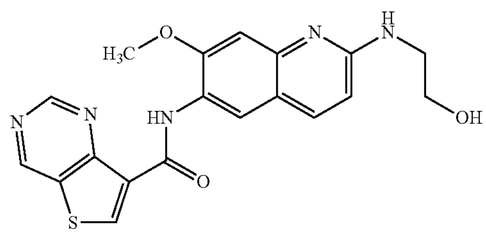 [SMILES: COc1cc2nc(NCCO)ccc2cc1NC(=O)c1csc2cncnc12] | Thieno[3,2-d]pyrimidine-7-carboxylic acid[2-(2-hydroxy-ethylamino)-7-methoxy-quinolin-6-yl]-amide | 0.010 | 0.20 | | 1 |
| 11 | 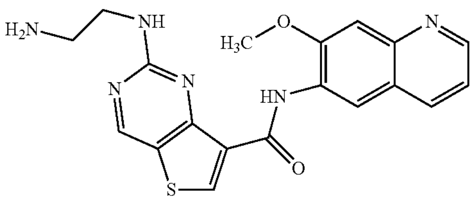 [SMILES: COc1cc2ncccc2cc1NC(=O)c1csc2cnc(NCCN)nc12] | 2-(2-Amino-ethylamino)-thieno[3,2-d]pyrimidine-7-carboxylic acid(7-methoxy-quinolin-6-yl)-amide | 0.010 | 0.712 | 0.017 | 12 |
| 12 | 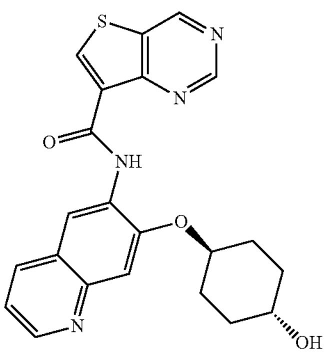 [SMILES: O=C(Nc1cc2cccnc2cc1O[C@H]1CC[C@H](O)CC1)c1csc2cncnc12] | Thieno[3,2-d]pyrimidine-7-carboxylic acid[7-(4-hydroxy-cyclohexyloxy)-quinolin-6-yl]-amide | 0.011 | 0.168 | | 5 |
| 13 | 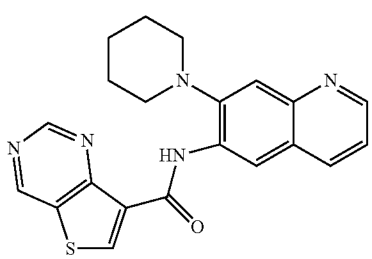 [SMILES: O=C(Nc1cc2cccnc2cc1N1CCCCC1)c1csc2cncnc12] | Thieno[3,2-d]pyrimidine-7-carboxylic acid piperidin-1-yl-quinolin-6-yl)-amide | 0.012 | | | 1 |

TABLE 1-continued

| # | Structure | Chemical Name | IRAK 4 | IRAK 1 | SYK | Ex. |
|---|-----------|---------------|--------|--------|-----|-----|
| 14 | 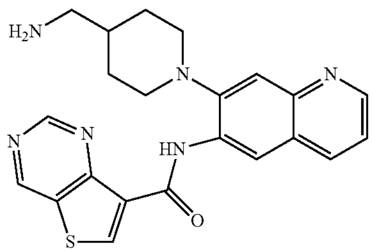 [SMILES: NCC1CCN(c2cc3ncccc3cc2NC(=O)c2csc3cncnc23)CC1] | Thieno[3,2-d]pyrimidine-7-carboxylic acid[7-(4-aminomethyl-piperidin-1-yl)-quinolin-6-yl]-amide hydrochloride | 0.012 | 0.85 | | 15 |
| 15 | 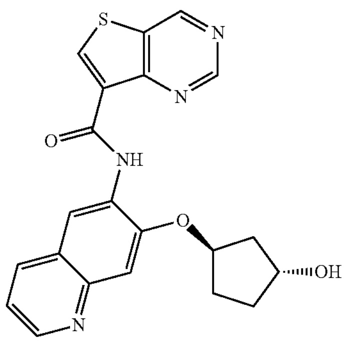 [SMILES: O=C(Nc1cc2cccnc2cc1O[C@@H]1CC[C@@H](O)C1)c1csc2cncnc12] | Thieno[3,2-d]pyrimidine-7-carboxylic acid[7-(3-hydroxy-cyclopentyloxy)-quinolin-6-yl]-amide hydrochloride | 0.015 | 0.246 | | 5 |
| 16 | 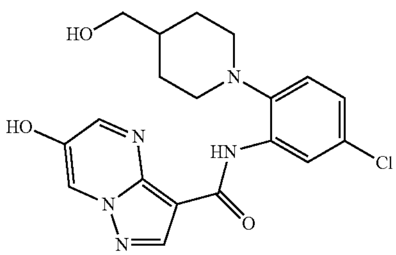 [SMILES: O=C(Nc1cc(Cl)ccc1N1CCC(CO)CC1)c1cnn2cc(O)cnc12] | 6-Hydroxy-pyrazolo[1,5-alpha]pyrimidine-3-carboxylic acid[5-chloro-2-(4-hydroxymethyl-piperidin-1-yl)-phenyl]-amide | 0.018 | 0.836 | | 14 |
| 17 | 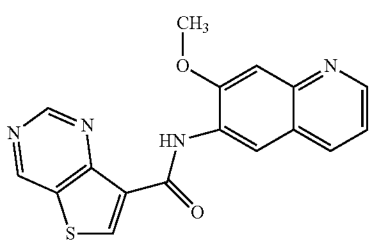 [SMILES: COc1cc2ncccc2cc1NC(=O)c1csc2cncnc12] | Thieno[3,2-d]pyrimidine-7-carboxylic acid(7-methoxy-quinolin-6-yl)-amide | 0.018 | 0.622 | | 1 |
| 18 | 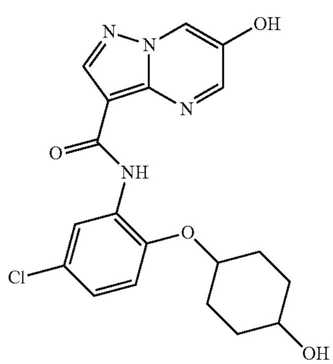 [SMILES: O=C(Nc1cc(Cl)ccc1OC1CCC(O)CC1)c1cnn2cc(O)cnc12] | 6-Hydroxy-pyrazolo[1,5-alpha]pyrimidine-3-carboxylic acid[5-chloro-2-(4-hydroxy-cyclohexyloxy)-phenyl]-amide | 0.023 | 0.163 | | 5 |

TABLE 1-continued

| # | Structure | Chemical Name | IRAK 4 | IRAK 1 | SYK | Ex. |
|---|---|---|---|---|---|---|
| 19 | 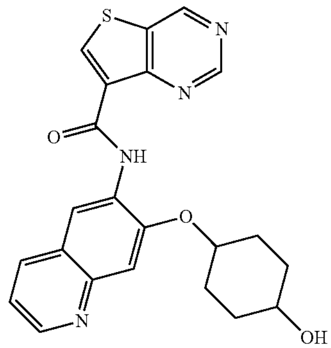 [SMILES: O=C(Nc1cc2cccnc2cc1OC1CCC(O)CC1)c1csc2cncnc12] | Thieno[3,2-d]pyrimidine-7-carboxylic acid[7-(4-hydroxy-cyclohexyloxy)-quinolin-6-yl]-amide | 0.024 | 0.123 | | 5 |
| 20 | 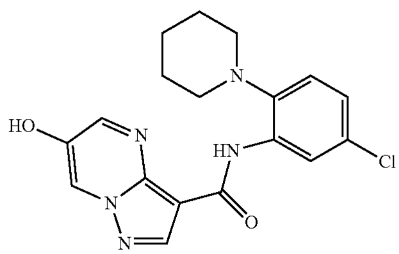 [SMILES: O=C(Nc1cc(Cl)ccc1N1CCCCC1)c1cnn2cc(O)cnc12] | 6-Hydroxy-pyrazolo[1,5-alpha]pyrimidine-3-carboxylic acid(5-chloro-2-piperidin-1-yl-phenyl)-amide | 0.024 | 0.644 | | 20 |
| 21 | 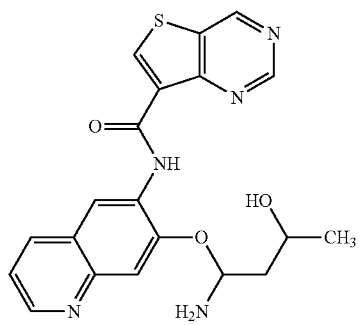 [SMILES: CC(O)CC(N)Oc1cc2ncccc2cc1NC(=O)c1csc2cncnc12] | Thieno[3,2-d]pyrimidine-7-carboxylic acid[7-(3-hydroxy-1-methyl-butoxy)-quinolin-6-yl]-amide | 0.024 | 0.76 | 0.449 | 5 |
| 22 | 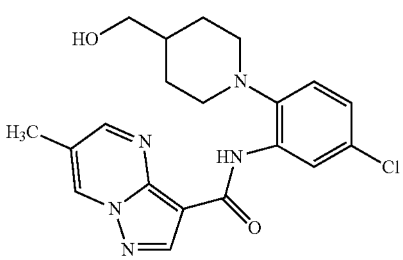 [SMILES: Cc1cnc2c(C(=O)Nc3cc(Cl)ccc3N3CCC(CO)CC3)cnn2c1] | 6-Methyl-pyrazolo[1,5-alpha]pyrimidine-3-carboxylic acid[5-chloro-2-(4-hydroxymethyl-piperidin-1-yl)-phenyl]-amide | 0.028 | | | 1 |
| 23 | 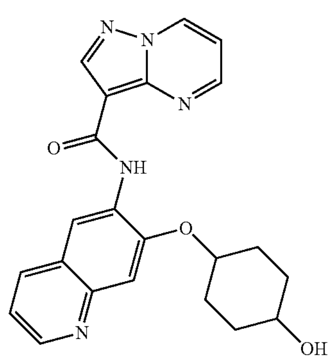 [SMILES: O=C(Nc1cc2cccnc2cc1OC1CCC(O)CC1)c1cnn2cccnc12] | Pyrazolo[1,5-alpha]pyrimidine-3-carboxylic acid[7-(4-hydroxy-cyclohexyloxy)-quinolin-6-yl]-amide | 0.029 | 0.103 | | 5 |

TABLE 1-continued

| # | Structure | Chemical Name | IRAK 4 | IRAK 1 | SYK | Ex. |
|---|---|---|---|---|---|---|
| 24 | 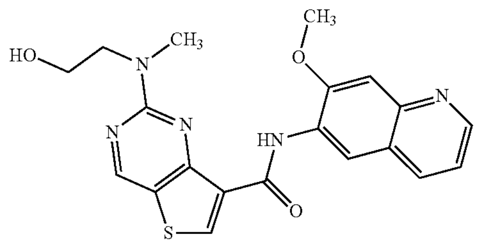 [SMILES: COc1cc2ncccc2cc1NC(=O)c1csc2cnc(N(C)CCO)nc12] | 2-[(2-Hydroxy-ethyl)-methyl-amino]-thieno[3,2-d]pyrimidine-7-carboxylic acid(7-methoxy-quinolin-6-yl)-amide | 0.029 | 0.3 | | 12 |
| 25 | 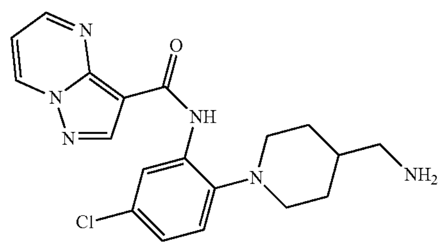 [SMILES: NCC1CCN(c2ccc(Cl)cc2NC(=O)c2cnn3cccnc23)CC1] | Pyrazolo[1,5alpha]pyrimidine-3-carboxylic acid[2-(4-aminomethyl-piperidin-1-yl)-5-chloro-phenyl]-amide | 0.031 | 0.92 | | 11 |
| 26 | 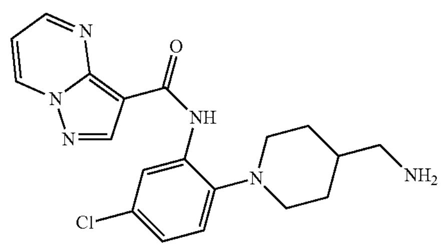 [SMILES: NCC1CCN(c2ccc(Cl)cc2NC(=O)c2cnn3cccnc23)CC1] | 2-Isopropylamino-thieno[3,2-d]pyrimidine-7-carboxylic acid(7-methoxy-quinolin-6-yl)-amide | 0.031 | 0.463 | 0.725 | 12 |
| 27 | 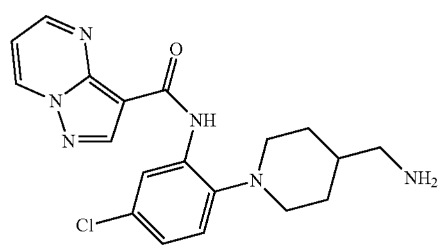 [SMILES: NCC1CCN(c2ccc(Cl)cc2NC(=O)c2cnn3cccnc23)CC1] | 2-Isopropylamino-thieno[3,2-d]pyrimidine-7-carboxylic acid(7-methoxy-quinolin-6-yl)-amide | 0.031 | | | 12 |
| 28 | 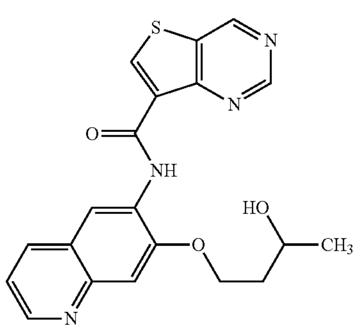 [SMILES: CC(O)CCOc1cc2ncccc2cc1NC(=O)c1csc2cncnc12] | Thieno[3,2-d]pyrimidine-7-carboxylic acid[7-(3-hydroxy-butoxy)-quinolin-6-yl]-amide | 0.033 | | | 1 |
| 29 | 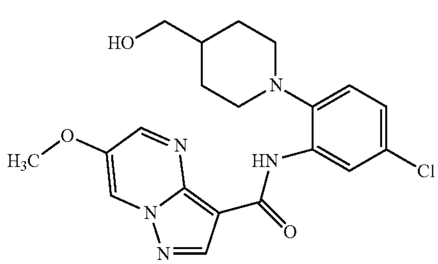 [SMILES: COc1cnc2c(C(=O)Nc3cc(Cl)ccc3N3CCC(CO)CC3)cnn2c1] | 6-Methoxy-pyrazolo[1,5alpha]pyrimidine-3-carboxylic acid[5-chloro-2-(4-hydroxymethyl-piperidin-1-yl)-phenyl]-amide | 0.033 | | | 1 |

TABLE 1-continued

| # | Structure | Chemical Name | IRAK 4 | IRAK 1 | SYK | Ex. |
|---|-----------|---------------|--------|--------|-----|-----|
| 30 | 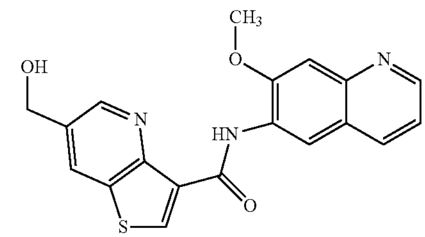 [SMILES: COc1cc2ncccc2cc1NC(=O)c1csc2cc(CO)cnc12] | 6-Hydroxymethyl-thieno[3,2beta]pyridine-3-carboxylic acid (7-methoxy-quinolin-6-yl)-amide | 0.035 | | 0.746 | 13 |
| 31 | 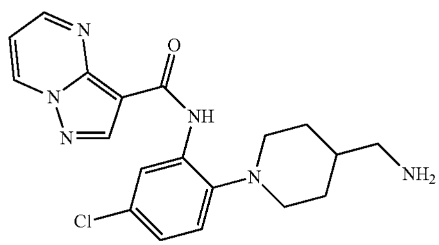 [SMILES: NCC1CCN(c2ccc(Cl)cc2NC(=O)c2cnn3cccnc23)CC1] | Pyrazolo[1,5alpha]pyrimidine-3-carboxylic acid[2-(4-aminomethyl-piperidin-1-yl)-5-chloro-phenyl]-amide | 0.037 | | | 11 |
| 32 | 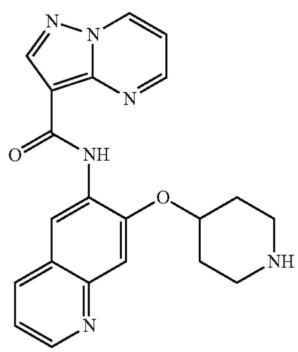 [SMILES: O=C(Nc1cc2cccnc2cc1OC1CCNCC1)c1cnn2cccnc12] | Pyrazolo[1,5-alpha]pyrimidine-3-carboxylic acid[7-(piperidin-4-yloxy)-quinolin-6-yl]-amide hydrochloride | 0.040 | | | 15 |
| 33 | 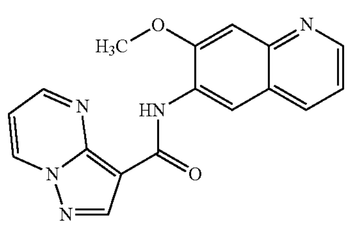 [SMILES: COc1cc2ncccc2cc1NC(=O)c1cnn2cccnc12] | Pyrazolo[1,5alpha]pyrimidine-3-carboxylic acid(7-methoxy-quinolin-6-yl)-amide | 0.043 | | | 1 |
| 34 | 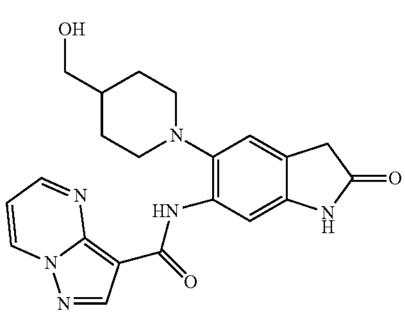 [SMILES: O=C1Cc2cc(N3CCC(CO)CC3)c(NC(=O)c3cnn4cccnc34)cc2N1] | Pyrazolo[1,5-alpha]pyrimidine-3-carboxylic acid[5-(4-hydroxymethyl-piperidin-1-yl)-2-oxo-2,3-dihydro-1H-indol-6-yl]-amide | 0.049 | | 0.478 | 1 |

TABLE 1-continued

| # | Structure | Chemical Name | IRAK 4 | IRAK 1 | SYK | Ex. |
|---|---|---|---|---|---|---|
| 35 | 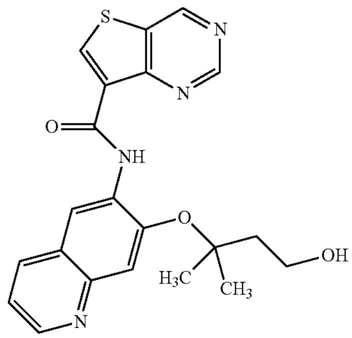 [SMILES: CC(C)(CCO)Oc1cc2ncccc2cc1NC(=O)c1csc2cncnc12] | Thieno[3,2-d]pyrimidine-7-carboxylic acid[7-(3-hydroxy-1,1-dimethyl-propoxy)-quinolin-6-yl]-amide hydrochloride | 0.049 | 0.364 | | 1 |
| 36 | 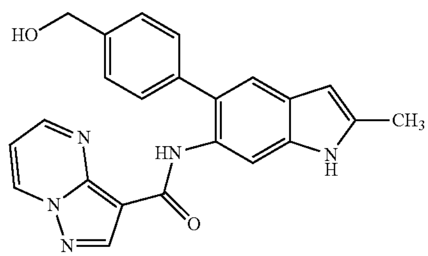 [SMILES: Cc1cc2cc(-c3ccc(CO)cc3)c(NC(=O)c3cnn4cccnc34)cc2[nH]1] | Pyrazolo[1,5-alpha]pyrimidine-3-carboxylic acid[5-(4-hydroxymethyl-phenyl)-2-methyl-1H-indol-6-yl]-amide | 0.052 | | | 1 |
| 37 | 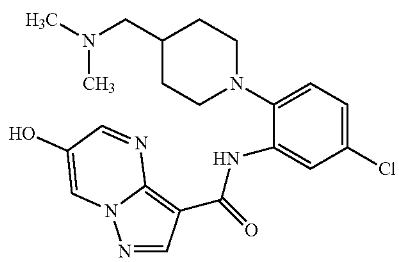 [SMILES: CN(C)CC1CCN(c2ccc(Cl)cc2NC(=O)c2cnn3cc(O)cnc23)CC1] | 6-Hydroxy-pyrazolo[1,5-alpha]pyrimidine-3-carboxylic acid[5-chloro-2-(4-dimethylaminomethyl-piperidin-1-yl)-phenyl]-amide | 0.053 | 0.307 | | 21 |
| 38 | 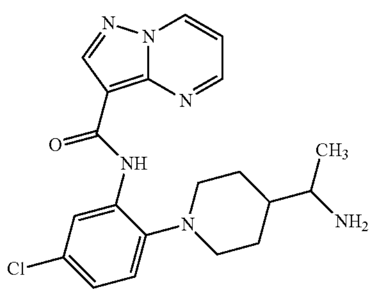 [SMILES: CC(N)C1CCN(c2ccc(Cl)cc2NC(=O)c2cnn3cccnc23)CC1] | Pyrazolo[1,5alpha]pyrimidine-3-carboxylic acid{2-[4-(1-amino-ethyl)-piperidin-1-yl]-5-chloro-phenyl}-amide | 0.053 | | | 15 |
| 39 | 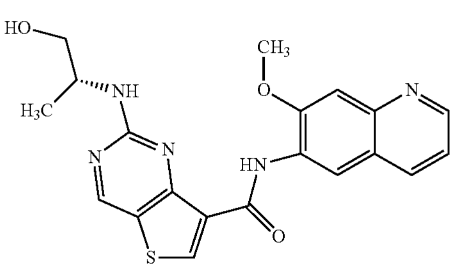 [SMILES: COc1cc2ncccc2cc1NC(=O)c1csc2cnc(N[C@H](C)CO)nc12] | 2-(2-Hydroxy-1-methyl-ethylamino)-thieno[3,2-d]pyrimidine-7-carboxylic acid(7-methoxy-quinolin-6-yl)-amide | 0.063 | | 0.492 | 12 |

TABLE 1-continued

| # | Structure | Chemical Name | IRAK 4 | IRAK 1 | SYK | Ex. |
|---|---|---|---|---|---|---|
| 40 | 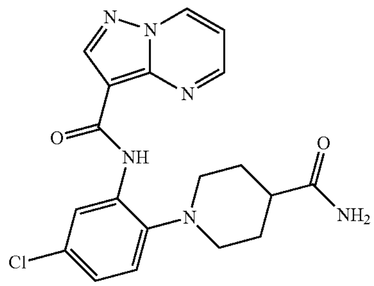 [SMILES: NC(=O)C1CCN(c2ccc(Cl)cc2NC(=O)c2cnn3cccnc23)CC1] | Pyrazolo[1,5-alpha]pyrimidine-3-carboxylic acid[2-(4-carbamoyl-piperidin-1-yl)-5-chloro-phenyl]-amide | 0.069 | | 0.5 | 1 |
| 41 | 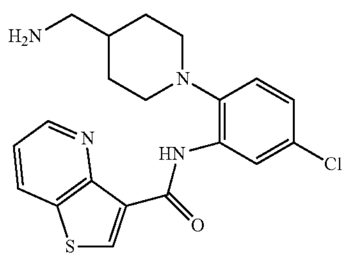 [SMILES: NCC1CCN(c2ccc(Cl)cc2NC(=O)c2csc3cccnc23)CC1] | Thieno[3,2-beta]pyridine-3-carboxylic acid[2-(4-aminomethyl-piperidin-1-yl)-5-chloro-phenyl]-amide | 0.070 | | | 11 |
| 42 | 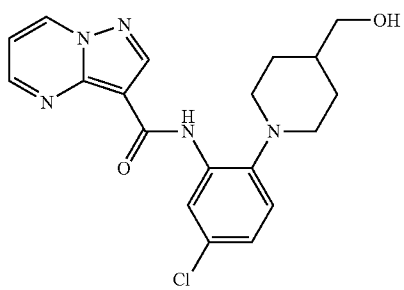 [SMILES: O=C(Nc1cc(Cl)ccc1N1CCC(CO)CC1)c1cnn2cccnc12] | Pyrazolo[1,5-alpha]pyrimidine-3-carboxylic acid[5-chloro-2-(4-hydroxymethyl-piperidin-1-yl)-phenyl]-amide | 0.072 | | | 1 |
| 43 | 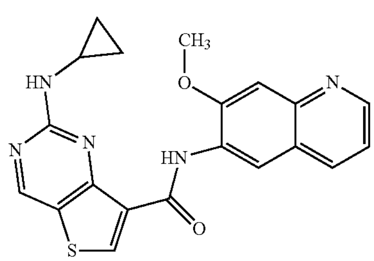 [SMILES: COc1cc2ncccc2cc1NC(=O)c1csc2cnc(NC3CC3)nc12] | 2-Cyclopropylamino-thieno[3,2-d]pyrimidine-7-carboxylic acid(7-methoxy-quinolin-6-yl)-amide | 0.074 | 0.575 | 0.81 | 12 |
| 44 | 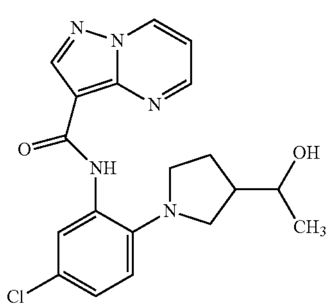 [SMILES: CC(O)C1CCN(c2ccc(Cl)cc2NC(=O)c2cnn3cccnc23)C1] | Pyrazolo[1,5alpha]pyrimidine-3-carboxylic acid{5-chloro-2-[3-(1-hydroxy-ethyl)-pyrrolidin-1-yl]-phenyl}-amide | 0.076 | 0.897 | | 1 |

TABLE 1-continued

| # | Structure | Chemical Name | IRAK 4 | IRAK 1 | SYK | Ex. |
|---|---|---|---|---|---|---|
| 45 | 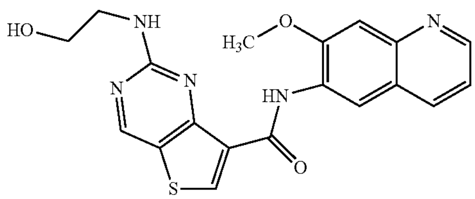 [SMILES: COc1cc2ncccc2cc1NC(=O)c1csc2cnc(NCCO)nc12] | 2-(2-Hydroxy-ethylamino)-thieno[3,2-d]pyrimidine-7-carboxylic acid(7-methoxy-quinolin-6-yl)-amide | 0.076 | | 0.216 | 12 |
| 46 | 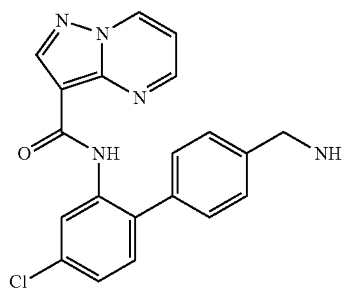 [SMILES: NCc1ccc(-c2ccc(Cl)cc2NC(=O)c2cnn3cccnc23)cc1] | Pyrazolo[1,5alpha]pyrimidine-3-carboxylic acid(4'-aminomethyl-4-chloro-biphenyl-2-yl)-amide | 0.081 | | | 15 |
| 47 | 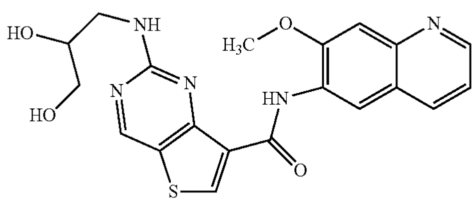 [SMILES: COc1cc2ncccc2cc1NC(=O)c1csc2cnc(NCC(O)CO)nc12] | 2-(2,3-Dihydroxy-propylamino)-thieno[3,2-d]pyrimidine-7-carboxylic acid(7-methoxy-quinolin-6-yl)-amide | 0.082 | 0.608 | | 12 |
| 48 | 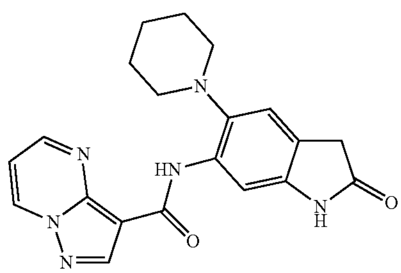 [SMILES: O=C1Cc2cc(N3CCCCC3)c(NC(=O)c3cnn4cccnc34)cc2N1] | Pyrazolo[1,5-alpha]pyrimidine-3-carboxylic acid(2-oxo-5-piperidin-1-yl-2,3-dihydro-1H-indol-6-yl)-amide | 0.098 | | | 1 |
| 49 | 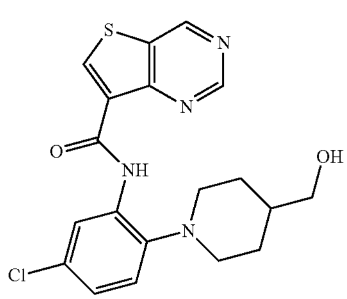 [SMILES: O=C(Nc1cc(Cl)ccc1N1CCC(CO)CC1)c1csc2cncnc12] | Thieno[3,2-d]pyrimidine-7-carboxylic acid[5-chloro-2-(4-hydroxymethyl-piperidin-1-yl)-phenyl]-amide | 0.100 | 0.70 | | 1 |
| 50 | 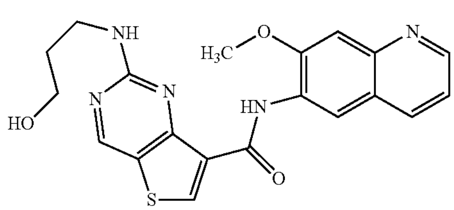 [SMILES: COc1cc2ncccc2cc1NC(=O)c1csc2cnc(NCCCO)nc12] | 2-(3-Amino-propylamino)-thieno[3,2-d]pyrimidine-7-carboxylic acid(7-methoxy-quinolin-6-yl)-amide | 0.101 | | | 12 |

TABLE 1-continued

| # | Structure | Chemical Name | IRAK 4 | IRAK 1 | SYK | Ex. |
|---|---|---|---|---|---|---|
| 51 | 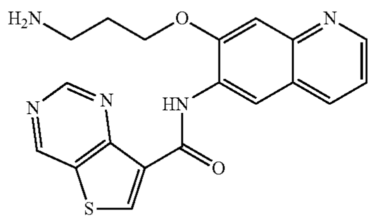 [SMILES: NCCCOc1cc2ncccc2cc1NC(=O)c1csc2cncnc12] | Thieno[3,2-d]pyrimidine-7-carboxylic acid[7-(3-amino-propoxy)-quinolin-6-yl]-amide | 0.103 | 0.529 | 0.376 | 15 |
| 52 | 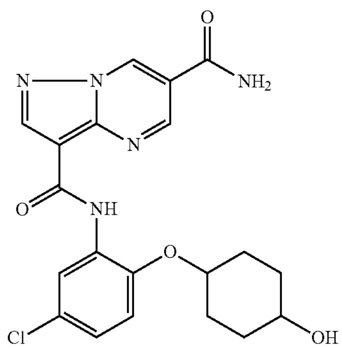 [SMILES: NC(=O)c1cnc2c(C(=O)Nc3cc(Cl)ccc3OC3CCC(O)CC3)cnn2c1] | Pyrazolo[1,5-alpha]pyrimidine-3,6-dicarboxylic acid 6-amide 3-{[5-chloro-2-(4-hydroxy-cyclohexyloxy)-phenyl]-amide] | 0.107 | | | 5 |
| 53 | 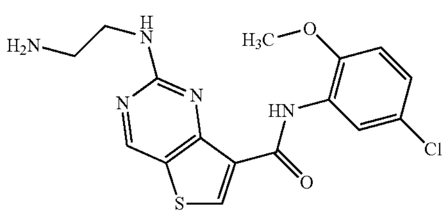 [SMILES: COc1ccc(Cl)cc1NC(=O)c1csc2cnc(NCCN)nc12] | 2-(2-Amino-ethylamino)-thieno[3,2-d]pyrimidine-7-carboxylic acid(5-chloro-2-methoxy-phenyl)-amide} | 0.107 | 0.813 | 0.35 | 12 |
| 54 | 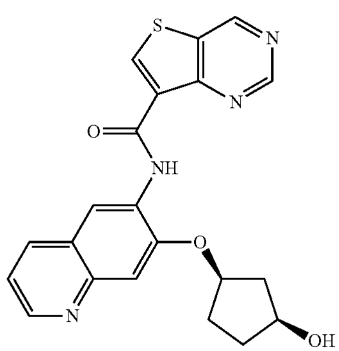 [SMILES: O=C(Nc1cc2cccnc2cc1O[C@@H]1CC[C@H](O)C1)c1csc2cncnc12] | Thieno[3,2-d]pyrimidine-7-carboxylic acid[7-(3-hydroxy-cyclopentyloxy)-quinolin-6-yl]-amide hydrochloride | 0.122 | | 0.5 | 5 |
| 55 | 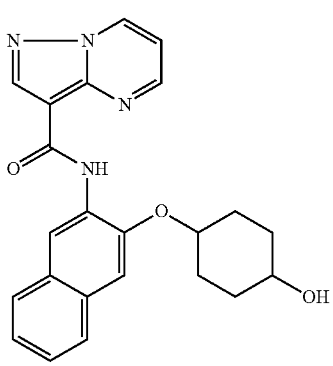 [SMILES: O=C(Nc1cc2ccccc2cc1OC1CCC(O)CC1)c1cnn2cccnc12] | Pyrazolo[1,5-alpha]pyrimidine-3-carboxylic acid[3-(4-hydroxy-cyclohexyloxy)-naphthalen-2-yl]-amide | 0.124 | 0.817 | 0.628 | 1 |

TABLE 1-continued

| # | Structure | Chemical Name | IRAK 4 | IRAK 1 | SYK | Ex. |
|---|---|---|---|---|---|---|
| 56 | 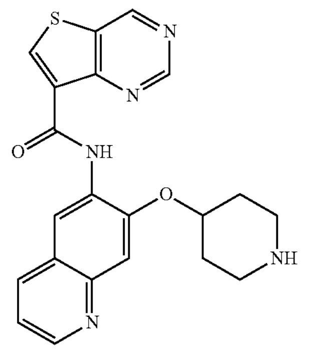 [SMILES: O=C(Nc1cc2cccnc2cc1OC1CCNCC1)c1csc2cncnc12] | Thieno[3,2-d]pyrimidine-7-carboxylic acid[7-(piperidin-4-yloxy)-quinolin-6-yl]-amide hydrochloride | 0.125 | | | 15 |
| 57 | 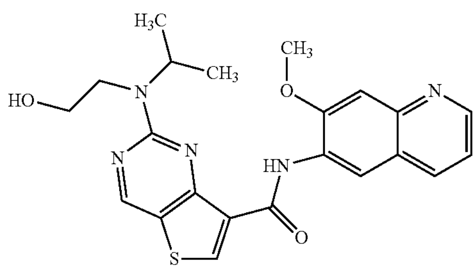 [SMILES: COc1cc2ncccc2cc1NC(=O)c1csc2cnc(N(CCO)C(C)C)nc12] | 2-[(2-Hydroxy-ethyl)-isopropyl-amino]-thieno[3,2-d]pyrimidine-7-carboxylic acid(7-methoxy-quinolin-6-yl)-amide | 0.127 | | | 12 |
| 58 | 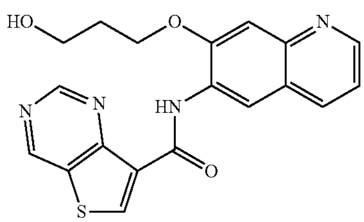 [SMILES: O=C(Nc1cc2cccnc2cc1OCCCO)c1csc2cncnc12] | Thieno[3,2-d]pyrimidine-7-carboxylic acid[7-(3-hydroxy-propoxy)-quinolin-6-yl]-amide | 0.131 | | | 5 |
| 59 | 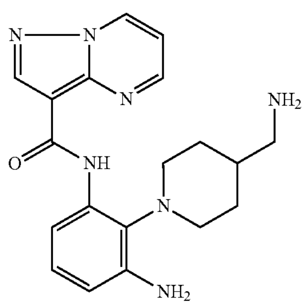 [SMILES: NCC1CCN(c2c(N)cccc2NC(=O)c2cnn3cccnc23)CC1] | Pyrazolo[1,5-alpha]pyrimidine-3-carboxylic acid[3-amino-2-(4-aminomethyl-piperidin-1-yl)-phenyl]-amide | 0.133 | | | 15 |
| 60 | 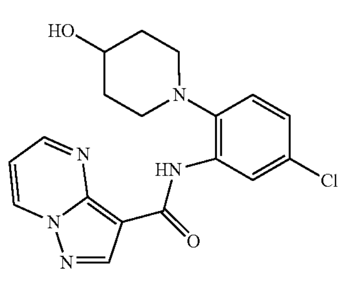 [SMILES: O=C(Nc1cc(Cl)ccc1N1CCC(O)CC1)c1cnn2cccnc12] | Pyrazolo[1,5-alpha]pyrimidine-3-carboxylic acid[5-chloro-2-(4-hydroxy-piperidin-1-yl)-phenyl]-amide | 0.136 | | | 1 |

TABLE 1-continued

| # | Structure | Chemical Name | IRAK 4 | IRAK 1 | SYK | Ex. |
|---|---|---|---|---|---|---|
| 61 | 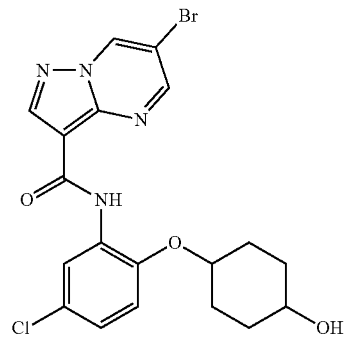 [SMILES: O=C(Nc1cc(Cl)ccc1OC1CCC(O)CC1)c1cnn2cc(Br)cnc12] | 6-Bromo-pyrazolo[1,5-alpha]pyrimidine-3-carboxylic acid[5-chloro-2-(4-hydroxy-cyclohexyloxy)-phenyl]-amide | 0.137 | | | 5 |
| 62 | 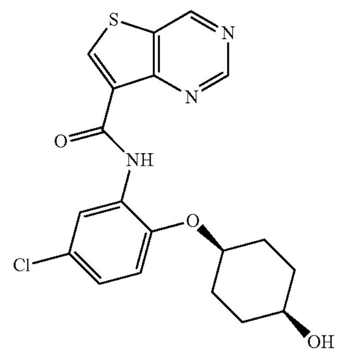 [SMILES: O=C(Nc1cc(Cl)ccc1O[C@H]1CC[C@@H](O)CC1)c1csc2cncnc12] | Thieno[3,2-d]pyrimidine-7-carboxylic acid[5-chloro-2-(4-hydroxy-cyclohexyloxy)-phenyl]-amide | 0.149 | 0.126 | | 1 |
| 63 | 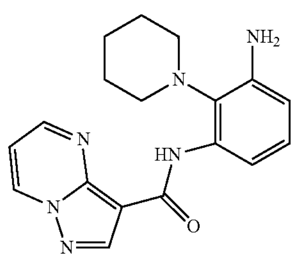 [SMILES: Nc1cccc(NC(=O)c2cnn3cccnc23)c1N1CCCCC1] | Pyrazolo[1,5-alpha]pyrimidine-3-carboxylic acid(3-amino-2-piperidin-1-yl-phenyl)-amide | 0.156 | | | 1 |
| 64 | 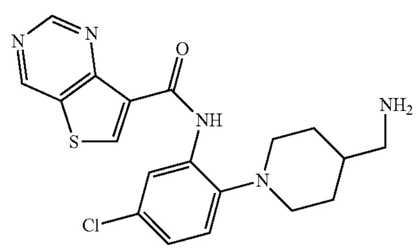 [SMILES: NCC1CCN(c2ccc(Cl)cc2NC(=O)c2csc3cncnc23)CC1] | Thieno[3,2-d]pyrimidine-7-carboxylic acid[2-(4-aminomethyl-piperidin-1-yl)-5-chloro-phenyl]-amide | 0.167 | 0.80 | | 11 |
| 65 | 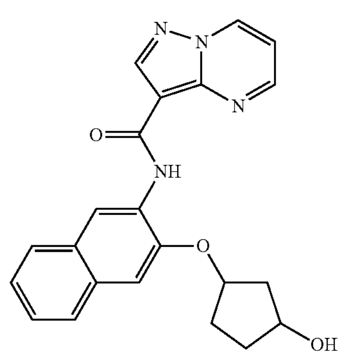 [SMILES: O=C(Nc1cc2ccccc2cc1OC1CCC(O)C1)c1cnn2cccnc12] | Pyrazolo[1,5-alpha]pyrimidine-3-carboxylic acid[3-(3-hydroxy-cyclopentyloxy)-naphthalen-2-yl]-amide | 0.177 | | | 1 |

TABLE 1-continued

| # | Structure | Chemical Name | IRAK 4 | IRAK 1 | SYK | Ex. |
|---|---|---|---|---|---|---|
| 66 | 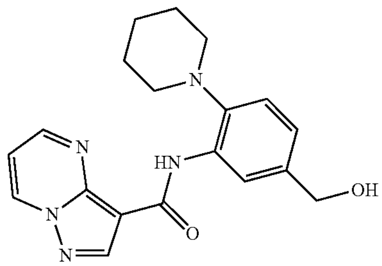 [SMILES: O=C(Nc1cc(CO)ccc1N1CCCCC1)c1cnn2cccnc12] | Pyrazolo[1,5-alpha]pyrimidine-3-carboxylic acid(5-hydroxymethyl-2-piperidin-1-yl-phenyl)-amide | 0.199 | | | 1 |
| 67 | 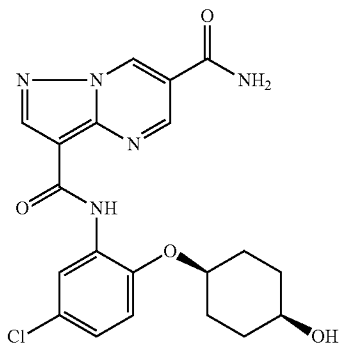 [SMILES: NC(=O)c1cnc2c(C(=O)Nc3cc(Cl)ccc3O[C@H]3CC[C@@H](O)CC3)cnn2c1] | Pyrazolo[1,5-alpha]pyrimidine-3,6-dicarboxylic acid 6-amide 3-{[5-chloro-2-(4-hydroxy-cyclohexyloxy)-phenyl]-amide} | 0.203 | | | 6 |
| 68 | 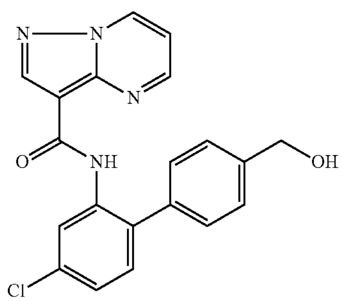 [SMILES: O=C(Nc1cc(Cl)ccc1-c1ccc(CO)cc1)c1cnn2cccnc12] | Pyrazolo[1,5-alpha]pyrimidine-3-carboxylic acid(4-chloro-4'-hydroxymethyl-biphenyl-2-yl)-amide | 0.218 | | | 1 |
| 69 | 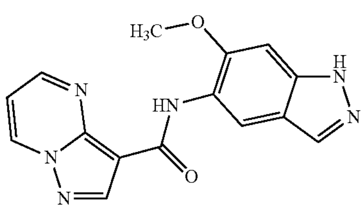 [SMILES: COc1cc2[nH]ncc2cc1NC(=O)c1cnn2cccnc12] | Pyrazolo[1,5-alpha]pyrimidine-3-carboxylic acid(6-methoxy-1H-indazol-5-yl)-amide | 0.231 | | | 1 |
| 70 | 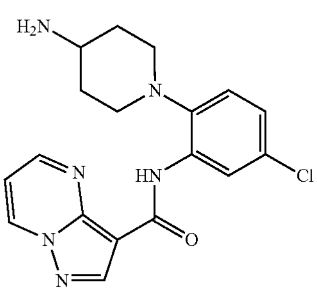 [SMILES: NC1CCN(c2ccc(Cl)cc2NC(=O)c2cnn3cccnc23)CC1] | Pyrazolo[1,5alpha]pyrimidine-3-carboxylic acid[2-(4-amino-piperidin-1-yl)-5-chloro-phenyl]-amide | 0.251 | | | 15 |

TABLE 1-continued

| # | Structure | Chemical Name | IRAK 4 | IRAK 1 | SYK | Ex. |
|---|---|---|---|---|---|---|
| 71 | 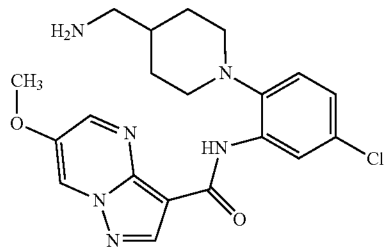 [SMILES: COc1cnc2c(C(=O)Nc3cc(Cl)ccc3N3CCC(CN)CC3)cnn2c1] | 6-Methoxy-pyrazolo[1,5-alpha]pyrimidine-3-carboxylic acid[2-(4-aminomethyl-piperidin-1-yl)-5-chloro-phenyl]-amide | 0.254 | | | 11 |
| 72 | 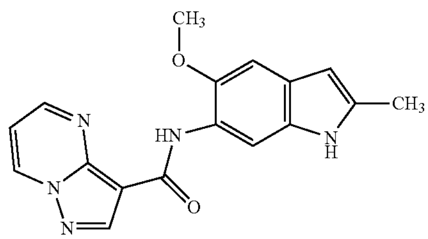 [SMILES: COc1cc2cc(C)[nH]c2cc1NC(=O)c1cnn2cccnc12] | Pyrazolo[1,5-alpha]pyrimidine-3-carboxylic acid(5-methoxy-2-methyl-1H-indol-6-yl)-amide | 0.255 | | | 1 |
| 73 | 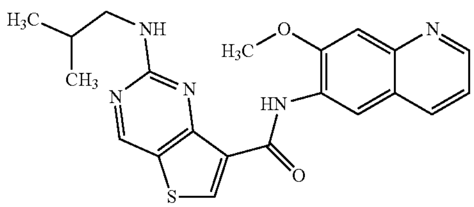 [SMILES: COc1cc2ncccc2cc1NC(=O)c1csc2cnc(NCC(C)C)nc12] | 2-Isobutylamino-thieno[3,2-d]pyrimidine-7-carboxylic acid(7-methoxy-quinolin-6-yl)-amide | 0.271 | | | 12 |
| 74 | 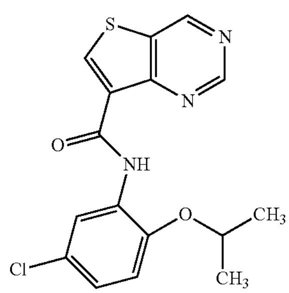 [SMILES: CC(C)Oc1ccc(Cl)cc1NC(=O)c1csc2cncnc12] | Thieno[3,2-d]pyrimidine-7-carboxylic acid(5-chloro-2-isopropoxy-phenyl)-amide | 0.290 | | | 1 |
| 75 | 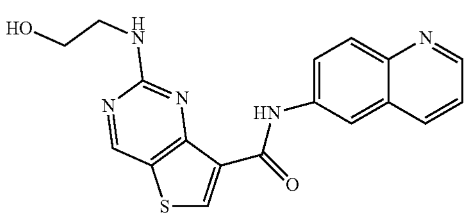 [SMILES: O=C(Nc1ccc2ncccc2c1)c1csc2cnc(NCCO)nc12] | 2-(2-Hydroxy-ethylamino)-thieno[3,2-d]pyrimidine-7-carboxylic acid quinolin-6-ylamide | 0.300 | | | 12 |
| 76 | 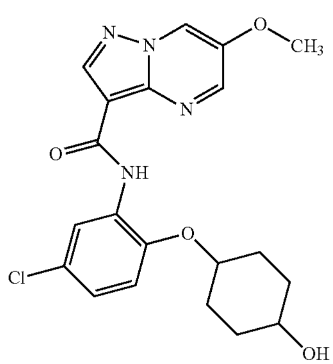 [SMILES: COc1cnc2c(C(=O)Nc3cc(Cl)ccc3OC3CCC(O)CC3)cnn2c1] | 6-Methoxy-pyrazolo[1,5-a]pyrimidine-3-carboxylic acid[5-chloro-2-(4-hydroxy-cyclohexyloxy)-phenyl]-amide | 0.301 | | | 5 |

TABLE 1-continued

| # | Structure | Chemical Name | IRAK 4 | IRAK 1 | SYK | Ex. |
|---|---|---|---|---|---|---|
| 77 | 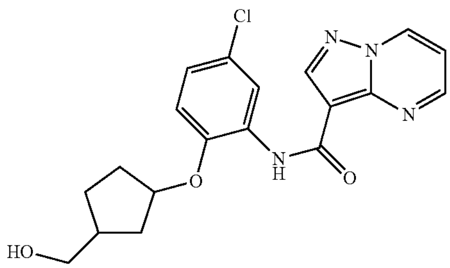 [SMILES: O=C(Nc1cc(Cl)ccc1OC1CCC(CO)C1)c1cnn2cccnc12] | Pyrazolo[1,5-alpha]pyrimidine-3-carboxylic acid[5-chloro-2-(3-hydroxymethyl-cyclopentyloxy)-phenyl]-amide | 0.306 | | | 1 |
| 78 | 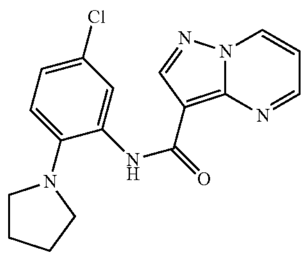 [SMILES: O=C(Nc1cc(Cl)ccc1N1CCCC1)c1cnn2cccnc12] | Pyrazolo[1,5-alpha]pyrimidine-3-carboxylic acid(5-chloro-2-pyrrolidin-1-yl-phenyl)-amide | 0.312 | | | 1 |
| 79 | 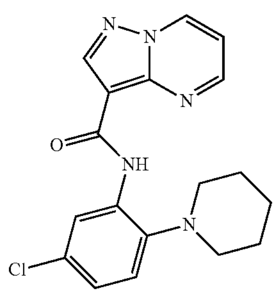 [SMILES: O=C(Nc1cc(Cl)ccc1N1CCCCC1)c1cnn2cccnc12] | Pyrazolo[1,5-alpha]pyrimidine-3-carboxylic acid(5-chloro-2-piperidin-1-yl-phenyl)-amide | 0.314 | | | 1 |
| 80 | 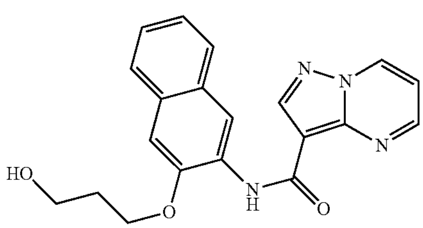 [SMILES: O=C(Nc1cc2ccccc2cc1OCCCO)c1cnn2cccnc12] | Pyrazolo[1,5-alpha]pyrimidine-3-carboxylic acid[3-(3-hydroxy-propoxy)-naphthalen-2-yl]-amide | 0.327 | | | 1 |
| 81 | 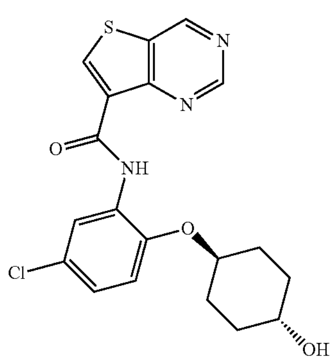 [SMILES: O=C(Nc1cc(Cl)ccc1O[C@H]1CC[C@H](O)CC1)c1csc2cncnc12] | Thieno[3,2-d]pyrimidine-7-carboxylic acid[5-chloro-2-(4-hydroxy-cyclohexyloxy)-phenyl]-amide | 0.338 | 0.60 | | 1 |

TABLE 1-continued

| # | Structure | Chemical Name | IRAK 4 | IRAK 1 | SYK | Ex. |
|---|---|---|---|---|---|---|
| 82 | 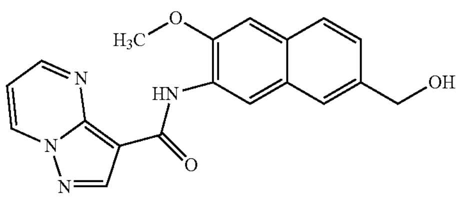 [SMILES: COc1cc2ccc(CO)cc2cc1NC(=O)c1cnn2cccnc12] | Pyrazolo[1,5-alpha]pyrimidine-3-carboxylic acid(7-hydroxymethyl-3-methoxy-naphthalen-2-yl)-amide | 0.358 | | | 1 |
| 83 | 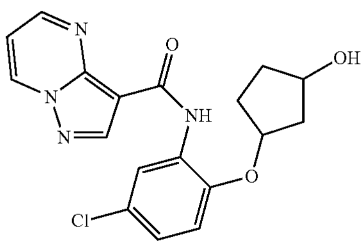 [SMILES: O=C(Nc1cc(Cl)ccc1OC1CCC(O)C1)c1cnn2cccnc12] | Pyrazolo[1,5-alpha]pyrimidine-3-carboxylic acid[5-chloro-2-(3-hydroxy-cyclopentyloxy)-phenyl]-amide | 0.361 | 0.656 | | 1 |
| 84 | 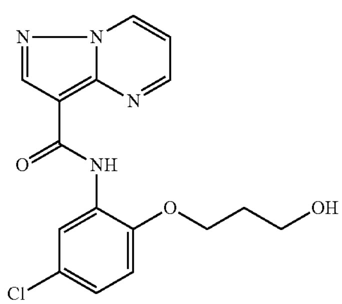 [SMILES: O=C(Nc1cc(Cl)ccc1OCCCO)c1cnn2cccnc12] | Pyrazolo[1,5-alpha]pyrimidine-3-carboxylic acid[5-chloro-2-(3-hydroxy-propoxy)-phenyl]-amide | 0.430 | | | 5 |
| 85 | 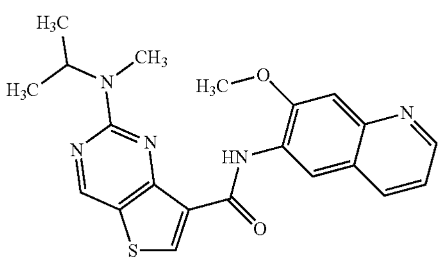 [SMILES: COc1cc2ncccc2cc1NC(=O)c1csc2cnc(N(C)C(C)C)nc12] | 2-(Isopropyl-methyl-amino)-thieno[3,2-d]pyrimidine-7-carboxylic acid(7-methoxy-quinolin-6-yl)-amide | 0.432 | | | 12 |
| 86 | 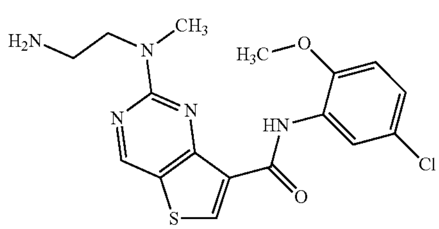 [SMILES: COc1ccc(Cl)cc1NC(=O)c1csc2cnc(N(C)CCN)nc12] | 2-[(2-Amino-ethyl)-methyl-amino]-thieno[3,2-d]pyrimidine-7-carboxylic acid(5-chloro-2-methoxy-phenyl)-amide | 0.436 | | | 12 |
| 87 | 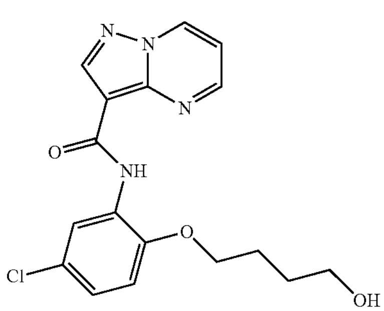 [SMILES: O=C(Nc1cc(Cl)ccc1OCCCCO)c1cnn2cccnc12] | Pyrazolo[1,5-alpha]pyrimidine-3-carboxylic acid[5-chloro-2-(4-hydroxy-butoxy)-phenyl]-amide | 0.437 | | | 1 |

TABLE 1-continued

| # | Structure | Chemical Name | IRAK 4 | IRAK 1 | SYK | Ex. |
|---|---|---|---|---|---|---|
| 88 | 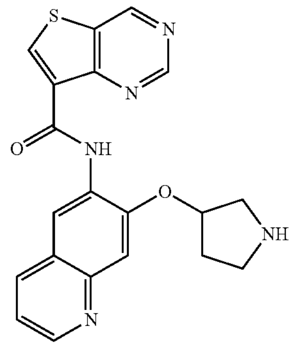 [SMILES: O=C(Nc1cc2cccnc2cc1OC1CCNC1)c1csc2cncnc12] | Thieno[3,2-d]pyrimidine-7-carboxylic acid[7-(pyrrolidin-3-yloxy)-quinolin-6-yl]-amide hydrochloride | 0.455 | | | 15 |
| 89 | 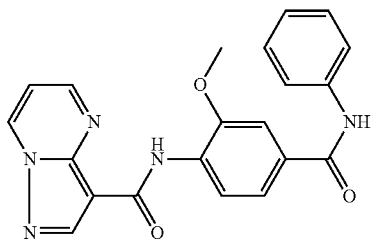 [SMILES: COc1cc(C(=O)Nc2ccccc2)ccc1NC(=O)c1cnn2cccnc12] | Pyrazolo[1,5-alpha]pyrimidine-3-carboxylic acid(2-methoxy-4-phenylcarbamoyl-phenyl)-amide | 0.455 | | | 1 |
| 90 | 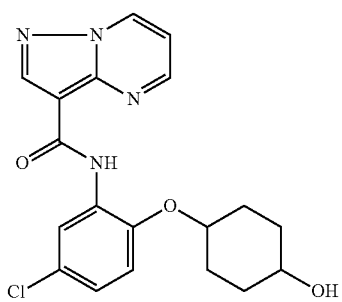 [SMILES: O=C(Nc1cc(Cl)ccc1OC1CCC(O)CC1)c1cnn2cccnc12] | Pyrazolo[1,5-alpha]pyrimidine-3-carboxylic acid[5-chloro-2-(4-hydroxy-cyclohexyloxy)-phenyl]-amide | 0.459 | 0.806 | | 1 |
| 91 | 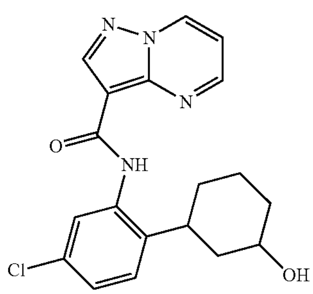 [SMILES: O=C(Nc1cc(Cl)ccc1C1CCCC(O)C1)c1cnn2cccnc12] | Pyrazolo[1,5-alpha]pyrimidine-3-carboxylic acid[5-chloro-2-(3-hydroxy-piperidin-1-yl)-phenyl]-amide | 0.474 | | | 1 |
| 92 | 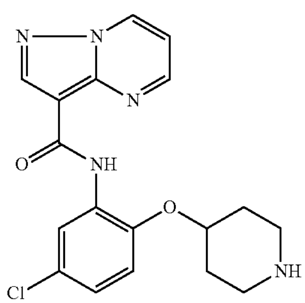 [SMILES: O=C(Nc1cc(Cl)ccc1OC1CCNCC1)c1cnn2cccnc12] | Pyrazolo[1,5-alpha]pyrimidine-3-carboxylic acid[5-chloro-2-(piperidin-4-yloxy)-phenyl]-amide hydrochloride | 0.476 | | | 15 |

TABLE 1-continued

| # | Structure | Chemical Name | IRAK 4 | IRAK 1 | SYK | Ex. |
|---|---|---|---|---|---|---|
| 93 | 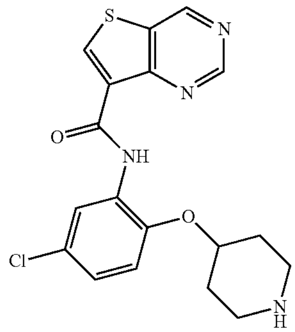 [SMILES: O=C(Nc1cc(Cl)ccc1OC1CCNCC1)c1csc2cncnc12] | Thieno[3,2-d]pyrimidine-7-carboxylic acid[5-chloro-2-(piperidin-4-yloxy)-phenyl]-amide trifluoro-acetic acid | 0.476 | 0.93 | | 11 |
| 94 | 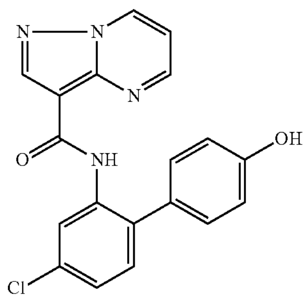 [SMILES: O=C(Nc1cc(Cl)ccc1-c1ccc(O)cc1)c1cnn2cccnc12] | Pyrazolo[1,5-alpha]pyrimidine-3-carboxylic acid(4-chloro-4'-hydroxy-biphenyl-2-yl)-amide | 0.477 | | | 5 |
| 95 | 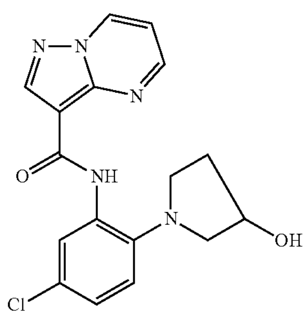 [SMILES: O=C(Nc1cc(Cl)ccc1N1CCC(O)C1)c1cnn2cccnc12] | Pyrazolo[1,5-alpha]pyrimidine-3-carboxylic acid[5-chloro-2-(3-hydroxy-pyrrolidin-1-yl)-phenyl]-amide | 0.493 | | | 1 |
| 96 | 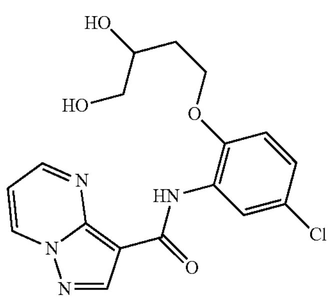 [SMILES: O=C(Nc1cc(Cl)ccc1OCCC(O)CO)c1cnn2cccnc12] | Pyrazolo[1,5-alpha]pyrimidine-3-carboxylic acid[5-chloro-2-(3,4-dihydroxy-butoxy)-phenyl]-amide | 0.506 | | | 18 |
| 97 | 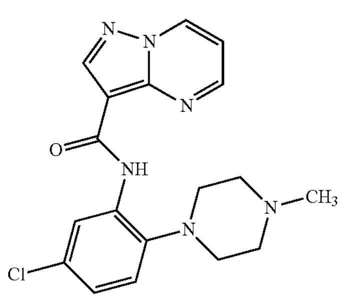 [SMILES: CN1CCN(c2ccc(Cl)cc2NC(=O)c2cnn3cccnc23)CC1] | Pyrazolo[1,5-alpha]pyrimidine-3-carboxylic acid[5-chloro-2-(4-methyl-piperazin-1-yl)-phenyl]-amide | 0.512 | | | 1 |

TABLE 1-continued

| # | Structure | Chemical Name | IRAK 4 | IRAK 1 | SYK | Ex. |
|---|---|---|---|---|---|---|
| 98 | 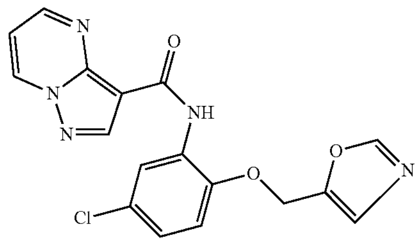 [SMILES: O=C(Nc1cc(Cl)ccc1OCc1cnco1)c1cnn2cccnc12] | Pyrazolo[1,5-alpha]pyrimidine-3-carboxylic acid[5-chloro-2-(oxazol-5-ylmethoxy)-phenyl]-amide | 0.516 | | | 16 |
| 99 | 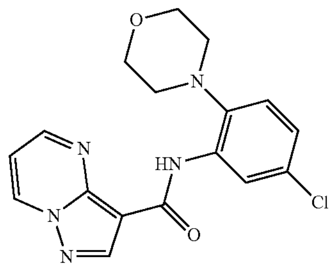 [SMILES: O=C(Nc1cc(Cl)ccc1N1CCOCC1)c1cnn2cccnc12] | Pyrazolo[1,5-alpha]pyrimidine-3-carboxylic acid(5-chloro-2-morpholin-4-yl-phenyl)-amide | 0.523 | | | 1 |
| 100 | 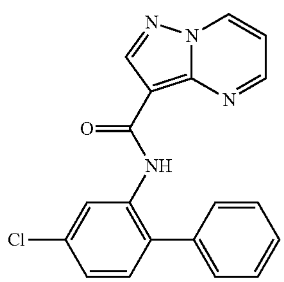 [SMILES: O=C(Nc1cc(Cl)ccc1-c1ccccc1)c1cnn2cccnc12] | Pyrazolo[1,5-alpha]pyrimidine-3-carboxylic acid(4-chloro-biphenyl-2-yl)-amide | 0.534 | | | 1 |
| 101 | 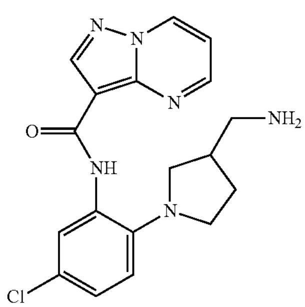 [SMILES: NCC1CCN(c2ccc(Cl)cc2NC(=O)c2cnn3cccnc23)C1] | Pyrazolo[1,5-alpha]pyrimidine-3-carboxylic acid[2-(3-aminomethyl-pyrrolidin-1-yl)-5-chloro-phenyl]-amide | 0.564 | | | 11 |
| 102 | 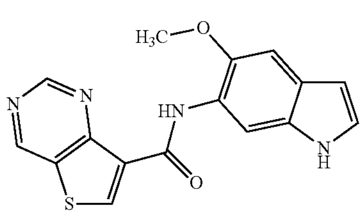 [SMILES: COc1cc2cc[nH]c2cc1NC(=O)c1csc2cncnc12] | Thieno[3,2-d]pyrimidine-7-carboxylic acid(5-methoxy-1H-indol-6-yl)-amide | 0.596 | | | 1 |

TABLE 1-continued

| # | Structure | Chemical Name | IRAK 4 | IRAK 1 | SYK | Ex. |
|---|---|---|---|---|---|---|
| 103 | 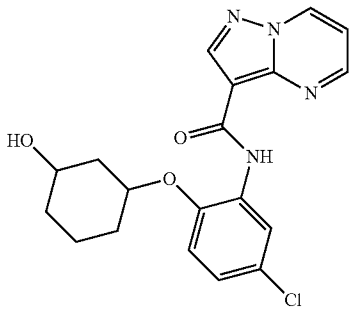 [SMILES: O=C(Nc1cc(Cl)ccc1OC1CCCC(O)C1)c1cnn2cccnc12] | Pyrazolo[1,5-alpha]pyrimidine-3-carboxylic acid[5-chloro-2-(3-hydroxy-cyclohexyloxy)-phenyl]-amide | 0.605 | | | 1 |
| 104 | 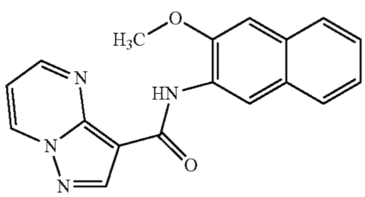 [SMILES: COc1cc2ccccc2cc1NC(=O)c1cnn2cccnc12] | Pyrazolo[1,5-alpha]pyrimidine-3-carboxylic acid(3-methoxy-naphthalen-2-yl)-amide | 0.613 | | | 1 |
| 105 | 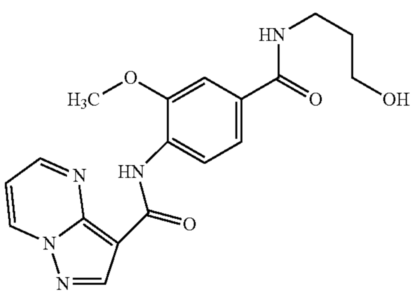 [SMILES: COc1cc(C(=O)NCCCO)ccc1NC(=O)c1cnn2cccnc12] | Pyrazolo[1,5-alpha]pyrimidine-3-carboxlic acid[4-(3-hydroxy-propylcarbamoyl)-2-methoxy-phenyl]-amide | 0.640 | | | 5 |
| 106 | 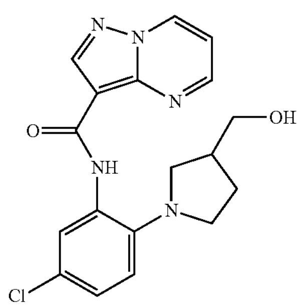 [SMILES: O=C(Nc1cc(Cl)ccc1N1CCC(CO)C1)c1cnn2cccnc12] | Pyrazolo[1,5-alpha]pyrimidine-3-carboxylic acid[5-chloro-2-(3-hydroxymethyl-pyrrolidin-1-yl)-phenyl]-amide | 0.650 | | | 1 |
| 107 | 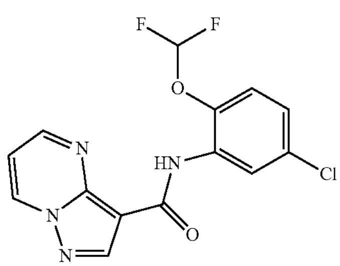 [SMILES: O=C(Nc1cc(Cl)ccc1OC(F)F)c1cnn2cccnc12] | Pyrazolo[1,5-alpha]pyrimidine-3-carboxylic acid(5-chloro-2-difluoromethoxy-phenyl)-amide | 0.717 | | | 1 |

TABLE 1-continued

| # | Structure | Chemical Name | IRAK 4 | IRAK 1 | SYK | Ex. |
|---|---|---|---|---|---|---|
| 108 | 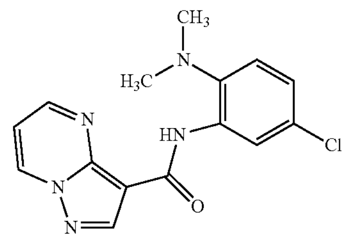 [SMILES: CN(C)c1ccc(Cl)cc1NC(=O)c1cnn2cccnc12] | Pyrazolo[1,5-alpha]pyrimidine-3-carboxylic acid(5-chloro-2-dimethylamino-phenyl)-amide | 0.739 | | | 1 |
| 109 | 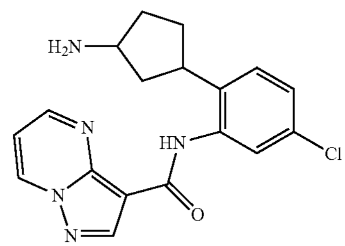 [SMILES: NC1CCC(c2ccc(Cl)cc2NC(=O)c2cnn3cccnc23)C1] | Pyrazolo[1,5-alpha]pyrimidine-3-carboxylic acid[2-(3-amino-pyrrolidin-1-yl)-5-chloro-phenyl]-amide | 0.766 | | | 19 |
| 110 | 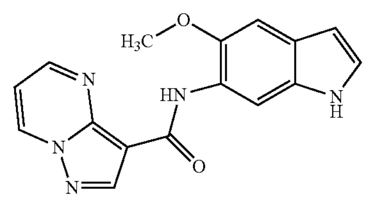 [SMILES: COc1cc2cc[nH]c2cc1NC(=O)c1cnn2cccnc12] | Pyrazolo[1,5-alpha]pyrimidine-3-carboxylic acid(5-methoxy-1H-indol-6-yl)-amide | 0.787 | | | 1 |
| 111 | 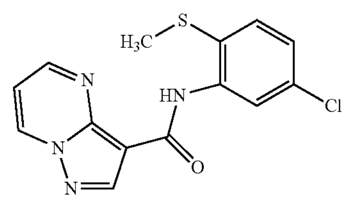 [SMILES: CSc1ccc(Cl)cc1NC(=O)c1cnn2cccnc12] | Pyrazolo[1,5-alpha]pyrimidine-3-carboxylic acid(5-chloro-2-methylsulfanyl-phenyl)-amide | 0.798 | | | 1 |
| 112 | 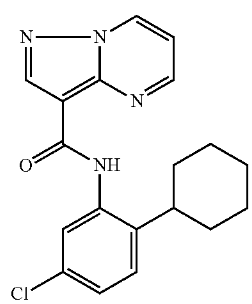 [SMILES: O=C(Nc1cc(Cl)ccc1C1CCCCC1)c1cnn2cccnc12] | Pyrazolo[1,5-alpha]pyrimidine-3-carboxylic acid(5-chloro-2-cyclohexyl-phenyl)-amide | 0.799 | | | 1 |
| 113 | 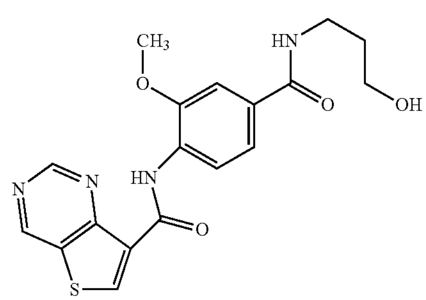 [SMILES: COc1cc(C(=O)NCCCO)ccc1NC(=O)c1csc2cncnc12] | Thieno[3,2-d]pyrimidine-7-carboxylic acid[4-(3-hydroxy-propylcarbamoyl)-2-methoxy-phenyl]-amide | 0.833 | | | 5 |

TABLE 1-continued

| # | Structure | Chemical Name | IRAK 4 | IRAK 1 | SYK | Ex. |
|---|---|---|---|---|---|---|
| 114 | 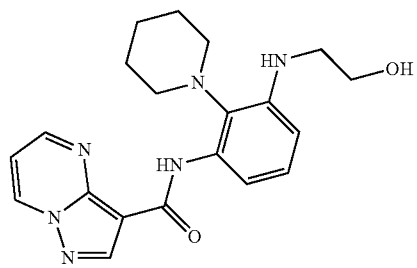 [SMILES: O=C(Nc1cccc(NCCO)c1N1CCCCC1)c1cnn2cccnc12] | Pyrazolo[1,5alpha]pyrimidine-3-carboxylic acid[3-(2-hydroxy-ethylamino)-2-piperidin-1-yl-phenyl]-amide | 1.029 | | | 1 |
| 115 | 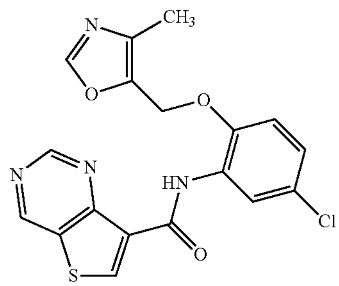 [SMILES: Cc1ncoc1COc1ccc(Cl)cc1NC(=O)c1csc2cncnc12] | Thieno[3,2-d]pyrimidine-7-carboxylic acid[5-chloro-2-(4-methyl-oxazol-5-ylmethoxy)-phenyl]-amide | 1.050 | | | 1 |
| 116 | 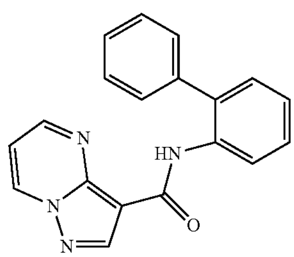 [SMILES: O=C(Nc1ccccc1-c1ccccc1)c1cnn2cccnc12] | Pyrazolo[1,5-alpha]pyrimidine-3-carboxylic acid biphenyl-2-ylamide | 1.224 | | | 1 |
| 117 | 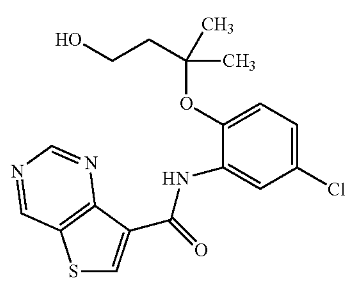 [SMILES: CC(C)(CCO)Oc1ccc(Cl)cc1NC(=O)c1csc2cncnc12] | Thieno[3,2-d]pyrimidine-7-carboxylic acid[5-chloro-2-(3-hydroxy-1,1-dimethyl-propoxy)-phenyl]-amide | 1.459 | | | 1 |
| 118 | 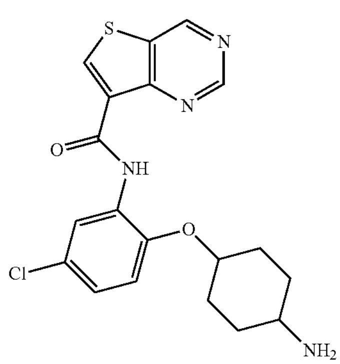 [SMILES: NC1CCC(Oc2ccc(Cl)cc2NC(=O)c2csc3cncnc23)CC1] | Thieno[3,2-d]pyrimidine-7-carboxylic acid[2-(4-amino-cyclohexyloxy)-5-chloro-phenyl]-amide | 1.471 | | | 15 |

TABLE 1-continued

| # | Structure | Chemical Name | IRAK 4 | IRAK 1 | SYK | Ex. |
|---|---|---|---|---|---|---|
| 119 | 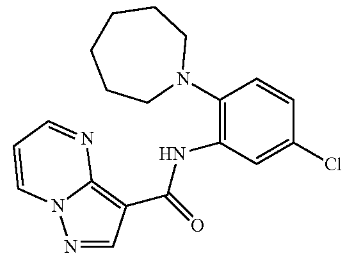 [SMILES: O=C(Nc1cc(Cl)ccc1N1CCCCCC1)c1cnn2cccnc12] | Pyrazolo[1,5-alpha]pyrimidine-3-carboxylic acid(2-azepan-1-yl-5-chloro-phenyl)-amide | 1.503 | | | 1 |
| 120 | 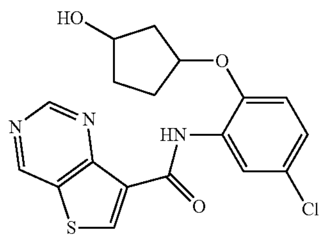 [SMILES: O=C(Nc1cc(Cl)ccc1OC1CCC(O)C1)c1csc2cncnc12] | Thieno[3,2-d]pyrimidine-7-carboxylic acid[5-chloro-2-(3-hydroxy-cyclopentyloxy)-phenyl]-amide | 1.521 | | | 5 |
| 121 | 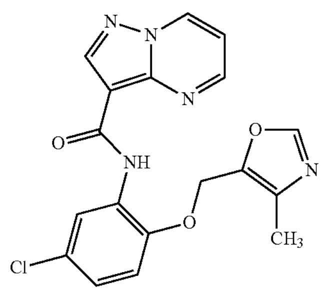 [SMILES: Cc1ncoc1COc1ccc(Cl)cc1NC(=O)c1cnn2cccnc12] | Pyrazolo[1,5-alpha]pyrimidine-3-carboxylic acid[5-chloro-2-(4-methyl-oxazol-5-ylmethoxy)-phenyl]-amide | 1.553 | | | 1 |
| 122 | 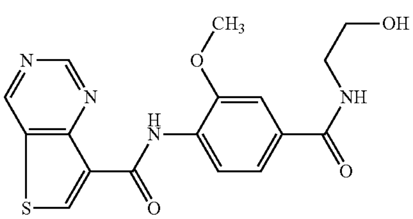 [SMILES: COc1cc(C(=O)NCCO)ccc1NC(=O)c1csc2cncnc12] | Thieno[3,2-d]pyrimidine-7-carboxylic acid[4-(2-hydroxy-ethylcarbamoyl)-2-methoxy-phenyl]-amide | 1.619 | | | 5 |
| 123 | 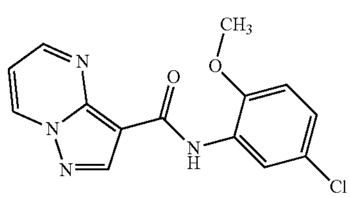 [SMILES: COc1ccc(Cl)cc1NC(=O)c1cnn2cccnc12] | Pyrazolo[1,5-alpha]pyrimidine-carboxylic acid(5 chloro-2-methoxy-phenyl)-amide | 1.633 | | | 1 |
| 124 | 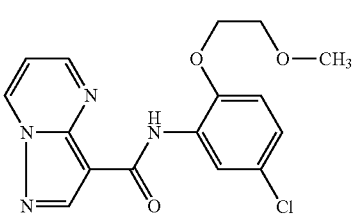 [SMILES: COCCOc1ccc(Cl)cc1NC(=O)c1cnn2cccnc12] | Pyrazolo[1,5-alpha]pyrimidine-3-carboxylic acid[5-chloro-2-(2-methoxy-ethoxy)-phenyl]-amide | 1.710 | | | 1 |

TABLE 1-continued

| # | Structure | Chemical Name | IRAK 4 | IRAK 1 | SYK | Ex. |
|---|---|---|---|---|---|---|
| 125 | 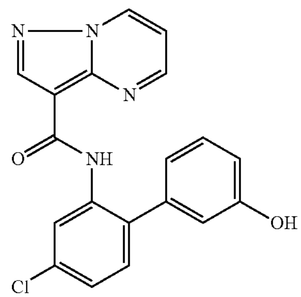 [SMILES: O=C(Nc1cc(Cl)ccc1-c1cccc(O)c1)c1cnn2cccnc12] | Pyrazolo[1,5-alpha]pyrimidine-3-carboxylic acid(4-chloro-3'-hydroxy-biphenyl-2-yl)-amide | 2.047 | | | 5 |
| 126 | 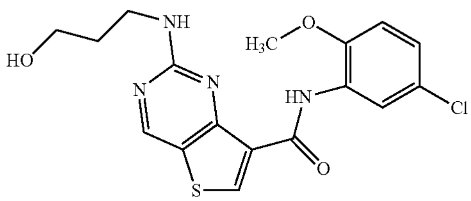 [SMILES: COc1ccc(Cl)cc1NC(=O)c1csc2cnc(NCCCO)nc12] | 2-(3-Hydroxy-propylamino)-thieno[3,2-d]pyrimidine-7-carboxylic acid(5-chloro-2-methoxy-phenyl)-amide | 2.062 | | | 12 |
| 127 | 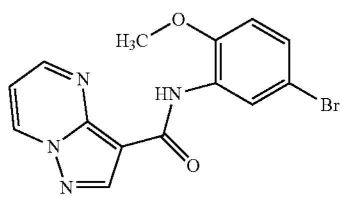 [SMILES: COc1ccc(Br)cc1NC(=O)c1cnn2cccnc12] | Pyrazolo[1,5-alpha]pyrimidine-3-carboxylic acid(5-bromo-2-methoxy-phenyl)-amide | 2.144 | | | 1 |
| 128 | 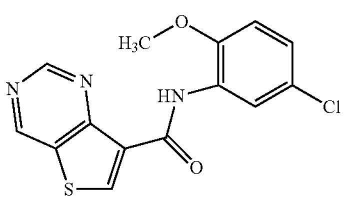 [SMILES: COc1ccc(Cl)cc1NC(=O)c1csc2cncnc12] | Thieno[3,2-d]pyrimidine-7-carboxylic acid(5-chloro-2-methoxy-phenyl)-amide | 2.200 | | | 1 |
| 129 | 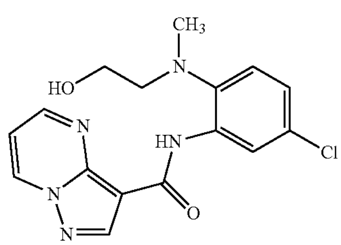 [SMILES: CN(CCO)c1ccc(Cl)cc1NC(=O)c1cnn2cccnc12] | Pyrazolo[1,5-alpha]pyrimidine-3-carboxylic acid{5-chloro-2-[(2-hydroxy-ethyl)-methyl-amino]-phenyl}-amide | 2.203 | | | 1 |
| 130 | 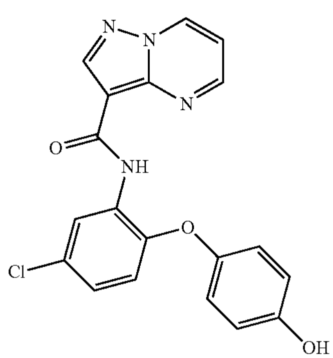 [SMILES: O=C(Nc1cc(Cl)ccc1Oc1ccc(O)cc1)c1cnn2cccnc12] | Pyrazolo[1,5-alpha]pyrimidine-3-carboxylic acid[5-chloro-2-(4-hydroxy-phenoxy)-phenyl]-amide | 2.221 | | | 1 |

TABLE 1-continued

| # | Structure | Chemical Name | IRAK 4 | IRAK 1 | SYK | Ex. |
|---|---|---|---|---|---|---|
| 131 | 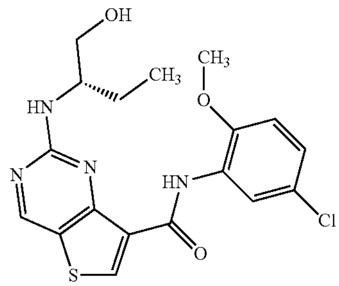 [SMILES: CC[C@@H](CO)Nc1ncc2scc(C(=O)Nc3cc(Cl)ccc3OC)c2n1] | 2-(1-Hydroxymethyl-propylamino)-thieno[3,2-d]pyrimidine-7-carboxylic acid(5-chloro-2-methoxy-phenyl)-amide | 2.226 | | | 12 |
| 132 | 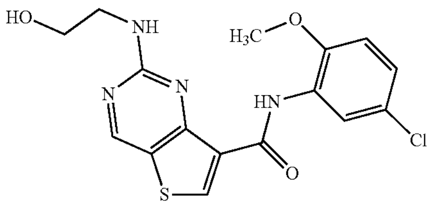 [SMILES: COc1ccc(Cl)cc1NC(=O)c1csc2cnc(NCCO)nc12] | 2-(2-Hydroxy-ethylamino)-thieno[3,2-d]pyrimidine-7-carboxylic acid(5-chloro-2-methoxy-phenyl)-amide | 2.237 | | | 12 |
| 133 | 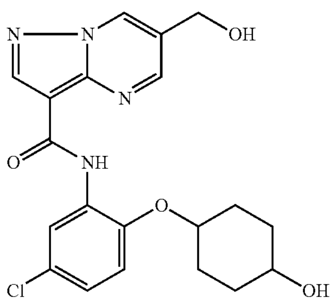 [SMILES: O=C(Nc1cc(Cl)ccc1OC1CCC(O)CC1)c1cnn2cc(CO)cnc12] | 6-Hydroxymethyl-pyrazolo[1,5-alpha]pyrimidine-3-carboxylic acid[5-chloro-2-(4-hydroxy-cyclohexyloxy)-phenyl]-amide | 2.253 | | | 6 |
| 134 | 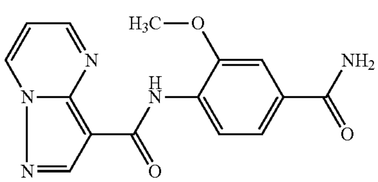 [SMILES: COc1cc(C(N)=O)ccc1NC(=O)c1cnn2cccnc12] | Pyrazolo[1,5-alpha]pyrimidine-3-carboxylic acid(4-carbamoyl-2-methoxy-phenyl)-amide | 2.256 | | | 3 |
| 135 | 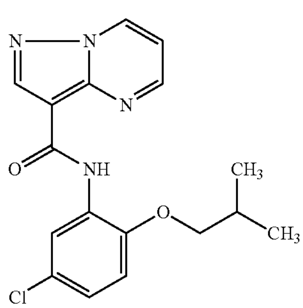 [SMILES: CC(C)COc1ccc(Cl)cc1NC(=O)c1cnn2cccnc12] | Pyrazolo[1,5-alpha]pyrimidine-3-carboxylic acid(5-chloro-2-isobutoxy-phenyl)-amide | 2.280 | | | 1 |
| 136 | 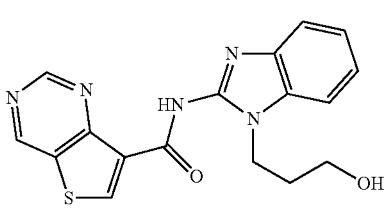 [SMILES: O=C(Nc1nc2ccccc2n1CCCO)c1csc2cncnc12] | Thieno[3,2-d]pyrimidine-7-carboxylic acid[1-(3-hydroxy-propyl)-1H-benzoimidazol-2-yl]-amide | 2.310 | | | 1 |

TABLE 1-continued

| # | Structure | Chemical Name | IRAK 4 | IRAK 1 | SYK | Ex. |
|---|---|---|---|---|---|---|
| 137 | 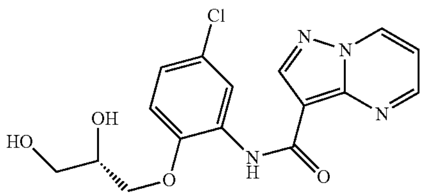 [SMILES: O=C(Nc1cc(Cl)ccc1OC[C@@H](O)CO)c1cnn2cccnc12] | Pyrazolo[1,5-alpha]pyrimidine-3-carboxylic acid[5-chloro-2-(2,3-dihydroxy-propoxy)-phenyl]-amide | 2.311 | | | 18 |
| 138 | 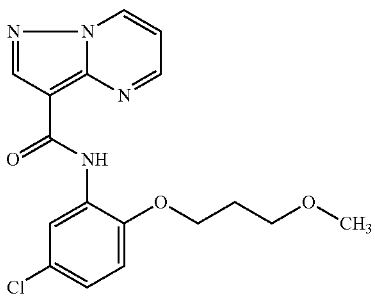 [SMILES: COCCCOc1ccc(Cl)cc1NC(=O)c1cnn2cccnc12] | Pyrazolo[1,5-alpha]pyrimidine-3-carboxylic acid[5-chloro-2-(3-methoxy-propoxy)-phenyl]-amide | 2.419 | | | 1 |
| 139 | 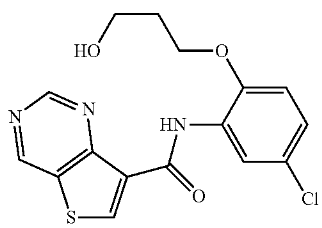 [SMILES: O=C(Nc1cc(Cl)ccc1OCCCO)c1csc2cncnc12] | Thieno[3,2-d]pyrimidine-7-carboxylic acid[5-chloro-2-(3-hydroxy-propoxy)-phenyl]-amide | 2.452 | | | 5 |
| 140 | 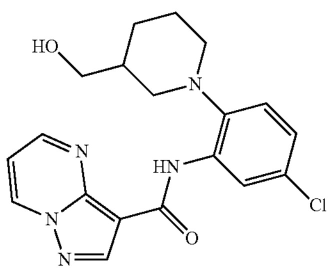 [SMILES: O=C(Nc1cc(Cl)ccc1N1CCCC(CO)C1)c1cnn2cccnc12] | Pyrazolo[1,5-alpha]pyrimidine-3-carboxylic acid[5-chloro-2-(3-hydroxymethyl-piperidin-1-yl)-phenyl]-amide | 2.465 | | | 1 |
| 141 | 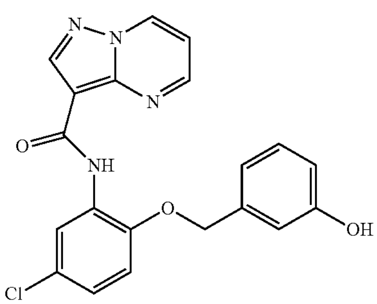 [SMILES: O=C(Nc1cc(Cl)ccc1OCc1cccc(O)c1)c1cnn2cccnc12] | Pyrazolo[1,5-alpha]pyrimidine-3-carboxylic acid[5-chloro-2-(3-hydroxy-benzyloxy)-phenyl]-amide | 2.626 | | | 7 |
| 142 | 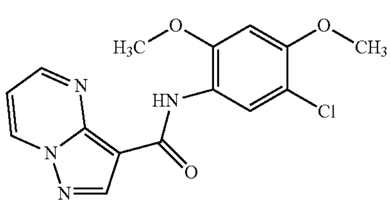 [SMILES: COc1cc(OC)c(NC(=O)c2cnn3cccnc23)cc1Cl] | Pyrazolo[1,5-alpha]pyrimidine-3-carboxylic acid(5-chloro-2,4-dimethoxy-phenyl)-amide | 2.738 | | | 1 |

TABLE 1-continued

| # | Structure | Chemical Name | IRAK 4 | IRAK 1 | SYK | Ex. |
|---|---|---|---|---|---|---|
| 143 | 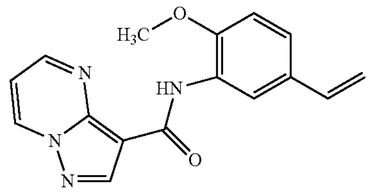 [SMILES: C=Cc1ccc(OC)c(NC(=O)c2cnn3cccnc23)c1] | Pyrazolo[1,5-alpha]pyrimidine-3-carboxylic acid(2-methoxy-5-vinyl-phenyl)-amide | 2.748 | | | 1 |
| 144 | 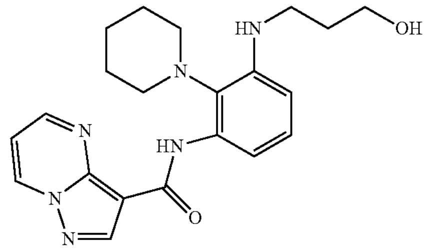 [SMILES: O=C(Nc1cccc(NCCCO)c1N1CCCCC1)c1cnn2cccnc12] | Pyrazolo[1,5-alpha]pyrimidine-3-carboxylic acid[3-(3-hydroxy-propylamino)-2-piperidin-1-yl-phenyl]-amide | 2.849 | | | 1 |
| 145 | 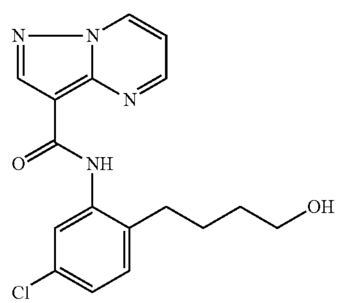 [SMILES: O=C(Nc1cc(Cl)ccc1CCCCO)c1cnn2cccnc12] | Pyrazolo[1,5-alpha]pyrimidine-3-carboxylic acid[5-chloro-2-(4-hydroxy-butyl)-phenyl]-amide | 2.949 | | | 1 |
| 146 | 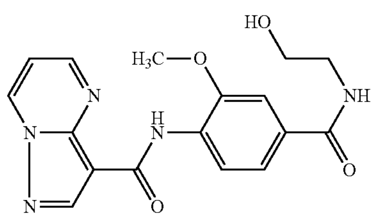 [SMILES: COc1cc(C(=O)NCCO)ccc1NC(=O)c1cnn2cccnc12] | Pyrazolo[1,5-alpha]pyrimidine-3-carboxylic acid[4-(2-hydroxy-ethylcarbamoyl)-2-methoxy-phenyl]-amide | 2.961 | | | 5 |
| 147 | 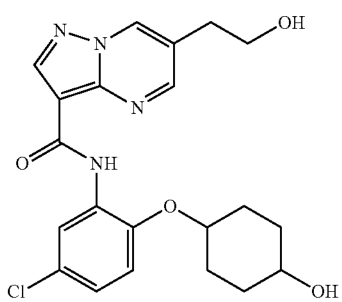 [SMILES: O=C(Nc1cc(Cl)ccc1OC1CCC(O)CC1)c1cnn2cc(CCO)cnc12] | 6-(2-Hydroxy-ethyl)-pyrazolo[1,5-alpha]pyrimidine-3-carboxylic acid[5-chloro-2-(4-hydroxy-cyclohexyloxy)-phenyl]-amide | 3.045 | | | 5 |
| 148 | 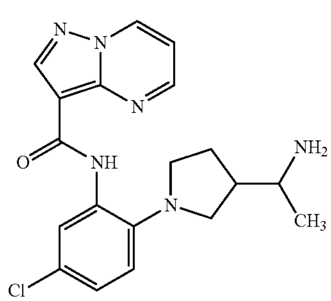 [SMILES: CC(N)C1CCN(c2ccc(Cl)cc2NC(=O)c2cnn3cccnc23)C1] | Pyrazolo[1,5-alpha]pyrimidine-3-carboxylic acid{2-[3-(1-amino-ethyl)-pyrrolidin-1-yl]-5-chloro-phenyl}-amide hydrochloride | 3.083 | | | 15 |

TABLE 1-continued

| # | Structure | Chemical Name | IRAK 4 | IRAK 1 | SYK | Ex. |
|---|-----------|---------------|--------|--------|-----|-----|
| 149 | 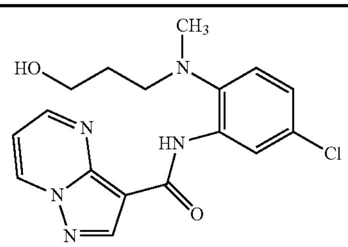 | Pyrazolo[1,5-alpha]pyrimidine-3-carboxylic acid{5-chloro-2-[(3-hydroxy-propyl)-methyl-amino]-phenyl}-amide | 3.395 | | | 1 |
| 150 | 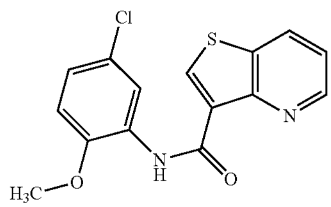 [SMILES: COc1ccc(Cl)cc1NC(=O)c1csc2cccnc12] | Thieno[3,2-beta]pyridine-3-carboxylic acid(5-chloro-2-methoxy-phenyl)-amide | 3.461 | | | 1 |
| 151 | 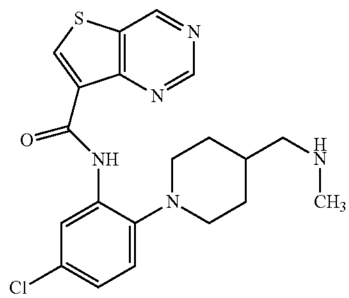 [SMILES: CNCC1CCN(c2ccc(Cl)cc2NC(=O)c2csc3cncnc23)CC1] | Thieno[3,2-d]pyrimidine-7-carboxylic acid[5-chloro-2-(4-methylaminomethyl-piperidin-1-yl)-phenyl]-amide | 3.545 | | | 8 |
| 152 | 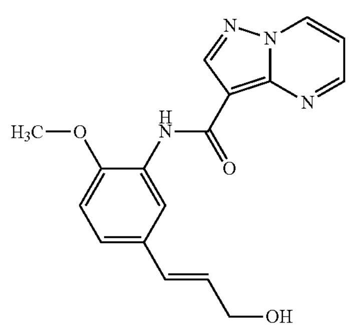 [SMILES: COc1ccc(/C=C/CO)cc1NC(=O)c1cnn2cccnc12] | Pyrazolo[1,5-alpha]pyrimidine-3-carboxylic acid[5-(3-hydroxy-propenyl)-2-methoxy-phenyl]-amide | 3.698 | | | 10 |
| 153 | 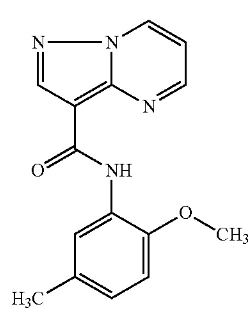 [SMILES: COc1ccc(C)cc1NC(=O)c1cnn2cccnc12] | Pyrazolo[1,5-alpha]pyrimidine-3-carboxylic acid(2-methoxy-5-methyl-phenyl)-amide | 3.769 | | | 1 |
| 154 | 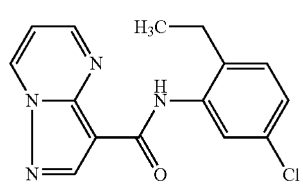 [SMILES: CCc1ccc(Cl)cc1NC(=O)c1cnn2cccnc12] | Pyrazolo[1,5-alpha]pyrimidine-3-carboxylic acid(5-chloro-2-ethyl-phenyl)-amide | 3.796 | | | 1 |

TABLE 1-continued

| # | Structure | Chemical Name | IRAK 4 | IRAK 1 | SYK | Ex. |
|---|---|---|---|---|---|---|
| 155 | 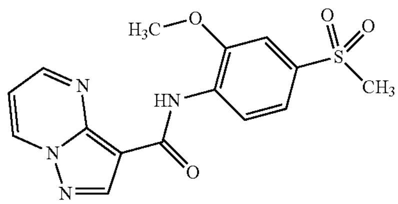 [SMILES: COc1cc(S(C)(=O)=O)ccc1NC(=O)c1cnn2cccnc12] | Pyrazolo[1,5-alpha]pyrimidine-3-carboxylic acid(4-methanesulfonyl-2-methoxy-phenyl)-amide | 4.011 | | | 1 |
| 156 | 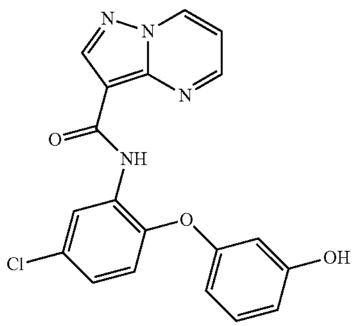 [SMILES: O=C(Nc1cc(Cl)ccc1Oc1cccc(O)c1)c1cnn2cccnc12] | Pyrazolo[1,5-alpha]pyrimidine-3-carboxylic acid[5-chloro-2-(3-hydroxy-phenoxy)-phenyl]-amide | 4.047 | | | 1 |
| 157 | 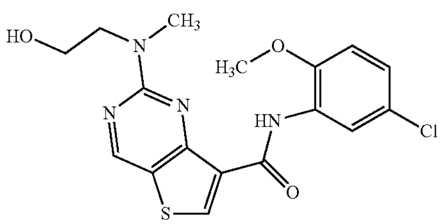 [SMILES: COc1ccc(Cl)cc1NC(=O)c1csc2cnc(N(C)CCO)nc12] | 2-[(2-Hydroxy-ethyl)-methyl-amino]-thieno[3,2-d]pyrimidine-7-carboxylic acid(5-chloro-2-methoxy-phenyl)-amide | 4.133 | | | 12 |
| 158 | 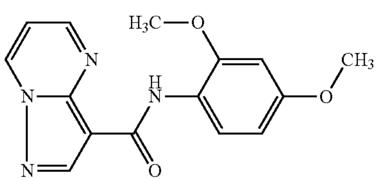 [SMILES: COc1ccc(NC(=O)c2cnn3cccnc23)c(OC)c1] | Pyrazolo[1,5-alpha]pyrimidine-3-carboxylic acid (2,4-dimethoxy-phenyl)-amide | 4.169 | | | 1 |
| 159 | 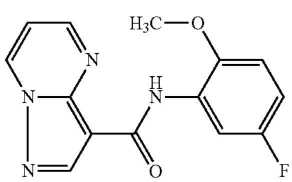 [SMILES: COc1ccc(F)cc1NC(=O)c1cnn2cccnc12] | Pyrazolo[1,5-alpha]pyrimidine-3-carboxylic acid(5-fluoro-2-methoxy-phenyl)-amide | 4.302 | | | 1 |
| 160 | 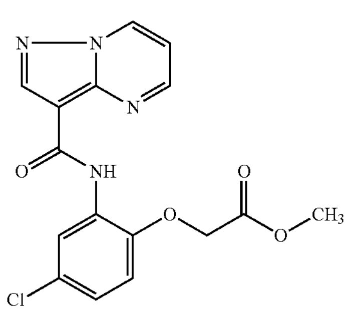 [SMILES: COC(=O)COc1ccc(Cl)cc1NC(=O)c1cnn2cccnc12] | {4-Chloro-2-[(pyrazolo[1,5-alpha]pyrimidine-3-carbonyl)-amino]-phenoxy}-acetic acid methyl ester | 4.305 | | | 2 |

TABLE 1-continued

| # | Structure | Chemical Name | IRAK 4 | IRAK 1 | SYK | Ex. |
|---|---|---|---|---|---|---|
| 161 | 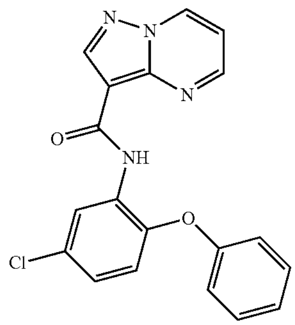 [SMILES: O=C(Nc1cc(Cl)ccc1Oc1ccccc1)c1cnn2cccnc12] | Pyrazolo[1,5-alpha]pyrimidine-3-carboxylic acid(5-chloro-2-phenoxy-phenyl)-amide | 4.647 | | | 1 |
| 162 | 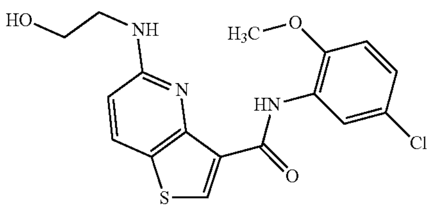 [SMILES: COc1ccc(Cl)cc1NC(=O)c1csc2ccc(NCCO)nc12] | 5-(2-Hydroxy-ethylamino)-thieno[3,2-beta]pyridine-3-carboxylic acid(5 chloro-2-methoxy-phenyl)-amide | 4.655 | | | 12 |
| 163 | 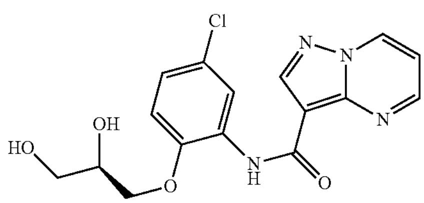 [SMILES: O=C(Nc1cc(Cl)ccc1OC[C@H](O)CO)c1cnn2cccnc12] | Pyrazolo[1,5-alpha]pyrimidine-3-carboxylic acid[5-chloro-2-(2,3-dihydroxy-propoxy)-phenyl]-amide | 4.664 | | | 18 |
| 164 | 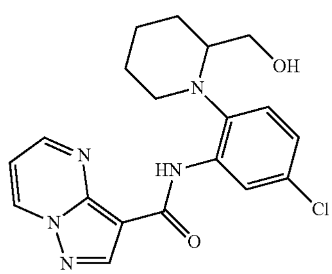 [SMILES: O=C(Nc1cc(Cl)ccc1N1CCCCC1CO)c1cnn2cccnc12] | Pyrazolo[1,5-alpha]pyrimidine-3-carboxylic acid[5-chloro-2-(2-hydroxymethyl-piperidin-1-yl)-phenyl]-amide | 4.848 | | | 1 |
| 165 | 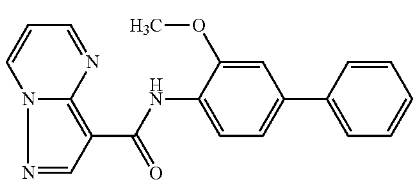 [SMILES: COc1cc(-c2ccccc2)ccc1NC(=O)c1cnn2cccnc12] | Pyrazolo[1,5-alpha]pyrimidine-3-carboxylic acid(3-methoxy-biphenyl-4-yl)-amide | 5.205 | | | 1 |
| 166 | 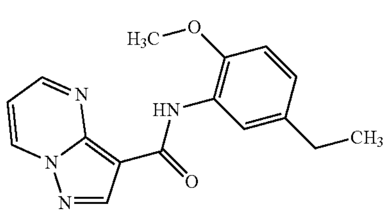 [SMILES: CCc1ccc(OC)c(NC(=O)c2cnn3cccnc23)c1] | Pyrazolo[1,5-alpha]pyrimidine-3-carboxylic acid(5-ethyl-2-methoxy-phenyl)-amide | 5.885 | | | 1 |

TABLE 1-continued

| # | Structure | Chemical Name | IRAK 4 | IRAK 1 | SYK | Ex. |
|---|---|---|---|---|---|---|
| 167 | 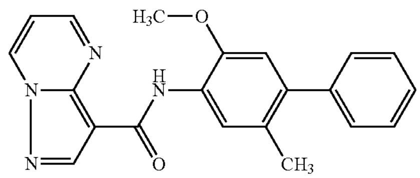 [SMILES: COc1cc(-c2ccccc2)c(C)cc1NC(=O)c1cnn2cccnc12] | Pyrazolo[1,5-alpha]pyrimidine-3-carboxylic acid(5-methoxy-2-methyl-biphenyl-4-yl)-amide | 5.941 | | | 1 |
| 168 | 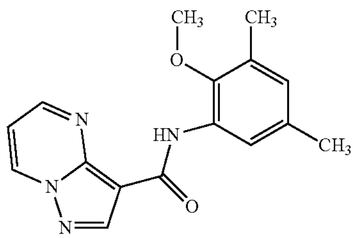 [SMILES: COc1c(C)cc(C)cc1NC(=O)c1cnn2cccnc12] | Pyrazolo[1,5-alpha]pyrimidine-3-carboxylic acid(2-methoxy-3,5-dimethyl-phenyl)-amide | 6.516 | | | 1 |
| 169 | 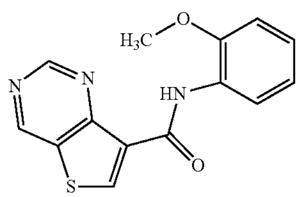 [SMILES: COc1ccccc1NC(=O)c1csc2cncnc12] | Thieno[3,2-d]pyrimidine-7-carboxylic acid(2-methoxy-phenyl)-amide | 6.559 | | | 1 |
| 170 | 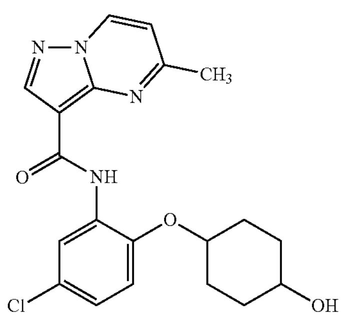 [SMILES: Cc1ccn2ncc(C(=O)Nc3cc(Cl)ccc3OC3CCC(O)CC3)c2n1] | 5-Methyl-pyrazolo[1,5-alpha]pyrimidine-3-carboxylic acid[5-chloro-2-(4-hydroxy-cyclohexyloxy)-phenyl]-amide | 6.561 | | | 9 |
| 171 | 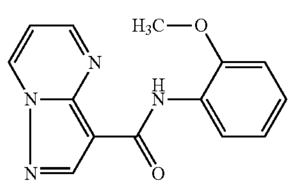 [SMILES: COc1ccccc1NC(=O)c1cnn2cccnc12] | Pyrazolo[1,5-alpha]pyrimidine-3-carboxylic acid(2-methoxy-phenyl)-amide | 7.337 | | | 1 |
| 172 | 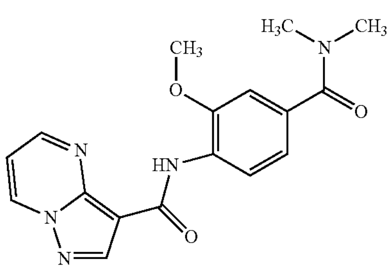 [SMILES: COc1cc(C(=O)N(C)C)ccc1NC(=O)c1cnn2cccnc12] | Pyrazolo[1,5-alpha]pyrimidine-3-carboxylic acid(4-dimethylcarbamoyl-2-methoxy-phenyl)-amide | 7.651 | | | 1 |

TABLE 1-continued

| # | Structure | Chemical Name | IRAK 4 | IRAK 1 | SYK | Ex. |
|---|---|---|---|---|---|---|
| 173 | 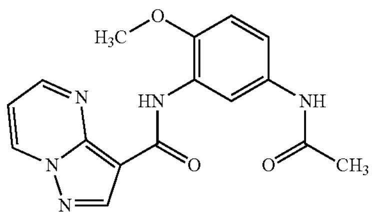 [SMILES: COc1ccc(NC(C)=O)cc1NC(=O)c1cnn2cccnc12] | Pyrazolo[1,5-alpha]pyrimidine-3-carboxylic acid(5-acetylamino-2-methoxy-phenyl)-amide | 7.697 | | | 1 |
| 174 | 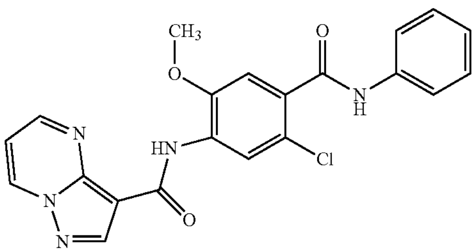 [SMILES: COc1cc(C(=O)Nc2ccccc2)c(Cl)cc1NC(=O)c1cnn2cccnc12] | Pyrazolo[1,5-alpha]pyrimidine-3-carboxylic acid(5-chloro-2-methoxy-4-phenylcarbamoyl-phenyl)-amide | 7.915 | | | 1 |
| 175 | 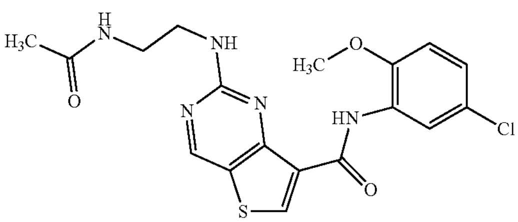 [SMILES: COc1ccc(Cl)cc1NC(=O)c1csc2cnc(NCCNC(C)=O)nc12] | 2-(2-Acetylamino-ethylamino)-thieno[3,2-d]pyrimidine-7-carboxylic acid-(5-chloro-2-methoxy-phenyl)-amide | 8.087 | | | 12 |
| 176 | 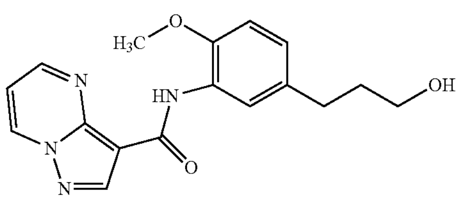 [SMILES: COc1ccc(CCCO)cc1NC(=O)c1cnn2cccnc12] | Pyrazolo[1,5-alpha]pyrimidine-3-carboxylic acid[5-(3-hydroxy-propyl)-2-methoxy-phenyl]-amide | 8.361 | | | 1 |
| 177 | 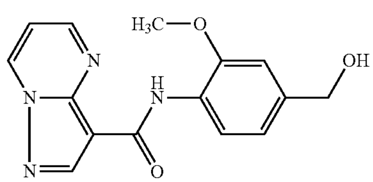 [SMILES: COc1cc(CO)ccc1NC(=O)c1cnn2cccnc12] | Pyrazolo[1,5-alpha]pyrimidine-3-carboxylic acid(4-hydroxymethyl-2-methoxy-phenyl)-amide | 8.673 | | | 5 |
| 178 | 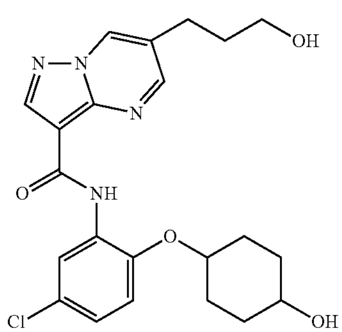 [SMILES: O=C(Nc1cc(Cl)ccc1OC1CCC(O)CC1)c1cnn2cc(CCCO)cnc12] | 6-(3-Hydroxy-propyl)-pyrazolo[1,5-alpha]pyrimidine-3-carboxylic acid[5-chloro-2-(4-hydroxy-cyclohexyloxy)-phenyl]-amide | 9.417 | | | 1 |

TABLE 1-continued

| # | Structure | Chemical Name | IRAK 4 | IRAK 1 | SYK | Ex. |
|---|---|---|---|---|---|---|
| 179 | 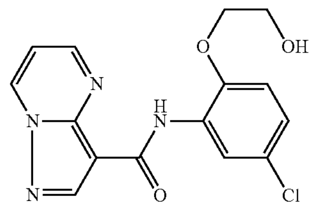 [SMILES: O=C(Nc1cc(Cl)ccc1OCCO)c1cnn2cccnc12] | Pyrazolo[1,5-alpha]pyrimidine-3-carboxylic acid[5-chloro-2-(2-hydroxy-ethoxy)-phenyl]-amide | 5 | | | 5 |
| 180 | 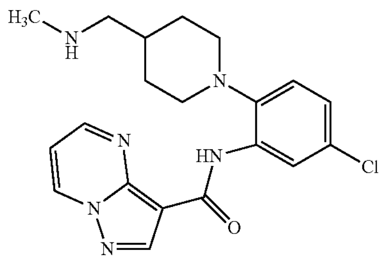 [SMILES: CNCC1CCN(c2ccc(Cl)cc2NC(=O)c2cnn3cccnc23)CC1] | Pyrazolo[1,5-alpha]pyrimidine-3-carboxylic acid[5-chloro-2-(4-methylaminomethyl-piperidin-1-yl)-phenyl]-amide | | | | 8 |
| 181 | 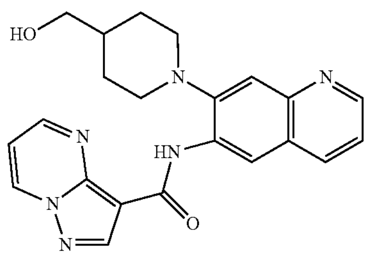 [SMILES: O=C(Nc1cc2cccnc2cc1N1CCC(CO)CC1)c1cnn2cccnc12] | Pyrazolo[1,5-alpha]pyrimidine-3-carboxylic acid[7-(4-hydroxymethyl-piperidin-1-yl)-quinolin-6-yl]-amide | | | | 1 |
| 182 | 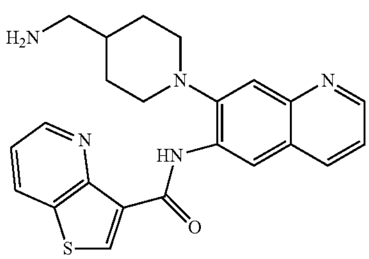 [SMILES: NCC1CCN(c2cc3ncccc3cc2NC(=O)c2csc3cccnc23)CC1] | Thieno[3,2-beta]pyridine-3-carboxylic acid[7-(4-aminomethyl-piperidin-1-yl)-quinolin-6-yl]-amide | | | | 11 |
| 183 | 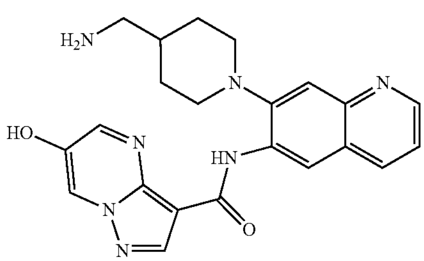 [SMILES: NCC1CCN(c2cc3ncccc3cc2NC(=O)c2cnn3cc(O)cnc23)CC1] | 6-Hydroxy-pyrazolo[1,5-alpha]pyrimidine-3-carboxylic acid[7-(4-aminomethyl-piperidin-1-yl)-quinolin-6-yl]-amide hydrochloride | | | | 14 |
| 184 | 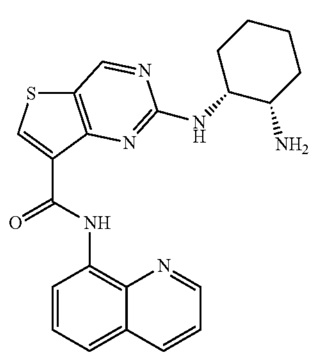 [SMILES: N[C@H]1CCCC[C@H]1Nc1ncc2scc(C(=O)Nc3cccc4cccnc34)c2n1] | 2-((1R,2S)-2-Amino-cyclohexylamino)-thieno[3,2-d]pyrimidine-7-carboxylic acid quinolin-8-ylamide | | | | 22 |

TABLE 1-continued

| # | Structure | Chemical Name | IRAK 4 | IRAK 1 | SYK | Ex. |
|---|-----------|---------------|--------|--------|-----|-----|
| 185 | 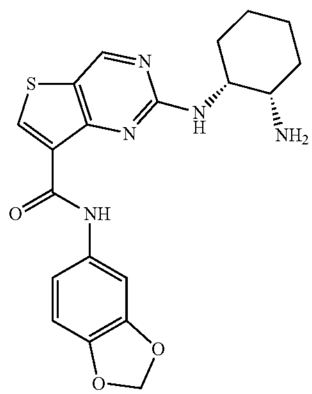 [SMILES: N[C@H]1CCCC[C@H]1Nc1ncc2scc(C(=O)Nc3ccc4c(c3)OCO4)c2n1] | 2-((1R,2S)-2-Amino-cyclohexylamino)-thieno[3,2-d]pyrimidine-7-carboxylic acid benzo[1,3]dioxol-5-ylamide | | | | 23 |
| 186 | 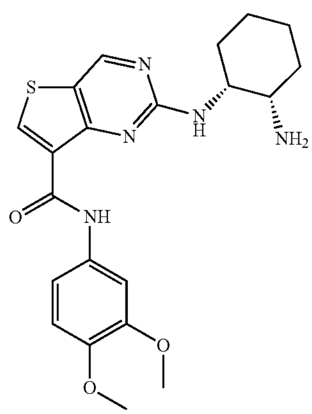 [SMILES: COc1ccc(NC(=O)c2csc3cnc(N[C@@H]4CCCC[C@@H]4N)nc23)cc1OC] | 2-((1R,2S)-2-Amino-cyclohexylamino)-thieno[3,2-d]pyrimidine-7-carboxylic acid (3,4-dimethoxy-phenyl)-amide | | | | 24 |
| 187 | 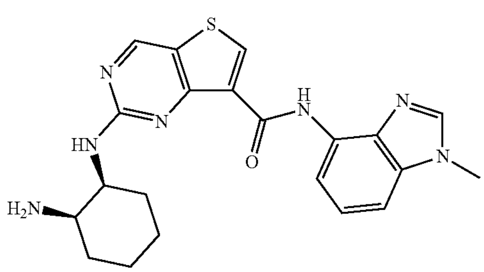 [SMILES: Cn1cnc2c(NC(=O)c3csc4cnc(N[C@H]5CCCC[C@H]5N)nc34)cccc21] | 2-((1S,2R)-2-Amino cyclohexylamino)-thieno[3,2-d]pyrimidine-7-carboxylic acid(1-methyl-1H-benzoimidazol-4-yl)-amide | | | | 25 |
| 188 | 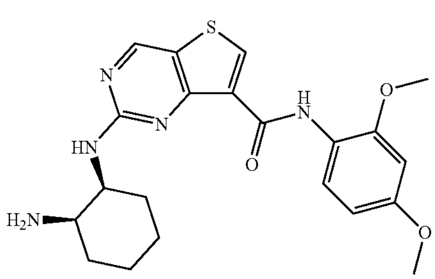 [SMILES: COc1ccc(NC(=O)c2csc3cnc(N[C@H]4CCCC[C@H]4N)nc23)c(OC)c1] | 2-((1S,2R)-2-Amino cyclohexylamino)-thieno[3,2-d]pyrimidine-7-carboxylic acid (2,4-dimethoxy-phenyl)-amide | | | | 26 |

TABLE 1-continued

| # | Structure | Chemical Name | IRAK 4 | IRAK 1 | SYK | Ex. |
|---|---|---|---|---|---|---|
| 189 | 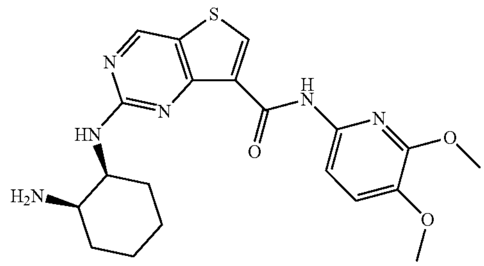 [SMILES: COc1ccc(NC(=O)c2csc3cnc(N[C@H]4CCCC[C@H]4N)nc23)nc1OC] | 2-((1S,2R)-2-Amino-cyclohexylamino)-thieno[3,2-d]pyrimidine-7-carboxylic acid (5,6-dimethoxy-pyridin-2-yl)-amide | | | | 27 |
| 190 | 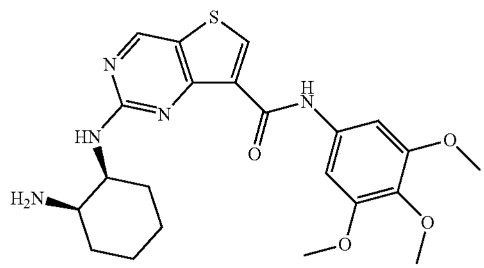 [SMILES: COc1cc(NC(=O)c2csc3cnc(N[C@H]4CCCC[C@H]4N)nc23)cc(OC)c1OC] | 2-((1S,2R)-2-Amino-cyclohexylamino)-thieno[3,2-d]pyrimidine-7-carboxylic acid (3,4,5-trimethoxy-phenyl)-amide | | | | 28 |
| 191 | 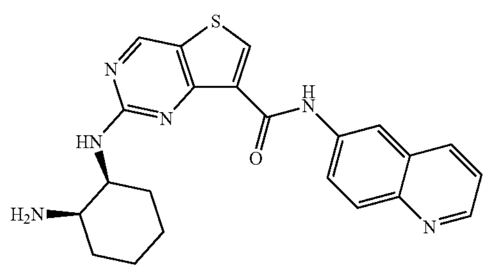 [SMILES: N[C@@H]1CCCC[C@@H]1Nc1ncc2scc(C(=O)Nc3ccc4ncccc4c3)c2n1] | 2-((1S,2R)-2-Amino-cyclohexylamino)-thieno[3,2-d]pyrimidine-7-carboxylic acid quinolin-6-ylamide | | | | 29 |
| 192 | 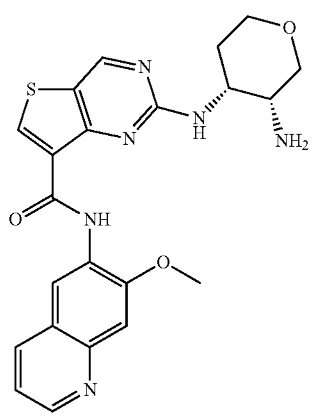 [SMILES: COc1cc2ncccc2cc1NC(=O)c1csc2cnc(N[C@@H]3CCOC[C@@H]3N)nc12] | 2-((3R,4R)-3-Amino-tetrahydro-pyran-4-ylamino)-thieno[3,2-d]pyrimidine-7-carboxylic acid(7-methoxy-quinolin-6-yl)-amide | | | | |

TABLE 1-continued

| # | Structure | Chemical Name | IRAK 4 | IRAK 1 | SYK | Ex. |
|---|---|---|---|---|---|---|
| 193 | 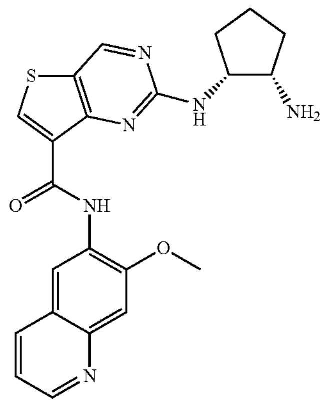 [SMILES: COc1cc2ncccc2cc1NC(=O)c1csc2cnc(N[C@@H]3CCC[C@@H]3N)nc12] | 2-((1R,2S)-2-Amino-cyclopentylamino)-thieno[3,2-d]pyrimidine-7-carboxylic acid(7-methoxy-quinolin-6-yl)-amide | | | | |

Synthesis

Compounds of the present invention can be made by a variety of methods depicted in the illustrative synthetic reaction schemes shown and described below.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1-15; *Rodd's Chemistry of Carbon Compounds*, Elsevier Science Publishers, 1989, Volumes 1-5 and Supplementals; and *Organic Reactions*, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Scheme A below illustrates one synthetic procedure usable to prepare specific compounds of formula I, wherein R is lower alkyl and may be the same or different in each occurrence, and Ar and $R^1$ and $R^2$ are as defined herein.

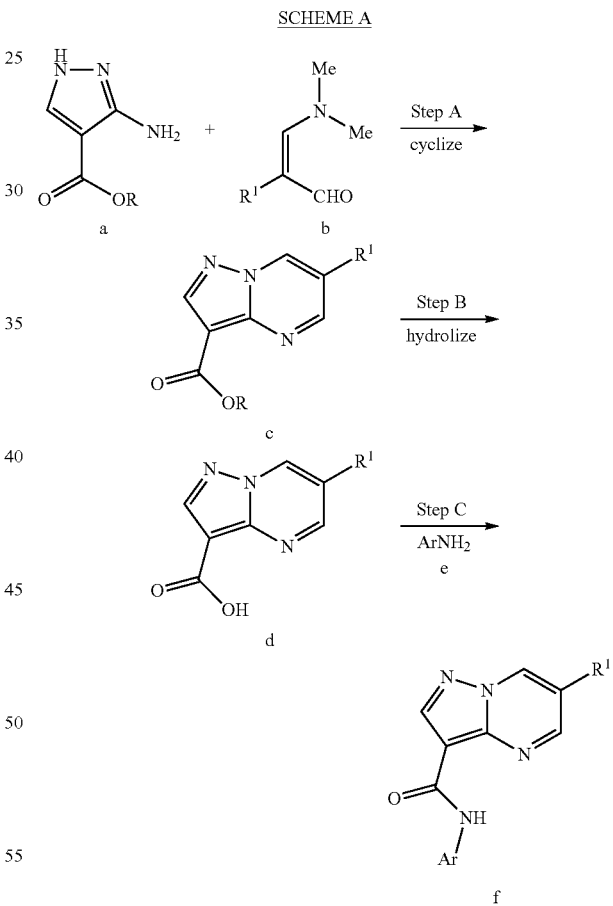

In step A of Scheme A, a cyclization reaction is carried out wherein aminopyrazole ester a is reacted with aminoenal compound b in the presence of base to afford pyrazolopyrimidine ester compound c. The reaction may be carried out under polar aprotic solvent conditions in the presence of sodium hydride. In step B, pyrazolopyrimidine ester c is hydrolyzed to yield the corresponding pyrazolopyrimidine carboxylic acid d. In step C, an amide coupling reaction is carried out by reaction of compound d with aryl amine e to provide pyrazolopyrimidine amide compound f, which is a compound of formula I in accordance with the invention. Amide coupling in step C may be carried out by forming an acid chloride intermediate by treatment of compound d with thionyl chloride, or may be effected using carbodiimides or other amide coupling reagents.

Scheme B below illustrates another procedure for preparation of the compounds of the invention, wherein R is lower alkyl and Ar and $R^1$ and $R^2$ are as defined herein.

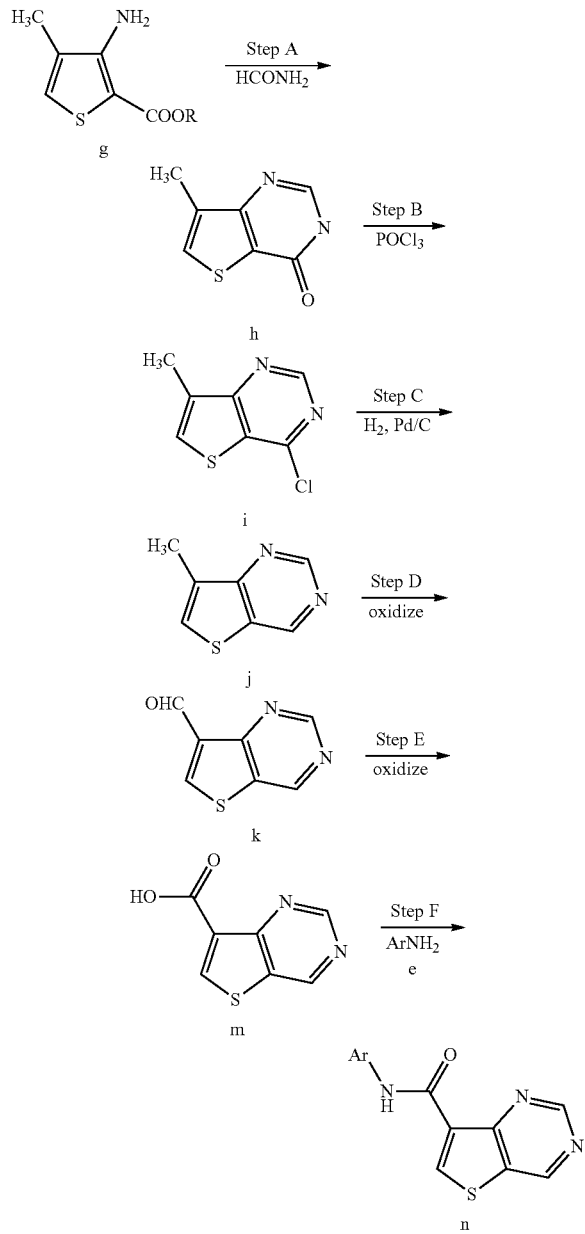

SCHEME B

In step A of Scheme B, a cyclization reaction is carried out wherein thienyl ester g is treated with formamide to afford oxo-thienopyrimidine compound h. Compound h is treated with phosphorus oxychloride or like chlorinating reagent in step B to provide chloro-thienopyrimidine compound i. In step C, chloro-thienopyrimidine compound undergoes reductive dechlorination by hydrogenation in the presence of catalyst to form thienopyrimidine compound j. A first oxidation is carried out in step D wherein the methyl group of thienopyrimidine compound j is oxidized to an aldehyde, thus affording thienopyrimidine carboxaldehyde compound k. In step E a second oxidation reaction is carried out on thienopyrimidine carboxaldehyde compound k give thienopyrimidine carboxylic acid compound m. The oxidation of step E may utilize, for example, sulfamic acid in the presence of sodium chlorite. In step F, compound m is treated with aryl amine e in an amide coupling reaction to afford thienopyrimidine amide compound n, which is a compound of formula II in accordance with the invention. Various amide coupling reagents as described above for Scheme A may be used in this step.

Many variations on the procedure of Scheme A and Scheme B are possible and will suggest themselves to those skilled in the art. Specific details for producing compounds of the invention are described in the Examples section below.

Utility

The compounds of the invention are usable for the treatment of a wide range of inflammatory diseases and conditions such as arthritis, including but not limited to, rheumatoid arthritis, spondyloarthropathies, gouty arthritis, osteoarthritis, systemic lupus erythematosus and juvenile arthritis, osteoarthritis, gouty arthritis and other arthritic conditions. The subject compounds would be useful for the treatment of pulmonary disorders or lung inflammation, including adult respiratory distress syndrome, pulmonary sarcoidosis, asthma, silicosis, bronchospasm and chronic pulmonary inflammatory diseases, including chronic obstructive pulmonary disorder (COPD). The subject compounds may further be useful for treatment of inflammatory bowel disease, multiple sclerosis, diabetes, obesity, allergic disease, psoriasis, asthma, graft rejection, cancer and sepsis.

Administration and Pharmaceutical Composition

The invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the invention will be administered in a therapeutically effective amount by any of the accepted modes of administration for agents that serve similar utilities. Suitable dosage ranges are typically 1-500 mg daily, preferably 1-100 mg daily, and most preferably 1-30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

Compounds of the invention may be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the invention may be formulated for vaginal administration. Pessaries, tampons, creams, gels, pastes, foams or sprays containing in addition to the active ingredient such carriers as are known in the art to be appropriate.

The subject compounds may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylazacycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described below.

EXAMPLES

The following preparations and examples are given to enable those skilled in the art to more clearly understand and to practice the present invention. They should not be considered as limiting the scope of the invention, but merely as being illustrative and representative thereof.

Unless otherwise stated, all temperatures including melting points (i.e., MP) are in degrees celsius (° C.). It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product. The following abbreviations may be used in the Preparations and Examples.

List of Abbreviations

AcOH—Acetic acid
AIBN—2,2'-Azobis(2-methylpropionitrile)
Atm. Atmosphere
$(BOC)_2O$—di-tert-Butyl dicarbonate
DCM—Dichloromethane/Methylene chloride
DIAD—Diisopropyl azodicarboxylate
DIPEA—Diisopropylethylamine
DMAP—4-Dimethylaminopyridine
DME—1,2-Dimethoxyethane
DMF—N,N-Dimethylformamide
DMSO—Dimethyl sulfoxide
$Et_2O$—Diethyl ether
EtOH—Ethanol/Ethyl alcohol
EtOAc—Ethyl acetate
HBTU—O-Benzotriazol-1-yl-N,N,N',N'-tetramethyluronium hexafluorophosphate
HOBT—1-Hydroxybenzotriazole
HPLC—High pressure liquid chromatography
i-PrOH—Isopropanol/isopropyl alcohol
MeOH—Methanol/Methyl alcohol
MW—Microwaves
NBS—N-Bromosuccinimide
NMP—1-Methyl-2-pyrrolidinone
PSI—Pound per square inch
RT—Room temperature
TBDMS—tert-Butyldimethylsilyl
TFA—Trifluoroacetic acid
THF—Tetrahydrofuran
TLC—Thin layer chromatography Preparation 1: Synthesis of 6-Formyl-pyrazolo[1,5-a]pyrimidine-3-carboxylic acid The synthesis of 6-formyl-pyrazolo[1,5-a]pyrimidine-3-carboxylic acid was carried out according to the process shown in Scheme 1.

SCHEME 1

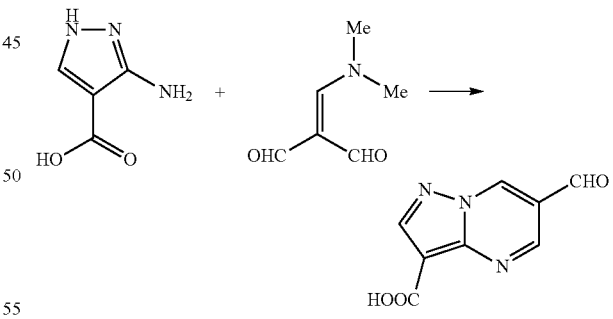

A mixture of 3-aminopyrazole-4-carboxylic acid (100 mg, 0.787 mmol) and 2-dimethylaminomethylene-malonaldehyde (Synthesis 1989 (11), 856-860) (100 mg, 0,787 mmol) in aqueous hydrochloric acid (6 M, 2 mL) was stirred at room temperature for 30 minutes; the resulting mixture was heated at 90° C. for 2 hours and was then stirred at room temperature for 64 hours. The solid formed was collected by filtration, washed twice with water, methanol and diethyl ether, dried in a vacuum oven to give 75 mg (50% yield) of 6-formyl-pyrazolo[1,5-a]pyrimidine-3-carboxylic acid as a light brown solid without further purifications.

Preparation 2: Synthesis of 2-[4-(tert-Butyl-dimethyl-silanyloxy)-cyclohexyloxy]-5-chloro-phenylamine The synthesis of 2-[4-(tert-butyl-dimethyl-silanyloxy)-cyclohexyloxy]-5-chloro-phenylamine was carried out according to the process shown in Scheme 2.

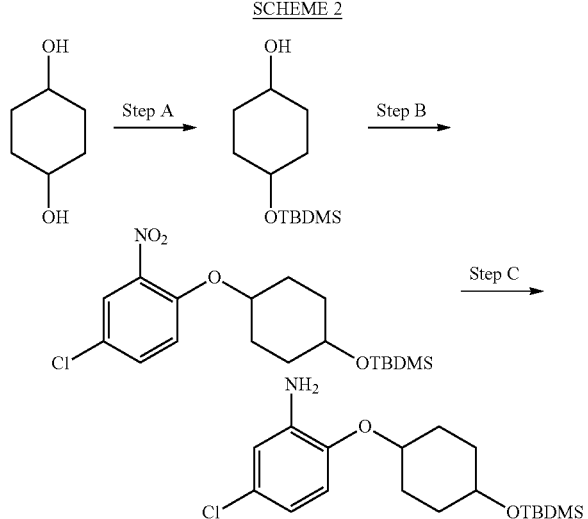

SCHEME 2

Step A: Synthesis of 4-(tert-butyl-dimethyl-silanyloxy)-cyclohexanol

A solution of tert-butyldimethylsilyl chloride (1.5 g, 9.9 mmol) in anhydrous N,N-dimethylformamide (5 mL) was added, dropwise, at 0° C., to a solution of 1,4-cyclohexanediol (1.0 g, 8.6 mmol) and imidazole (1.5 g, 22.0 mmol) in anhydrous tetrahydrofuran (5 mL). After completion of the addition brine was added and the resulting mixture was extracted 3 times with ethyl acetate. The combined organic extracts were washed with water and brine, dried over anhydrous sodium sulfate, filtered and evaporated under reduced pressure. The crude residue was purified on a silica gel plug (hexane/EtOAc, 80/20) to afford 1.3 g (66% yield) of 4-(tert-butyl-dimethyl-silanyloxy)-cyclohexanol as a colorless oil.

Step B: Synthesis of tert-butyl-[4-(4-chloro-2-nitrophenoxy)-cyclohexyloxy]-dimethyl-silane A solution of diisopropylazadicarboxylate (1.65 g, 8.16 mmol) in anhydrous tetrahydrofuran (5 mL) was added, dropwise, at 0° C., to a solution of 4-chloro-2-nitrophenol (0.75 g, 4.32 mmol), 4-(tert-butyl-dimethyl-silanyloxy)-cyclohexanol (1.2 g, 5.21 mmol) and triphenylphosphine (2.27 g, 8.65 mmol) in anhydrous tetrahydrofuran (10 mL). The resulting mixture was stirred at 0° C. for 1 hour and at room temperature overnight. The reaction mixture was then sonicated for 20 minutes at room temperature and for 30 minutes at 40° C. and then was stirred at room temperature for 24 hours. The solvent was evaporated under reduced pressure and the residue was partitioned between ethyl acetate and an aqueous solution of sodium bicarbonate (5%), the organic layer was separated and the aqueous layer was extracted 3 times with ethyl acetate. The combined organic extracts were washed with brine, dried over anhydrous sodium sulfate, filtered and evaporated under reduced pressure. The yellow oily residue was purified on a silica gel plug (hexane/EtOAc, from 99/1 to 90/10) to give a yellow oil. This material was dissolved in a mixture of ethyl acetate and hexane (1/1) and the resulting solution was washed twice with an aqueous solution of sodium hydroxide (3 M) and once with brine, dried over anhydrous sodium sulfate, filtered and evaporated under reduced pressure to give 1.28 g (79% yield) of tert-butyl-[4-(4-chloro-2-nitro-phenoxy)-cyclohexyloxy]-dimethyl-silane as a light yellow oil.

Step C: Synthesis of 2-[4-(tert-butyl-dimethyl-silanyloxy)-cyclohexyloxy]-5-chloro-phenylamine Stannous chloride (3.2 g, 16.98 mmol) was added to a solution of tert-butyl-[4-(4-chloro-2-nitro-phenoxy)-cyclohexyloxy]-dimethyl-silane (1.28 g, 3.32 mmol) in a mixture of ethanol and ethyl acetate (1/1, 40 mL) and the resulting mixture was stirred at room temperature for 24 hours. Ice and an aqueous solution of sodium bicarbonate (5%, 150 mL) were added and the solid formed was filtered, washed with ethyl acetate and discarded. The layers of the filtrate were separated and the aqueous layer was extracted 3 times with ethyl acetate. The combined organic extracts were washed with brine, dried over anhydrous sodium sulfate, filtered through a CELITE™ pad and evaporated under reduced pressure. The yellow oily residue was purified by flash chromatography (EtOAc/hexane, from 5/95 to 80/20) to give 0.5 g (42% yield) of 2-[4-(tert-butyl-dimethyl-silanyloxy)-cyclohexyloxy]-5-chloro-phenylamine as a yellow oil and 803 mg (16% yield) of 4-(2-amino-4-chloro-phenoxy)-cyclohexanol.

Utilizing the appropriate starting materials and the above described procedure the following compounds were prepared:

cis-2-[4-(tert-butyl-dimethyl-silanyloxy)-cyclohexyloxy]-5-chloro-phenylamine;
trans-2-[4-(tert-butyl-dimethyl-silanyloxy)-cyclohexyloxy]-5-chloro-phenylamine;
2-[3-(tert-butyl-dimethyl-silanyloxy)-cyclopentyloxy]-5-chloro-phenylamine;
3-(6-amino-quinolin-7-yloxy)-3-methyl-butan-1-ol (Step B and Step C);
3-(2-amino-4-chloro-phenoxy)-3-methyl-butan-1-ol (Step B and Step C);
5-chloro-2-cyclohexyloxy-phenylamine (Step B and Step C);
5-chloro-2-isopropoxy-phenylamine (Step B and Step C);
5-chloro-2-((S)-2,2-dimethyl-[1,3]dioxolan-4-ylmethoxy)-phenylamine (Step B and Step C);
5-chloro-2-((R)-2,2-dimethyl-[1,3]dioxolan-4-ylmethoxy)-phenylamine (Step B and Step C);
[3-(2-amino-4-chloro-phenoxy)-cyclopentyl]-methanol (Step B and Step C);
3-(2-amino-4-chloro-phenoxy)-cyclohexanol (Step B and Step C);
1-(2-amino-4-chloro-phenyl)-pyrrolidin-3-ol (Step B and Step C);
2-[3-(tert-butyl-dimethyl-silanyloxy)-propoxy]-5-chloro-phenylamine;
2-[2-(tert-butyl-dimethyl-silanyloxy)-ethoxy]-5-chloro-phenylamine;
[4-(2-amino-4-chloro-phenoxy)-cyclohexyl]-carbamic acid tert-butyl ester (Step B and Step C);
5-chloro-2-[2-(2,2-dimethyl-[1,3]dioxolan-4-yl)-ethoxy]-phenylamine (Step B and Step C); and
4-(2-amino-phenoxy)-cyclohexanol (Step B and Step C).

Preparation 3: Synthesis of 4-Amino-3-methoxy-benzoic acid methyl ester

The synthesis of 4-amino-3-methoxy-benzoic acid methyl ester was carried out according to the process shown in Scheme 3.

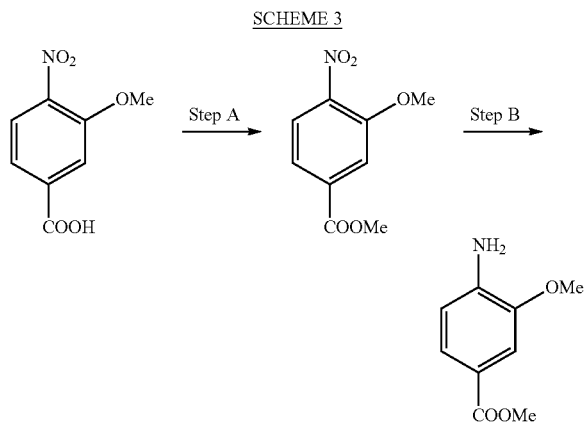

Step A: Synthesis of 3-methoxy-4-nitro-benzoic acid methyl ester

Boron trifluoride diethyl etherate (2 mL, 16.3 mmol) was added to a suspension of 3-methoxy-4-nitrobenzoic acid (1.0 g, 5.07 mmol) in anhydrous methanol (15 mL) and the resulting mixture was heated at reflux for 24 hours. The solvent was evaporated under reduced pressure and the residue was partitioned between water and dichloromethane; the aqueous layer was extracted 3 times with dichloromethane. The combined organic extracts were dried over anhydrous sodium sulfate, filtered and evaporated under reduced pressure. The residue was purified over a silica gel plug (EtOAc/hexane from 40/60 to 50/50) to give 1.09 g of 3-methoxy-4-nitro-benzoic acid methyl ester as a pale yellow solid.

Step B: Synthesis of 4-amino-3-methoxy-benzoic acid methyl ester

Palladium on carbon (10%, catalytic amount) was added to a solution of 3-methoxy-4-nitro-benzoic acid methyl ester (1.08 g, 5.11 mmol) in a mixture of methanol (40 mL) and dichloromethane (a few drops). The resulting mixture was stirred under nitrogen atmosphere (balloon pressure) overnight. The catalyst was filtered off on a CELITE™ pad and the solvent was evaporated to give 0.929 g of 4-amino-3-methoxy-benzoic acid methyl ester as a yellow solid.

Utilizing the above described procedure and the appropriate starting materials 3-methoxy-4-nitro-N-phenyl-benzamide was reduced to give 4-amino-3-methoxy-N-phenyl-benzamide.

Preparation 4: Synthesis of 4-(tert-Butyl-dimethyl-silanyloxymethyl)-2-methoxy-phenylamine The synthesis of 4-(tert-butyl-dimethyl-silanyloxymethyl)-2-methoxy-phenylamine was carried out according to the process shown in Scheme 4.

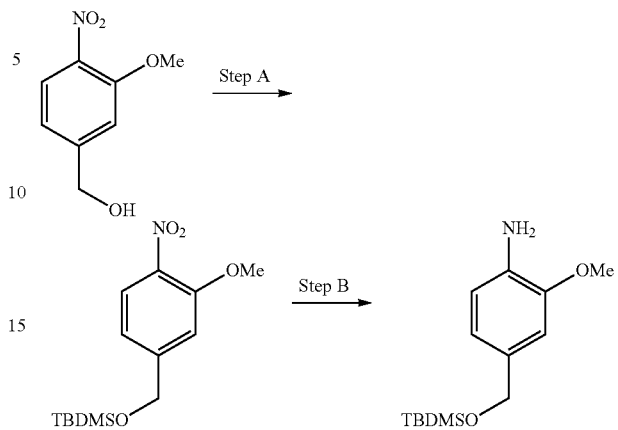

Step A: Synthesis of tert-butyl-(3-methoxy-4-nitrobenzyloxy)-dimethyl-silane tert-Butyldimethylsilyl chloride (0.9 g, 5.97 mmol) was added to a solution of 2-methoxy-4-nitrobenzylalcohol (1.0 g, 5.46 mmol) and imidazole (0.9 g, 13.2 mmol) in anhydrous dichloromethane (15 mL) and the resulting mixture was stirred at room temperature overnight. The reaction mixture was then partitioned between water and dichloromethane, the organic layer was separated and the aqueous layer was extracted 3 times with dichloromethane. The combined organic extracts were dried over anhydrous sodium sulfate, filtered and evaporated under reduced pressure. The crude residue was purified on a silica gel plug (hexane/EtOAc, 80/20) to afford 1.58 g (97% yield) of tert-butyl-(3-methoxy-4-nitro-benzyloxy)-dimethyl-silane as a light yellow solid.

Step B: Synthesis of 4-(tert-butyl-dimethyl-silanyloxymethyl)-2-methoxy-phenylamine tert-Butyl-(3-methoxy-4-nitro-benzyloxy)-dimethyl-silane was reduced by hydrogenation as described in Preparation 3, Step B, to give 4-(tert-butyl-dimethyl-silanyloxymethyl)-2-methoxy-phenylamine.

Preparation 5: Synthesis of 3-Methoxy-biphenyl-4-ylamine

The synthesis of 3-methoxy-biphenyl-4-ylamine was carried out according to the process shown in Scheme 5.

SCHEME 5

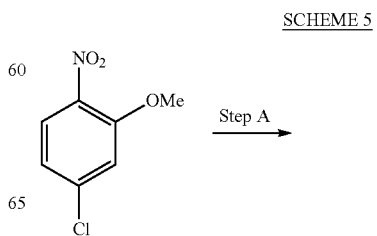

-continued

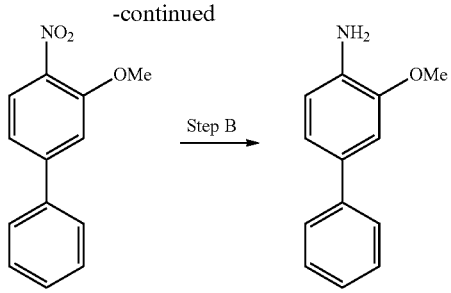

Step A: Synthesis of 3-methoxy-4-nitro-biphenyl

A solution of potassium methoxyde (0.56 g, 7.98 mmol) in anhydrous methanol (5 mL) was added at 0° C. to a mixture of 5-chloro-2-nitroanisole (0.5 g, 2.66 mmol), phenylboronic acid (0.42 g, 3.44 mmol), bis(dibenzylideneacetone)palladium (47 mg, 0.082 mmol), 1,3-bis(2,6-diisopropylphenyl)imidazolium chloride (35 mg, 0.082 mmol) and tetrabutylammonium bromide (86 mg, 0.267 mmol) in anhydrous toluene (20 mL). The reaction mixture was stirred at 60° C. for 24 hours, and then was partitioned between ethyl acetate and water. The organic layer was separated and washed with brine, dried over anhydrous sodium sulfate, filtered and evaporated under reduced pressure. The crude residue was purified on a silica gel plug (EtOAc/hexane, 20/80) to give 0.7 g of 3-methoxy-4-nitro-biphenyl as a yellow oil.

Step B: Synthesis of 3-methoxy-biphenyl-4-ylamine

3-Methoxy-4-nitro-biphenyl was reduced by hydrogenation as described in Preparation 3, Step B, to give 3-methoxy-biphenyl-4-ylamine.

4-Chloro-biphenyl-2-ylamine was synthesized utilizing the appropriate starting materials and the above described procedure, the reduction step was conducted in presence of stannous chloride as described in Preparation 9, Step D.

Preparation 6: Synthesis of 6-Carbamoyl-pyrazolo[1,5-a]pyrimidine-3-carboxylic acid The synthesis of 6-carbamoyl-pyrazolo[1,5-a]pyrimidine-3-carboxylic acid was carried out according to the process shown in Scheme 6.

SCHEME 6

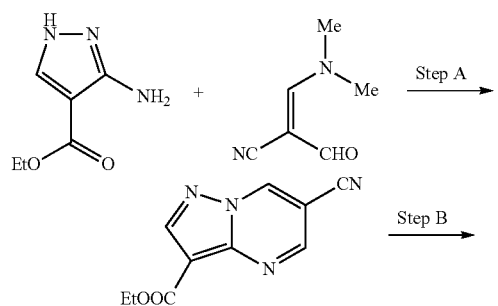

-continued

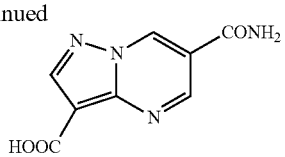

Step A: Synthesis of 6-cyano-pyrazolo[1,5-a]pyrimidine-3-carboxylic acid ethyl ester Sodium hydride (60% dispersion in mineral oil, 0.52 g, 13.0 mmol) was added, at 0° C., to a mixture of 3-amino-1H-pyrazole-4-carboxylic acid ethyl ester (0.9 g, 5.8 mmol) and 3-dimethylamino-2-formyl-acrylonitrile (0.72 g, 5.8 mmol) in anhydrous tetrahydrofuran (30 mL) and the reaction mixture was stirred overnight while warming up to room temperature. Ice-water was added and the resulting mixture was partitioned between water and ethyl acetate; the organic layer was separated and the aqueous layer was extracted 3 times with ethyl acetate. The combined organic extracts were washed with brine, dried over anhydrous sodium sulfate, filtered and evaporated. The yellow crude residue was purified twice on a silica gel plug (EtOAc/hexane) to afford 0.4 g (32% yield) of 6-cyano-pyrazolo[1,5-a]pyrimidine-3-carboxylic acid ethyl ester.

Step B: Synthesis of 6-carbamoyl-pyrazolo[1,5-a]pyrimidine-3-carboxylic acid An aqueous solution of sodium hydroxide (10%, 5 mL) was added to a suspension of 6-cyano-pyrazolo[1,5-a]pyrimidine-3-carboxylic acid ethyl ester (0.35 mg, 1.62 mmol) in ethanol (5 mL) and the reaction mixture was heated at 60° C. for 5 hours. Ice-water was added and the resulting mixture was acidified until pH<1 by addition of an aqueous solution of hydrochloric acid (3 M). The solid which crashed out was collected by filtration, washed twice with water, methanol and diethyl ether, dried under reduced pressure to afford 0.25 g (75% yield) of 6-carbamoyl-pyrazolo[1,5-a]pyrimidine-3-carboxylic acid.

Preparation 7: Synthesis of 2-Methoxy-benzene-1,3-diamine

The synthesis 2-methoxy-benzene-1,3-diamine was carried out according to the process shown in Scheme 7.

SCHEME 7

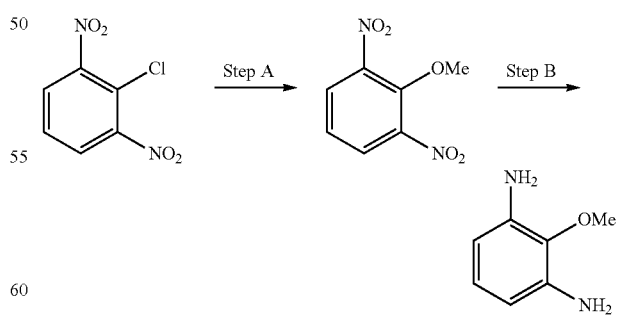

Step A: Synthesis of 2-methoxy-1,3-dinitro-benzene

A solution of sodium methoxyde in methanol (25%, 2.25 mL) was added to a suspension of 2-chloro-2,3-dinitrobenzene (3.26 g) in anhydrous methanol (30 mL) and the resulting mixture was stirred at room temperature overnight. The light yellow solid formed was collected by filtration to give 1.59 g of 2-methoxy-1,3-dinitro-benzene without further purifications.

Step B: Synthesis of 2-methoxy-benzene-1,3-diamine

A mixture of 2-methoxy-1,3-dinitro-benzene (1.49 g) and palladium on carbon (10%, 150 mg) in ethanol (75 mL) was stirred under hydrogen atmosphere (1 atm.) overnight. The catalyst was filtered off on a CELITE™ pad and the filter cake was washed with ethanol. The filtrate was evaporated under reduced pressure to afford 1.1 g of 2-methoxy-benzene-1,3-diamine as a light yellow solid without further purifications.

Preparation 8: Synthesis of 3-(3-Amino-2-piperidin-1-yl-phenylamino)-propan-1-ol The synthesis 3-(3-amino-2-piperidin-1-yl-phenylamino)-propan-1-ol was carried out according to the process shown in Scheme 8.

SCHEME 8

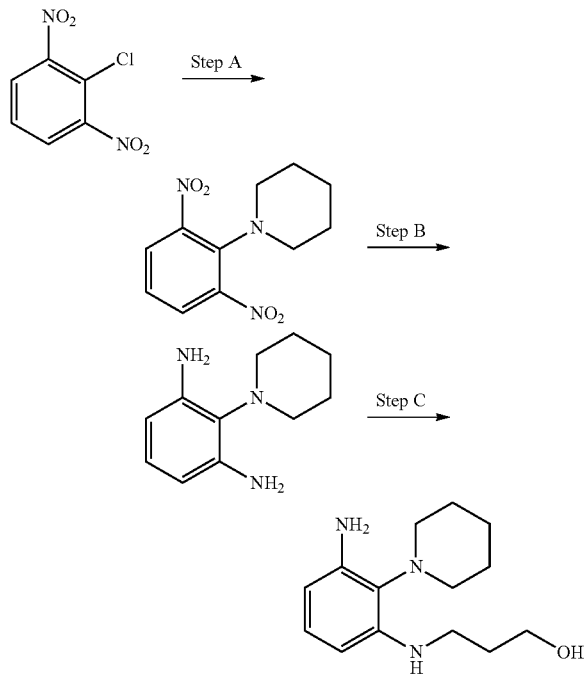

Step A: Synthesis of 1-(2,6-dinitro-phenyl)-piperidine

Piperidine (1.96 mL, 19.75 mmol) was added to a solution of 2-chloro-2,3-dinitrobenzene (2.0 g, 9.87 mmol) in anhydrous dichloromethane (80 mL) and the reaction mixture was stirred for 2 hours. The solvent was evaporated under reduced pressure and the orange solid residue was washed with water to give after drying 2.31 g of 1-(2,6-dinitro-phenyl)-piperidine as a light orange solid without further purifications.

Step B: Synthesis of 2-piperidin-1-yl-benzene-1,3-diamine

A mixture of 1-(2,6-dinitro-phenyl)-piperidine (2.31 g) and palladium on carbon (10%, 230 mg) in ethanol (80 mL) was stirred under hydrogen atmosphere (1 atm.), at room temperature, for 40 hours. The catalyst was filtered off on a CELITE™ pad. The filtrate was evaporated under reduced pressure and the residue was purified by flash chromatography (hexane/EtOAc, 80/20) to afford 1.29 g of 2-piperidin-1-yl-benzene-1,3-diamine as an orange solid without further purifications.

Utilizing the above described procedure and the appropriate starting materials, the following compounds were prepared:

[1-(2,6-diamino-phenyl)-piperidin-4-ylmethyl]-carbamic acid tert-butyl ester; and 5-chloro-2-piperidin-1-yl-phenylamine.

Step C: Synthesis of 3-(3-amino-2-piperidin-1-yl-phenylamino)-propan-1-ol

To a solution of 2-piperidin-1-yl-benzene-1,3-diamine (300 mg, 1.57 mmol) in N,N-dimethylformamide (4 mL) was added sodium hydride (60% suspension in mineral oil, 63 mg, 1.57 mmol) followed by 3-bromo-1-propanol (0.14 mL, 1.57 mmol) and the reaction mixture was stirred at 60° C. overnight. The resulting mixture was then extracted with ethyl acetate (150 mL) and the organic layer was washed twice with water (80 mL) and once with brine (80 mL), dried over anhydrous sodium sulfate, filtered and evaporated under reduced pressure. The crude residue was purified by flash chromatography (hexane/EtOAc, 60/40) to give 22 mg of 3-(3-amino-2-piperidin-1-yl-phenylamino)-propan-1-ol.

2-(3-Amino-2-piperidin-1-yl-phenylamino)-ethanol was prepared utilizing the above described procedure and the appropriate starting materials.

Preparation 9: Synthesis of 4-Amino-2-chloro-5-methoxy-N-phenyl-benzamide

The synthesis 4-amino-2-chloro-5-methoxy-N-phenyl-benzamide was carried out according to the process shown in Scheme 9.

SCHEME 9

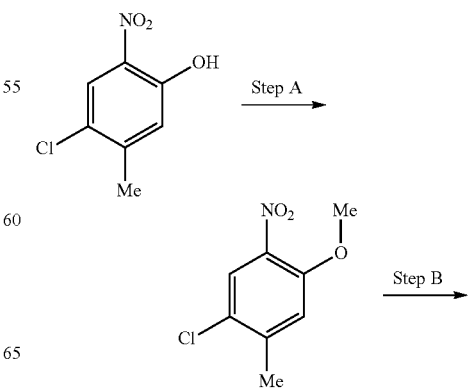

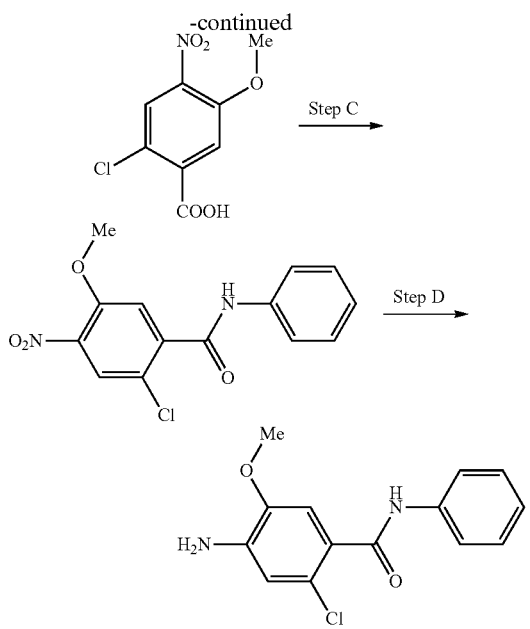

Step A: Synthesis of 1-chloro-4-methoxy-2-methyl-5-nitro-benzene

A solution of (trimethylsilyl)diazomethane (2.0 M in hexane, 13.3 mL, 26.6 mmol) was added to a mixture of 4-chloro-5-methyl-2-nitro-phenol (1.0 g, 5.33 mmol) and diisopropylethylamine (1.04 mL, 6.13 mmol) in a mixture of anhydrous methanol and anhydrous acetonitrile (1/1, 50 mL) and the reaction mixture was stirred for 1 hour. Glacial acetic acid (5 drops) was then added and the resulting mixture was evaporated under reduced pressure. The residue was partitioned between diethyl ether (100 mL) and water (50 mL); the organic layer was separated, dried over anhydrous sodium sulfate, filtered and evaporated under reduced pressure to afford 1.07 g of 1-chloro-4-methoxy-2-methyl-5-nitro-benzene as a light orange solid without further purifications.

2-Methoxy-1,5-dimethyl-3-nitro-benzene was prepared utilizing the above described procedure and the appropriate starting materials.

Step B: Synthesis of 2-chloro-5-methoxy-4-nitro-benzoic acid

A suspension of 1-chloro-4-methoxy-2-methyl-5-nitro-benzene (1.05 g, 5.21 mmol) in a mixture of pyridine and water (1/2, 15 mL) was heated to 97° C. and then potassium permanganate (4.53 g, 28.64 mmol) was added. The reaction mixture was heated at 100° C. for 4 hours; a second aliquot of the mixture pyridine/water (1/1, 10 mL) was added and was followed by potassium permanganate (1 g); the resulting mixture was heated to 100° C. overnight. The hot reaction mixture was filtered through a CELITE™ pad, the filter cake was washed with hot water and the filtrate was acidified, until pH 1, by addition of an aqueous solution of hydrochloric acid (6 M). The resulting mixture was extracted with ethyl acetate; the organic layer was dried over anhydrous sodium sulfate, filtered and evaporated under reduced pressure. The light yellow solid residue (903 mg) was washed twice with a small aliquot of dichloromethane to give 2-chloro-5-methoxy-4-nitro-benzoic acid as an off-white solid without further purifications.

Step C: Synthesis of 2-chloro-5-methoxy-4-nitro-N-phenyl-benzamide

To a solution of 2-chloro-5-methoxy-4-nitro-benzoic acid (200 mg, 0.86 mmol) in acetonitrile (10 mL) was added HBTU (327 mg, 0.86 mmol) followed by aniline (0.08 mL, 0.86 mmol) and diisopropylethylamine (0.56 mL, 3.20 mmol) and the resulting mixture was stirred at room temperature overnight. The reaction mixture was then heated at 60° C. for 24 hours and concentrated under reduced pressure. The residue was partitioned between ethyl acetate (50 mL) and water (50 mL); the organic layer was separated and washed with water (50 mL) and brine (50 mL), dried over anhydrous sodium sulfate, filtered and evaporated under reduced pressure. The crude residue was purified by flash chromatography (hexane/EtOAc, 75/25) to give 182 mg of 2-chloro-5-methoxy-4-nitro-N-phenyl-benzamide as a light yellow solid.

Step D: Synthesis of 4-amino-2-chloro-5-methoxy-N-phenyl-benzamide

Stannous chloride (334 mg, 1.76 mmol) was added to a solution of 2-chloro-5-methoxy-4-nitro-N-phenyl-benzamide (180 mg, 0.59 mmol) in a mixture of ethyl acetate and ethanol (1/1, 8 mL) and the reaction mixture was stirred at room temperature overnight. The resulting mixture was partitioned between ethyl acetate (50 mL) and an aqueous solution of potassium carbonate (5%, 30 mL); the organic layer was separated, washed with brine (30 mL), dried over anhydrous sodium sulfate, filtered and evaporate under reduced pressure. The crude residue was purified by flash chromatography (hexane/EtOAc, 70/30) to give 82 mf of 4-amino-2-chloro-5-methoxy-N-phenyl-benzamide as an off-white solid.

Preparation 10: Synthesis of 4-Amino-3-methoxy-N,N-dimethyl-benzamide

The synthesis of 4-amino-3-methoxy-N,N-dimethyl-benzamide was carried out according to the process shown in Scheme 10.

SCHEME 10

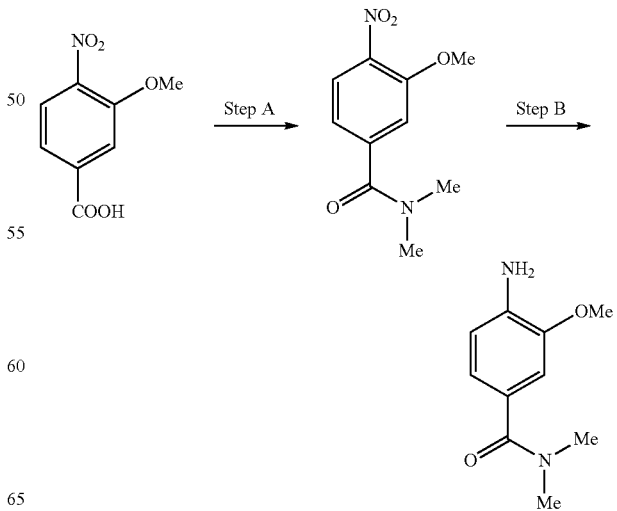

Step A: Synthesis of 3-methoxy-N,N-dimethyl-4-nitro-benzamide

N,N-Dimethylphosphoramidodichloridate (1.8 mL, 15.22 mmol) was added to a solution of 3-methoxy-4-nitrobenzoic acid (300 mg, 1.52 mmol) in anhydrous 1,2-dimethoxyethane (15 mL) and the resulting mixture was heated at reflux for 110 hours ca. The reaction mixture was then cooled and poured into ice-water (50 mL); the resulting mixture was extracted with diethyl ether (50 mL), the organic layer was separated and the aqueous layer was extracted with dichloromethane (50 mL). The combined organic extracts were concentrated under reduced pressure; the residue was dissolved in dichloromethane and washed with water (30 mL), dried over anhydrous sodium sulfate, filtered and evaporated under reduced pressure. The tan liquid residue was purified by flash chromatography (DCM/MeOH, 98/2) to give 185 mg of 3-methoxy-N,N-dimethyl-4-nitro-benzamide as a yellow oil.

Step B: Synthesis of 4-amino-3-methoxy-N,N-dimethyl-benzamide

A mixture of 3-methoxy-N,N-dimethyl-4-nitro-benzamide (185 mg) and palladium on carbon (10%, 20 mg) in ethanol (6 mL) was stirred under hydrogen atmosphere (balloon pressure), at room temperature, overnight. The reaction mixture was filtered on a CELITE™ pad and the filtrate was concentrated under reduced pressure. The crude residue was purified by flash chromatography (DCM/MeOH, 98/2) to afford 60 mg of 4-amino-3-methoxy-N,N-dimethyl-benzamide.

2-Methoxy-1,5-dimethyl-3-nitro-benzene was reduced utilizing the above described procedure to give 2-methoxy-3,5-dimethyl-phenylamine.

Preparation 11: Synthesis of 6-chloro-thieno[2,3-b]pyridine-3-carboxylic acid The synthesis of 6-chloro-thieno[2,3-b]pyridine-3-carboxylic acid was carried out according to the process shown in Scheme 11.

SCHEME 11

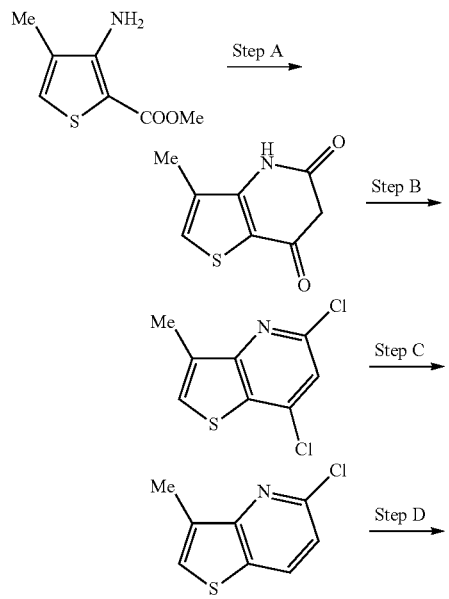

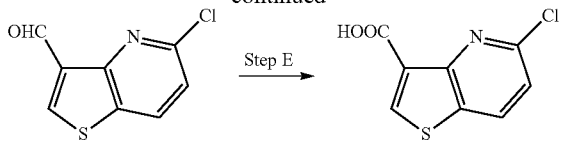

Step A: Synthesis of 3-methyl-4H-thieno[3,2-b]pyridine-5,7-dione

Ethyl malonyl chloride (4.29 g, 28 mmol) was added to a solution of methyl 3-amino-4-methylthiophene-2-carboxylate (4 g, 23 mmol) and triethylamine (4.2 mL, 30 mmol) in dichloromethane (50 mL) and the resulting mixture was stirred for 30 minutes. The reaction mixture was diluted with dichloromethane, washed with water and brine, dried over anhydrous sodium sulfate, filtered and evaporated under reduced pressure. To the oily residue was added a freshly prepared ethanolic solution of sodium ethoxyde (0.5 g in 25 mL of EtOH) and the reaction mixture was heated at reflux overnight. The solvent was evaporated under reduced pressure and water (50 mL) was added to the residue, followed by sodium hydroxide (1.5 g). The resulting mixture was heated at reflux overnight, then was cooled and acidified by addition of an aqueous solution of hydrochloric acid (6 M). The solid formed was collected by filtration, washed with water and dried under reduced pressure to afford 2.0 g of 3-methyl-4H-thieno[3,2-b]pyridine-5,7-dione.

Step B: Synthesis of 5,7-dichloro-3-methyl-thieno[3,2-b]pyridine

A mixture of 3-methyl-4H-thieno[3,2-b]pyridine-5,7-dione (0.8 g) and phosphorus oxychloride (2.5 mL) was heated to 180° C. in a microwave reactor for 15 minutes. The cooled reaction mixture was poured into a mixture of ice-water and ethyl acetate, the organic layer was separated, washed with brine, dried over anhydrous sodium sulfate, filtered and evaporated under reduced pressure. The crude residue was purified by flash chromatography (DCM) to give 5,7-dichloro-3-methyl-thieno[3,2-b]pyridine.

Step C: Synthesis of 5-chloro-3-methyl-thieno[3,2-b]pyridine

A mixture of 5,7-dichloro-3-methyl-thieno[3,2-b]pyridine (1.2 g), palladium hydroxide on carbon (20%, 600 mg) and sodium acetate (1.0 g) in ethyl acetate (50 mL) was shaken in a Parr apparatus under hydrogen atmosphere (55 PSI) for 62 hours. The resulting mixture was filtered on a CELITE™ pad, the filter cake was washed with dichloromethane and the filtrate was evaporated under reduced pressure. The crude residue was purified by flash chromatography (acetone/hexane) to afford 0.4 g of 5-chloro-3-methyl-thieno[3,2-b]pyridine and 0.2 g of 3-methyl-thieno[3,2-b]pyridine.

Step D: Synthesis of 5-chloro-thieno[3,2-b]pyridine-3-carbaldehyde

A mixture of 5-chloro-3-methyl-thieno[3,2-b]pyridine (0.5 g, 2.7 mmol), N-bromosuccinimide (0.48 g, 2.7 mmol) and benzoyl peroxide (50 mg) in carbon tetrachloride (3 mL) was heated at 100° C. in a microwave reactor for 15 minutes. The supernatant was decanted and evaporated under reduced pressure, the residue was suspended in toluene (3 mL) and pyridine-N-oxide (0.5 g) was added, followed by sodium bicarbonate (0.4 g) and diisopropylethylamine (3 drops). The reaction mixture was heated at 150° C. in a microwave reactor for 5 minutes, was then diluted with ethyl acetate, washed with water and brine, dried over anhydrous sodium sulfate, filtered and evaporated under reduced pressure. The crude residue was purified by flash chromatography (EtOAc/hexane, 20/80) to give 150 mg of 5-chloro-thieno[3,2-b]pyridine-3-carbaldehyde.

Step E: Synthesis of 6-chloro-thieno[2,3-b]pyridine-3-carboxylic acid

Sulfamic acid (150 mg) was added to a solution of 5-chloro-thieno[3,2-b]pyridine-3-carbaldehyde (150 mg, 0.76 mmol) in a mixture of tetrahydrofuran, tert-butanol and water (1/1/1, 6 mL). A solution of sodium chlorite (100 mg) and potassium dihydrogen phosphate (300 mg) in water (2 mL) was then added and the resulting mixture was stirred for 30 minutes. The reaction mixture was then concentrated under reduced pressure to the remove the volatiles, the solid formed was collected by filtration, washed with water and ethyl acetate, dried in a vacuum oven to give 70 mg of 6-chloro-thieno[2,3-b]pyridine-3-carboxylic acid without further purifications.

Preparation 12: Synthesis of thieno[3,2-d]pyrimidine-7-carboxylic acid

The synthesis of thieno[3,2-d]pyrimidine-7-carboxylic acid was carried out according to the process shown in Scheme 12.

SCHEME 12

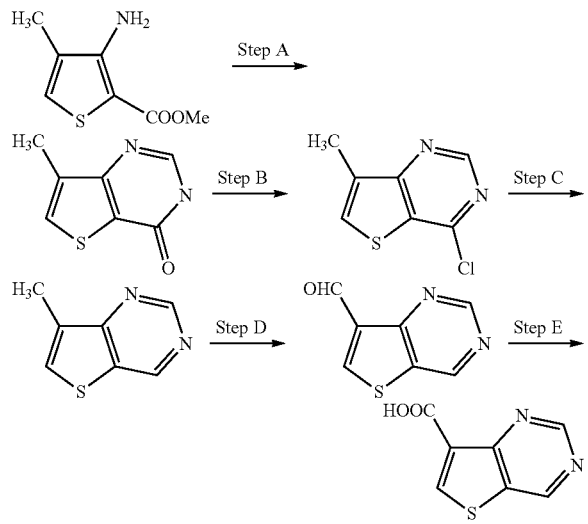

Step A: Synthesis of 7-methyl-3H-thieno[3,2-d]pyrimidin-4-one

A mixture of 3-amino-4-methyl-thiophene-2-carboxylic acid methyl ester (3.0 g) and formamide (50 mL) was heated to 150° C. overnight. The reaction mixture was then cooled and diluted with water. The solid formed was collected by filtration, washed with water and dried under reduced pressure to give 2.1 g of 7-methyl-3H-thieno[3,2-d]pyrimidin-4-one without further purifications.

Step B: Synthesis of 4-chloro-7-methyl-thieno[3,2-d]pyrimidine

A suspension of 7-methyl-3H-thieno[3,2-d]pyrimidin-4-one (2.1 g) in phosphorus oxychloride (10 mL) was heated at 100° C. for 1 hour. The reaction mixture was then cooled and poured into a mixture of ice-water and ethyl acetate. The organic layer was separated, washed with brine, dried over anhydrous sodium sulfate, filtered and evaporated under reduced pressure. The crude residue was purified by flash chromatography (DCM) to afford 2.0 g of 4-chloro-7-methyl-thieno[3,2-d]pyrimidine.

Step C: Synthesis of 7-methyl-thieno[3,2-d]pyrimidine

A mixture of 4-chloro-7-methyl-thieno[3,2-d]pyrimidine (2 g), palladium hydroxide on carbon (20%, 1 g) and sodium acetate (2 g) in a mixture of ethyl acetate and isopropanol (5/1, 30 mL) was shaken in a Parr apparatus under hydrogen atmosphere (50 PSI) overnight. The resulting mixture was filtered on a CELITE™ pad, the filter cake was washed with dichloromethane and the filtrate was evaporated under reduced pressure. The crude residue was purified by flash chromatography (acetone/DCM, 3/97) to afford 1 g of 7-methyl-thieno[3,2-d]pyrimidine.

Step D: Synthesis of thieno[3,2-d]pyrimidine-7-carbaldehyde

A mixture of 7-methyl-thieno[3,2-d]pyrimidine (1.2 g) and N-bromosuccinimide (2.9 g) in carbon tetrachloride (50 mL) was heated at reflux for 1 hour. The reaction mixture was then cooled, the solid formed was filtered off and the filtrate was concentrated under reduced pressure. The residue was suspended in water (10 mL) and the suspension was heated at reflux for 1 hour. The resulting mixture was basified by addition of a saturated aqueous solution of sodium bicarbonate and extracted twice with dichloromethane (100 mL). The combined organic layers were washed with brine, dried over anhydrous sodium sulfate, filtered and evaporated under reduced pressure. The solid residue was triturated with ethyl acetate and hexane and then collected by filtration to give 0.8 g of thieno[3,2-d]pyrimidine-7-carbaldehyde.

Step E: Synthesis of thieno[3,2-d]pyrimidine-7-carboxylic acid

Thieno[3,2-d]pyrimidine-7-carbaldehyde was oxidized using the procedure described in Preparation 11, Step E, to give the corresponding carboxylic acid.

Preparation 13: Synthesis of 2-Chloro-thieno[3,2-d]pyrimidine-7-carboxylic acid

The synthesis of 2-chloro-thieno[3,2-d]pyrimidine-7-carboxylic acid was carried out according to the process shown in Scheme 13.

SCHEME 13

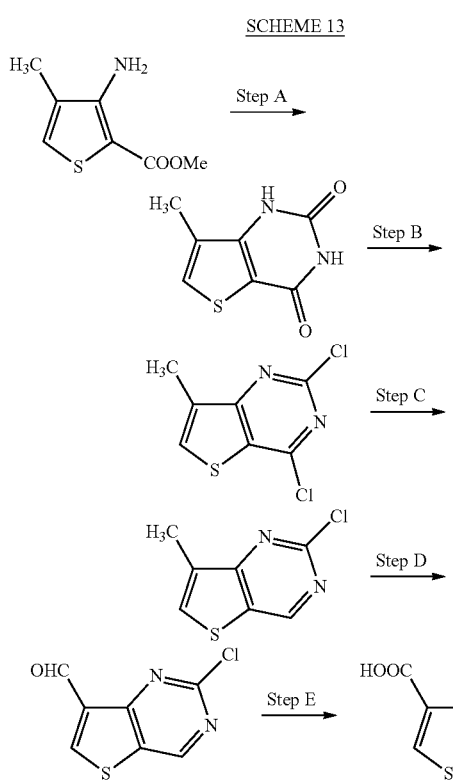

Step A: Synthesis of 7-methyl-1H-thieno[3,2-d]pyrimidine-2,4-dione

Trichloroacetyl isocyanate (2.0 g) was added to a solution of methyl 3-amino-4-methylthiophene-2-carboxylate (1.3 g) in acetonitrile (10 mL) and the resulting mixture was stirred for 15 minutes. The solid, which crashed out, was collected by filtration and suspended in methanol (5 mL), a solution of ammonia in methanol (7 M, 5 mL) was then added and the resulting mixture was heated at 70° C. for 15 minutes. The reaction mixture was cooled, the solid formed was collected by filtration, dried under reduced pressure to give 0.8 g of 7-methyl-1H-thieno[3,2-d]pyrimidine-2,4-dione.

Step B: Synthesis of 2,4-dichloro-7-methyl-thieno[3,2-d]pyrimidine

A mixture of 7-methyl-1H-thieno[3,2-d]pyrimidine-2,4-dione (2.8 g) and phosphorus oxychloride (5 mL) was split in 2 portions and both portions were heated at 180° C. in a microwave reactor for 15 minutes. The combined reaction mixtures were cooled and partitioned between ice-water and ethyl acetate. The organic layer was separated, washed with water and brine, dried over anhydrous sodium sulfate, filtered and evaporated under reduced pressure. The crude residue was triturated with hexane and the solid was collected by filtration to afford 2.5 g of 2,4-dichloro-7-methyl-thieno[3,2-d]pyrimidine.

Step C: Synthesis of 2-chloro-7-methyl-thieno[3,2-d]pyrimidine

A mixture of 2,4-dichloro-7-methyl-thieno[3,2-d]pyrimidine (2.5 g), palladium hydroxide on carbon (20%, 0.5 g) and sodium acetate (2.0 g) in a mixture of ethyl acetate (40 mL) and isopropyl alcohol (5 mL) was shaken in a Parr apparatus under hydrogen atmosphere (50 PSI) overnight. The reaction mixture was filtered on a CELITE™ pad and the filtrate was evaporated under reduced pressure. The crude residue was purified by flash chromatography (DCM) to give 1.8 g of 2-chloro-7-methyl-thieno[3,2-d]pyrimidine.

Step D: Synthesis of 2-chloro-thieno[3,2-d]pyrimidine-7-carbaldehyde

A mixture of 2-chloro-7-methyl-thieno[3,2-d]pyrimidine (1.8 g), N-bromosuccinimide (1.8 g), 2,2'-azobis(2-methylpropionitrile) (0.1 g) in carbon tetrachloride (50 mL) was heated at reflux for 1 hour. The resulting mixture was cooled, the solid was filtered off and the filtrate was evaporated under reduced pressure. The residue was dissolved in acetonitrile (20 mL) and diisopropylethylamine (2.0 mL) was added, followed by pyridine-N-oxide (3 g) and the resulting mixture was heated at 100° C. for 30 minutes. The reaction mixture was cooled, diluted with ethyl acetate, washed with water and brine, dried over anhydrous sodium sulfate, filtered and evaporated under reduced pressure. The crude residue was purified by flash chromatography (hexane/EtOAc) to afford 0.25 g of 2-chloro-thieno[3,2-d]pyrimidine-7-carbaldehyde and 1 g of 2-chloro-7-methyl-thieno[3,2-d]pyrimidine starting material.

Step E: Synthesis of 2-chloro-thieno[3,2-d]pyrimidine-7-carboxylic acid

To a solution of 2-chloro-thieno[3,2-d]pyrimidine-7-carbaldehyde (0.6 g) in a mixture of tert-butanol/tertrahydrofuran/water (1/1/1, 45 mL) was added sulfamic acid (1.0 g) followed by a solution of sodium chlorite (0.9 g) and potassium dihydrogen phosphate (3.0 g) in water (10 mL) and the resulting mixture was stirred for 1 hour. The reaction mixture was then diluted with ethyl acetate; the organic layer was separated and washed with brine, dried over anhydrous sodium sulfate, filtered and evaporated under reduced pressure. The residue was triturated with ethyl acetate and the solid was collected by filtration to give 0.5 g of 2-chloro-thieno[3,2-d]pyrimidine-7-carboxylic acid.

Preparation 14: Synthesis of 5-Methyl-pyrazolo[1,5-a]pyrimidine-3-carboxylic acid The synthesis of 5-methyl-pyrazolo[1,5-a]pyrimidine-3-carboxylic acid was carried out according to the process shown in Scheme 14.

SCHEME 14

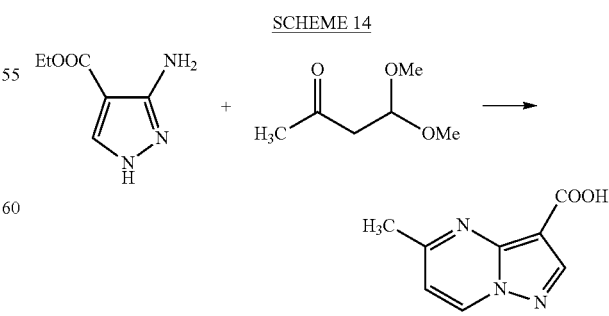

A mixture of ethyl 3-amino-4-pyrazolecarboxylate (1.0 g, 6.4 mmol) and acetylacetaldehyde dimethyl acetal (1.7 g, 13 mmol) in toluene (5 mL) was heated at reflux overnight. The resulting mixture was cooled and purified by flash chromatography (hexane/ethyl acetate) to obtain 0.7 g of the ester. The ester was then dissolved in a mixture of methanol and water (1/1, 10 mL) and sodium hydroxide (0.7 g) and heated at reflux overnight. The reaction mixture was cooled, neutralized with an aqueous solution of hydrochloric acid (6 M) to pH 7 and extracted with ethyl acetate. The organic layer was separated, washed with brine, dried over anhydrous sodium sulfate, filtered and evaporated under reduced pressure to afford 5-methyl-pyrazolo[1,5-a]pyrimidine-3-carboxylic acid without further purifications.

Preparation 15: Synthesis of 7-Methyl-pyrazolo[1,5-a]pyrimidine-3-carboxylic acid The synthesis of 7-methyl-pyrazolo[1,5-a]pyrimidine-3-carboxylic acid was carried out according to the process shown in Scheme 15.

SCHEME 15

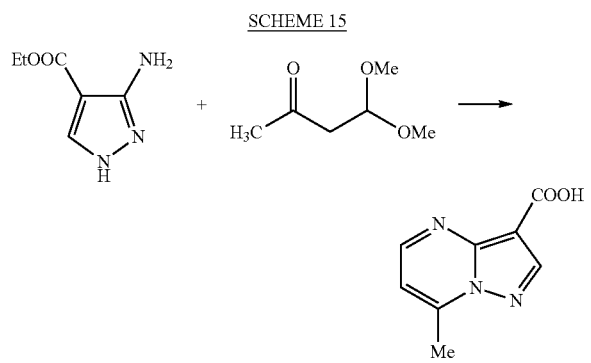

A mixture of ethyl 3-amino-4-pyrazolecarboxylate (250 mg), acetylacetaldehyde dimethyl acetale (200 μL) and concentrated hydrochloric acid (0.5 mL) was heated at 60° C. for 15 minutes. The resulting mixture was cooled and the solid which crashed out was collected by filtration, washed with ethyl acetate and dried in a vacuum oven to give 200 mg of 7-methyl-pyrazolo[1,5-a]pyrimidine-3-carboxylic acid.

Preparation 16: Synthesis of (E)-3-(4-Methoxy-3-nitro-phenyl)-acrylic acid methyl ester The synthesis of (E)-3-(4-methoxy-3-nitro-phenyl)-acrylic acid methyl ester was carried out according to the process shown in Scheme 16.

SCHEME 16

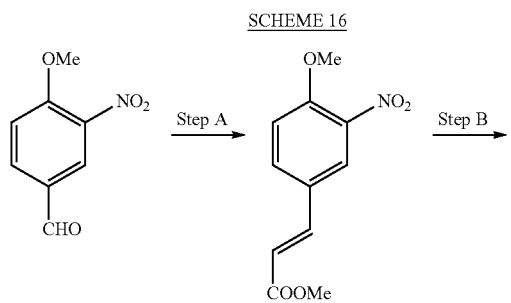

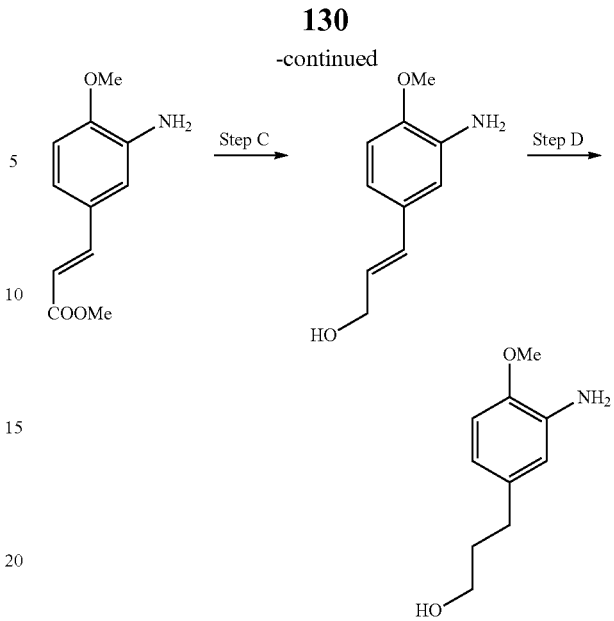

Step A: Synthesis of (E)-3-(4-methoxy-3-nitro-phenyl)-acrylic acid methyl ester

A mixture of 4-methoxy-3-nitrobenzaldehyde (1.5 g, 8.2 mmol) and methyl (triphenylphosphoranylidene)acetate (4.4 g, 13 mmol) in tetrahydrofuran (30 mL) was heated at reflux overnight. The reaction mixture was cooled and evaporated under reduced pressure; the crude residue was purified by flash chromatography (acetone/hexane, 20/80) to afford 0.5 g of (E)-3-(4-methoxy-3-nitro-phenyl)-acrylic acid methyl ester.

Step B: Synthesis of (E)-3-(3-amino-4-methoxy-phenyl)-acrylic acid methyl ester

To a solution of (E)-3-(4-methoxy-3-nitro-phenyl)-acrylic acid methyl ester (0.5 g) in dichloromethane (5 mL) was added zinc dust (2 g), followed by acetic acid (1 mL) and the resulting mixture was stirred at room temperature for 30 minutes. The solid was filtered off and washed with dichloromethane. The filtrate was evaporated under reduced pressure and the residue was purified by flash chromatography (DCM/acetone, 95/5) to give (E)-3-(3-amino-4-methoxy-phenyl)-acrylic acid methyl ester.

Step C: Synthesis of (E)-3-(3-amino-4-methoxy-phenyl)-prop-2-en-1-ol

A solution of lithium aluminum hydride (1 M in THF, 4 mL) was added at 0° C. to a solution of (E)-3-(3-amino-4-methoxy-phenyl)-acrylic acid methyl ester (400 mg) in tetrahydrofuran (10 mL) and the resulting mixture was stirred for 15 minutes. The reaction mixture was then quenched by addition of a saturated aqueous solution of ammonium chloride, the resulting mixture was filtered and the filter cake was washed with ethyl acetate. The filtrate was separated and the organic layer was dried over anhydrous sodium sulfate, filtered and evaporated under reduced pressure to afford 90 mg of (E)-3-(3-amino-4-methoxy-phenyl)-prop-2-en-1-ol without further purifications.

Step D: Synthesis of 3-(3-amino-4-methoxy-phenyl)-propan-1-ol

A mixture of (E)-3-(3-amino-4-methoxy-phenyl)-prop-2-en-1-ol (250 mg) and palladium hydroxide on carbon (20%, 50 mg) in ethyl acetate (10 mL) was stirred under hydrogen atmosphere (balloon pressure) overnight. The resulting mixture was filtered over a CELITE™ pad, the filter cake was washed with dichloromethane and the filtrate was evaporated under reduced pressure to give 100 mg of 3-(3-amino-4-methoxy-phenyl)-propan-1-ol without further purifications.

Preparation 17: Synthesis of 5-Ethyl-2-methoxy-phenylamine

The synthesis of 5-ethyl-2-methoxy-phenylamine was carried out according to the process shown in Scheme 17.

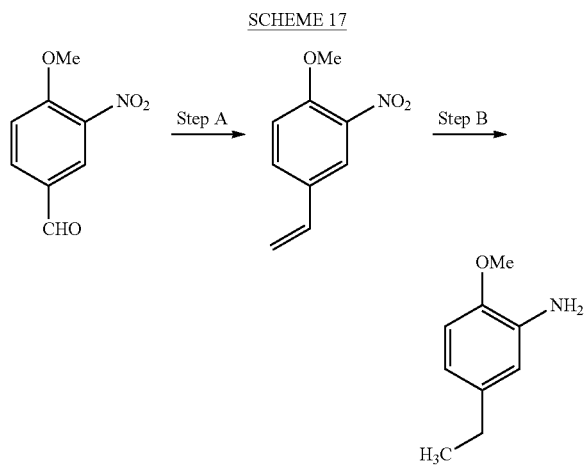

Step A: Synthesis of 1-methoxy-2-nitro-4-vinyl-benzene

To a solution of 4-methoxy-3-nitrobenzaldehyde (0.6 g) in tetrahydrofuran (10 mL) was added sodium hydride (50% suspension in mineral oil, 0.5 g) followed by methyltriphenylphosphonium bromide (1.8 g) and the resulting mixture was heated at reflux for 1 hour. The reaction mixture was cooled, diluted with water, extracted with brine, dried over anhydrous sodium sulfate, filtered and evaporated under reduced pressure. The crude residue was purified by flash chromatography (hexane/EtOAc, 90/10) to give 150 mg of 1-methoxy-2-nitro-4-vinyl-benzene.

Step B: Synthesis of 5-ethyl-2-methoxy-phenylamine

A mixture of 1-methoxy-2-nitro-4-vinyl-benzene (150 mg) and palladium on carbon (10%, 25 mg) in ethyl acetate (10 mL) was stirred under hydrogen atmosphere (balloon pressure) at room temperature overnight. The reaction mixture was filtered on a CELITE™ pad and the filtrate was evaporated to give 5-ethyl-2-methoxy-phenylamine without further purifications.

Preparation 18: Synthesis of 2-Methoxy-5-vinyl-phenylamine

The synthesis of 2-methoxy-5-vinyl-phenylamine was carried out according to the process shown in Scheme 18.

SCHEME 18

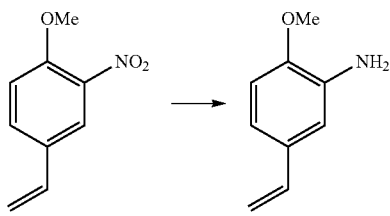

To a solution of 1-methoxy-2-nitro-4-vinyl-benzene (100 mg) in dichloromethane (2 mL) was added zinc dust (large excess), followed by acetic acid (0.5 mL) and the resulting mixture was stirred at room temperature for 30 minutes. The solid was filtered, washed with dichloromethane and discarded. The filtrate was evaporated under reduced pressure and the residue was purified by flash chromatography (hexane/EtOAc, 90/10) to give 50 mg of 2-methoxy-5-vinyl-phenylamine.

Preparation 19: Synthesis of [1-(2-Amino-4-chloro-phenyl)-piperidin-4-yl]-methanol The synthesis of [1-(2-amino-4-chloro-phenyl)-piperidin-4-yl]-methanol was carried out according to the process shown in Scheme 19.

SCHEME 19

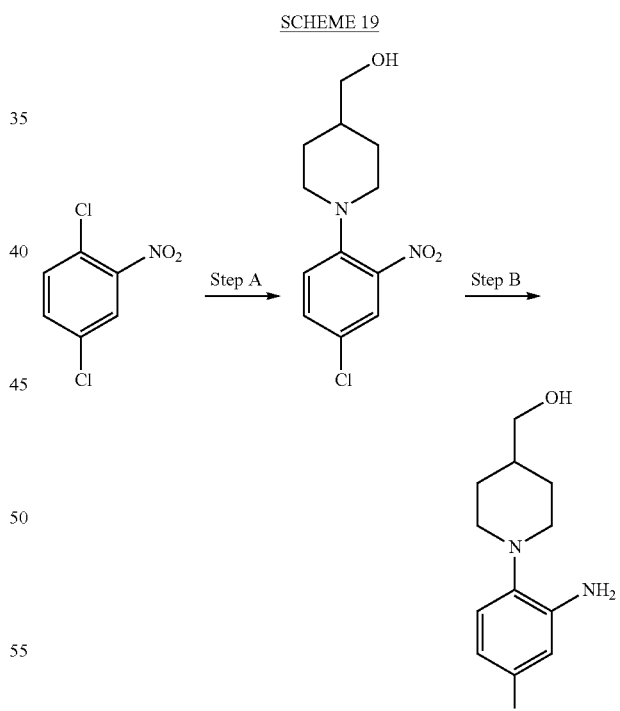

Step A: Synthesis of [1-(4-chloro-2-nitro-phenyl)-piperidin-4-yl]-methanol

A mixture of 2,5-dichloronitrobenzene (0.7 g), 4-piperidinemethanol (0.6 g) and potassium carbonate (1 g) in N,N-dimethylformamide (10 mL) was heated at 80° C. for 1 hour. The reaction mixture was cooled, diluted with water and extracted with ethyl acetate. The combined organic extracts were washed with water and brine, dried over anhydrous sodium sulfate, filtered and evaporated under reduced pressure. The crude residue was purified by flash chromatography (DCM/Acetone, 90/10) to afford 0.8 g of [1-(4-chloro-2-nitro-phenyl)-piperidin-4-yl]-methanol.

Step B: Synthesis of [1-(2-amino-4-chloro-phenyl)-piperidin-4-yl]-methanol

[1-(4-Chloro-2-nitro-phenyl)-piperidin-4-yl]-methanol (200 mg) was reduced following the procedure described in Preparation 16, Step B, to afford 90 mg of [1-(2-amino-4-chloro-phenyl)-piperidin-4-yl]-methanol.

Utilizing the above described procedure and the appropriate starting materials, the following compounds were prepared:
[1-(2-amino-4-chloro-phenyl)-piperidin-4-ylmethyl]-carbamic acid tert-butyl ester;
1-(2-amino-4-chloro-phenyl)-piperidine-4-carboxylic acid amide;
[1-(2-amino-4-chloro-phenyl)-piperidin-3-yl]-methanol;
2-azepan-1-yl-5-chloro-phenylamine;
(3-amino-4-piperidin-1-yl-phenyl)-methanol;
5-chloro-2-pyrrolidin-1-yl-phenylamine;
[1-(2-amino-4-chloro-phenyl)-pyrrolidin-3-yl]-methanol;
5-chloro-2-(4-methyl-piperazin-1-yl)-phenylamine;
4-(2-amino-4-chloro-phenoxy)-piperidine-1-carboxylic acid tert-butyl ester;
2-[4-(tert-butyl-dimethyl-silanyloxymethyl)-piperidin-1-yl]-5-chloro-phenylamine;
5-chloro-2-piperidin-1-yl-phenylamine;
2-[(2-amino-4-chloro-phenyl)-methyl-amino]-ethanol;
1-(2-amino-4-chloro-phenyl)-piperidin-4-ol;
1-(2-amino-4-chloro-phenyl)-piperidin-3-ol;
[1-(2-amino-4-chloro-phenyl)-piperidin-2-yl]-methanol;
3-[(2-amino-4-chloro-phenyl)-methyl-amino]-propan-1-ol; and
1-[1-(2-amino-4-chloro-phenyl)-pyrrolidin-3-yl]-ethanol.

Preparation 20: Synthesis of 3-(2-Amino-4-chloro-phenoxy)-cyclopentanecarboxylic acid ethyl ester The synthesis of 3-(2-amino-4-chloro-phenoxy)-cyclopentanecarboxylic acid ethyl ester was carried out according to the process shown in Scheme 20.

Step A: Synthesis of 3-(4-chloro-2-nitro-phenoxy)-cyclopentanecarboxylic acid ethyl ester A mixture of 1,4-dichloro-2-nitro-benzene (190 mg, 1.1 mmol), 3-hydroxy-cyclopentanecarboxylic acid ethyl ester (180 mg, 1.14 mmol), triphenylphosphine (448 mg) and DIAD (345 mg) in dichloromethane (10 mL) was stirred at room temperature overnight. The reaction mixture was then evaporated under reduced pressure and the crude residue was purified by flash chromatography to afford 280 mg of 3-(4-chloro-2-nitro-phenoxy)-cyclopentanecarboxylic acid ethyl ester.

Step B: Synthesis of 3-(2-amino-4-chloro-phenoxy)-cyclopentanecarboxylic acid ethyl ester To a solution of 3-(4-chloro-2-nitro-phenoxy)-cyclopentanecarboxylic acid ethyl ester (280 mg) in dichloromethane (20 mL) was added zinc dust (2 g) followed by glacial acetic acid (1 mL) and the resulting mixture was stirred at room temperature for 20 minutes. The solid was filtered, washed with dichloromethane and discarded. The filtrate was evaporated under reduced pressure and the residue was purified by flash chromatography (hexane/acetone, 80/20) to afford 200 mg of 3-(2-amino-4-chloro-phenoxy)-cyclopentanecarboxylic acid ethyl ester.

1-Methoxy-naphthalen-2-ylamine was prepared utilizing the above described procedure and the appropriate starting materials.

Preparation 21: Synthesis of Pyrrolo[2,1-f][1,2,4]triazine-7-carboxylic acid

The synthesis of pyrrolo[2,1-J][1,2,4]triazine-7-carboxylic acid was carried out according to the process shown in Scheme 21.

SCHEME 20

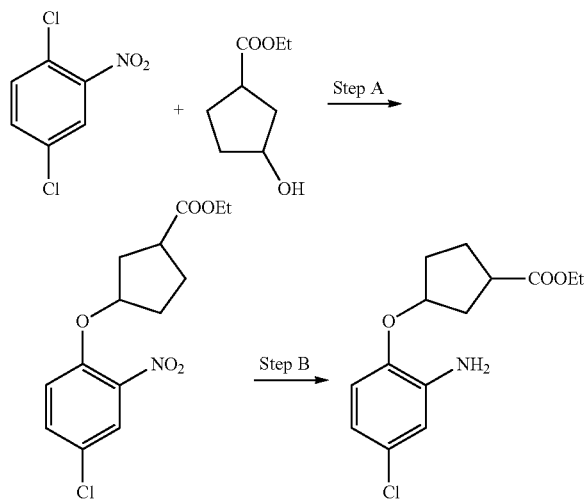

SCHEME 21

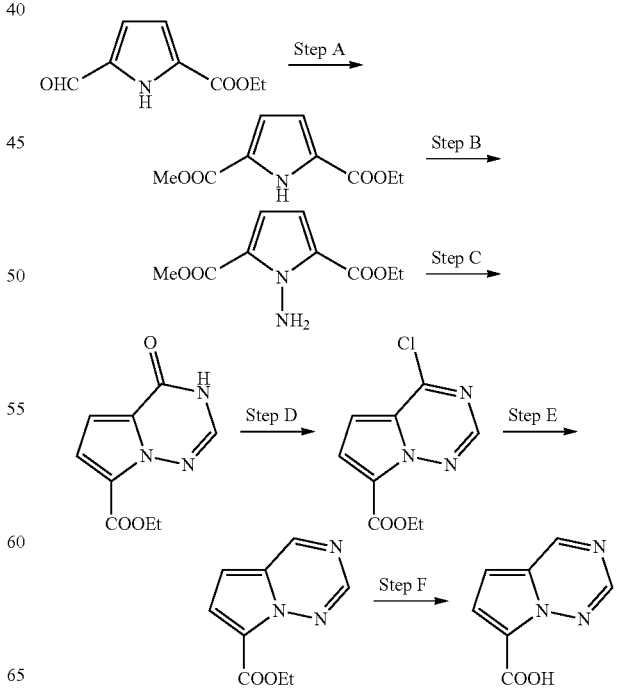

Step A: Synthesis of 1H-pyrrole-2,5-dicarboxylic acid 2-ethyl ester 5-methyl ester To a solution of 5-formyl-1H-pyrrole-2-carboxylic acid ethyl ester (1 g, 6 mmol) in a mixture of tert-butanol/tetrahydrofuran/water (1/1/1, 60 mL) was added sulfamic acid (1.0 g, 9 mmol) and the resulting mixture was stirred for 10 minutes. A solution of sodium chlorite (0.76 g, 8.4 mmol) and potassium dihydrogen phosphate (1.6 g, 12 mmol) in water (5 mL) was then added and the reaction mixture was stirred for 30 minutes. The resulting mixture was then extracted with ethyl acetate and the organic extracts were washed with water and brine, dried over anhydrous sodium sulfate, filtered and evaporated under reduced pressure. The residue was dissolved in dichloromethane (20 mL) and a solution of trimetisilidiazomethane (2 M in hexane, 5 mL) was added; the resulting mixture was stirred until the gas evolution ceased. Glacial acetic acid (a few drops) was added and the resulting mixture was evaporated under reduced pressure. The residue was purified by flash chromatography (hexane/EtOAc, 85/15) to give 0.7 g of 1H-pyrrole-2,5-dicarboxylic acid 2-ethyl ester 5-methyl ester.

Step B: Synthesis of 1-amino-1H-pyrrole-2,5-dicarboxylic acid 2-ethyl ester 5-methyl ester Sodium hydride (60% suspension in mineral oil, 90 mg) was added to a solution of 1H-pyrrole-2,5-dicarboxylic acid 2-ethyl ester 5-methyl ester (100 mg) in N,N-dimethylformamide (2 mL) and the resulting mixture was stirred for 5 minutes. 2,4,6-Trimethyl-benzenesulfonylhydroxylamine (prepared from 0.5 g of mesitilene oxamate as described in JOC 1973, 1239) was then added and the mixture was stirred for 5 minutes. The reaction mixture was then quenched by addition of water and the resulting mixture was extracted with ethyl acetate.

The combined organic layers were washed with water and brine, dried over anhydrous sodium sulfate, filtered and evaporated under reduced pressure. The crude residue was purified by flash chromatography (hexane/EtOAc, 90/10) to afford 100 mg of 1-amino-1H-pyrrole-2,5-dicarboxylic acid 2-ethyl ester 5-methyl ester.

Step C: Synthesis of 4-oxo-3,4-dihydro-pyrrolo[2,1-f][1,2,4]triazine-7-carboxylic acid ethyl ester A mixture of 1-amino-1H-pyrrole-2,5-dicarboxylic acid 2-ethyl ester 5-methyl ester (140 mg) and formamide (1 mL) was stirred at 140° C. overnight. The reaction mixture was then cooled and diluted with water, the solid which crashed out was collected by filtration and dried under vacuum to give 60 mg of 4-oxo-3,4-dihydro-pyrrolo[2,1-f][1,2,4]triazine-7-carboxylic acid ethyl ester.

Step D: Synthesis of 4-chloro-pyrrolo[2,1-f][1,2,4]triazine-7-carboxylic acid ethyl ester A mixture of 4-oxo-3,4-dihydro-pyrrolo[2, 1-J][1,2,4]triazine-7-carboxylic acid ethyl ester (300 mg) and phosphorus oxychloride (1 mL) was heated at 160° C. for 15 minutes in a microwave reactor. The resulting mixture was cooled and poured into a mixture of ice-water and ethyl acetate. The organic layer was separated, washed with brine, dried over anhydrous sodium sulfate, filtered and evaporated under reduced pressure. The residue was purified by flash chromatography (hexane/EtOAc, 90/10) to afford 120 mg of 4-chloro-pyrrolo[2,1-J][1,2,4]triazine-7-carboxylic acid ethyl ester containing 4-chloro-pyrrolo[2, l-J][1,2,4]triazine-7-carbonitrile.

Step E: Synthesis of pyrrolo[2,1-f][1,2,4]triazine-7-carboxylic acid ethyl ester A mixture of 4-chloro-pyrrolo[2,1-f][1,2,4]triazine-7-carboxylic acid ethyl ester (120 mg), palladium hydroxide on carbon (20%, 40 mg) and sodium acetate (600 mg) in a mixture of ethyl acetate and isopropanol (5/1, 12 mL) was stirred at room temperature under hydrogen atmosphere (balloon pressure) overnight. The resulting mixture was filtered and a CELITE™ pad, the filtrate was evaporated under reduced pressure. The crude residue was purified by flash chromatography to give 45 mg of pyrrolo[2,1-f][1,2,4]triazine-7-carboxylic acid ethyl ester.

Step F: Synthesis of pyrrolo[2,1-f][1,2,4]triazine-7-carboxylic acid

A mixture of pyrrolo[2,1-f][1,2,4]triazine-7-carboxylic acid ethyl ester (40 mg) and an aqueous solution of sodium hydroxide (6 M, 1 mL) in a mixture of tetrahydrofuran and methanol (1/1, 1 mL) was heated at 70° C. for 1 hour. The reaction mixture was then cooled, acidified by addition of an aqueous solution of hydrochloric acid (6 M) and evaporated under reduced pressure. The residue was dissolved in a mixture of dichloromethane and water (10/1, 5.5 mL), the organic layer was separated, dried over anhydrous sodium sulfate, filtered and evaporated under reduced pressure to give 15 mg of pyrrolo[2,1-f][1,2,4]triazine-7-carboxylic acid.

Preparation 22: Synthesis of 6-Amino-5-piperidin-1-yl-1,3-dihydro-indol-2-one The synthesis of 6-amino-5-piperidin-1-yl-1,3-dihydro-indol-2-one was carried out according to the process shown in Scheme 22.

SCHEME 22

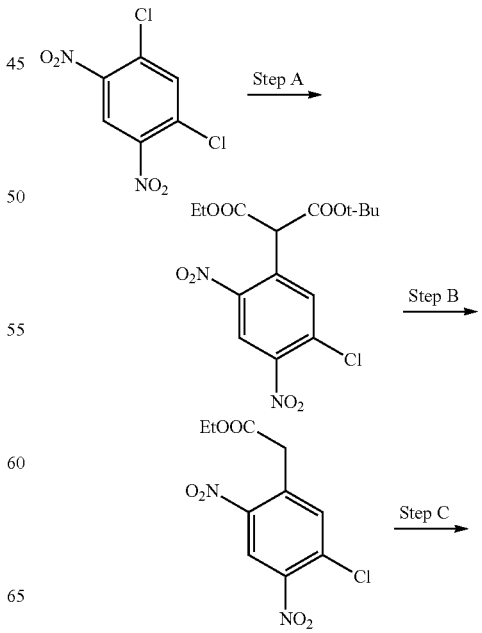

-continued

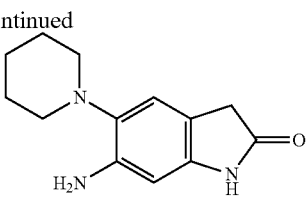

Step A: Synthesis of 2-(5-chloro-2,4-dinitro-phenyl)-malonic acid tert-butyl ester ethyl ester Sodium hydride (60% suspension in mineral oil, 1.60 mmol) was added to a mixture of tert-butyl ethyl malonate (300 mg) in 1-methyl-2-pyrrolidinone (3 mL) and was followed by 1,5-dichloro-2,4-dinitrobenzene (0.45 g). The reaction mixture was stirred for 15 minutes and was then quenched by addition of a diluted aqueous solution of hydrochloric acid. The resulting mixture was extracted with ethyl acetate; the combined organic extracts were washed with brine, dried over anhydrous sodium sulfate, filtered and evaporated under reduced pressure. The residue was purified by flash chromatography (EtOAc/hexane, 5/95 to 15/85) to give 0.4 g of 2-(5-chloro-2,4-dinitro-phenyl)-malonic acid tert-butyl ester ethyl ester.

Step B: Synthesis of (5-chloro-2,4-dinitro-phenyl)-acetic acid ethyl ester

A solution of 2-(5-chloro-2,4-dinitro-phenyl)-malonic acid tert-butyl ester ethyl ester (0.4 g) in a mixture of dichloromethane (3 mL) and trifluoroacetic acid (0.5 mL) was heated at 70° C. for 30 minutes in a sealed tube. The reaction mixture was then evaporated under reduced pressure and the residue was purified by flash chromatography (EtOac/hexane, 10/90) to afford 150 mg of (5-chloro-2,4-dinitro-phenyl)-acetic acid ethyl ester.

Step C: Synthesis of 6-amino-5-piperidin-1-yl-1,3-dihydro-indol-2-one

Piperidine (120 mg) was added to a solution of (5-chloro-2,4-dinitro-phenyl)-acetic acid ethyl ester (150 mg) in dichloromethane (5 mL) and the resulting mixture was stirred at room temperature for 10 minutes. Glacial acetic acid (0.3 mL) and zinc dust (1 scoop) were added and the reaction mixture was stirred at room temperature for 20 minutes. The resulting mixture was filtered through a CELITE™ pad, the filter cake was washed with dichloromethane and the filtrate was evaporated under reduced pressure. The residue was then diluted with ethyl acetate, washed with brine, dried over anhydrous sodium sulfate, filtered and evaporated under reduced pressure to give (2,4-diamino-5-piperidin-1-yl-phenyl)-acetic acid ethyl ester. This material was dissolved in toluene (2.5 mL) and heated at 150° C. in a microwave reactor for 10 minutes. The reaction mixture was then cooled, evaporated under reduced pressure and the residue was purified by flash chromatography (DCM/MeOH, 95/5) to give 30 mg of 6-amino-5-piperidin-1-yl-1,3-dihydro-indol-2-one. MS=232 [M+H]$^+$.

6-Amino-5-(4-hydroxymethyl-piperidin-1-yl)-1,3-dihydro-indol-2-one was prepared following the above described procedure and utilizing the appropriate starting materials.

Preparation 23: Synthesis of [4-(6-Amino-2-methyl-1H-indol-5-yl)-phenyl]-methanol The synthesis of [4-(6-amino-2-methyl-1H-indol-5-yl)-phenyl]-methanol was carried out according to the process shown in Scheme 23.

SCHEME 23

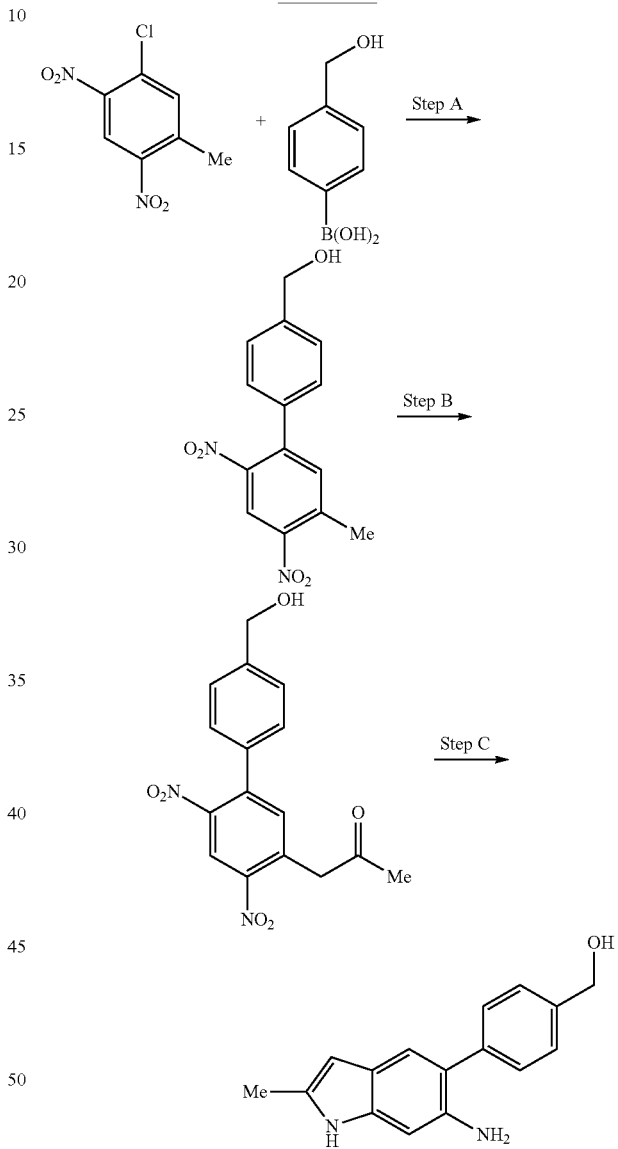

Step A: Synthesis of (5'-methyl-2',4'-dinitro-biphenyl-4-yl)-methanol

A mixture of 5-chloro-2,4-dinitrotoluene (1.0 g), 4-(hydroxymethyl)phenylboronic acid (0.84 g), bis(triphenylphosphine)palladium(II) chloride (150 mg) and potassium carbonate (2.0 g) in a mixture of 1,4-dioxane and water (10/1, 11 mL) was heated at 170° C. in a microwave reactor for 10 minutes. The reaction mixture was then cooled and diluted with ethyl acetate. The organic layer was washed with water and brine, dried over anhydrous sodium sulfate, filtered and evaporated under reduced pressure. The crude residue was purified by flash chromatography (acetone/DCM, 3/97) to give 0.6 g of (5'-methyl-2',4'-dinitro-biphenyl-4-yl)-methanol.

Step B: Synthesis of 1-(4'-hydroxymethyl-4,6-dinitro-biphenyl-3-yl)-propan-2-one A solution of (5'-methyl-2',4'-dinitro-biphenyl-4-yl)-methanol (0.6 g) in N,N-dimethylacetamide dimethylacetal (5 mL) was heated at 100° C. for 2 hour. The reaction mixture was then cooled, diluted with ethyl acetate, washed with a diluted aqueous solution of hydrochloric acid, water and brine, dried over anhydrous sodium sulfate, filtered and evaporated under reduced pressure. The crude residue was purified by flash chromatography (acetone/DCM, 3/97) to afford 1-(4'-hydroxymethyl-4,6-dinitro-biphenyl-3-yl)-propan-2-one.

Step C: Synthesis of [4-(6-amino-2-methyl-1H-indol-5-yl)-phenyl]-methanol

A mixture of 1-(4'-hydroxymethyl-4,6-dinitro-biphenyl-3-yl)-propan-2-one (200 mg) and palladium on carbon (10%, 80 mg) in ethyl acetate was shaken in a Parr apparatus under hydrogen atmosphere (50 PSI) overnight. The reaction mixture was then filtered on a CELITE™ pad, the filtrate was evaporated under reduced pressure and the crude residue was purified by flash chromatography to afford [4-(2-methyl-6-nitro-1H-indol-5-yl)-phenyl]-methanol and [4-(6-hydroxyamino-2-methyl-1H-indol-5-yl)-phenyl]-methanol. The two products were combined and dissolved in dichloromethane (5 mL). Zinc dust (a large excess) and glacial acetic acid (1 mL) were added and the resulting mixture was heated at 70° C. for 30 minutes. The reaction mixture was then filtered on a CELITE™ pad, the filter cake was washed with ethyl acetate. The filtrate was washed with brine, dried over anhydrous sodium sulfate, filtered and evaporated under reduced pressure. The crude residue was purified by flash chromatography (MeOH/DCM, 5/95) to give 55 mg of [4-(6-amino-2-methyl-1H-indol-5-yl)-phenyl]-methanol. MS=253 [M+H]$^+$.

Preparation 24: Synthesis of Thieno[3,2-b]pyridine-3,6-dicarboxylic acid 6-ethyl ester The synthesis of thieno[3,2-b]pyridine-3,6-dicarboxylic acid 6-ethyl ester was carried out according to the process shown in Scheme 24.

SCHEME 24

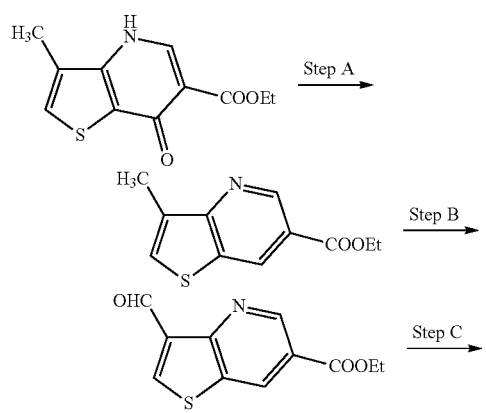

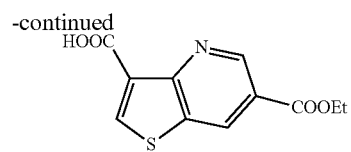

Step A: Synthesis of 3-methyl-thieno[3,2-b]pyridine-6-carboxylic acid ethyl ester A mixture of 3-methyl-7-oxo-4,7-dihydro-thieno[3,2-b]pyridine-6-carboxylic acid ethyl ester (WO 2003/059878 A2) (1.0 g) and phosphorus oxychloride (3 mL) was heated at 150° C. for 15 minutes in a microwave reactor. The reaction mixture was then cooled and poured into a mixture of ice-water and ethyl acetate. The resulting mixture was stirred for 10 minutes; the organic layer was separated, washed twice with water (50 mL) and with brine, dried over anhydrous sodium sulfate, filtered and evaporated under reduced pressure. To the solid residue dissolved in a mixture of ethyl acetate and isopropanol (10/1, 55 mL) sodium acetate trihydrate (2.0 g) and palladium hydroxide on carbon (20%, 0.3 g) were added and the resulting mixture was shaken in a Parr apparatus under hydrogen atmosphere (50 PSI) overnight. The reaction mixture was then filtered on a CELITE™ pad, the filtrate was evaporated under reduced pressure and the crude residue was purified by flash chromatography (EtOAc/hexane, 10/90) to afford 0.78 g of 3-methyl-thieno[3,2-b]pyridine-6-carboxylic acid ethyl ester.

Step B: Synthesis of 3-formyl-thieno[3,2-b]pyridine-6-carboxylic acid ethyl ester To a solution of 3-methyl-thieno[3,2-b]pyridine-6-carboxylic acid ethyl ester (1.2 g) in carbon tetrachloride (50 mL) was added N-bromosuccinimide (2.4 g) followed by AIBN (50 mg) and the resulting mixture was heated at reflux for 4 hours. The reaction mixture was cooled; the solids were removed by filtrations and copiously washed with carbon tetrachloride. The filtrate was evaporated under reduced pressure, the residue was dissolved in dimethyl sulfoxide (20 mL) and the resulting mixture was heated at 80° C. for 1 hour. The reaction mixture was cooled, diluted with water, basified by addition of a saturated aqueous solution of sodium bicarbonate and extracted with ethyl acetate. The combined organic layers were washed with brine, dried over anhydrous sodium sulfate, filtered and evaporated under reduced pressure. The residue was purified by flash chromatography (acetone/DCM, 5/95) to give 0.8 g of 3-formyl-thieno[3,2-b]pyridine-6-carboxylic acid ethyl ester.

Step C: Synthesis of thieno[3,2-b]pyridine-3,6-dicarboxylic acid 6-ethyl ester

A mixture of 3-formyl-thieno[3,2-b]pyridine-6-carboxylic acid ethyl ester (0.8 g, 3.4 mmol) and sulfamic acid (0.66 g, 6.8 mmol) in a mixture of tert-butanol/tetrahydrofuran/water (1/1/1, 60 mL) was stirred for 20 minutes. A solution of sodium chlorite (0.55 g, 6 mmol) and potassium dihydrogen phosphate (1.36 g, 10 mmol) in water (5 mL) was added and the resulting yellow solution was stirred for 20 minutes. The reaction mixture was diluted with water and ethyl acetate, the solid formed was collected by filtration, washed with water and dried in a vacuum oven at 60° C. The filtrate was extracted with ethyl acetate; the organic layer was washed with brine, dried over anhydrous sodium sulfate, filtered and evaporated under reduced pressure to afford combined with the solid previously collected 0.5 g of thieno[3,2-b]pyridine-3,6-dicarboxylic acid 6-ethyl ester.

Preparation 25: Synthesis of 5-Chloro-2-ethyl-phenylamine

The synthesis of 5-chloro-2-ethyl-phenylamine was carried out according to the process shown in Scheme 25.

SCHEME 25

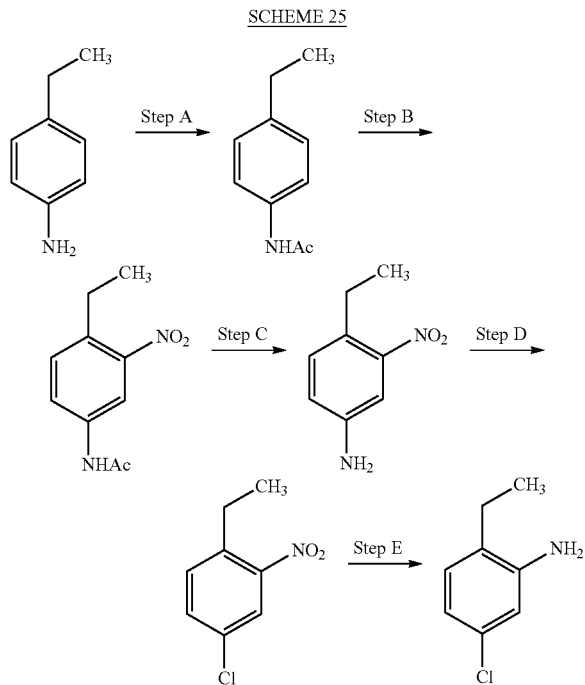

Step A: Synthesis of N-(4-ethyl-phenyl)-acetamide

Acetic anhydride (4.3 mL, 45.45 mmol) was added to a mixture of 4-ethylaniline (5.0 g, 41.32 mmol) and pyridine (20 mL) and the resulting mixture was stirred at room temperature overnight. The reaction mixture was partitioned between dichloromethane and an aqueous solution of hydrochloric acid. The organic layer was separated, dried over anhydrous sodium sulfate, filtered and evaporated under reduced pressure to give 6.857 g of N-(4-ethyl-phenyl)-acetamide as a brown solid without further purifications.

Step B: Synthesis of N-(4-ethyl-3-nitro-phenyl)-acetamide

To concentrate sulfuric acid (8 mL) was added portionwise N-(4-ethyl-phenyl)-acetamide (2.0 g, 12.27 mmol) and the mixture was cooled to −15° C., fuming nitric acid (0.505 mL, 12.27 mmol) was then added dropwise. The reaction mixture was stirred at a temperature ranging between −20 and −10° C. for 75 minutes. The reaction mixture was then poured into ice, neutralized by addition of sodium carbonate and extracted twice with diethyl ether. The combined organic extracts were dried over anhydrous sodium sulfate, filtered and evaporated under reduced pressure. The crude residue was purified by flash chromatography (hexane/ EtOAc, 100/0 to 70/30) to give 2.231 g (88% yield) of N-(4-ethyl-3-nitro-phenyl)-acetamide.

Step C: Synthesis of 4-ethyl-3-nitro-phenylamine

A mixture of N-(4-ethyl-3-nitro-phenyl)-acetamide (1.0 g) and concentrated hydrochloric acid (5 mL) was heated at reflux for 4 hours. The reaction mixture was then cooled, basified by addition of sodium hydroxide and extracted twice with diethyl ether. The combined organic extracts were dried over anhydrous sodium sulfate, filtered and evaporated under reduced pressure to afford 0.601 g of 4-ethyl-3-nitro-phenylamine without further purifications. MS=167 [M+H]$^+$.

Step D: Synthesis of 4-chloro-1-ethyl-2-nitro-benzene (page 32042-86)

A solution of sodium nitrite (0.11 g, 1.32 mmol) in water (1 mL) was added, dropwise, at 0° C., to a suspension of 4-ethyl-3-nitro-phenylamine (80%, 0.25 g, 1.20 mmol) in a mixture of concentrated hydrochloric acid (2 mL) and water (4 mL). The reaction mixture was stirred at 0° C. for 5 minutes and then urea (15 mg, 0.24 mmol) was added. The resulting mixture was stirred for 10 minutes and then was poured into a suspension of cuprous chloride (0.18 g, 1.8 mmol) in a mixture of concentrated hydrochloric acid (1.5 mL) and water (0.6 mL) at 80° C. The reaction mixture was stirred at 80° C. for 2 hours and then was extracted with ethyl acetate. The organic extracts were washed with an aqueous solution of sodium hydroxide (1 M) and water, dried over anhydrous sodium sulfate, filtered and evaporated under reduced pressure to give 200 mg (90% yield) of 4-chloro-1-ethyl-2-nitro-benzene as an oil.

4-Chloro-1-(4-methoxy-butyl)-2-nitro-benzene was prepared utilizing the above described procedure and the appropriate starting materials.

Step E: Synthesis of 5-chloro-2-ethyl-phenylamine

To a solution of 4-chloro-1-ethyl-2-nitro-benzene (0.57 g, 3.08 mmol) in a mixture of ethyl acetate and ethanol (1/1, 30 mL) was added stannous chloride (1.7 g, 9.24 mmol) and the resulting mixture was stirred at room temperature overnight. The reaction mixture was then poured into water and basified by addition of potassium carbonate until pH>10. The resulting mixture was extracted with dichloromethane; the organic extracts were dried over anhydrous sodium sulfate, filtered and evaporated under reduced pressure. The crude residue was purified by flash chromatography to afford 0.503 g of 5-chloro-2-ethyl-phenylamine as a brown oil.

Preparation 26: Synthesis of (7-Amino-6-methoxy-naphthalen-2-yl)-methanol

The synthesis of (7-amino-6-methoxy-naphthalen-2-yl)-methanol was carried out according to the process shown in Scheme 26.

SCHEME 26

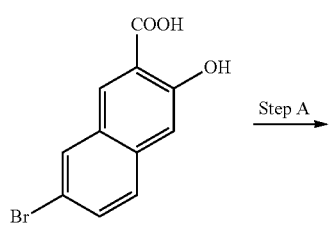

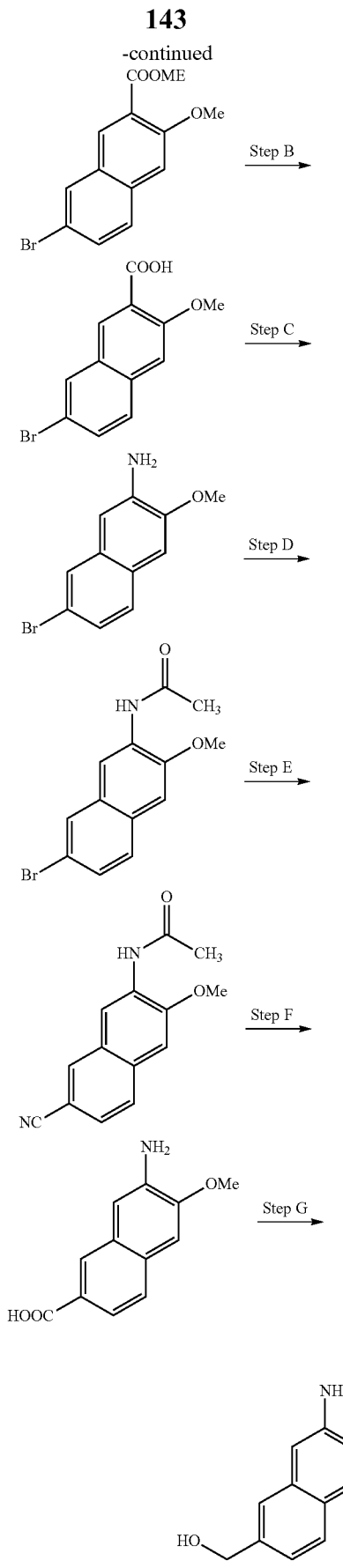

Step A: Synthesis of 7-bromo-3-methoxy-naphthalene-2-carboxylic acid methyl ester A mixture of 7-bromo-3-hydroxy-naphthalene-2-carboxylic acid (J. Med. Chem. 1990, 33(1), 171) (5.3 g, 19.85 mmol), potassium carbonate (13.7 g, 99.25 mmol) and dimethylsulfate (3.8 mL, 45.66 mmol) in acetone (50 mL) was heated at reflux for 3.5 hours. The reaction mixture was then filtered; the filtrate was treated with water (5 mL) and the resulting mixture was stirred for 10 minutes. The reaction mixture was concentrated under reduced pressure; the residue was dissolved in dichloromethane, dried over anhydrous sodium sulfate, filtered and evaporated under reduced pressure to afford 5.946 g of 7-bromo-3-methoxy-naphthalene-2-carboxylic acid methyl ester without further purifications.

Step B: Synthesis of 7-bromo-3-methoxy-naphthalene-2-carboxylic acid

A solution of sodium hydroxide (1.6 g, 40 mmol) in water (30 mL) was added to a solution of 7-bromo-3-methoxy-naphthalene-2-carboxylic acid methyl ester (5.9 g, 20 mmol) in ethanol (100 mL) and the resulting mixture was heated at reflux for 2 hours. The reaction mixture was then cooled and concentrated under reduced pressure. The residue was acidified until pH 3 ca. by addition of an aqueous solution of hydrochloric acid. The resulting mixture was extracted twice with dichloromethane and the combined organic extracts were dried over anhydrous sodium sulfate, filtered and evaporated under reduced pressure to give 5.329 g of 7-bromo-3-methoxy-naphthalene-2-carboxylic acid as a cream colored solid.

Step C: Synthesis of 7-bromo-3-methoxy-naphthalen-2-ylamine

A mixture of 7-bromo-3-methoxy-naphthalene-2-carboxylic acid (1.0 g, 3.56 mmol) and thionyl chloride (5 mL) was heated at reflux for 2 hours. The reaction mixture was evaporated under reduced pressure and the residue was dissolved in acetone (30 mL). To this solution was added, dropwise, a solution of sodium azide (0.23 g) in water (0.5 mL) and the resulting mixture was stirred for 15 minutes at room temperature. Water (100 mL) was added and the resulting mixture was extracted twice with benzene (50 mL). The combined organic extracts were dried over anhydrous sodium sulfate, filtered and heated to reflux for 1 hour. An aqueous solution of potassium hydroxide (50%, 100 mL) was then added and the resulting mixture was heated at reflux for 1 hour. The reaction mixture was cooled, the organic layer was separated and the aqueous layer was extracted twice with dichloromethane. The combined organic extracts were dried over anhydrous sodium sulfate, filtered and evaporated under reduced pressure. The crude residue was purified by flash chromatography (hexane/EtOAc) to give 0.678 g of 7-bromo-3-methoxy-naphthalen-2-ylamine as a cream colored solid.

Step D: Synthesis of N-(7-bromo-3-methoxy-naphthalen-2-yl)-acetamide

A mixture of 7-bromo-3-methoxy-naphthalen-2-ylamine (2.2 g, 8.76 mmol), acetic anhydride (1.4 g, 13.14 mmol) and pyridine (20 mL) was stirred at room temperature for 3 hours. Water (300 mL) was added and the solid precipitate was collected by filtration and copiously washed with water. The solid residue was dissolved in dichloromethane, dried over anhydrous sodium sulfate, filtered and evaporated under reduced pressure to give 2.569 g of N-(7-bromo-3-methoxy-naphthalen-2-yl)-acetamide as a light pink solid.

Step E: Synthesis of N-(7-cyano-3-methoxy-naphthalen-2-yl)-acetamide

To a solution of N-(7-bromo-3-methoxy-naphthalen-2-yl)-acetamide (1.2 g, 4.0 mmol) in a previously degassed mixture of water and N,N-dimethylformamide (3/1, 40 mL) was added zinc cyanide (0.28 g, 2.4 mmol) followed by tris(dibenzylideneacetone)dipalladium(0) (0.18 g, 0.22 mmol) and 1,1'-bis(diphenylphosphino)ferrocene (0.27 g, 0.48 mmol) and the resulting mixture was heated at 120° C. overnight. The reaction mixture was poured into water and extracted with ethyl acetate. The organic extracts were washed 3 times with water, dried over anhydrous sodium sulfate, filtered and evaporated under reduced pressure. The crude residue was purified by flash chromatography (hexane/EtOAc) to afford 0.621 g of N-(7-cyano-3-methoxy-naphthalen-2-yl)-acetamide as a cream colored solid. MS=241 [M+H]$^+$.

Step F: Synthesis of 7-amino-6-methoxy-naphthalene-2-carboxylic acid

Sodium hydroxide (0.17 g, 4.17 mmol) was added to a suspension of N-(7-cyano-3-methoxy-naphthalen-2-yl)-acetamide (0.2 g, 0.83 mmol) in ethylene glycol (2 mL) and the resulting mixture was heated at reflux (195° C.) overnight. The reaction mixture was then cooled, water was added and the pH was adjusted to 4. The precipitate was collected by filtration and dried to give 0.156 g of 7-amino-6-methoxy-naphthalene-2-carboxylic acid as a brown solid. MS=218 [M+H]$^+$.

Step G: Synthesis of (7-amino-6-methoxy-naphthalen-2-yl)-methanol

Borane tetrahydrofuran complex (1 mL, 0.92 mmol) was added, at 0° C., to a suspension of 7-amino-6-methoxy-naphthalene-2-carboxylic acid (0.1 g, 0.46 mmol) in anhydrous tetrahydrofuran (2 mL) and the resulting mixture was stirred at room temperature overnight. The reaction mixture was quenched by addition of methanol and then was stirred for 2 hours at room temperature. The resulting mixture was concentrated under reduced pressure, partitioned between dichloromethane and a saturated aqueous solution of sodium bicarbonate. The organic layer was separated, dried over anhydrous sodium sulfate, filtered and evaporated under reduced pressure to afford (7-amino-6-methoxy-naphthalen-2-yl)-methanol without further purifications. MS=204 [M+H]$^+$.

Preparation 27: Synthesis of 1-(4-Methoxy-butyl)-4-nitro-benzene

The synthesis of 1-(4-methoxy-butyl)-4-nitro-benzene was carried out according to the process shown in Scheme 27.

SCHEME 27

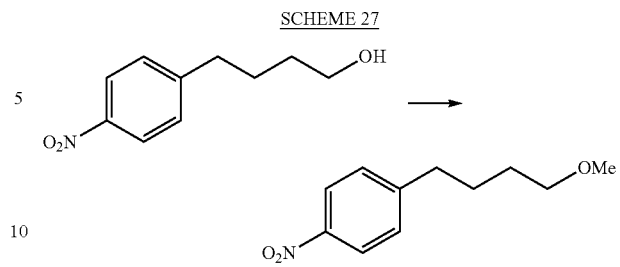

4-(4-Nitrophenyl)-1-butanol (2 g, 10.26 mmol) was added, dropwise, to a suspension of sodium hydride (60% dispersion in mineral oil, 0.49 g, 12.30 mmol) in anhydrous tetrahydrofuran and the resulting mixture was stirred at room temperature for 10 minutes. Methyl iodide (2 mL) was added and the resulting mixture was stirred for 62 hours. The reaction mixture was evaporated under reduced pressure; the residue was partitioned between dichloromethane and water. The organic layer was separated, dried over anhydrous sodium sulfate, filtered and evaporated under reduced pressure. The residue was purified by flash chromatography (EtOAc/hexane, 1/1) to give 1.996 g of 1-(4-methoxy-butyl)-4-nitro-benzene as an oil.

Preparation 28: Synthesis of 4-(4-Chloro-2-nitro-phenyl)-butan-1-ol

The synthesis of 4-(4-chloro-2-nitro-phenyl)-butan-1-ol was carried out according to the process shown in Scheme 33.

SCHEME 28

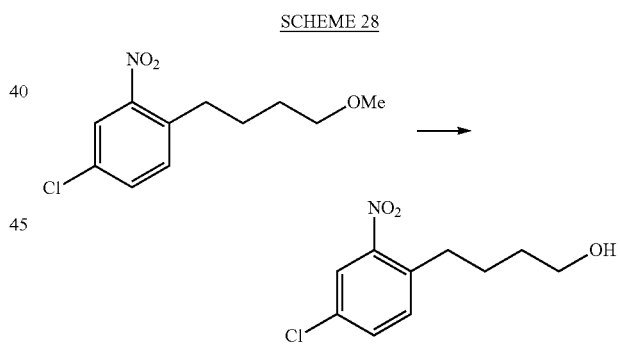

Boron tribromide (1.24 g, 4.925 mmol) was added to a cooled mixture of 4-chloro-1-(4-methoxy-butyl)-2-nitro-benzene (0.2 g, 0.995 mmol) in dichloromethane (10 mL) and the resulting mixture was stirred at room temperature overnight. The reaction mixture was extracted with ethyl acetate and the organic extracts were dried over anhydrous sodium sulfate, filtered and evaporated under reduced pressure to give 80 mg of 4-(4-chloro-2-nitro-phenyl)-butan-1-ol as an oil without further purifications.

Preparation 29: Synthesis of 7-Methoxy-quinolin-6-ylamine

The synthesis of 7-methoxy-quinolin-6-ylamine was carried out according to the process shown in Scheme 29.

SCHEME 29

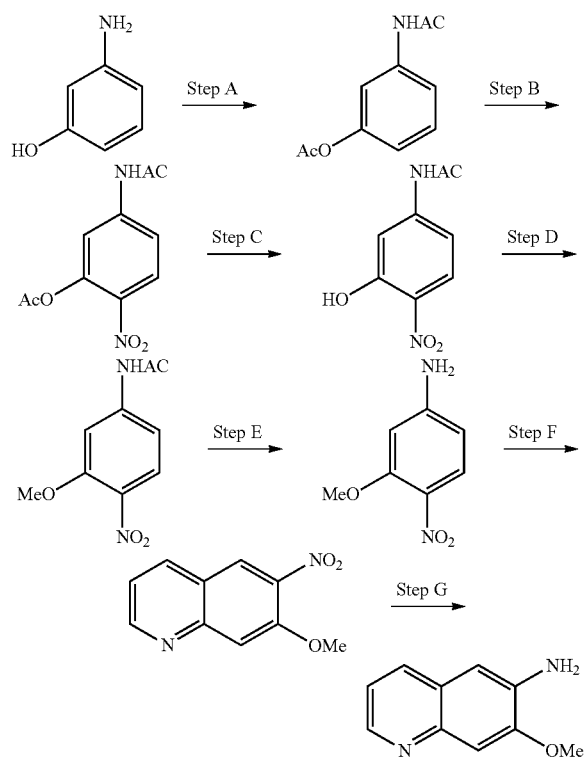

Step A: Synthesis of acetic acid 3-acetylamino-phenyl ester

Acetic anhydride (53 mL, 572.0 mmol) was slowly added to a mixture of 3-aminophenol (25 g, 225.0 mmol) and 4-dimethylaminopyridine (catalytic quantity) in pyridine (100 mL) at 0° C. and the reaction mixture was stirred at room temperature for 62 hours. Water (1 L) was added and the resulting mixture was extracted with ethyl acetate. The organic extracts were washed with an aqueous solution of hydrochloric acid, a saturated aqueous solution of sodium bicarbonate and water, dried over anhydrous sodium sulfate, filtered and evaporated under reduced pressure to give 21.79 g of acetic acid 3-acetylamino-phenyl ester as a solid without further purifications. A second batch (2.978 g) of this material crashed out of the aqueous layer upon standing and was collected by filtration.

Step B: Synthesis of acetic acid 5-acetylamino-2-nitro-phenyl ester

Acetic acid 3-acetylamino-phenyl ester (21.7 g, 112.4 mmol) was added portionwise, at −15° C., to fuming nitric acid (109 mL) maintaining the temperature below −10° C. The reaction mixture was stirred at −10° C. for 3 hours and then was poured into ice. The resulting mixture was extracted 3 times with ethyl acetate and the combined organic extracts were washed with brine, dried over anhydrous sodium sulfate, filtered and evaporated under reduced pressure. The crude residue was purified by flash chromatography (EtOAc/hexane, 1/1) to afford 20.608 g (77% yield) of acetic acid 5-acetylamino-2-nitro-phenyl ester as a cream colored solid.

Step C: Synthesis of N-(3-hydroxy-4-nitro-phenyl)-acetamide

A mixture of acetic acid 5-acetylamino-2-nitro-phenyl ester (20.5 g, 85.77 mmol) and potassium carbonate (26 g, 188.4 mmol) in methanol (200 mL) was stirred at room temperature for 3 hours. The reaction mixture was concentrated under reduced pressure, water (250 mL) was added and the resulting mixture was acidified by addition of concentrated hydrochloric acid. The solid which crushed out was triturated, collected by filtration, washed with water and dried under vacuum to afford N-(3-hydroxy-4-nitro-phenyl)-acetamide.

Step D: Synthesis of N-(3-methoxy-4-nitro-phenyl)-acetamide

To a solution of N-(3-hydroxy-4-nitro-phenyl)-acetamide (2 g, 10.15 mmol) in anhydrous N,N-dimethyformamide (5 mL) was added potassium carbonate (2.6 g, 18.88 mmol) followed by methyl iodide (0.71 mL, 11.16 mmol) and the reaction mixture was stirred at room temperature for 1 hour. A second aliquot of methyl iodide (0.15 mL) was then added and the resulting mixture was stirred for 1 hour. Ethyl acetate (100 mL) and brine (100 mL) were added, the organic layer was separated, washed twice with water, dried over anhydrous sodium sulfate, filtered and evaporated under reduced pressure to give N-(3-methoxy-4-nitro-phenyl)-acetamide.

Step E: Synthesis of 3-methoxy-4-nitro-phenylamine

A mixture of N-(3-methoxy-4-nitro-phenyl)-acetamide (16.6 g, 78.67 mmol) and an aqueous solution of hydrochloric acid (1.5 M, 200 mL) was refluxed until a clear solution was obtained. The reaction mixture was basified by addition of an aqueous solution of potassium carbonate and then was extracted four times with dichloromethane (200 mL); the combined organic extracts were dried over anhydrous sodium sulfate, filtered and evaporated under reduced pressure to give 13.56 g (quantitative yield) of 3-methoxy-4-nitro-phenylamine as a yellow solid. MS=169 [M+H]$^+$.

Step F: Synthesis of 7-methoxy-6-nitro-quinoline

To a mixture of 3-methoxy-4-nitro-phenylamine (13.4 g, 80.0 mmol), arsenic pentoxide (11.0 g, 48.0 mmol) and glycerol (33 mL, 216.0 mmol) at 100° C., was added, dropwise, concentrated sulfuric acid (4.7 mL, 88.0 mmol). The reaction mixture was then heated at a temperature ranging between 150 and 160° C. for 2 hours and then was cooled. Water (200 mL) was added and the resulting mixture was extracted four times with ethyl acetate. The combined organic extracts were dried over anhydrous sodium sulfate, filtered and evaporated under reduced pressure. The crude residue was purified by flash chromatography (EtOAc) to give 9.00 g (61% yield) of 7-methoxy-6-nitro-quinoline as an orange solid.

Step G: Synthesis of 7-methoxy-quinolin-6-ylamine

A mixture of 7-methoxy-6-nitro-quinoline (5 g, 24.0 mmol), iron powder (9.8 g, 172 mmol) and ammonium chloride (9.1 g, 172 mmol) in a mixture of ethanol and water (3/1, 160 mL) was heated at reflux overnight. The resulting mixture was filtered through a CELITE™ pad, the filtrate was evaporated under reduced pressure and the residue was partitioned between water and ethyl acetate. The organic layer was separated, dried over anhydrous sodium sulfate, filtered and evaporated under reduced pressure. The residue was purified by flash chromatography (EtOAc) to afford 3.551 g of 7-methoxy-quinolin-6-ylamine as a grey solid.

Preparation 30: Synthesis of N²-[2-(tert-Butyl-dimethyl-silanyloxy)-ethyl]-7-methoxy-quinoline-2,6-diamine The synthesis of N²-[2-(tert-butyl-dimethyl-silanyloxy)-ethyl]-7-methoxy-quinoline-2,6-diamine was carried out according to the process shown in Scheme 30.

SCHEME 30

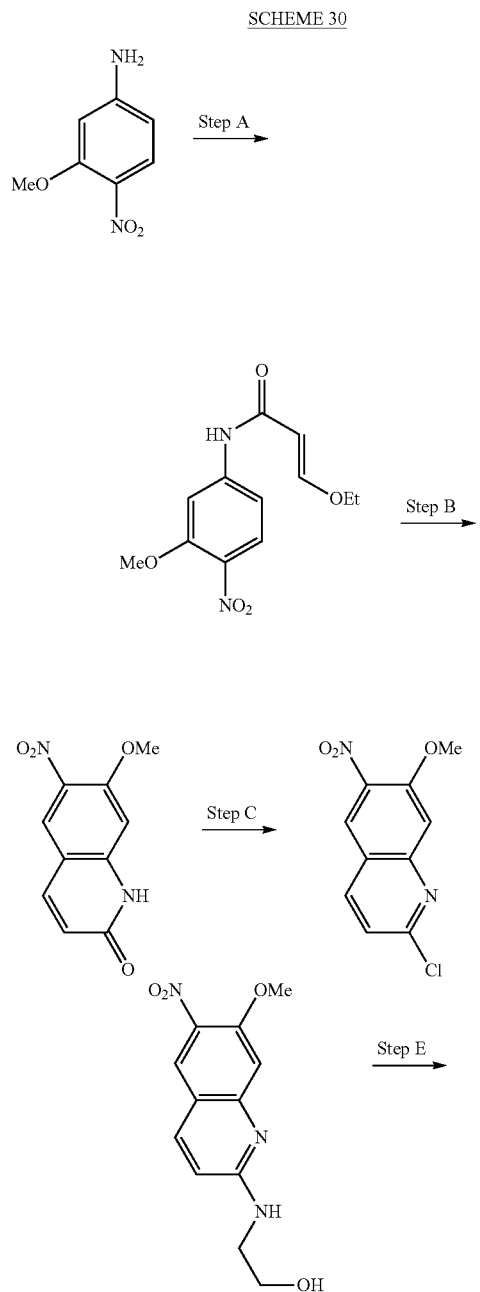

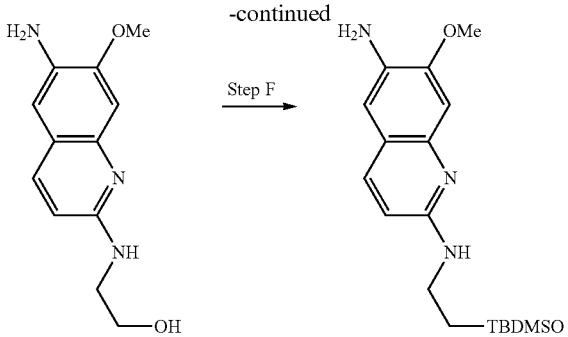

Step A: Synthesis of (E)-3-ethoxy-N-(3-methoxy-4-nitro-phenyl)-acrylamide

Thionyl chloride (1 mL) was added to 3,3-diethoxy-propionic acid (Eur. J. Org. Chem. 2001, 2041) (0.20 g, 1.10 mmol) and the resulting mixture was heated at 80° C. for 1 hour. The reaction mixture was then evaporated under reduced pressure and the residue was dissolved in dichloromethane (2 mL). The resulting solution was added to a mixture of 3-methoxy-4-nitro-phenylamine (0.13 g, 0.77 mmol) and pyridine (0.12 g, 1.54 mmol) in dichloromethane (5 mL) at 0° C. The reaction mixture was stirred at room temperature overnight and then the pH was then neutralized by addition of an aqueous solution of hydrochloric acid (6 M). The resulting mixture was extracted twice with ethyl acetate and the combined organic extracts were washed with water, dried over anhydrous sodium sulfate, filtered and evaporated under reduced pressure to give 225 mg of (E)-3-ethoxy-N-(3-methoxy-4-nitro-phenyl)-acrylamide as an orange solid.

Step B: Synthesis of 7-methoxy-6-nitro-1H-quinolin-2-one

Concentrated sulfuric acid (1 mL) was added to (E)-3-ethoxy-N-(3-methoxy-4-nitro-phenyl)-acrylamide (225 mg) with cooling and the resulting mixture was stirred at room temperature for 1.5 hours. The reaction mixture was then poured into ice-water and stirred for 1 hour. The solid which crushed out was collected by filtration and dried under vacuum to give 142 mg of 7-methoxy-6-nitro-1H-quinolin-2-one as a brown solid. MS=221 [M+H]⁺.

Step C: Synthesis of 2-chloro-7-methoxy-6-nitro-quinoline

A mixture of 7-methoxy-6-nitro-1H-quinolin-2-one (0.13 g) and phosphorus oxychloride (1 mL) was heated at 110° C. for 2 hours. The resulting mixture was then cooled and poured into ice. The solid which formed was collected by filtration and dried under vacuum to afford 0.119 g of 2-chloro-7-methoxy-6-nitro-quinoline as a brown solid.

Step D: Synthesis of 2-(7-methoxy-6-nitro-quinolin-2-ylamino)-ethanol

A mixture of 2-chloro-7-methoxy-6-nitro-quinoline (0.1 g, 0.42 mmol) and 2-aminoethanol (38 μL, 0.63 mmol) in anhydrous 1,4-dioxane (5 mL) was heated at 90° C. overnight. A second aliquot of 2-aminoethanol (38 μL, 0.63 mmol) was added and the resulting mixture was heated at 90° C. overnight. The reaction mixture was then concentrated under reduced pressure, the residue was washed with water, dried over anhydrous sodium sulfate, filtered and evaporated under reduced pressure to give 70 mg of 2-(7-methoxy-6-nitro-quinolin-2-ylamino)-ethanol as a solid without further purifications. MS=264 [M+H]$^+$.

Step E: Synthesis of 2-(6-amino-7-methoxy-quinolin-2-ylamino)-ethanol

A mixture of 2-(7-methoxy-6-nitro-quinolin-2-ylamino)-ethanol (0.5 g, 1.90 mmol), iron powder (0.32 g, 5.70 mmol) and ammonium chloride (0.32 g, 5.70 mmol) in a mixture of ethanol and water (3/1, 16 mL) was heated at reflux for 2 hours. The reaction mixture was then filtered through a CELITE™ pad, the filtrate was evaporated under reduced pressure and the residue was triturated ten times with a mixture of dichloromethane and methanol (9/1, 50 mL). The residue was concentrated under reduced pressure to afford 0.425 g of 2-(6-amino-7-methoxy-quinolin-2-ylamino)-ethanol as a brown solid.

Step F: Synthesis of N$^2$-[2-(tert-butyl-dimethyl-silanyloxy)-ethyl]-7-methoxy-quinoline-2,6-diamine A mixture of 2-(6-amino-7-methoxy-quinolin-2-ylamino)-ethanol (0.4 g, 1.72 mmol), tert-butyldimethylchlorosilane (0.8 g, 5.15 mmol) and imidazole (0.4 g, 5.15 mmol) in dichloromethane (20 mL) was stirred at room temperature for 62 hours. The resulting mixture was washed with water and the organic layer was separated, dried over anhydrous sodium sulfate, filtered and evaporated under reduced pressure. The crude residue was purified by flash chromatography (EtOAc/hexane, 3/7) to afford 206 mg of N$^2$-[2-(tert-butyl-dimethyl-silanyloxy)-ethyl]-7-methoxy-quinoline-2,6-diamine as a brown oil. MS=348 [M+H]$^+$.

Preparation 31: Synthesis of (2'-Amino-4'-chloro-biphenyl-4-yl)-methanol

The synthesis of (2'-amino-4'-chloro-biphenyl-4-yl)-methanol was carried out according to the process shown in Scheme 31.

Step A: Synthesis of (4'-chloro-2'-nitro-biphenyl-4-yl)-methanol

Nitrogen was bubbled through a mixture of 1-bromo-4-chloro-2-nitro-benzene (1.25 g, 5.3 mmol), bis(triphenylphosphine)palladium(II) chloride (90 mg, 0.13 mmol) and potassium phosphate tribasic (4.2 g, 19.7 mmol) in anhydrous 1,2-dimethoxyethane (30 mL) for 15 minutes. A solution of 4-(hydroxymethyl)phenylboronic acid (0.8 g, 5.3 mmol) in anhydrous 1,2-dimethoxyethane (1.5 mL) was added and the resulting mixture was heated at 80° C. overnight.

The reaction mixture was then poured into water and extracted twice with ethyl acetate. The combined organic extracts were dried over anhydrous sodium sulfate, filtered and evaporated under reduced pressure. The crude residue was purified by flash chromatography (hexane/EtOAc, 70/30) to give 0.367 g of (4'-chloro-2'-nitro-biphenyl-4-yl)-methanol as a solid.

Step B: Synthesis of (2'-amino-4'-chloro-biphenyl-4-yl)-methanol (4'-Chloro-2'-nitro-biphenyl-4-yl)-methanol was reduced utilizing the procedure described in Preparation 9, Step D.

Utilizing the above described procedure and the appropriate starting materials, the following compounds were prepared:
(2'-amino-4'-chloro-biphenyl-3-yl)-methanol; and
(2'-amino-4'-chloro-biphenyl-4-ylmethyl)-carbamic acid tert-butyl ester.

Preparation 32: Synthesis of 6-(3-Hydroxy-propyl)-pyrazolo[1,5-a]pyrimidine-3-carboxylic acid The synthesis of 6-(3-hydroxy-propyl)-pyrazolo[1,5-a]pyrimidine-3-carboxylic acid was carried out according to the process shown in Scheme 32.

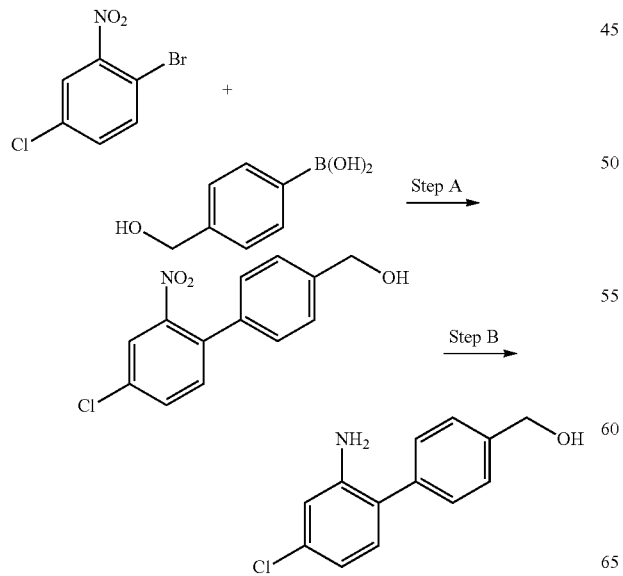

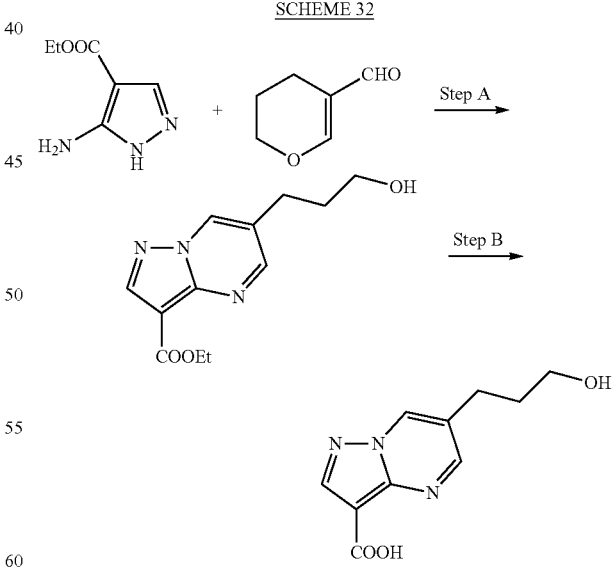

Step A: Synthesis of 6-(3-hydroxy-propyl)-pyrazolo[1,5-a]pyrimidine-3-carboxylic acid ethyl ester Sodium hydride (60% suspension in mineral oil, 350 mg, 8.78 mmol) was added, at 0° C., to a solution of 5-amino- 1H-pyrazole-4-carboxylic acid ethyl ester (1.4 g, 8.9 mmol) and 5,6-dihydro-4H-pyran-3-carbaldehyde (0.5 g, 4.5 mmol) in anhydrous N,N-dimethylformamide (10 mL) and the resulting mixture was stirred, at 0° C., for 30 minutes. The reaction mixture was stirred at room temperature overnight and then heated at 50° C. for 2 hours. The resulting mixture was partitioned between water and ethyl acetate and the organic layer was separated, dried over anhydrous sodium sulfate, filtered and evaporated under reduced pressure. The crude residue was purified by flash chromatography to afford 0.24 g of 6-(3-hydroxy-propyl)-pyrazolo[1,5-a]pyrimidine-3-carboxylic acid ethyl ester as a white solid. MS=250 [M+H]$^+$.

Step B: Synthesis of 6-(3-hydroxy-propyl)-pyrazolo[1,5-a]pyrimidine-3-carboxylic acid A mixture of 6-(3-hydroxy-propyl)-pyrazolo[1,5-a]pyrimidine-3-carboxylic acid ethyl ester (5 mg) and an aqueous solution of sodium hydroxide (5 drops) was stirred at room temperature for 16 hours. The reaction mixture was then acidified by addition of an aqueous solution of hydrochloric acid (3 M). The precipitate was collected by filtration to give 6-(3-hydroxy-propyl)-pyrazolo[1,5-a]pyrimidine-3-carboxylic acid. MS=222 [M+H]$^+$.

Preparation 33: Synthesis of 6-Benzyloxy-pyrazolo[1,5-a]pyrimidine-3-carboxylic acid The synthesis of 6-benzyloxy-pyrazolo[1,5-a]pyrimidine-3-carboxylic acid was carried out according to the process shown in Scheme 33.

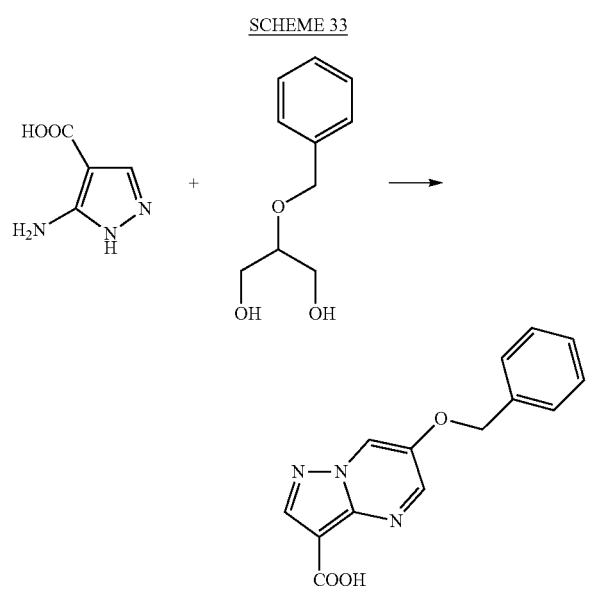

To solution of oxalyl chloride (0.6 mL, 6.87 mmol) in anhydrous dichloromethane (15 mL), cooled at −78° C., was added, dropwise, a solution of anhydrous dimethyl sulfoxide (1.2 mL, 16.5 mmol) in dichloromethane (2 mL) and the resulting mixture was stirred for 10 minutes at −78° C. A solution of 2-benzyloxy-1,3-propanediol (0.5 g, 2.75 mmol) in dichloromethane (2 mL) was then added dropwise at −78° C. and the reaction mixture was stirred for 15 minutes. Triethylamine (4.6 mL, 33 mmol) was then added dropwise at −78° C. and the resulting mixture was stirred for 1 hour. The cold bath was removed and an aqueous solution of hydrochloric acid (6 M, 6 mL, 36 mmol) was added, followed by 5-amino-1H-pyrazole-4-carboxylic acid (0.35 g, 2.75 mmol) and the reaction mixture was heated at 70° C. for 1 hour. The solid formed was collected by filtration, washed with water and dried under vacuum. The solid residue (0.53 g) was then washed with dichloromethane to give 65 mg (9% yield) of 6-benzyloxy-pyrazolo[1,5-a]pyrimidine-3-carboxylic acid. MS=270 [M+H]$^+$.

Preparation 34: Synthesis of 5-chloro-2-(3-methoxy-propoxy)-phenylamine

The synthesis of 5-chloro-2-(3-methoxy-propoxy)-phenylamine was carried out according to the process shown in Scheme 34.

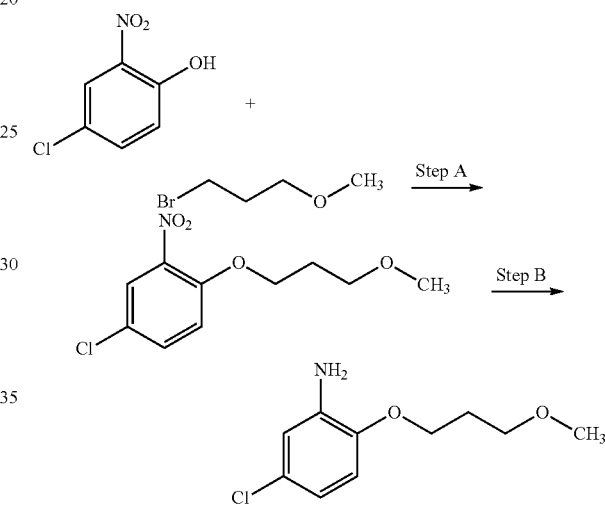

Step A: Synthesis of 4-chloro-1-(3-methoxy-propoxy)-2-nitro-benzene

Sodium hydride (60% suspension in mineral oil, 0.15 g, 3.75 mmol) was added, at room temperature, to a solution of 4-chloro-2-nitrophenol (0.5 g, 2.88 mmol) in anhydrous N,N-dimethylformamide (15 mL) and the resulting mixture was stirred for 5 minutes. 1-Bromo-3-methoxy-propane (0.485 g, 3.17 mmol) was then added and the reaction mixture was heated at 80° C. for 62 hours. The resulting mixture was partitioned between an aqueous solution of sodium hydroxide (3 M) and ethyl acetate, the organic layer was separated, washed twice with an aqueous solution of sodium hydroxide (3 M) and once with brine, dried over anhydrous sodium sulfate, filtered and evaporated under reduced pressure. The crude residue was purified by flash chromatography (hexane/EtOAc, 90/10 to 50/50) to give 0.455 g (64% yield) of 4-chloro-1-(3-methoxy-propoxy)-2-nitro-benzene as a yellow solid.

Step B: Synthesis of 5-chloro-2-(3-methoxy-propoxy)-phenylamine

Stannous chloride (1.04 g, 5.49 mmol) was added to a solution of 4-chloro-1-(3-methoxy-propoxy)-2-nitro-benzene (0.448 g, 1.82 mmol) in a mixture of ethanol and ethyl acetate (1/1, 20 mL) and the resulting mixture was stirred at room temperature overnight. More stannous chloride (0.76 g, 4 mmol) was added and the reaction mixture was stirred for 1 day. The resulting mixture was partitioned between an aqueous solution of sodium bicarbonate (5%) and ethyl acetate, the aqueous solution was separated and extracted twice with ethyl acetate, the combined organic extracts were washed with brine, dried over anhydrous sodium sulfate, filtered and evaporated under reduced pressure. The yellow oily residue was purified by flash chromatography (hexane/EtOAc, 80/20 to 60/40) to give 0.29 g (74% yield) of 5-chloro-2-(3-methoxy-propoxy)-phenylamine as a yellow oil.

The following compounds were prepared utilizing the above described procedure and the appropriate starting materials:
5-chloro-2-(2-methoxy-ethoxy)-phenylamine; and
5-chloro-2-isobutoxy-phenylamine.

Preparation 35: Synthesis of 4-(2-Amino-4-chloro-phenoxy)-piperidine-1-carboxylic acid tert-butyl ester The synthesis of 4-(2-amino-4-chloro-phenoxy)-piperidine-1-carboxylic acid tert-butyl ester was carried out according to the process shown in Scheme 35.

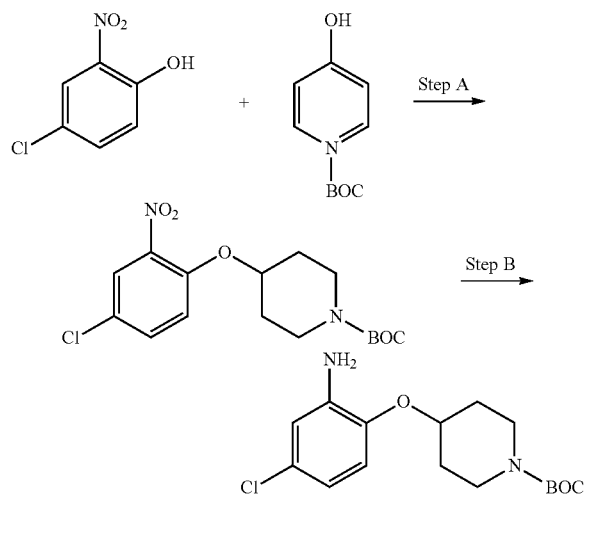

SCHEME 35

Step A: Synthesis of 4-(4-chloro-2-nitro-phenoxy)-piperidine-1-carboxylic acid tert-butyl ester A solution of diisopropylazodicarboxylate (3.4 mL, 17.55 mmol) in anhydrous tetrahydrofuran (5 mL) was added, at 0° C., to a solution of 4-chloro-2-nitrophenol (2.0 g, 11.52 mmol), 1-BOC-4-hydroxypiperidine (3.48 g, 17.3 mmol) and triphenylphosphine (4.6 g, 17.5 mmol) in anhydrous tetrahydrofuran (25 mL) and the resulting mixture was stirred at 0° C. for 1 hour. Then the reaction mixture was stirred at room temperature for 24 hours; the residue was partitioned between water and ethyl acetate. The organic layer was separated and the aqueous layer was extracted twice with ethyl acetate; the combined organic extracts were washed with brine, dried over anhydrous sodium sulfate, filtered and evaporated under reduced pressure. The crude residue was purified by flash chromatography (hexane/EtOAc, 90/10 to 70/30) to give an oily residue which was washed with hexane to afford 6.5 g of an off-white solid material. This solid residue was repurified by flash chromatography to give 3.61 g (88% yield) of 4-(4-chloro-2-nitro-phenoxy)-piperidine-1-carboxylic acid tert-butyl ester as a white solid.

Step B: Synthesis of 4-(2-amino-4-chloro-phenoxy)-piperidine-1-carboxylic acid tert-butyl ester 4-(4-Chloro-2-nitro-phenoxy)-piperidine-1-carboxylic acid tert-butyl ester was reduced following the procedure described in Preparation 37, Step E, to afford 4-(2-amino-4-chloro-phenoxy)-piperidine-1-carboxylic acid tert-butyl ester as a light yellow oil in 76% yield.
4-(6-amino-quinolin-7-yloxy)-butan-2-ol;
4-(2-amino-4-chloro-phenoxy)-phenol; and
3-(2-amino-4-chloro-phenoxy)-phenol.

Preparation 36: Synthesis of 3'-(tert-Butyl-dimethyl-silanyloxy)-4-chloro-biphenyl-2-ylamine Utilizing the above described procedure and the appropriate starting materials the following compounds were prepared:
The synthesis of 3'-(tert-butyl-dimethyl-silanyloxy)-4-chloro-biphenyl-2-ylamine was carried out according to the process shown in Scheme 36.

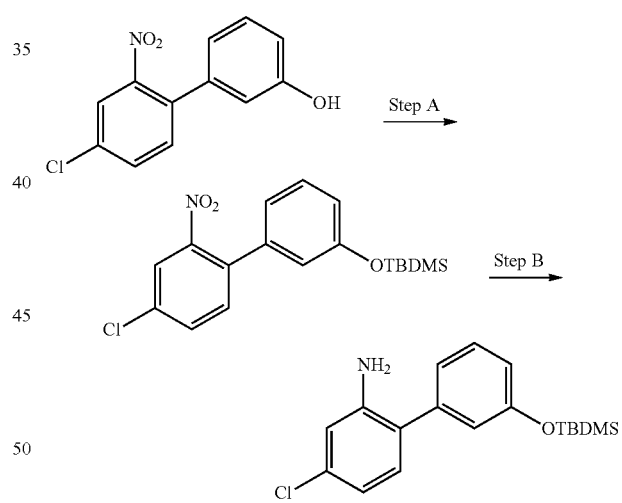

SCHEME 36

Step A: Synthesis of tert-butyl-(4'-chloro-2'-nitro-biphenyl-3-yloxy)-dimethyl-silane tert-Butyldimethylchlorosilane (0.82 g, 5.44 mmol) was added at room temperature to a solution of 4'-chloro-2'-nitro-biphenyl-3-ol (1.05 g, 4.21 mmol) and imidazole (0.58, 8.52 mmol) in anhydrous N,N-dimethylformamide (30 mL) and the resulting mixture was stirred at room temperature for 4 days. The reaction mixture was then partitioned between water and ethyl acetate, the organic layer was separated and the aqueous layer was extracted twice with ethyl acetate. The combined organic extracts were washed with water and brine, dried over anhydrous sodium sulfate, filtered and evaporated under reduced pressure. The crude residue was purified on a silica gel plug (hexane/EtOAc, 90/10) to give 1.43 g (94% yield) of tert-butyl-(4'-chloro-2'-nitro-biphenyl-3-yloxy)-dimethyl-silane as a yellow oil.

Step B: Synthesis of 3'-(tert-butyl-dimethyl-silanyloxy)-4-chloro-biphenyl-2-ylamine tert-Butyl-(4'-chloro-2'-nitro-biphenyl-3-yloxy)-dimethyl-silane was reduced following the procedure described in Preparation 37, Step E, to afford 3'-(tert-butyl-dimethyl-silanyloxy)-4-chloro-biphenyl-2-ylamine in 88% yield as a colorless oil.

4'-(tert-Butyl-dimethyl-silanyloxy)-4-chloro-biphenyl-2-ylamine was prepared following the above described procedure and utilizing the appropriate starting materials.

Preparation 37: Synthesis of [1-(2-Amino-5-phenyl-carbamoyl-phenyl)-piperidin-4-ylmethyl]-carbamic acid tert-butyl ester The synthesis of [1-(2-amino-5-phenylcarbamoyl-phenyl)-piperidin-4-ylmethyl]-carbamic acid tert-butyl ester was carried out according to the process shown in Scheme 37.

SCHEME 37

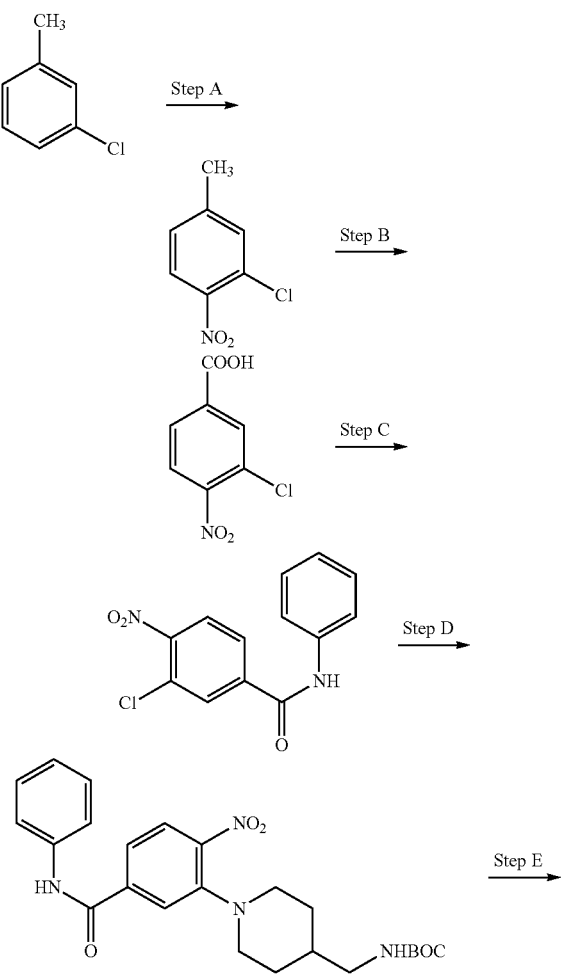

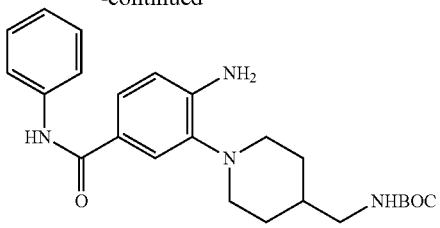

Step A: Synthesis of 2-chloro-4-methyl-1-nitro-benzene

Concentrated nitric acid (16 mL) was slowly added, at 0° C., to a solution of 3-chlorotoluene (3 mL, 25.4 mmol) and concentrated sulfuric acid (6 mL) in glacial acetic acid (20 mL) and the resulting mixture was stirred for 24 hours allowing the temperature to rise until room temperature. The reaction mixture was then poured into ice-water and partitioned between water and diethyl ether. The aqueous phase was separated and extracted twice with diethyl ether; the combined organic extracts were washed with water and brine, dried over anhydrous sodium sulfate, filtered and evaporated under reduced pressure. The yellow oily residue was purified on a silica gel plug and twice by flash chromatography to give 1.22 g (14% yield) of 2-chloro-4-methyl-1-nitro-benzene as a yellow oil and 3.39 g (39% yield) of 4-chloro-2-methyl-1-nitro-benzene.

Step B: Synthesis of 3-chloro-4-nitro-benzoic acid

2-Chloro-4-methyl-1-nitro-benzene (1.2 g, 6.99 mmol) in a mixture of water and pyridine (2/1, 30 mL) was heated at 90° C. then potassium permanganate (5.2 g, 32.9 mmol) was added in 4 portions at intervals of 1.5 hours. The reaction mixture was heated at 90° C. for 8 hours and then more potassium permanganate (2 g) was added and the resulting mixture was stirred at 90° C. overnight. More potassium permanganate (2 g) was added and the resulting mixture was stirred at 90° C. for 1 hour, the solid was filtered off on a CELITE™ pad. Water (50 mL) was added to the filtrate; the resulting mixture was acidified until pH<2 and was extracted 3 times with ethyl acetate. The combined organic extracts were washed with water and brine, dried over anhydrous sodium sulfate, filtered and evaporated under reduced pressure to give 1.19 g (84% yield) of 3-chloro-4-nitro-benzoic acid as a light yellow solid without further purifications Step C: Synthesis of 3-chloro-4-nitro-N-phenyl-benzamide Diisopropylethylamine (0.65 mL, 3.7 mmol) was added to a mixture of 3-chloro-4-nitro-benzoic acid (0.2 g, 0.992 mmol), aniline (0.1 mL, 1.1 mmol) and HBTU (0.42 g, 1.1 mmol) in acetonitrile (20 mL) and the reaction mixture was stirred at 80° C. for 8 hours and then at room temperature for 62 hours. The resulting mixture was then partitioned between water and ethyl acetate, the organic layer was separated and the aqueous layer was extracted twice with ethyl acetate. The combined organic extracts were washed with brine, dried over anhydrous sodium sulfate, filtered and evaporated under reduced pressure. The crude residue was purified on a silica gel plug (hexane/EtOAc, 80/20) to afford 135 mg (49% yield) of 3-chloro-4-nitro-N-phenyl-benzamide as a yellow solid.

Step D: Synthesis of [1-(2-nitro-5-phenylcarbamoyl-phenyl)-piperidin-4-ylmethyl]-carbamic acid tert-butyl ester To a solution of 3-chloro-4-nitro-N-phenyl-benzamide (0.13 g, 0.47 mmol) in N,N-dimethylformamide (10 mL) were added piperidin-4-ylmethyl-carbamic acid tert-butyl ester (0.12 g, 0.56 mmol) and potassium carbonate (0.1 g, 0.72 mmol) and the resulting mixture was heated at 50° C. overnight. The reaction mixture was then heated at 80° C. for 8 hours; then more piperidin-4-ylmethyl-carbamic acid tert-butyl ester (0.33 mmol) and potassium carbonate (0.14 g, 1 mmol) were added and the resulting mixture was heated at 85° C. overnight. The reaction mixture was partitioned between water and ethyl acetate, the organic layer was separated and the aqueous layer was extracted twice with ethyl acetate. The combined organic extracts were washed with water and brine, dried over anhydrous sodium sulfate, filtered and evaporated under reduced pressure. The crude residue was purified on a silica gel plug (hexane/EtOAc, 20/80 to 40/60) to give 0.13 g, (61% yield) of [1-(2-nitro-5-phenylcarbamoyl-phenyl)-piperidin-4-ylmethyl]-carbamic acid tert-butyl ester as on orange colored solid.

Step E: Synthesis of [1-(2-amino-5-phenylcarbamoyl-phenyl)-piperidin-4-ylmethyl]-carbamic acid tert-butyl ester To a solution of [1-(2-nitro-5-phenylcarbamoyl-phenyl)-piperidin-4-ylmethyl]-carbamic acid tert-butyl ester (0.13 g, 0.286 mmol) in a mixture of ethanol (8 mL), ethyl acetate (3 mL) and water (3 mL) were added ammonium chloride (0.12 g, 7.6 mmol) and iron powder (0.12 g, 7.5 mmol) and the resulting mixture was heated at 80° C. for 4 hours. The reaction mixture was filtered through a CELITE™ pad, the filter cake was washed with ethyl acetate. The filtrate was washed with and aqueous solution of sodium bicarbonate (5%) and with brine, dried over anhydrous sodium sulfate, filtered and evaporated under reduced pressure to afford 0.12 g (quantitative yield) of [1-(2-amino-5-phenylcarbamoyl-phenyl)-piperidin-4-ylmethyl]-carbamic acid tert-butyl ester as light yellow foam.

Preparation 38: Synthesis of 7-[4-(tert-Butyl-dimethyl-silanyloxy)-cyclohexyloxy]-quinolin-6-ylamine The synthesis of 7-[4-(tert-butyl-dimethyl-silanyloxy)-cyclohexyloxy]-quinolin-6-ylamine was carried out according to the process shown in Scheme 38.

SCHEME 38

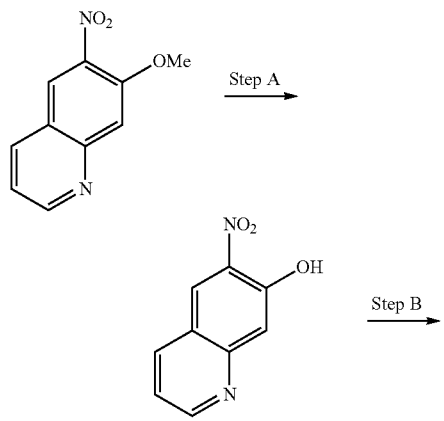

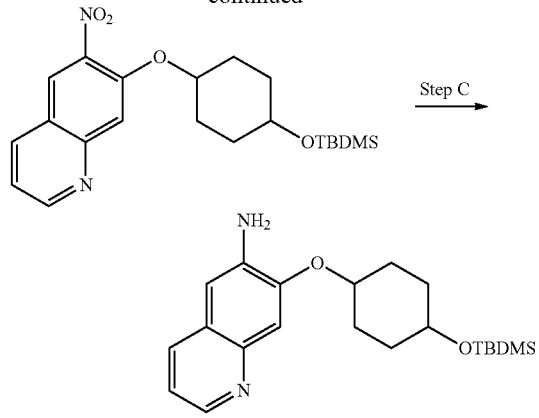

Step A: Synthesis of 6-nitro-quinolin-7-ol

A mixture of 7-methoxy-6-nitro-quinoline (1.5 g, 7.35 mmol) and pyridine hydrochloride (2.6 g, 22.58 mmol) was heated at 150° C. for ca. 5 hours. The residue was dissolved in an aqueous solution of sodium hydroxide (3 M) and extracted twice with ethyl acetate. The combined organic extract were washed twice with an aqueous solution of sodium hydroxide (3 M) and then discarded. The combined aqueous layers were neutralized (pH 7) by addition of concentrated hydrochloric acid and extracted 4 times with ethyl acetate. The combined organic extracts were dried over anhydrous sodium sulfate, filtered and evaporated under reduced pressure. The yellow solid residue was purified on a silica gel plug to give 1.29 g (69% yield) of 6-nitro-quinolin-7-ol as a yellow solid.

Step B: Synthesis of 7-[4-(tert-butyl-dimethyl-silanyloxy)-cyclohexyloxy]-6-nitro-quinoline 7-[4-(tert-Butyl-dimethyl-silanyloxy)-cyclohexyloxy]-6-nitro-quinoline was synthesized following the procedure described in Preparation 2, Step B.

Step C: Synthesis of 7-[4-(tert-butyl-dimethyl-silanyloxy)-cyclohexyloxy]-quinolin-6-ylamine 7-[4-(tert-Butyl-dimethyl-silanyloxy)-cyclohexyloxy]-6-nitro-quinoline was reduced as described in Preparation 37, Step E, to afford 7-[4-(tert-butyl-dimethyl-silanyloxy)-cyclohexyloxy]-quinolin-6-ylamine in 31% yield.

Utilizing the above described procedure and the appropriate strating materials, the following compounds were prepared:

7-[3-(tert-butyl-dimethyl-silanyloxy)-cyclopentyloxy]-quinolin-6-ylamine;
7-[3-(tert-butyl-dimethyl-silanyloxy)-1-methyl-butoxy]-quinolin-6-ylamine;
7-[3-(tert-butyl-dimethyl-silanyloxy)-propoxy]-quinolin-6-ylamine;
[3-(6-amino-quinolin-7-yloxy)-propyl]-carbamic acid tert-butyl ester;
3-(6-amino-quinolin-7-yloxy)-pyrrolidine-1-carboxylic acid tert-butyl ester;—trans-7-[4-(tert-butyl-diphenyl-silanyloxy)-cyclohexyloxy]-quinolin-6-ylamine, (4-(trans-tert-butyl-diphenyl-silanyloxy)-cyclohexanol and cis-tert-butyl-diphenyl-silanyloxy)-cyclohexanol were prepared as described in Preparation 2, Step A, and were separated by flash-chromatography (EtOAc/hexane, 1/1)); and cis-7-[4-(tert-butyl-diphenyl-silanyloxy)-cyclohexyloxy]-quinolin-6-ylamine.

Preparation 39: Synthesis of 4-Amino-N-[2-(tert-butyl-dimethyl-silanyloxy)-ethyl]-3-methoxy-benzamide The synthesis 4-amino-N-[2-(tert-butyl-dimethyl-silanyloxy)-ethyl]-3-methoxy-benzamide was carried out according to the process shown in Scheme 39.

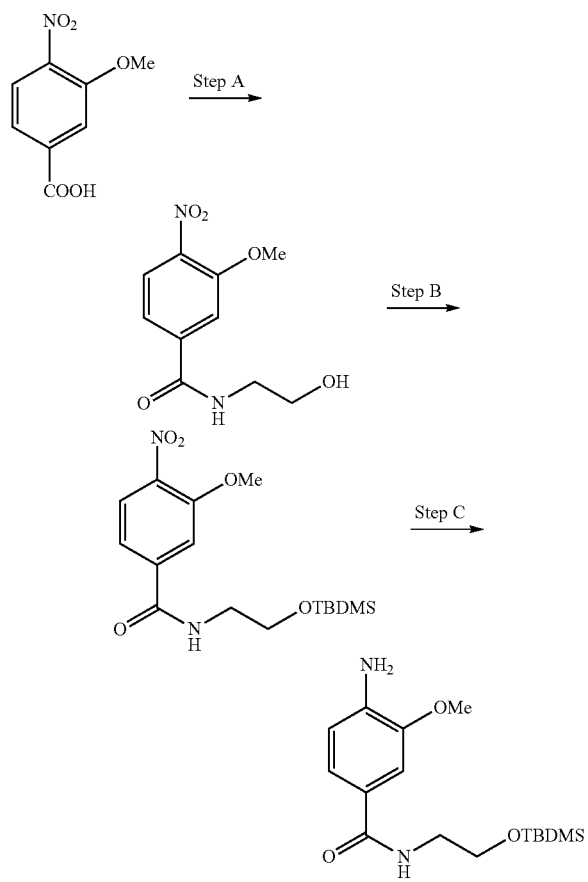

Step A: Synthesis of N-(2-hydroxy-ethyl)-3-methoxy-4-nitro-benzamide

A suspension of 3-methoxy-4-nitro-benzoic acid (1.5 g, 7.61 mmol) in thionyl chloride (20 mL) and N,N-dimethylformamide (2 drops) was heated at reflux for 2 hours. The solvent was then evaporated under reduced pressure to give a light yellow solid. A portion of this residue (3.8 mmol) was dissolved in acetone (previously dried over anhydrous sodium sulfate) (20 mL) and cooled in an ice bath. Then a solution of ethylendiamine (0.46 mL, 7.62 mmol) in water (10 mL) was added at 0° C. and the resulting mixture was stirred at room temperature for 30 minutes. The reaction mixture was partitioned between water and ethyl acetate; the aqueous phase was separated and extracted twice with ethyl acetate. The combined organic extracts were washed with brine, dried over anhydrous sodium sulfate, filtered and evaporated under reduced pressure. The crude residue was purified on a silica gel plug (EtOAc/MeOH, 100/0 to 98/2) to afford 0.42 g (46% 2 steps yield) of N-(2-hydroxy-ethyl)-3-methoxy-4-nitro-benzamide.

Step B: Synthesis of N-[2-(tert-butyl-dimethyl-silanyloxy)-ethyl]-3-methoxy-4-nitro-benzamide N-[2-(tert-butyl-dimethyl-silanyloxy)-ethyl]-3-methoxy-4-nitro-benzamide was synthesized, utilizing the appropriate starting materials, as described in Preparation 36, Step A, and was obtained in quantitative yield as a pale yellow solid.

Step C: Synthesis of 4-amino-N-[2-(tert-butyl-dimethyl-silanyloxy)-ethyl]-3-methoxy-benzamide N-[2-(tert-Butyl-dimethyl-silanyloxy)-ethyl]-3-methoxy-4-nitro-benzamide was reduced, utilizing the appropriate starting materials, as described in Preparation 37, Step E, to afford 4-amino-N-[2-(tert-butyl-dimethyl-silanyloxy)-ethyl]-3-methoxy-benzamide as a colorless oil in 91% yield.

4-Amino-N-[3-(tert-butyl-dimethyl-silanyloxy)-propyl]-3-methoxy-benzamide was prepared utilizing the above described procedure and the appropriate starting materials.

Preparation 40: Synthesis of 2-[3-(tert-Butyl-dimethyl-silanyloxy)-propoxy]-5-chloro-phenylamine The synthesis 2-[3-(tert-butyl-dimethyl-silanyloxy)-propoxy]-5-chloro-phenylamine was carried out according to the process shown in Scheme 40.

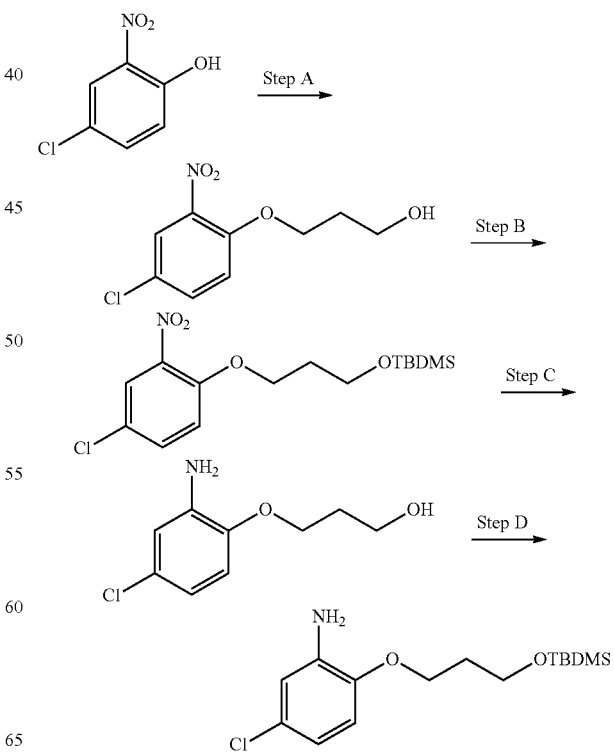

Step A: Synthesis of 3-(4-chloro-2-nitro-phenoxy)-propan-1-ol 3-(4-Chloro-2-nitro-phenoxy)-propan-1-ol was synthesized, utilizing the appropriate starting materials, following the procedure described in Preparation 2, Step B, and was obtained as a yellow oil in 48% yield.

Step B: Synthesis of tert-butyl-[3-(4-chloro-2-nitro-phenoxy)-propoxy]-dimethyl-silane tert-Butyl-[3-(4-chloro-2-nitro-phenoxy)-propoxy]-dimethyl-silane was synthesized, utilizing the appropriate starting materials, as described in Preparation 36, Step A, and was obtained in 82% yield as a yellow oil.

Step C: Synthesis of 3-(2-amino-4-chloro-phenoxy)-propan-1-ol

To a solution of tert-butyl-[3-(4-chloro-2-nitro-phenoxy)-propoxy]-dimethyl-silane (0.37 g, 1.07 mmol), in a mixture of ethanol (10 mL) and water (3 mL), were added ammonium chloride (0.3 g, 5.37 mmol) and iron powder (0.3 g, 5.6 mmol) and the resulting mixture was heated at 80° C. overnight. The solid was filtered through a CELITE™ pad, the filter cake was washed with ethyl acetate. The filtrate was washed with water and brine, dried over anhydrous sodium sulfate, filtered and evaporated under reduced pressure. The crude residue was purified on a silica gel plug to give 0.188 g (87% yield) of 3-(2-amino-4-chloro-phenoxy)-propan-1-ol as a yellow oil.

Step D: Synthesis of 2-[3-(tert-butyl-dimethyl-silanyloxy)-propoxy]-5-chloro-phenylamine 2-[3-(tert-Butyl-dimethyl-silanyloxy)-propoxy]-5-chloro-phenylamine was synthesized, utilizing the appropriate starting materials, as described in Preparation 36, Step A.

Preparation 41: Synthesis of [1-(6-Amino-quinolin-7-yl)-piperidin-4-ylmethyl]-carbamic acid tert-butyl ester The synthesis of [1-(6-amino-quinolin-7-yl)-piperidin-4-ylmethyl]-carbamic acid tert-butyl ester was carried out according to the process shown in Scheme 41.

SCHEME 41

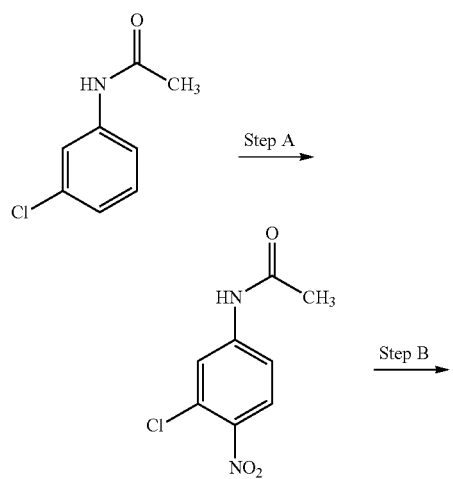

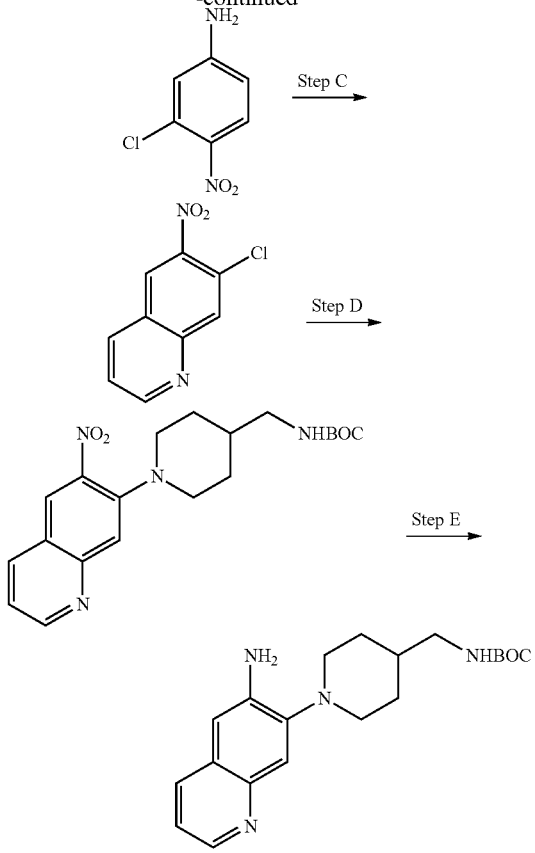

Step A: Synthesis of N-(3-chloro-4-nitro-phenyl)-acetamide

Fuming nitric acid (150 mL) was slowly added, at −50° C., over a period of 50 minutes to N-(3-chloro-phenyl)-acetamide (45 g). The reaction mixture was allowed to warm up to −20° C. and then was poured into ice-water. The solid formed was collected by filtration, washed with water, and dried under reduced pressure. The residue was washed with dichloromethane and dried under reduced pressure to afford 14 g of N-(3-chloro-4-nitro-phenyl)-acetamide as a light pink solid.

Step B: Synthesis of 3-chloro-4-nitro-phenylamine

A mixture of N-(3-chloro-4-nitro-phenyl)-acetamide (18.55 g, 86.4 mmol) and an aqueous solution of hydrochloric acid (6 M, 120 mL) was heated at reflux for 2 hours. The resulting mixture was cooled and poured into water (800 mL); the yellow solid which crushed out was collected by filtration, washed with water and dried under reduced pressure to give 5 g of 3-chloro-4-nitro-phenylamine. The water layer was basified until pH 8 by addition of potassium carbonate and then was extracted with dichloromethane. The organic layer was dried over anhydrous sodium sulfate, filtered and evaporated under reduced pressure to give 7.2 g of 3-chloro-4-nitro-phenylamine.

Step C: Synthesis of 7-chloro-6-nitro-quinoline

To a mixture of 3-chloro-4-nitro-phenylamine (10.6 g, 61.4 mmol), arsenic pentoxide (8.79 g, 38.2 mmol) and glycerol (26 mL, 172.1 mmol) at 100° C., was added, dropwise, concentrated sulfuric acid (10.5 mL, 197.6 mmol). The reaction mixture was heated at 150° C. for 2 hours and then was cooled at 80° C. Water (300 mL) was added and the resulting mixture was extracted 3 times with ethyl acetate. The combined organic extracts were dried over anhydrous sodium sulfate, filtered and evaporated under reduced pressure to give 8.7 g of a brown solid residue. A portion (2.7 g) of this crude material was purified by flash chromatography (DCM) to afford 974 mg of 7-chloro-6-nitro-quinoline as a light yellow solid and 1.108 g of 5-chloro-6-nitro-quinoline.

Step D: Synthesis of [1-(6-nitro-quinolin-7-yl)-piperidin-4-ylmethyl]-carbamic acid tert-butyl ester To a solution of 7-chloro-6-nitro-quinoline (974 mg, 4.67 mmol) in N,N-dimethylformamide (25 mL) were added potassium carbonate (1.93 g, 14.01 mmol) and piperidin-4ylmethyl-carbamic acid tert-butyl ester (1.00 g, 4.67 mmol) and the resulting mixture was heated at 100° C. overnight. The reaction mixture was cooled and partitioned between water (500 mL) and ethyl acetate (300 mL). The organic layer was separated, washed twice with water (500 mL), dried over anhydrous sodium sulfate, filtered and evaporated under reduced pressure.

The crude residue was purified twice by flash chromatography to afford 415 mg of [1-(6-nitro-quinolin-7-yl)-piperidin-4-ylmethyl]-carbamic acid tert-butyl ester as an orange solid.

Step E: Synthesis of [1-(6-amino-quinolin-7-yl)-piperidin-4-ylmethyl]-carbamic acid tert-butyl ester

[1-(6-Nitro-quinolin-7-yl)-piperidin-4-ylmethyl]-carbamic acid tert-butyl ester was reduced as described in Preparation 37, Step E, to give [1-(6-amino-quinolin-7-yl)-piperidin-4-ylmethyl]-carbamic acid tert-butyl ester as a light yellow solid in 93% yield.

Utilizing the above described procedure and the appropriate strating materials, the following compounds were prepared:
7-piperidin-1-yl-quinolin-6-ylamine;
[1-(2-amino-4-chloro-phenyl)-pyrrolidin-3-ylmethyl]-carbamic acid tert-butyl ester (Step D and Step E);
[1-(2-amino-4-chloro-phenyl)-piperidin-4-ylmethyl]-carbamic acid tert-butyl ester (Step D and Step E); and
[1-(6-amino-quinolin-7-yl)-piperidin-4-yl]-methanol (Step D and Step E).

Preparation 42: Synthesis of 3-(2-Amino-4-chloro-phenoxy)-propan-1-ol

The synthesis of 3-(2-amino-4-chloro-phenoxy)-propan-1-ol was carried out according to the process shown in Scheme 42.

SCHEME 42

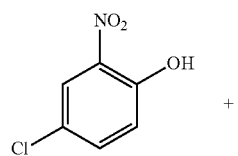

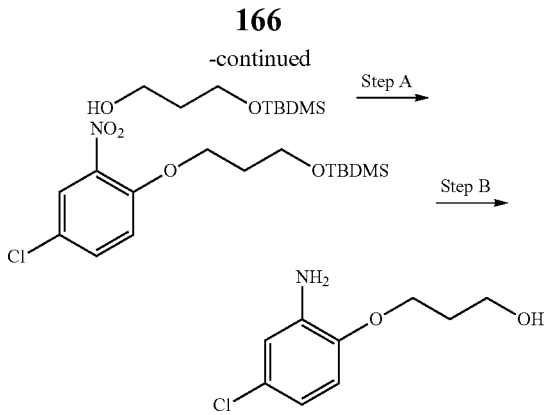

Step A: Synthesis of 2-[3-(tert-butyl-dimethyl-silanyloxy)-propoxy]-5-chloro-phenylamine 2-[3-(tert-Butyl-dimethyl-silanyloxy)-propoxy]-5-chloro-phenylamine was synthesized, utilizing the appropriate starting materials, as described in Preparation 2, Step B, and was obtained as a light yellow oil in 71% yield.

Step B: Synthesis of 3-(2-amino-4-chloro-phenoxy)-propan-1-ol

2-[3-(tert-butyl-dimethyl-silanyloxy)-propoxy]-5-chloro-phenylamine was reduced as described in Preparation 34, Step B, to afford 3-(2-amino-4-chloro-phenoxy)-propan-1-ol as a yellow oil in 42% yield.

Preparation 43: Synthesis of 5-Chloro-2-(2-triisopropylsilanyl-oxazol-5-ylmethoxy)-phenylamine The synthesis of 5-chloro-2-(2-triisopropylsilanyl-oxazol-5-ylmethoxy)-phenylamine was carried out according to the process shown in Scheme 43.

SCHEME 43

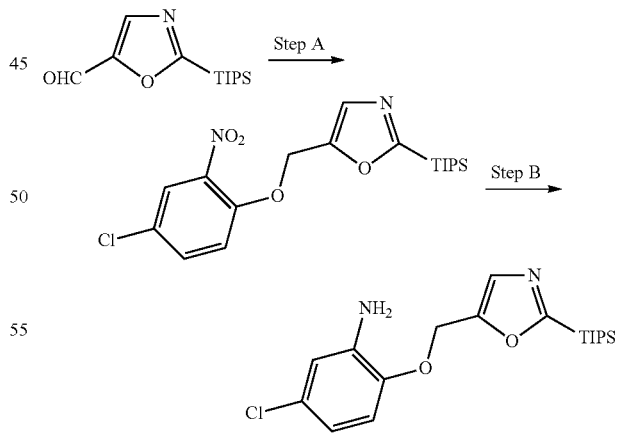

Step A: Synthesis of 5-(4-chloro-2-nitro-phenoxymethyl)-2-triisopropylsilanyl-oxazole Sodiumboron hydride (200 mg, 5.5 mmol) was added to a solution of 2-triisopropylsilyl-oxazole-5-carboxaldehyde (0.7 g, 2.7 mmol) in a mixture of methanol and tetrahydrofuran (1/1, 20 mL) and the resulting mixture was stirred at room temperature for 20 minutes. The reaction mixture was then diluted with ethyl acetate, washed with water and brine, dried over anhydrous sodium sulfate, filtered and evaporated under reduced pressure to give (2-triisopropylsilanyl-oxazol-5-yl)-methanol without further purifications. This material was treated with 4-chloro-2-nitro-phenol as described in Preparation 20, Step A, to give 0.7 g of 5-(4-chloro-2-nitro-phenoxymethyl)-2-triisopropylsilanyl-oxazole.

Step B: Synthesis of 5-chloro-2-(2-triisopropylsilanyl-oxazol-5-ylmethoxy)-phenylamine 5-(4-Chloro-2-nitro-phenoxymethyl)-2-triisopropylsilanyl-oxazole was reduced utilizing zinc dust as described in Preparation 20, Step B, to give 100 mg of 5-chloro-2-(2-triisopropylsilanyl-oxazol-5-ylmethoxy)-phenylamine.

Preparation 44: Synthesis of 3-[4-(tert-Butyl-dimethyl-silanyloxy)-cyclohexyloxy]-naphthalen-2-ylamine The synthesis of 3-[4-(tert-butyl-dimethyl-silanyloxy)-cyclohexyloxy]-naphthalen-2-ylamine was carried out according to the process shown in Scheme 44.

SCHEME 44

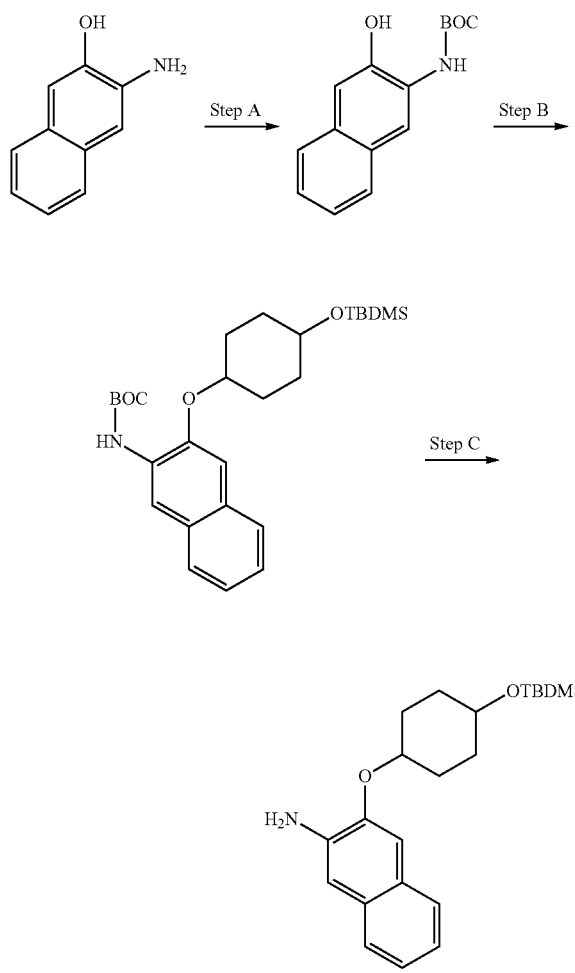

Step A: Synthesis of (3-hydroxy-naphthalen-2-yl)-carbamic acid tert-butyl ester

Di-tert-butyldicarbonate (1.37 g, 6.28 mmol) was added to a solution of 3-amino-2-naphthol (0.5 g, 3.14 mmol) in tetrahydrofuran (15 mL) and the resulting mixture was stirred at room temperature for 62 hours. The reaction mixture was then partitioned between water and ethyl acetate; the aqueous layer was separated and extracted twice with ethyl acetate. The combined organic extracts were washed with brine, dried over anhydrous sodium sulfate, filtered and evaporated under reduced pressure. The crude residue was purified on a silica gel plug (hexane/EtOAc, 80/20) to give a brown solid which was washed twice with hexane to give 0.69 g (85% yield) of (3-hydroxy-naphthalen-2-yl)-carbamic acid tert-butyl ester as a gray solid.

Step B: Synthesis of [3-(4-hydroxy-cyclohexyloxy)-naphthalen-2-yl]-carbamic acid tert-butyl ester

[3-(4-Hydroxy-cyclohexyloxy)-naphthalen-2-yl]-carbamic acid tert-butyl ester (colorless oil) was synthesized (68% yield) following the procedure described in Preparation 2, Step B.

Step C: Synthesis of 4-(3-amino-naphthalen-2-yloxy)-cyclohexanol

A mixture of [3-(4-hydroxy-cyclohexyloxy)-naphthalen-2-yl]-carbamic acid tert-butyl ester (0.15 g, 0.58 mmol) and trifluoroacetic acid (0.2 mL) in dichloromethane (5 mL) was stirred at room temperature for 16 hours. The reaction mixture was basified by addition of an aqueous solution of sodium hydroxide and was extracted twice with dichloromethane. The combined organic extracts were dried over anhydrous sodium sulfate, filtered and evaporated under reduced pressure. The crude residue was purified by flash chromatography (hexane/EtOAc, 75/25) to give 38 mg of 4-(3-amino-naphthalen-2-yloxy)-cyclohexanol and 66 mg of trifluoroacetic acid 4-(3-amino-naphthalen-2-yloxy)-cyclohexyl ester. The trifluoroacetate was treated with a solution of sodium hydroxide (11 mg) in ethanol (2 mL) and water and the resulting mixture was stirred at room temperature overnight. The reaction mixture was concentrated and the residue was partitioned between water and dichloromethane, the organic layer was dried over anhydrous sodium sulfate, filtered and evaporated under reduced pressure to afford additional 40 mg of 4-(3-amino-naphthalen-2-yloxy)-cyclohexanol.

Utilizing the above described procedure and the appropriate starting materials, the following compounds were prepared:

3-(3-amino-naphthalen-2-yloxy)-propan-1-ol; and 3-(3-amino-naphthalen-2-yloxy)-cyclopentanol.

Preparation 45: Synthesis of [3-(2-Amino-4-chloro-phenoxy)-cyclopentyl]-methanol The synthesis of [3-(2-amino-4-chloro-phenoxy)-cyclopentyl]-methanol was carried out according to the process shown in Scheme 45.

SCHEME 45

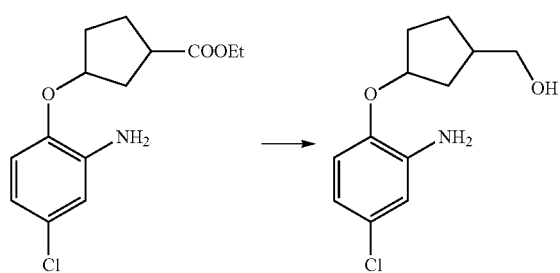

A solution of lithium aluminum hydride (1 M, 3 mL) was added to a cooled (0° C.) solution of 3-(2-amino-4-chloro-phenoxy)-cyclopentanecarboxylic acid ethyl ester (0.2 g) in tetrahydrofuran (5 mL) and the resulting mixture was stirred for 30 minutes. The reaction mixture was then quenched by addition of a saturated aqueous solution of ammonium chloride and filtered. The filter cake was washed with ethyl acetate and the filtrate was dried over anhydrous sodium sulfate, filtered and evaporated under reduced pressure to give 180 mg of [3-(2-amino-4-chloro-phenoxy)-cyclopentyl]-methanol without further purifications.

Preparation 46: Synthesis of 6-Methoxy-1H-indazol-5-ylamine

The synthesis of 6-methoxy-1H-indazol-5-ylamine was carried out according to the process shown in Scheme 46.

SCHEME 46

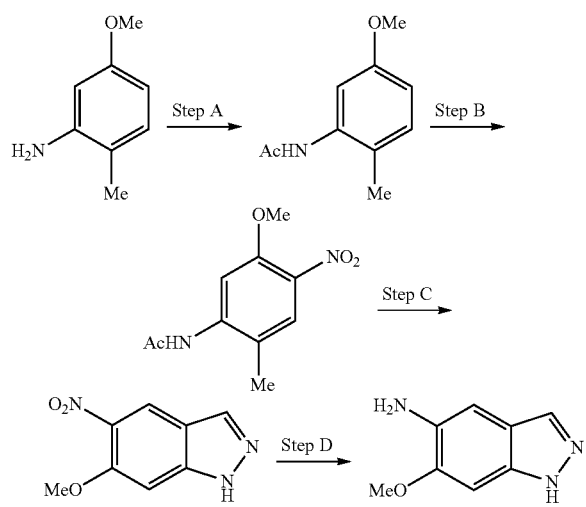

Step A: Synthesis of N-(5-methoxy-2-methyl-phenyl)-acetamide

Acetic anhydride (5.6 g, 54.66 mmol) was added to a solution of 5-methoxy-2-methyl-phenylamine (5.0 g, 36.44 mmol) in pyridine (30 mL) and the resulting mixture was stirred at room temperature overnight. Water was added and the pH was adjusted to 5 by addition of an aqueous solution of hydrochloric acid (3 M). The resulting mixture was extracted with dichloromethane; the organic layer was separated and washed with a saturated aqueous solution of sodium bicarbonate and with brine, dried over anhydrous sodium sulfate, filtered and evaporated under reduced pressure to afford 5.93 g of N-(5-methoxy-2-methyl-phenyl)-acetamide as a white solid without further purifications.

Step B: Synthesis of N-(5-methoxy-2-methyl-4-nitro-phenyl)-acetamide

Nitric acid (70%, 2.5 mL, 25.14 mmol) was added, dropwise, at a temperature ranging between 5 and 10° C., to a mixture of N-(5-methoxy-2-methyl-phenyl)-acetamide (3.0 g, 16.76 mmol) and concentrated sulfuric acid (10 mL) in glacial acetic acid (20 mL) and the resulting mixture was stirred for 3 hours. The reaction mixture was poured into ice-water and the solid formed was collected by filtration. The residue was dissolved in dichloromethane, dried over anhydrous sodium sulfate, filtered and evaporated under reduced pressure to give 2.135 g of N-(5-methoxy-2-methyl-4-nitro-phenyl)-acetamide as an off-white solid.

Step C: Synthesis of 6-methoxy-5-nitro-1H-indazole

To a mixture of N-(5-methoxy-2-methyl-4-nitro-phenyl)-acetamide (0.5 g, 2.23 mmol), potassium carbonate (0.26 g, 2.68 mmol), glacial acetic acid (0.15 mL, 2.68 mmol) and acetic anhydride (0.42 mL, 4.46 mmol) in chloroform (20 mL) was added, dropwise, at 40° C., isoamyl nitrile (0.6 mL, 4.46 mmol) and the resulting mixture was heated at 60° C. overnight. The reaction mixture was then basified by addition of a saturated aqueous solution of sodium bicarbonate and extracted twice with dichloromethane. The combined organic extracts were dried over anhydrous sodium sulfate, filtered and evaporated under reduced pressure. To the residue was added a mixture of an aqueous solution of hydrochloric acid (3 M, 10 mL) and methanol (10 mL) and the resulting mixture was heated at 80° C. for 2 hours. The reaction mixture was cooled, basified by addition of a saturated aqueous solution of sodium bicarbonate and extracted with dichloromethane. The organic extracts were dried over anhydrous sodium sulfate, filtered and evaporated under reduced pressure. The crude residue was purified by flash chromatography (EtOAc/hexane, 0/100 to 70/30) to afford 169 mg of 6-methoxy-5-nitro-1H-indazole as orange solid.

Step D: Synthesis of 6-methoxy-1H-indazol-5-ylamine

To a mixture of 6-methoxy-5-nitro-1H-indazole (0.16 g, 0.83 mmol), an aqueous solution of hydrochloric acid (6 M, 5 mL) and concentrated hydrochloric acid (2 mL) was added, in portions, at 0° C., stannous chloride (0.31 g, 1.66 mmol) and the resulting mixture was warmed up to room temperature. The reaction mixture was stirred at room temperature for 4 hours and then was quenched by addition of a saturated aqueous solution of sodium bicarbonate. The resulting mixture was extracted with dichloromethane; the organic extracts were dried over anhydrous sodium sulfate, filtered and evaporated under reduced pressure. The crude residue was triturated with dichloromethane to give a 2/1 mixture of 6-methoxy-1H-indazol-5-ylamine and 3-chloro-6-methoxy-1H-indazol-5-ylamine.

Preparation 47: Synthesis of 6-[2-(tert-Butyl-dimethyl-silanyloxy)-ethyl]-pyrazolo[1,5-a]pyrimidine-3-carboxylic acid The synthesis of 6-[2-(tert-butyl-dimethyl-silanyloxy)-ethyl]-pyrazolo[1,5-a]pyrimidine-3-carboxylic acid was carried out according to the process shown in Scheme 47.

SCHEME 47

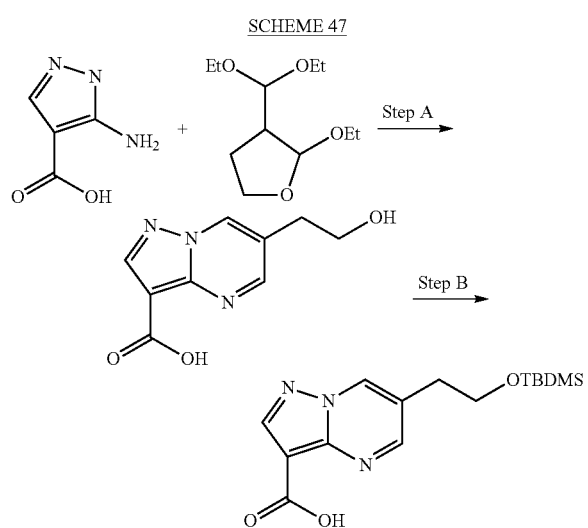

Step A: Synthesis of 6-(2-hydroxy-ethyl)-pyrazolo[1,5-a]pyrimidine-3-carboxylic acid To a cooled (0° C.) solution of 3-diethoxymethyl-2-ethoxy-tetrahydro-furan (prepared accordingly to WO2005/095317) (350 mg, 1.61 mmol) in dichloromethane (2 mL) was added an aqueous solution of hydrochloric acid (6 M, 2 mL) followed by 5-amino-1H-pyrazole-4-carboxylic acid (250 mg, 1.97 mmol) and the resulting mixture was gradually heated at 70° C. for 1 hour. The organic solvent evaporated while heating and the solid formed was collected by filtration of the aqueous layer to give 50 mg of 5-amino-1H-pyrazole-4-carboxylic acid residual. The filtrate was repeatedly triturated with diethyl ether, decanted and lyophilized to give 6-(2-hydroxy-ethyl)-pyrazolo[1,5-a]pyrimidine-3-carboxylic acid.

Step B: Synthesis of 6-[2-(tert-butyl-dimethyl-silanyloxy)-ethyl]-pyrazolo[1,5-a]pyrimidine-3-carboxylic acid 6-(2-Hydroxy-ethyl)-pyrazolo[1,5-a]pyrimidine-3-carboxylic acid was protected following the procedure described in Preparation 2, Step A.

Preparation 48: Synthesis of 6-methyl-pyrazolo[1,5-a]pyrimidine-3-carboxylic acid The synthesis of 6-methyl-pyrazolo[1,5-a]pyrimidine-3-carboxylic acid was carried out according to the process shown in Scheme 48.

SCHEME 48

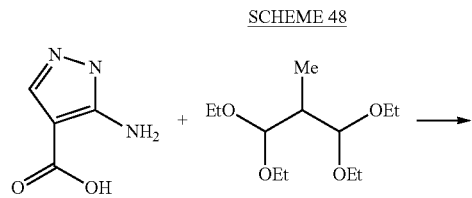

A suspension of 5-amino-1H-pyrazole-4-carboxylic acid (271 mg, 2.1 mmol) and 1,1,3,3-tetraethoxy-2-methyl-propane (prepared accordingly to the procedure described in JACS 126(7), 2004, 2194) (0.5 g, 2.1 mmol) in an aqueous solution of hydrochloric acid (6 M, 1.3 mL) was heated at 95° C. in a sealed tube. The solid material completely dissolved when the temperature reached 82° C. and then a solid precipitate crushed out of solution, stirring was continued for 5 minutes. The resulting mixture was cooled to room temperature and the solid was collected by filtration, rinsed with water and dried in vacuum oven to afford 305.1 mg (81% yield) of 6-methyl-pyrazolo[1,5-a]pyrimidine-3-carboxylic acid.

Preparation 49: Synthesis of 6-Methoxy-pyrazolo[1,5-a]pyrimidine-3-carboxylic acid The synthesis of 6-methoxy-pyrazolo[1,5-a]pyrimidine-3-carboxylic acid was carried out according to the process shown in Scheme 49.

SCHEME 49

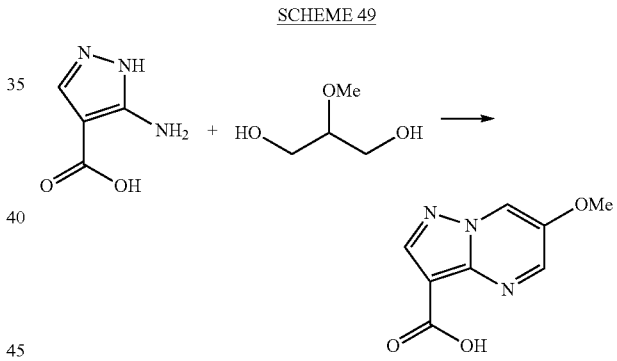

To a solution of oxalyl chloride (6.9 mL) in dichloromethane (65 mL), cooled at −78° C., was added, dropwise, a solution of dimethyl sulfoxide (13 mL) in dichloromethane (16 mL) and the resulting mixture was stirred for 10 minutes. A solution of 2-O-methyl-glycerol (3.3 g, 31.5 mmol) in dichloromethane (16 mL) was then added dropwise and the reaction mixture was stirred for 15 minutes. Triethylamine (52 mL) was then added dropwise and the resulting mixture was stirred for 1 hour. The reaction mixture was warmed up to room temperature and an aqueous solution of hydrochloric acid (6 M, 35 mL) was added followed by 5-amino-1H-pyrazole-4-carboxylic acid (4 g, 31.5 mmol) and the resulting mixture was heated to 95° C. over 20 minutes, the temperature was maintained at 95° C. for 20 minutes. The resulting mixture was cooled to room temperature and stored at room temperature for 24 hours and at 4° C. for 62 hours. The solid formed was collected by filtration and dried in a vacuum oven to afford 1.087 g (18% yield) of 6-methoxy-pyrazolo[1,5-a]pyrimidine-3-carboxylic acid.

Preparation 50: Synthesis of 6-Bromo-pyrazolo[1,5-a]pyrimidine-3-carboxylic acid The synthesis of 6-bromo-pyrazolo[1,5-a]pyrimidine-3-carboxylic acid was carried out according to the process shown in Scheme 50.

SCHEME 50

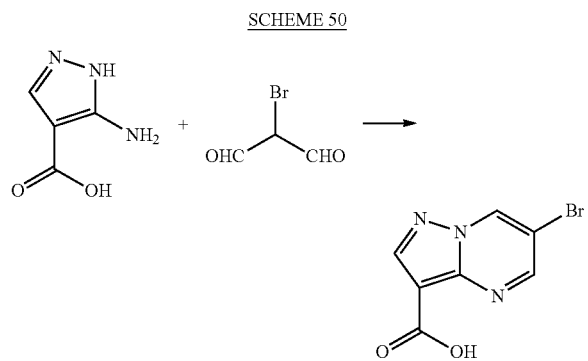

A suspension of 5-amino-1H-pyrazole-4-carboxylic acid (1 g, 7.8 mmol) and 2-bromomalonaldehyde (1.2 g, 7.8 mmol) in an aqueous solution of hydrochloric acid (6 M, 20 mL) was heated at 95° C. for 15 minutes. The resulting mixture was cooled to room temperature and the solid formed was collected by filtration, rinsed with water and dried in vacuum oven to give 6-bromo-pyrazolo[1,5-a]pyrimidine-3-carboxylic acid.

Preparation 51: Synthesis of 1-pyrrolidin-3-yl-ethanol trifluoroacetate

The synthesis of 1-pyrrolidin-3-yl-ethanol trifluoroacetate was carried out according to the process shown in Scheme 51.

SCHEME 51

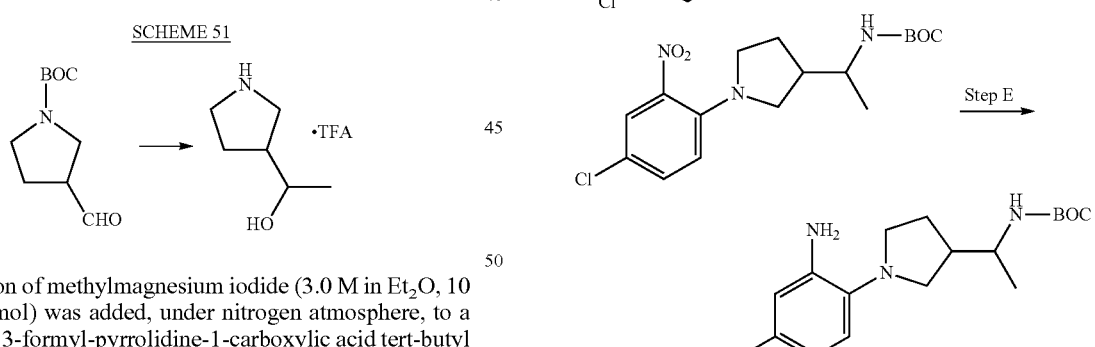

A solution of methylmagnesium iodide (3.0 M in Et$_2$O, 10 mL, 30 mmol) was added, under nitrogen atmosphere, to a solution of 3-formyl-pyrrolidine-1-carboxylic acid tert-butyl ester (2 g, 10.0 mmol) in tetrahydrofuran (15 mL) at 0° C. and the resulting mixture was stirred at room temperature for 1 hour. A second aliquot of tetrahydrofuran (55 mL) was then added. The reaction mixture was quenched by addition of a saturated aqueous solution of ammonium chloride until dissolution of the solids. The volatiles were evaporated under reduced pressure and the residue was extracted twice with dichloromethane. The combined organic extracts were washed with a saturated aqueous solution of sodium bicarbonate, dried over anhydrous sodium sulfate, filtered and evaporated under reduced pressure to give 2.149 of 3-(1-hydroxy-ethyl)-pyrrolidine-1-carboxylic acid tert-butyl ester. To a portion of this material (875 mg, 4.1 mmol) was added a solution of trifluoroacetic acid (5% in DCM, 10 mL) and the resulting mixture was stirred at room temperature for 30 minutes. The reaction mixture was then evaporated under reduced pressure to give 1-pyrrolidin-3-yl-ethanol trifluoroacetate which was used without further purifications.

Preparation 52: Synthesis of {1-[1-(2-amino-4-chloro-phenyl)-pyrrolidin-3-yl]-ethyl}-carbamic acid tert-butyl ester The synthesis of {1-[1-(2-amino-4-chloro-phenyl)-pyrrolidin-3-yl]-ethyl}-carbamic acid tert-butyl ester was carried out according to the process shown in Scheme 52.

SCHEME 52

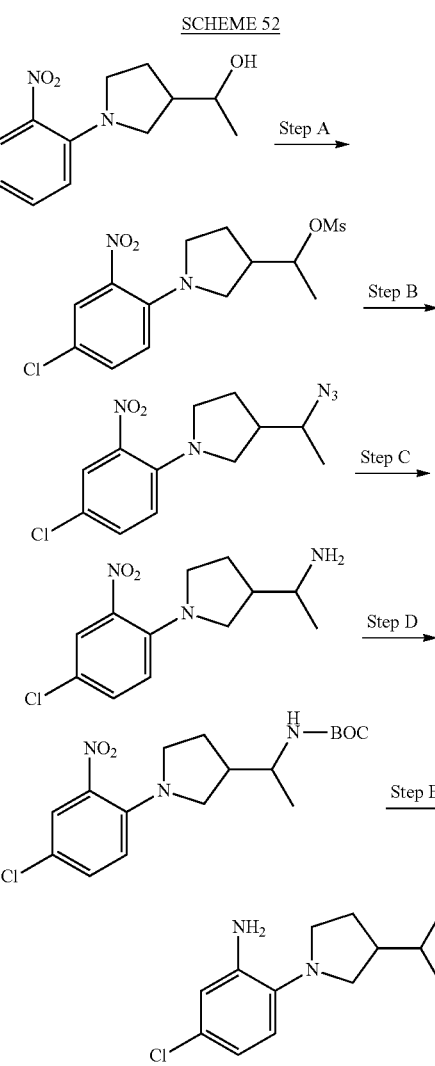

Step A: Synthesis of methanesulfonic acid 1-[1-(4-chloro-2-nitro-phenyl)-pyrrolidin-3-yl]-ethyl ester A mixture of 1-[1-(2-amino-4-chloro-phenyl)-pyrrolidin-3-yl]-ethanol (320.7 mg, 1.2 mmol), triethylamine (0.5 mL) and p-toluenesulfonylchloride (272 mg) in dichloromethane (15 mL) was stirred, under nitrogen atmosphere, at room temperature, for 62 hours. 4-Dimethylaminopyridine (catalytic quantity) was then added and the reaction mixture was heated at reflux for 3 hours. The resulting mixture was evaporated under reduced pressure; the residue was dissolved in pyridine and more p-toluenesulfonylchloride (272 mg) was added. The reaction mixture was stirred at room temperature overnight and then was evaporated under reduced pressure. The residue was diluted with water and extracted 3 times with ethyl acetate. The combined organic extracts were washed with brine, dried over anhydrous sodium sulfate, filtered and evaporated under reduced pressure. To a solution of this material in dichloromethane (15 mL) was added triethylamine (0.5 mL) followed by methanesulfonylchloride (0.26 mL) and the resulting mixture was stirred, under nitrogen atmosphere, at room temperature, for 2 hours. The reaction mixture was washed twice with water and the aqueous layer was extracted 3 times with dichloromethane. The combined organic extracts were washed with brine, dried over anhydrous sodium sulfate, filtered and evaporated under reduced pressure. The crude residue was purified by flash chromatography (hexane/EtOAc, 90/10 to 50/50) to afford 285.9 mg of methanesulfonic acid 1-[1-(4-chloro-2-nitro-phenyl)-pyrrolidin-3-yl]-ethyl ester and 55.2 mg of toluene-4-sulfonic acid 1-[1-(4-chloro-2-nitro-phenyl)-pyrrolidin-3-yl]-ethyl ester.

Step B: Synthesis of 3-(1-Azido-ethyl)-1-(4-chloro-2-nitro-phenyl)-pyrrolidine

A mixture of methanesulfonic acid 1-[1-(4-chloro-2-nitrophenyl)-pyrrolidin-3-yl]-ethyl ester (285.9 mg), toluene-4-sulfonic acid 1-[1-(4-chloro-2-nitro-phenyl)-pyrrolidin-3-yl]-ethyl ester (55.2 mg) and sodium azide (185 mg) in N,N-dimethylformamide (ca. 5 mL) was heated at 80° C. overnight. The reaction mixture was cooled, diluted with water and extracted 3 times with ethyl acetate. The combined organic extracts were washed with brine, dried over anhydrous sodium sulfate, filtered and evaporated under reduced pressure. The crude residue was purified by flash chromatography (hexane/EtOAc, 90/10) to give 214 mg (76% yield) of 3-(1-azido-ethyl)-1-(4-chloro-2-nitro-phenyl)-pyrrolidine.

Step C: Synthesis of 1-[1-(4-chloro-2-nitro-phenyl)-pyrrolidin-3-yl]-ethylamine

A mixture of 3-(1-azido-ethyl)-1-(4-chloro-2-nitro-phenyl)-pyrrolidine (214 mg, 0.7 mmol), triphenylphosphine (500 mg) and water (0.171 mL) in tetrahydrofuran (20 mL) was heated at 50° C. overnight. The resulting mixture was evaporated under reduced pressure; the residue was diluted with ethyl acetate, washed twice with water and once with brine, dried over anhydrous sodium sulfate, filtered and evaporated under reduced pressure. The crude residue was purified by flash chromatography (DCM/MeOH) to give 127 mg (65% yield) of 1-[1-(4-chloro-2-nitro-phenyl)-pyrrolidin-3-yl]-ethylamine.

Step D: Synthesis of {1-[1-(4-Chloro-2-nitro-phenyl)-pyrrolidin-3-yl]-ethyl}-carbamic acid tert-butyl ester To a mixture of 1-[1-(4-chloro-2-nitro-phenyl)-pyrrolidin-3-yl]-ethylamine (127 mg, 0.47 mmol) in dichloromethane (ca. 5 mL) cooled at 0° C. was added di-tert-butyl-dicarbonate (113 mg) and the resulting mixture was stirred for 30 minutes at 0° C. The reaction mixture was then warmed up to room temperature and stirred for 2.5 hours. The resulting mixture was washed with a saturated aqueous solution of sodium bicarbonate and with brine, dried over anhydrous sodium sulfate, filtered and evaporated under reduced pressure. The crude residue was purified by flash chromatography (hexane/EtOAc, 90/10 to 50/50) to give 146 mg (84% yield) of {1-[1-(4-chloro-2-nitro-phenyl)-pyrrolidin-3-yl]-ethyl}-carbamic acid tert-butyl ester.

Step E: Synthesis of {1-[1-(2-amino-4-chloro-phenyl)-pyrrolidin-3-yl]-ethyl}-carbamic acid tert-butyl ester {1-[1-(4-Chloro-2-nitro-phenyl)-pyrrolidin-3-yl]-ethyl}-carbamic acid tert-butyl ester was reduced following the procedure described in Preparation 20, Step B, to give {1-[1-(2-amino-4-chloro-phenyl)-pyrrolidin-3-yl]-ethyl}-carbamic acid tert-butyl ester in quantitative yield.

Example 1

Synthesis of Pyrazolo[1,5-a]pyrimidine-3-carboxylic acid [5-chloro-2-(4-hydroxy-cyclohexyloxy)-phenyl]-amide The synthesis of pyrazolo[1,5-a]pyrimidine-3-carboxylic acid [5-chloro-2-(4-hydroxy-cyclohexyloxy)-phenyl]-amide was carried out according to the process shown in Scheme 53.

SCHEME 53

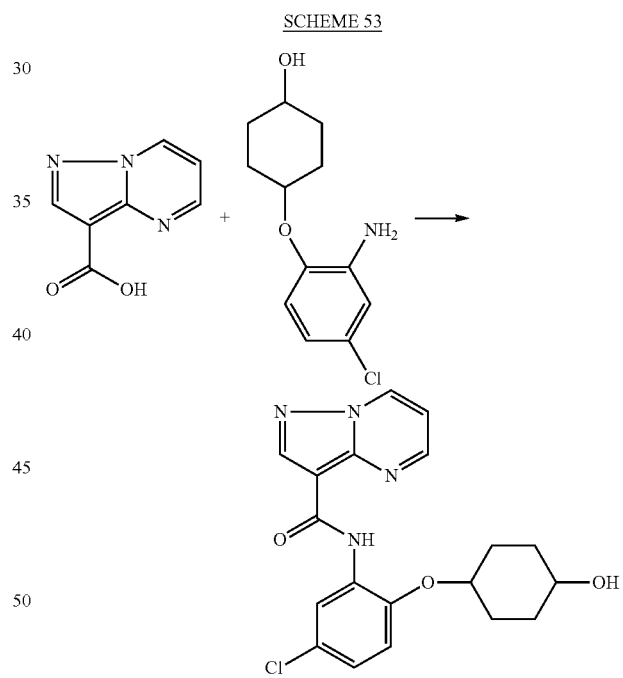

Diisopropylethylamine (0.35 mL, 2.01 mmol) was added at room temperature to a suspension of 4-(2-amino-4-chloro-phenoxy)-cyclohexanol (127 mg, 0.525 mmol), pyrazolo[1,5-a]pyrimidine-3-carboxylic acid (85 mg, 0.521 mmol) and HBTU (0.21 g, 0.55 mmol) in anhydrous acetonitrile (15 mL) and the resulting solution was heated at 80° C. overnight. The resulting mixture was partitioned between ethyl acetate and an aqueous solution of sodium bicarbonate (5%). The aqueous layer was extracted 3 times with ethyl acetate and the combined organic extracts were washed with brine, dried over anhydrous sodium sulfate, filtered and evaporated under reduced pressure. The brown oily residue was purified on a silica gel plug and by flash chromatography (DCM/

MeOH/NH₄OH) to give a pale yellow solid which was washed with dichloromethane and methanol to give 75 mg (38% yield) of pyrazolo[1,5-a]pyrimidine-3-carboxylic acid [5-chloro-2-(4-hydroxy-cyclohexyloxy)-phenyl]-amide as a white powder. MS=387 [M+H]⁺.

In a similar manner, utilizing the appropriate starting materials, the following compounds were prepared:

3-methoxy-4-[(pyrazolo[1,5-a]pyrimidine-3-carbonyl)-amino]-benzoic acid methyl ester;
pyrazolo[1,5-a]pyrimidine-3-carboxylic acid [4-(tert-butyl-dimethyl-silanyloxymethyl)-2-methoxy-phenyl]-amide;
6-formyl-pyrazolo[1,5-a]pyrimidine-3-carboxylic acid {2-[4-(tert-butyl-dimethyl-silanyloxy)-cyclohexyloxy]-5-chloro-phenyl}-amide;
pyrazolo[1,5-a]pyrimidine-3-carboxylic acid (3-methoxy-biphenyl-4-yl)-amide (light yellow solid); MS=345 [M+H]⁺;
pyrazolo[1,5-a]pyrimidine-3,6-dicarboxylic acid 6-amide 3-({2-[4-(tert-butyl-dimethyl-silanyloxy)-cyclohexyloxy]-5-chloro-phenyl}-amide);
3-methoxy-4-nitro-N-phenyl-benzamide;
pyrazolo[1,5-a]pyrimidine-3-carboxylic acid (2-methoxy-4-phenylcarbamoyl-phenyl)-amide (light yellow crystalline solid); MS=388 [M+H]⁺;
pyrazolo[1,5-a]pyrimidine-3-carboxylic acid (3-amino-2-methoxy-phenyl)-amide (light yellow powder); MS=284 [M+H]⁺;
pyrazolo[1,5-a]pyrimidine-3-carboxylic acid [3-(3-hydroxy-propylamino)-2-piperidin-1-yl-phenyl]-amide (light yellow powder); MS=395 [M+H]⁺;
pyrazolo[1,5-a]pyrimidine-3-carboxylic acid [3-(2-hydroxy-ethylamino)-2-piperidin-1-yl-phenyl]-amide (light yellow powder); MS=381 [M+H]⁺;
pyrazolo[1,5-a]pyrimidine-3-carboxylic acid (5-chloro-2-methoxy-4-phenylcarbamoyl-phenyl)-amide (white powder); MS=422 [M+H]⁺;
pyrazolo[1,5-a]pyrimidine-3-carboxylic acid (4-dimethylcarbamoyl-2-methoxy-phenyl)-amide (white powder); MS=340 [M+H]⁺;
pyrazolo[1,5-a]pyrimidine-3-carboxylic acid (2-methoxy-3,5-dimethyl-phenyl)-amide (light yellow powder); MS=297 [M+H]⁺;
5-methyl-pyrazolo[1,5-a]pyrimidine-3-carboxylic acid {2-[4-(tert-butyl-dimethyl-silanyloxy)-cyclohexyloxy]-5-chloro-phenyl}-amide;
7-methyl-pyrazolo[1,5-a]pyrimidine-3-carboxylic acid {2-[4-(tert-butyl-dimethyl-silanyloxy)-cyclohexyloxy]-5-chloro-phenyl}-amide;
pyrazolo[1,5-a]pyrimidine-3-carboxylic acid [5-(3-hydroxy-propyl)-2-methoxy-phenyl]-amide (light brown crystalline solid); MS=327 [M+H]⁺; MP=189.7-190.2° C.;
pyrazolo[1,5-a]pyrimidine-3-carboxylic acid (2-methoxy-5-vinyl-phenyl)-amide (light yellow solid); MS=295 [M+H]⁺;
pyrazolo[1,5-a]pyrimidine-3-carboxylic acid (5-ethyl-2-methoxy-phenyl)-amide (pink powder); MS=297 [M+H]⁺;
pyrazolo[1,5-a]pyrimidine-3-carboxylic acid [5-chloro-2-(4-hydroxymethyl-piperidin-1-yl)-phenyl]-amide (off-white solid); MS=386 [M+H]⁺;
(1-{4-chloro-2-[(pyrazolo[1,5-a]pyrimidine-3-carbonyl)-amino]-phenyl}-piperidin-4-ylmethyl)-carbamic acid tert-butyl ester;
pyrrolo[2,1-f][1,2,4]triazine-7-carboxylic acid [5-chloro-2-(4-hydroxy-cyclohexyloxy)-phenyl]-amide (off-white solid); MS=386 [M+H]⁺;
2-chloro-thieno[3,2-d]pyrimidine-7-carboxylic acid (7-methoxy-quinolin-6-yl)-amide;
pyrazolo[1,5-a]pyrimidine-3-carboxylic acid (2-oxo-5-piperidin-1-yl-2,3-dihydro-1H-indol-6-yl)-amide (black solid); MS=377 [M+H]⁺;
pyrazolo[1,5-a]pyrimidine-3-carboxylic acid (5-methoxy-2-methyl-1H-indol-6-yl)-amide (yellow solid); MS=322 [M+H]⁺;
3-(7-methoxy-quinolin-6-ylcarbamoyl)-thieno[3,2-b]pyridine-6-carboxylic acid ethyl ester;
thieno[3,2-d]pyrimidine-7-carboxylic acid [2-(2-hydroxy-ethylamino)-7-methoxy-quinolin-6-yl]-amide hydrochloride (the hydrochloride salt was generated utilizing HCl in Et₂O) (yellow powder); MS=396 [M+H]⁺; MP=265.1-269.9° C.;
4-{4-chloro-2-[(pyrazolo[1,5-a]pyrimidine-3-carbonyl)-amino]-phenoxy}-piperidine-1-carboxylic acid tert-butyl ester;
pyrazolo[1,5-a]pyrimidine-3-carboxylic acid [3'-(tert-butyl-dimethyl-silanyloxy)-4-chloro-biphenyl-2-yl]-amide;
(1-{5-phenylcarbamoyl-2-[(pyrazolo[1,5-a]pyrimidine-3-carbonyl)-amino]-phenyl}-piperidin-4-ylmethyl)-carbamic acid tert-butyl ester;
pyrazolo[1,5-a]pyrimidine-3-carboxylic acid {7-[4-(tert-butyl-dimethyl-silanyloxy)-cyclohexyloxy]-quinolin-6-yl}-amide;
(1-{2-amino-6-[(pyrazolo[1,5-a]pyrimidine-3-carbonyl)-amino]-phenyl}-piperidin-4-ylmethyl)-carbamic acid tert-butyl ester;
pyrazolo[1,5-a]pyrimidine-3-carboxylic acid [5-chloro-2-(4-hydroxy-butoxy)-phenyl]-amide (white powder); MS=361 [M+H]⁺;
pyrazolo[1,5-a]pyrimidine-3-carboxylic acid (3-amino-2-piperidin-1-yl-phenyl)-amide (off-white powder); MS=337 [M+H]⁺;
pyrazolo[1,5-a]pyrimidine-3-carboxylic acid (4-chloro-biphenyl-2-yl)-amide (light yellow powder); MS=349 [M+H]⁺;
pyrazolo[1,5-a]pyrimidine-3-carboxylic acid (7-piperidin-1-yl-quinolin-6-yl)-amide hydrochloride (orange powder) (the hydrochloride salt was prepared adding 3 equivalents of HCl in Et₂O to a solution of the free base in a mixture 1/1 of dichloromethane and methanol); MS=373 [M+H]⁺; MP=285-287° C.;
pyrazolo[1,5-a]pyrimidine-3-carboxylic acid (2-methoxy-phenyl)-amide (light yellow powder); MS=268 [M]⁺;
pyrazolo[1,5-a]pyrimidine-3-carboxylic acid (2,4-dimethoxy-phenyl)-amide (light yellow powder); MS=298 [M]⁺;
pyrazolo[1,5-a]pyrimidine-3-carboxylic acid (2-methoxy-4-methyl-phenyl)-amide (light yellow powder); MS=283 [M+H]⁺;
pyrazolo[1,5-a]pyrimidine-3-carboxylic acid (5-chloro-2-fluoro-phenyl)-amide (light yellow powder); MS=291 [M+H]⁺;
pyrazolo[1,5-a]pyrimidine-3-carboxylic acid (2-methoxy-5-methyl-phenyl)-amide (light yellow solid); MS=283 [M+H]⁺;
pyrazolo[1,5-a]pyrimidine-3-carboxylic acid (5-fluoro-2-methoxy-phenyl)-amide (light yellow powder); MS=287 [M+H]⁺;
pyrazolo[1,5-a]pyrimidine-3-carboxylic acid [5-chloro-2-(3-methoxy-propoxy)-phenyl]-amide (off-white powder); MS=361 [M+H]⁺;
pyrazolo[1,5-a]pyrimidine-3-carboxylic acid (5-methoxy-2-methyl-biphenyl-4-yl)-amide (light yellow powder); MS=359 [M+H]⁺;

pyrazolo[1,5-a]pyrimidine-3-carboxylic acid (2,5-dimethoxy-phenyl)-amide (light yellow crystalline solid); MS=299 [M+H]$^+$;

pyrazolo[1,5-a]pyrimidine-3-carboxylic acid (7-methoxy-quinolin-6-yl)-amide (off-white powder); MS=320 [M+H]$^+$; MP=256-257.3° C.;

pyrazolo[1,5-a]pyridine-3-carboxylic acid (5-chloro-2-piperidin-1-yl-phenyl)-amide (white crystalline solid); MS=355 [M+H]$^+$; MP=186.4-188.5° C.;

pyrazolo[1,5-a]pyridine-3-carboxylic acid (7-methoxy-quinolin-6-yl)-amide hydrochloride (yellow powder) (the hydrochloride salt was prepared adding 3 equivalents of HCl in Et$_2$O to a solution of the free base in a mixture 1/1 of dichloromethane and methanol); MS=319 [M+H]$^+$;

cis-thieno[3,2-d]pyrimidine-7-carboxylic acid [5-chloro-2-(4-hydroxy-cyclohexyloxy)-phenyl]-amide (light yellow powder); MS=404 [M+H]$^+$;

trans-thieno[3,2-d]pyrimidine-7-carboxylic acid [5-chloro-2-(4-hydroxy-cyclohexyloxy)-phenyl]-amide (yellow powder); MS=404 [M+H]$^+$;

pyrazolo[1,5-a]pyrimidine-3-carboxylic acid {4-[2-(tert-butyl-dimethyl-silanyloxy)-ethylcarbamoyl]-2-methoxy-phenyl}-amide;

thieno[3,2-d]pyrimidine-7-carboxylic acid {4-[2-(tert-butyl-dimethyl-silanyloxy)-ethylcarbamoyl]-2-methoxy-phenyl}-amide;

thieno[3,2-d]pyrimidine-7-carboxylic acid {4-[3-(tert-butyl-dimethyl-silanyloxy)-propylcarbamoyl]-2-methoxy-phenyl}-amide;

pyrazolo[1,5-a]pyrimidine-3-carboxylic acid {4-[3-(tert-butyl-dimethyl-silanyloxy)-propylcarbamoyl]-2-methoxy-phenyl}-amide;

(1-{4-chloro-2-[(pyrazolo[1,5-a]pyrimidine-3-carbonyl)-amino]-phenyl}-piperidin-4-yl)-carbamic acid tert-butyl ester;

pyrazolo[1,5-a]pyrimidine-3-carboxylic acid [2-(4-carbamoyl-piperidin-1-yl)-5-chloro-phenyl]-amide (off-white powder); MS=399 [M+H]$^+$;

{4'-chloro-2'-[(pyrazolo[1,5-a]pyrimidine-3-carbonyl)-amino]-biphenyl-4-ylmethyl}-carbamic acid tert-butyl ester;

pyrazolo[1,5-a]pyrimidine-3-carboxylic acid [3-(3-hydroxy-cyclopentyloxy)-naphthalen-2-yl]-amide (off-white solid); MS=389 [M+H]$^+$;

pyrazolo[1,5-a]pyrimidine-3-carboxylic acid (1-methoxy-naphthalen-2-yl)-amide (off-white solid); MS=319 [M+H]$^+$;

pyrazolo[1,5-a]pyrimidine-3-carboxylic acid [5-(4-hydroxymethyl-piperidin-1-yl)-2-oxo-2,3-dihydro-1H-indol-6-yl]-amide (black solid); MS=407 [M+H]$^+$;

pyrazolo[1,5-a]pyrimidine-3-carboxylic acid (5-bromo-2-methoxy-phenyl)-amide (light brown powder); MS=347 [M+H]$^+$;

pyrazolo[1,5-a]pyrimidine-3-carboxylic acid biphenyl-2-yl-amide (light yellow powder); MS=315 [M+H]$^+$;

pyrazolo[1,5-a]pyrimidine-3-carboxylic acid (5-chloro-2-morpholin-4-yl-phenyl)-amide (white powder); MS=358 [M+H]$^+$;

pyrazolo[1,5-a]pyrimidine-3-carboxylic acid (5-chloro-2-methylsulfanyl-phenyl)-amide (light yellow needles); MS=319 [M+H]$^+$;

(1-{6-[(pyrazolo[1,5-a]pyrimidine-3-carbonyl)-amino]-quinolin-7-yl}-piperidin-4-ylmethyl)-carbamic acid tert-butyl ester;

thieno[3,2-d]pyrimidine-7-carboxylic acid (7-piperidin-1-yl-quinolin-6-yl)-amide (light yellow powder); MS=390 [M+H]$^+$; MP=234.0-236.0° C.;

thieno[3,2-d]pyrimidine-7-carboxylic acid [7-(3-hydroxy-1,1-dimethyl-propoxy)-quinolin-6-yl]-amide hydrochloride (the hydrochloride salt was generated utilizing HCl in Et$_2$O) (light yellow powder); MS=400 [M+H]$^+$; MP>300° C.;

thieno[3,2-d]pyrimidine-7-carboxylic acid [7-(3-hydroxy-butoxy)-quinolin-6-yl]-amide (light yellow powder); MS=395 [M+H]$^+$; MP=256.0-257.0° C.;

thieno[3,2-d]pyrimidine-7-carboxylic acid [5-chloro-2-(3-hydroxy-1,1-dimethyl-propoxy)-phenyl]-amide (yellow waxy solid); MS=392 [M+H]$^+$; MP=52.0-54.0° C.;

thieno[3,2-d]pyrimidine-7-carboxylic acid (5-chloro-2-cyclohexyloxy-phenyl)-amide (white powder); MS=388 [M+H]$^+$; MP=153.4-155.7° C.;

thieno[3,2-d]pyrimidine-7-carboxylic acid (5-chloro-2-isopropoxy-phenyl)-amide (white powder); MS=348 [M+H]$^+$; MP=149.6-150.6° C.;

pyrazolo[1,5-a]pyrimidine-3-carboxylic acid [2-(2-hydroxy-ethylamino)-7-methoxy-quinolin-6-yl]-amide (light brown powder); MS=379 [M+H]$^+$; MP=261.3-264.8° C.;

pyrazolo[1,5-a]pyrimidine-3-carboxylic acid [5-chloro-2-(3-hydroxymethyl-pyrrolidin-1-yl)-phenyl]-amide (yellow powder); MS=372 [M+H]$^+$; MP=174.4-175.9° C.;

pyrazolo[1,5-a]pyrimidine-3-carboxylic acid [7-(4-hydroxymethyl-piperidin-1-yl)-quinolin-6-yl]-amide (light yellow powder); MS=403 [M+H]$^+$; MP=247.7-249.0° C.;

pyrazolo[1,5-a]pyrimidine-3-carboxylic acid [3-(3-hydroxy-propoxy)-naphthalen-2-yl]-amide (light brown solid); MS=363 [M+H]$^+$; MP=227.7-230.2° C.;

pyrazolo[1,5-a]pyrimidine-3-carboxylic acid [3-(4-hydroxy-cyclohexyloxy)-naphthalen-2-yl]-amide (light brown solid); MS=403 [M+H]$^+$;

pyrazolo[1,5-a]pyrimidine-3-carboxylic acid [5-chloro-2-(3-hydroxy-cyclopentyloxy)-phenyl]-amide (light brown powder); MS=373 [M+H]$^+$; MP=256.9-258.4° C.;

pyrazolo[1,5-a]pyrimidine-3-carboxylic acid [5-chloro-2-(3-hydroxymethyl-cyclopentyloxy)-phenyl]-amide (off-white solid); MS=387 [M+H]$^+$;

pyrazolo[1,5-a]pyrimidine-3-carboxylic acid [5-chloro-2-(3-hydroxy-cyclohexyloxy)-phenyl]-amide (off-white solid); MS=387 [M+H]$^+$;

thieno[3,2-d]pyrimidine-7-carboxylic acid (5-chloro-2-methoxy-phenyl)-amide (orange crystalline solid); MS=320 [M+H]$^+$; MP=213.1-214.0° C.;

pyrazolo[1,5-a]pyrimidine-3-carboxylic acid [5-chloro-2-(3-hydroxymethyl-piperidin-1-yl)-phenyl]-amide (dark brown solid); MS=386 [M+H]$^+$;

pyrazolo[1,5-a]pyrimidine-3-carboxylic acid (2-azepan-1-yl-5-chloro-phenyl)-amide (pink solid); MS=370 [M+H]$^+$;

pyrazolo[1,5-a]pyrimidine-3-carboxylic acid (5-hydroxymethyl-2-piperidin-1-yl-phenyl)-amide (light yellow solid); MS=352 [M+H]$^+$; MP=196.6-197.9° C.;

thieno[3,2-d]pyrimidine-7-carboxylic acid [5-chloro-2-(4-hydroxymethyl-piperidin-1-yl)-phenyl]-amide (off-white solid); MS=403 [M+H]$^+$;

thieno[3,2-d]pyrimidine-7-carboxylic acid (2-methoxy-phenyl)-amide (orange solid); MS=286 [M+H]$^+$;

thieno[3,2-b]pyridine-3-carboxylic acid (5-chloro-2-methoxy-phenyl)-amide (light yellow powder); MS=319 [M+H]$^+$;

pyrazolo[1,5-a]pyrimidine-3-carboxylic acid (5-chloro-2-pyrrolidin-1-yl-phenyl)-amide (crystalline off-white solid); MS=342 [M+H]$^+$;

pyrazolo[1,5-a]pyrimidine-3-carboxylic acid [5-(4-hydroxymethyl-phenyl)-2-methyl-1H-indol-6-yl]-amide (orange semisolid); MS=398 [M+H]+;

pyrazolo[1,5-a]pyrimidine-3-carboxylic acid (5-methoxy-1H-indol-6-yl)-amide (light green powder); MS=308 [M+H]+;

thieno[3,2-d]pyrimidine-7-carboxylic acid (5-methoxy-1H-indol-6-yl)-amide (light green powder); MS=325 [M+H]+;

pyrazolo[1,5-a]pyrimidine-3-carboxylic acid [5-chloro-2-(4-methyl-piperazin-1-yl)-phenyl]-amide (off-white solid); MS=371 [M+H]+;

pyrazolo[1,5-a]pyrimidine-3-carboxylic acid [5-chloro-2-(4-methyl-oxazol-5-ylmethoxy)-phenyl]-amide (off-white solid); MS=384 [M+H]+; MP=240.9-242.5° C.;

thieno[3,2-d]pyrimidine-7-carboxylic acid [5-chloro-2-(4-methyl-oxazol-5-ylmethoxy)-phenyl]-amide (light brown crystalline solid); MS=401 [M+H]+; MP=233.3-234.3° C.;

pyrazolo[1,5-a]pyrimidine-3-carboxylic acid [5-chloro-2-(3-hydroxy-pyrrolidin-1-yl)-phenyl]-amide (off-white solid); MS=358 [M+H]+;

(1-{6-[(thieno[3,2-b]pyridine-3-carbonyl)-amino]-quinolin-7-yl}-piperidin-4-ylmethyl)-carbamic acid tert-butyl ester;

pyrazolo[1,5-a]pyrimidine-3-carboxylic acid {5-chloro-2-[3-(2,2,2-trifluoro-acetylamino)-pyrrolidin-1-yl]-phenyl}-amide;

pyrazolo[1,5-a]pyrimidine-3-carboxylic acid (5-chloro-2-methoxy-phenyl)-amide (crystalline off-white solid); MS=303 [M+H]+;

pyrazolo[1,5-a]pyrimidine-3-carboxylic acid {2-[3-(tert-butyl-dimethyl-silanyloxy)-propoxy]-5-chloro-phenyl}-amide;

pyrazolo[1,5-a]pyrimidine-3-carboxylic acid {2-[2-(tert-butyl-dimethyl-silanyloxy)-ethoxy]-5-chloro-phenyl}-amide;

pyrazolo[1,5-a]pyrimidine-3-carboxylic acid [5-chloro-2-(2-methoxy-ethoxy)-phenyl]-amide (off-white solid); MS=347 [M+H]+;

pyrazolo[1,5-a]pyrimidine-3-carboxylic acid (5-chloro-2-ethyl-phenyl)-amide (off-white powder); MS=301 [M+H]+;

pyrazolo[1,5-a]pyrimidine-3-carboxylic acid (5-chloro-2-isobutoxy-phenyl)-amide (off-white powder); MS=345 [M+H]+;

pyrazolo[1,5-a]pyrimidine-3-carboxylic acid [5-chloro-2-(4-hydroxy-butyl)-phenyl]-amide (white powder); MS=345 [M+H]+;

pyrazolo[1,5-a]pyrimidine-3-carboxylic acid (5-chloro-2-cyclohexyl-phenyl)-amide (white powder); MS=355 [M+H]+;

pyrazolo[1,5-a]pyrimidine-3-carboxylic acid (4-chloro-4'-hydroxymethyl-biphenyl-2-yl)-amide (off-white powder); MS=379 [M+H]+;

pyrazolo[1,5-a]pyrimidine-3-carboxylic acid (7-hydroxymethyl-3-methoxy-naphthalen-2-yl)-amide (off-white powder); MS=349 [M+H]+;

pyrazolo[1,5-a]pyrimidine-3-carboxylic acid (4-methanesulfonyl-2-methoxy-phenyl)-amide (off-white powder) (4-methanesulfonyl-2-methoxy-phenylamine was prepared accordingly to the procedure reported in *Eur. J. Med. Chem.* 37, 2002, 461); MS=347 [M+H]+;

pyrazolo[1,5-a]pyrimidine-3-carboxylic acid (6-methoxy-1H-indazol-5-yl)-amide (yellow powder); MS=309 [M+H]+;

thieno[3,2-d]pyrimidine-7-carboxylic acid (7-methoxy-quinolin-6-yl)-amide (off-white powder); MS=337 [M+H]+; MP=249.0-252.2° C.;

cis-thieno[3,2-d]pyrimidine-7-carboxylic acid {7-[4-(tert-butyl-diphenyl-silanyloxy)-cyclohexyloxy]-quinolin-6-yl}-amide;

3-{6-[(thieno[3,2-d]pyrimidine-7-carbonyl)-amino]-quinolin-7-yloxy}-pyrrolidine-1-carboxylic acid tert-butyl ester;

(3-{6-[(thieno[3,2-d]pyrimidine-7-carbonyl)-amino]-quinolin-7-yloxy}-propyl)-carbamic acid tert-butyl ester;

thieno[3,2-d]pyrimidine-7-carboxylic acid {7-[3-(tert-butyl-dimethyl-silanyloxy)-propoxy]-quinolin-6-yl}-amide;

4-{6-[(thieno[3,2-d]pyrimidine-7-carbonyl)-amino]-quinolin-7-yloxy}-piperidine-1-carboxylic acid tert-butyl ester;

(1-{6-[(thieno[3,2-d]pyrimidine-7-carbonyl)-amino]-quinolin-7-yl}-piperidin-4-ylmethyl)-carbamic acid tert-butyl ester;

(1-{6-[(pyrazolo[1,5-a]pyrimidine-3-carbonyl)-amino]-quinolin-7-yl}-piperidin-4-ylmethyl)-carbamic acid tert-butyl ester;

thieno[3,2-d]pyrimidine-7-carboxylic acid {7-[4-(tert-butyl-dimethyl-silanyloxy)-cyclohexyloxy]-quinolin-6-yl}-amide;

(4-{4-chloro-2-[(thieno[3,2-d]pyrimidine-7-carbonyl)-amino]-phenoxy}-cyclohexyl)-carbamic acid tert-butyl ester;

4-{6-[(pyrazolo[1,5-a]pyrimidine-3-carbonyl)-amino]-quinolin-7-yloxy}-piperidine-1-carboxylic acid tert-butyl ester;

6-(3-hydroxy-propyl)-pyrazolo[1,5-a]pyrimidine-3-carboxylic acid [5-chloro-2-(4-hydroxy-cyclohexyloxy)-phenyl]-amide (off-white powder); MS=445 [M+H]+; MP=236.7-237.7° C.;

6-[2-(tert-butyl-dimethyl-silanyloxy)-ethyl]-pyrazolo[1,5-a]pyrimidine-3-carboxylic acid {2-[4-(tert-butyl-dimethyl-silanyloxy)-cyclohexyloxy]-5-chloro-phenyl}-amide;

pyrazolo[1,5-a]pyrimidine-3-carboxylic acid (2-{4-[1-(tert-butyl-dimethyl-silanyloxy)-ethyl]-piperidin-1-yl}-5-chloro-phenyl)-amide (1-piperidin-4-yl-ethanol was prepared accordingly to the procedure described in WO2005/080394);

[1-(1-{4-chloro-2-[(pyrazolo[1,5-a]pyrimidine-3-carbonyl)-amino]-phenyl}-piperidin-4-yl)-ethyl]-carbamic acid tert-butyl ester (1-piperidin-4-yl-ethylamine was prepared accordingly to the procedure described in WO2005/080394);

pyrazolo[1,5-a]pyrimidine-3-carboxylic acid (5-acetylamino-2-methoxy-phenyl)-amide (light brown powder); MS=326 [M+H]+; MP=232.3-233.8° C.;

pyrazolo[1,5-a]pyrimidine-3-carboxylic acid (3-methoxy-naphthalen-2-yl)-amide (light yellow powder); MS=319 [M+H]+; MP=202.3-205.0° C.;

pyrazolo[1,5-a]pyrimidine-3-carboxylic acid (5-chloro-2,4-dimethoxy-phenyl)-amide (light brown powder); MS=333 [M+H]+; MP=243.0-247.0° C.;

pyrazolo[1,5-a]pyrimidine-3-carboxylic acid (5-chloro-2-phenoxy-phenyl)-amide (white powder); MS=365 [M+H]+; MP=184.5-186.0° C.;

pyrazolo[1,5-a]pyrimidine-3-carboxylic acid (5-chloro-2-piperidin-1-yl-phenyl)-amide (light yellow powder); MS=356 [M+H]+; MP=171.2-172.5° C.;

pyrazolo[1,5-a]pyrimidine-3-carboxylic acid {5-chloro-2-[(2-hydroxy-ethyl)-methyl-amino]-phenyl}-amide (off-white powder); MS=346 [M+H]+; MP=150.2-151.7° C.;

pyrazolo[1,5-a]pyrimidine-3-carboxylic acid (5-chloro-2-dimethylamino-phenyl)-amide (off-white powder); MS=316 [M+H]⁺; MP=179.8-180.6° C.;
pyrazolo[1,5-a]pyrimidine-3-carboxylic acid [5-chloro-2-(4-hydroxy-piperidin-1-yl)-phenyl]-amide (off-white powder); MS=372 [M+H]⁺; MP=130.7-132.0° C.;
pyrazolo[1,5-a]pyrimidine-3-carboxylic acid [5-chloro-2-(3-hydroxy-piperidin-1-yl)-phenyl]-amide (off-white powder); MS=372 [M+H]⁺; MP=185.7-186.9° C.;
pyrazolo[1,5-a]pyrimidine-3-carboxylic acid [5-chloro-2-(2-hydroxymethyl-piperidin-1-yl)-phenyl]-amide (off-white powder); MS=386 [M+H]⁺; MP=232.0-235.0° C.;
pyrazolo[1,5-a]pyrimidine-3-carboxylic acid [5-chloro-2-(4-hydroxy-phenoxy)-phenyl]-amide (white powder); MS=381 [M+H]⁺; MP=284.7-285.4° C.;
pyrazolo[1,5-a]pyrimidine-3-carboxylic acid [5-chloro-2-(3-hydroxy-phenoxy)-phenyl]-amide (off-white powder); MS=381 [M+H]⁺; MP=245.3-247.0° C.;
(1-{4-chloro-2-[(pyrazolo[1,5-a]pyrimidine-3-carbonyl)-amino]-phenyl}-piperidin-4-ylmethyl)-carbamic acid tert-butyl ester;
pyrazolo[1,5-a]pyrimidine-3-carboxylic acid {5-chloro-2-[(3-hydroxy-propyl)-methyl-amino]-phenyl}-amide (white powder); MS=360 [M+H]⁺;
6-methyl-pyrazolo[1,5-a]pyrimidine-3-carboxylic acid [5-chloro-2-(4-hydroxymethyl-piperidin-1-yl)-phenyl]-amide (off-white powder); MS=400 [M+H]⁺;
6-methoxy-pyrazolo[1,5-a]pyrimidine-3-carboxylic acid {2-[4-(tert-butyl-dimethyl-silanyloxy)-cyclohexyloxy]-5-chloro-phenyl}-amide;
6-bromo-pyrazolo[1,5-a]pyrimidine-3-carboxylic acid {2-[4-(tert-butyl-dimethyl-silanyloxy)-cyclohexyloxy]-5-chloro-phenyl}-amide;
imidazo[1,2-a]pyridine-8-carboxylic acid {2-[4-(tert-butyl-dimethyl-silanyloxy)-cyclohexyloxy]-5-chloro-phenyl}-amide;
6-methoxy-pyrazolo[1,5-a]pyrimidine-3-carboxylic acid (5-chloro-2-piperidin-1-yl-phenyl)-amide;
[1,2,4]triazolo[4,3-a]pyridine-8-carboxylic acid {2-[4-(tert-butyl-dimethyl-silanyloxy)-cyclohexyloxy]-5-chloro-phenyl}-amide;
6-methoxy-pyrazolo[1,5-a]pyrimidine-3-carboxylic acid [5-chloro-2-(4-hydroxymethyl-piperidin-1-yl)-phenyl]-amide (white solid); MS=416 [M+H]⁺; MP=257.5-258.3° C.;
(1-{4-chloro-2-[(6-methoxy-pyrazolo[1,5-a]pyrimidine-3-carbonyl)-amino]-phenyl}-piperidin-4-ylmethyl)-carbamic acid tert-butyl ester;
(1-{4-chloro-2-[(6-methoxy-pyrazolo[1,5-a]pyrimidine-3-carbonyl)-amino]-phenyl}-piperidin-4-ylmethyl)-carbamic acid tert-butyl ester;
pyrazolo[1,5-a]pyrimidine-3-carboxylic acid {5-chloro-2-[3-(1-hydroxy-ethyl)-pyrrolidin-1-yl]-phenyl}-amide (light yellow solid); MS=386 [M+H]⁺; MP=175.5-175.9° C.;
pyrazolo[1,5-a]pyrimidine-3-carboxylic acid (5-chloro-2-difluoromethoxy-phenyl)-amide (white solid); MS=339 [M+H]⁺; MP=228.0-230.5° C.;
[1-(1-{4-chloro-2-[(pyrazolo[1,5-a]pyrimidine-3-carbonyl)-amino]-phenyl}-pyrrolidin-3-yl)-ethyl]-carbamic acid tert-butyl ester;
thieno[3,2-d]pyrimidine-7-carboxylic acid [1-(3-hydroxy-propyl)-1H-benzoimidazol-2-yl]-amide (yellow foam)(3-(2-amino-benzoimidazol-1-yl)-propan-1-ol was prepared accordingly to the procedure described in WO03/030902 A1); MS=354 [M+H]⁺; and
thieno[3,2-d]pyrimidine-7-carboxylic acid {7-[4-(tert-butyl-dimethyl-silanyloxy)-cyclohexyloxy]-quinolin-6-yl}-amide.

Example 2

Synthesis of {4-Chloro-2-[(pyrazolo[1,5-a]pyrimidine-3-carbonyl)-amino]-phenoxy}-acetic acid methyl ester The synthesis of {4-chloro-2-[(pyrazolo[1,5-a]pyrimidine-3-carbonyl)-amino]-phenoxy}-acetic acid methyl ester was carried out according to the process shown in Scheme 54.

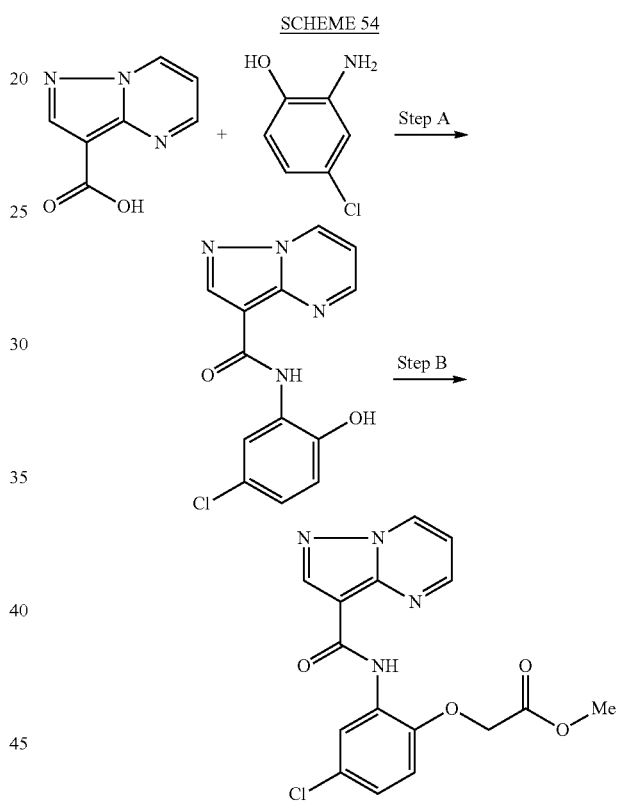

Step A: Synthesis of pyrazolo[1,5-a]pyrimidine-3-carboxylic acid (5-chloro-2-hydroxy-phenyl)-amide Pyrazolo[1,5-a]pyrimidine-3-carboxylic acid (0.5 g, 3.06 mmol) was suspended in thionyl chloride (25 mL) and the resulting mixture was heated at 85° C. for 1.5 hours. The volatiles were then evaporated under high vacuum and the residue was suspended in pyridine (25 mL). 2-Amino-4-chlorophenol (0.46 g, 3.2 mmol) was added and the resulting mixture was heated at reflux overnight. The volatiles were then evaporated under high vacuum, water and dichloromethane were added to the residue and the mixture was evaporated under reduced pressure. The solid residue was washed with a mixture of dichloromethane and methanol (96/4) to give 0.588 g (67% yield) of pyrazolo[1,5-a]pyrimidine-3-carboxylic acid (5-chloro-2-hydroxy-phenyl)-amide in mixture with pyrazolo[1,5-a]pyrimidine-3-carboxylic acid 4-chloro-2-[(pyrazolo[1,5-a]pyrimidine-3-carbonyl)-amino]-phenyl ester.

Step B: Synthesis of {4-chloro-2-[(pyrazolo[1,5-a]pyrimidine-3-carbonyl)-amino]-phenoxy}-acetic acid methyl ester To a solution of pyrazolo[1,5-a]pyrimidine-3-carboxylic acid (5-chloro-2-hydroxy-phenyl)-amide (200 mg, 0.693 mmol) in anhydrous N,N-dimethylformamide (15 mL), was added potassium carbonate (1.0 g, 7.2 mmol) followed by methyl bromoacetate (0.2 mL, 2.11 mmol) and the resulting mixture was heated at 60° C. for 6 hours. The reaction mixture was cooled to room temperature and partitioned between water and ethyl acetate; the organic layer was separated and washed with water and brine, dried over anhydrous sodium sulfate, filtered and evaporated under reduced pressure. The crude residue was purified twice by flash chromatography (DCM/MeOH/NH$_4$OH and hexane/EtOAc) to give 80 mg of a brown solid. This material was washed with acetonitrile, diethyl ether and ethyl acetate to afford 28 mg of {4-chloro-2-[(pyrazolo[1,5-a]pyrimidine-3-carbonyl)-amino]-phenoxy}-acetic acid methyl ester as a light pink powder. MS=361 [M+H]$^+$.

Pyrazolo[1,5-a]pyrimidine-3-carboxylic acid [2-(3-hydroxy-benzyloxy)-phenyl]-amide was prepared utilizing the above described procedure and the appropriate starting materials.

Example 3

Synthesis of Pyrazolo[1,5-a]pyrimidine-3-carboxylic acid (4-carbamoyl-2-methoxy-phenyl)-amide The synthesis of pyrazolo[1,5-a]pyrimidine-3-carboxylic acid (4-carbamoyl-2-methoxy-phenyl)-amide was carried out according to the process shown in Scheme 55.

SCHEME 55

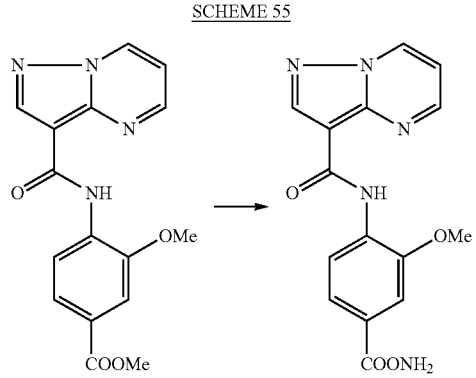

A mixture of 3-methoxy-4-[(pyrazolo[1,5-a]pyrimidine-3-carbonyl)-amino]-benzoic acid methyl ester (5 mg) and an aqueous solution of ammonium hydroxide (concentrated, 1 mL) and a mixture of 3-methoxy-4-[(pyrazolo[1,5-a]pyrimidine-3-carbonyl)-amino]-benzoic acid methyl ester (5 mg) and a solution of ammonia (2 M in MeOH, 1 mL) were stirred at room temperature for 2 days. The two mixtures were then combined and dimethyl sulfoxide (1 mL) was added followed by acetonitrile (1 mL). A solution of ammonia (2 M in MeOH, 1 mL) and an aqueous solution of ammonium hydroxide (concentrated, 2 mL) were then added and the resulting mixture was heated to 50° C. for 24 hours. A second portion of 3-methoxy-4-[(pyrazolo[1,5-a]pyrimidine-3-carbonyl)-amino]-benzoic acid methyl ester (35 mg) was added followed by dimethyl sulfoxide (5 mL), acetonitrile (5 mL), a solution of ammonia (2 M in MeOH, 5 mL) and an aqueous solution of ammonium hydroxide (concentrated, 5 mL) and the resulting mixture was heated to 85° C. for 3 days. The white precipitate which formed was collected by filtration, washed with water, methanol and diethyl ether to afford after drying 15 mg (35% yield) of pyrazolo[1,5-a]pyrimidine-3-carboxylic acid (4-carbamoyl-2-methoxy-phenyl)-amide as light yellow solid. MS=312 [M+H]$^+$.

Example 4

Synthesis of Pyrazolo[1,5-a]pyrimidine-3-carboxylic acid (2-methoxy-4-methoxymethyl-phenyl)-amide The synthesis of pyrazolo[1,5-a]pyrimidine-3-carboxylic acid (2-methoxy-4-methoxymethyl-phenyl)-amide was carried out according to the process shown in Scheme 56.

SCHEME 56

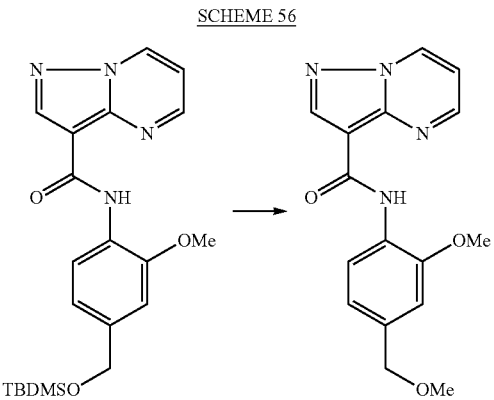 [SMILES: COc1cc(CO[Si](C)(C)C(C)(C)C)ccc1NC(=O)c1cnn2cccnc12 ; COCc1ccc(NC(=O)c2cnn3cccnc23)c(OC)c1]

A solution of hydrochloric acid (1 M in Et$_2$O, 2 mL) was added to a solution of pyrazolo[1,5-a]pyrimidine-3-carboxylic acid [4-(tert-butyl-dimethyl-silanyloxymethyl)-2-methoxy-phenyl]-amide (160 mg, 0.388 mmol) in dichloromethane (20 mL) and the resulting mixture was stirred at room temperature for 10 minutes. A second aliquot of solution of hydrochloric acid (1 M in Et$_2$O, 2 mL) was added and the reaction mixture was stirred for 1 hour.

The resulting mixture was evaporated under reduced pressure and the yellow solid residue was washed with hexane, ethyl acetate, diethyl ether and dichloromethane. The solid and the filtrate were then combined and partitioned between dichloromethane and aqueous solution of sodium bicarbonate (5%). The organic layer was separated and the aqueous layer was extracted 3 times with dichloromethane. The combined organic extracts were washed with brine, dried over anhydrous sodium sulfate, filtered and evaporated under reduced pressure. The yellow solid residue was purified by flash chromatography (DCM/MeOH/NH$_4$OH) to give 80 mg of pyrazolo[1,5-a]pyrimidine-3-carboxylic acid (2-methoxy-4-methoxymethyl-phenyl)-amide and 40 mg of pyrazolo[1,5-a]pyrimidine-3-carboxylic acid (4-hydroxymethyl-2-methoxy-phenyl)-amide. Pyrazolo[1,5-a]pyrimidine-3-carboxylic acid (2-methoxy-4-methoxymethyl-phenyl)-amide compound was repurified by preparative TLC (DCM/MeOH/NH$_4$OH) and was washed with diethyl ether

Example 5

Synthesis of Pyrazolo[1,5-a]pyrimidine-3-carboxylic acid (4-hydroxymethyl-2-methoxy-phenyl)-amide The synthesis of pyrazolo[1,5-a]pyrimidine-3-carboxylic acid (4-hydroxymethyl-2-methoxy-phenyl)-amide was carried out according to the process shown in Scheme 57.

SCHEME 57

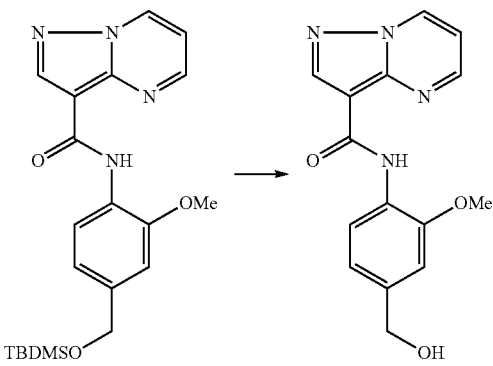

A solution of hydrochloric acid (1 M in Et$_2$O, 3 mL) was added to a solution of pyrazolo[1,5-a]pyrimidine-3-carboxylic acid [4-(tert-butyl-dimethyl-silanyloxymethyl)-2-methoxy-phenyl]-amide (150 mg, 0.364 mmol) in dichloromethane (20 mL) and the resulting mixture was stirred at room temperature for 2 hours. Ice and water were then added and the pH of the mixture was neutralized by addition of an aqueous solution of sodium hydroxide (5%). The resulting mixture was extracted 3 times with dichloromethane. The combined organic extracts were washed with brine, dried over anhydrous sodium sulfate, filtered and evaporated under reduced pressure. The crude residue was purified by flash chromatography and by preparative TLC to give a yellow solid which was washed with water, methanol, dichloromethane, hexane and diethyl ether to give after drying pyrazolo[1,5-a]pyrimidine-3-carboxylic acid (4-hydroxymethyl-2-methoxy-phenyl)-amide as a light yellow solid. MS=299 [M+H]$^+$.

Utilizing the above described procedure and the appropriate starting materials, the following compounds were prepared:

pyrazolo[1,5-a]pyrimidine-3,6-dicarboxylic acid 6-amide 3-{[5-chloro-2-(4-hydroxy-cyclohexyloxy)-phenyl]-amide}(yellow powder); MS=430 [M+H]$^+$;

pyrazolo[1,5-a]pyrimidine-3-carboxylic acid (4-chloro-3'-hydroxy-biphenyl-2-yl)-amide (off-white powder); MS=365 [M+H]$^+$;

pyrazolo[1,5-a]pyrimidine-3-carboxylic acid [7-(4-hydroxy-cyclohexyloxy)-quinolin-6-yl]-amide (white powder); MS=404 [M+H]$^+$; MP=273.8-275.1° C.;

pyrazolo[1,5-a]pyrimidine-3-carboxylic acid (4-chloro-4'-hydroxy-biphenyl-2-yl)-amide (light yellow powder); MS=365 [M+H]$^+$;

pyrazolo[1,5-a]pyrimidine-3,6-dicarboxylic acid 6-amide 3-{[5-chloro-2-(4-cis-hydroxy-cyclohexyloxy)-phenyl]-amide}(yellow powder); MS=430 [M+H]$^+$;

thieno[3,2-d]pyrimidine-7-carboxylic acid [7-((1R,3R)-3-hydroxy-cyclopentyloxy)-quinolin-6-yl]-amide hydrochloride (light yellow powder); MS=407 [M+H]$^+$;

thieno[3,2-d]pyrimidine-7-carboxylic acid [7-((1R,3S)-3-hydroxy-cyclopentyloxy)-quinolin-6-yl]-amide hydrochloride salt (light yellow powder); MS=407 [M+H]$^+$;

thieno[3,2-d]pyrimidine-7-carboxylic acid [7-(3-hydroxy-1-methyl-butoxy)-quinolin-6-yl]-amide bishydrochloride salt (off-white powder); MS=409 [M+H]$^+$;

thieno[3,2-d]pyrimidine-7-carboxylic acid [5-chloro-2-(3-hydroxy-cyclopentyloxy)-phenyl]-amide hydrochloride salt (yellow powder); MS=390 [M+H]$^+$; MP=220.0-221.5° C.;

thieno[3,2-d]pyrimidine-7-carboxylic acid [5-chloro-2-(3-hydroxy-propoxy)-phenyl]-amide hydrochloride salt (yellow powder); MS=364 [M+H]$^+$; MP=215.5-218.0° C.;

pyrazolo[1,5-a]pyrimidine-3-carboxylic acid [4-(2-hydroxy-ethylcarbamoyl)-2-methoxy-phenyl]-amide (brown powder); MS=356 [M+H]$^+$; MP=267.5-268.5° C.;

thieno[3,2-d]pyrimidine-7-carboxylic acid [4-(2-hydroxy-ethylcarbamoyl)-2-methoxy-phenyl]-amide hydrochloride (yellow powder); MS=373 [M+H]$^+$; MP=223-226° C.;

thieno[3,2-d]pyrimidine-7-carboxylic acid [4-(3-hydroxy-propylcarbamoyl)-2-methoxy-phenyl]-amide (white powder); MS=387 [M+H]$^+$; MP=229.3-229.8° C.;

pyrazolo[1,5-a]pyrimidine-3-carboxylic acid [4-(3-hydroxy-propylcarbamoyl)-2-methoxy-phenyl]-amide (white powder); MS=370 [M+H]$^+$; MP=230.8-232.3° C.;

pyrazolo[1,5-a]pyrimidine-3-carboxylic acid [5-chloro-2-(3-hydroxy-propoxy)-phenyl]-amide (white powder); MS=347 [M+H]$^+$;

pyrazolo[1,5-a]pyrimidine-3-carboxylic acid [5-chloro-2-(2-hydroxy-ethoxy)-phenyl]-amide (white powder); MS=333 [M+H]$^+$;

thieno[3,2-d]pyrimidine-7-carboxylic acid [7-(4-hydroxy-cyclohexyloxy)-quinolin-6-yl]-amide (off-white powder); MS=421 [M+H]$^+$;

thieno[3,2-d]pyrimidine-7-carboxylic acid [7-(3-hydroxy-propoxy)-quinolin-6-yl]-amide hydrochloride (yellow crystalline solid); MS=381 [M+H]$^+$; MP=269.9-271.0° C.;

cis-thieno[3,2-d]pyrimidine-7-carboxylic acid [7-(4-hydroxy-cyclohexyloxy)-quinolin-6-yl]-amide hydrochloride (white powder); MS=421 [M+H]$^+$; MP=281.1-283.6° C.;

6-(2-hydroxy-ethyl)-pyrazolo[1,5-a]pyrimidine-3-carboxylic acid [5-chloro-2-(4-hydroxy-cyclohexyloxy)-phenyl]-amide (light yellow powder); MS=431 [M+H]$^+$;

pyrazolo[1,5-a]pyrimidine-3-carboxylic acid {5-chloro-2-[4-(1-hydroxy-ethyl)-piperidin-1-yl]-phenyl}-amide (off-white powder); MS=400 [M+H]$^+$; MP=180.6-181.8° C.;

6-methoxy-pyrazolo[1,5-a]pyrimidine-3-carboxylic acid [5-chloro-2-(4-hydroxy-cyclohexyloxy)-phenyl]-amide (off-white solid); MS=417 [M+H]$^+$; MP=258.9-260.7° C.;

6-bromo-pyrazolo[1,5-a]pyrimidine-3-carboxylic acid [5-chloro-2-(4-hydroxy-cyclohexyloxy)-phenyl]-amide (off-white solid); MS=465 [M+H]$^+$; MP=289.4-290.8° C.;

[1,2,4]triazolo[4,3-a]pyridine-8-carboxylic acid [5-chloro-2-(4-hydroxy-cyclohexyloxy)-phenyl]-amide (yellow solid); MS=387 [M+H]$^+$; MP=216.3-217.3° C.;

6-hydroxy-pyrazolo[1,5-a]pyrimidine-3-carboxylic acid [5-chloro-2-(4-hydroxy-cyclohexyloxy)-phenyl]-amide (yellow solid); MS=403 [M+H]$^+$; and thieno[3,2-d]pyrimidine-7-carboxylic acid [7-(4-hydroxy-cyclohexyloxy)-quinolin-6-yl]-amide hydrochloride (off-white powder); MS=421 [M+H]+.

Example 6

Synthesis of 6-hydroxymethyl-pyrazolo[1,5-a]pyrimidine-3-carboxylic acid [5-chloro-2-(4-hydroxy-cyclohexyloxy)-phenyl]-amide The synthesis of 6-hydroxymethyl-pyrazolo[1,5-a]pyrimidine-3-carboxylic acid [5-chloro-2-(4-hydroxy-cyclohexyloxy)-phenyl]-amide was carried out according to the process shown in Scheme 58.

SCHEME 58

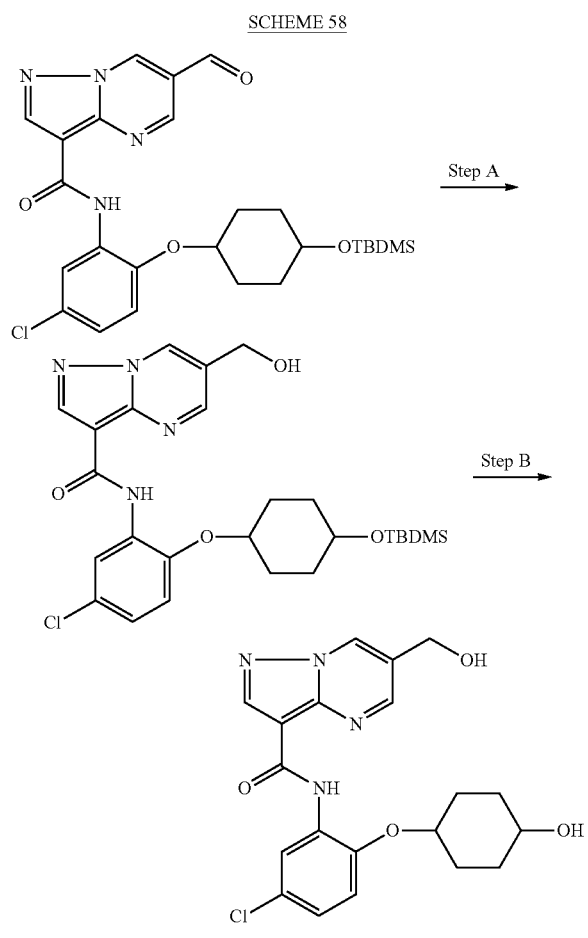

Step A: Synthesis of 6-hydroxymethyl-pyrazolo[1,5-a]pyrimidine-3-carboxylic acid {2-[4-(tert-butyl-dimethyl-silanyloxy)-cyclohexyloxy]-5-chloro-phenyl}-amide Sodium borohydride (30 mg, 0.079 mmol) was added to a solution of 6-formyl-pyrazolo[1,5-a]pyrimidine-3-carboxylic acid {2-[4-(tert-butyl-dimethyl-silanyloxy)-cyclohexyloxy]-5-chloro-phenyl}-amide (20 mg, 0.038 mmol) in a mixture of tetrahydrofuran (1.5 mL) and water (0.1 mL) and the resulting mixture was stirred at room temperature for 2.5 hours. The solvent was evaporated under reduced pressure to give 6-hydroxymethyl-pyrazolo[1,5-a]pyrimidine-3-carboxylic acid {2-[4-(tert-butyl-dimethyl-silanyloxy)-cyclohexyloxy]-5-chloro-phenyl}-amide as an oily residue.

Step B: Synthesis of 6-hydroxymethyl-pyrazolo[1,5-a]pyrimidine-3-carboxylic acid [5-chloro-2-(4-hydroxy-cyclohexyloxy)-phenyl]-amide 6-Hydroxymethyl-pyrazolo[1,5-a]pyrimidine-3-carboxylic acid {2-[4-(tert-butyl-dimethyl-silanyloxy)-cyclohexyloxy]-5-chloro-phenyl}-amide was deprotected as described in Example 5 to give 6-hydroxymethyl-pyrazolo[1,5-a]pyrimidine-3-carboxylic acid [5-chloro-2-(4-hydroxy-cyclohexyloxy)-phenyl]-amide as a yellow powder. MS=417 [M+H]+.

Example 7

Synthesis of Pyrazolo[1,5-a]pyrimidine-3-carboxylic acid [5-chloro-2-(3-hydroxy-benzyloxy)-phenyl]-amide The synthesis of pyrazolo[1,5-a]pyrimidine-3-carboxylic acid [5-chloro-2-(3-hydroxy-benzyloxy)-phenyl]-amide was carried out according to the process shown in Scheme 59.

SCHEME 59

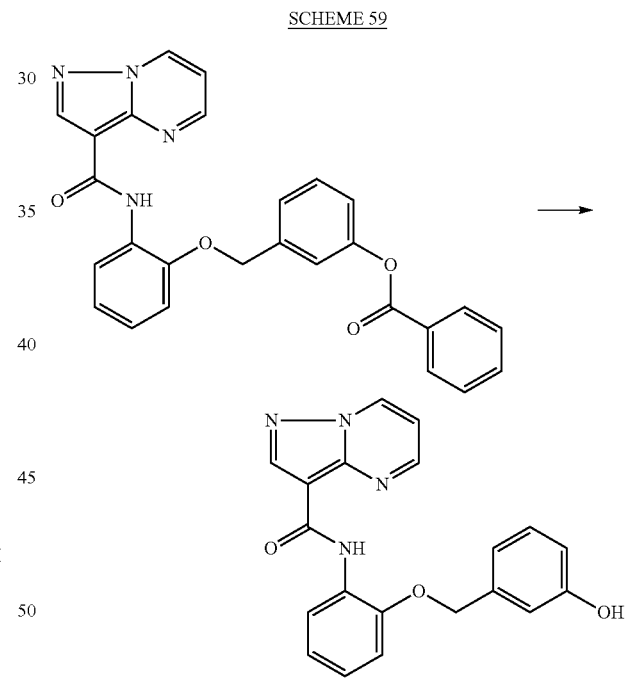

An aqueous solution of sodium hydroxide (2 M, 0.14 mL, 0.28 mmol) was added to a suspension of pyrazolo[1,5-a]pyrimidine-3-carboxylic acid [2-(3-hydroxy-benzyloxy)-phenyl]-amide (70 mg, 0.14 mmol) in a mixture of ethanol and water (1/1, 6 mL) and the resulting mixture was stirred at room temperature for 1 hour. The reaction mixture was heated at 60° C. for 1.5 hours, and then was evaporated under reduced pressure. The residue was acidified (pH 5) by addition of an aqueous solution of hydrochloric acid (1 M) and was extracted with dichloromethane (50 mL). The organic layer was separated, dried over anhydrous sodium sulfate, filtered and evaporated under reduced pressure. The crude residue was purified by preparative TLC (DCM/

MeOH, 96/4) to afford pyrazolo[1,5-a]pyrimidine-3-carboxylic acid [5-chloro-2-(3-hydroxy-benzyloxy)-phenyl]-amide as a white solid. MS=395.

Example 8

Synthesis of Thieno[3,2-d]pyrimidine-7-carboxylic acid [5-chloro-2-(4-methylaminomethyl-piperidin-1-yl)-phenyl]-amide The synthesis of thieno[3,2-d]pyrimidine-7-carboxylic acid [5-chloro-2-(4-methylaminomethyl-piperidin-1-yl)-phenyl]-amide was carried out according to the process shown in Scheme 60.

SCHEME 60

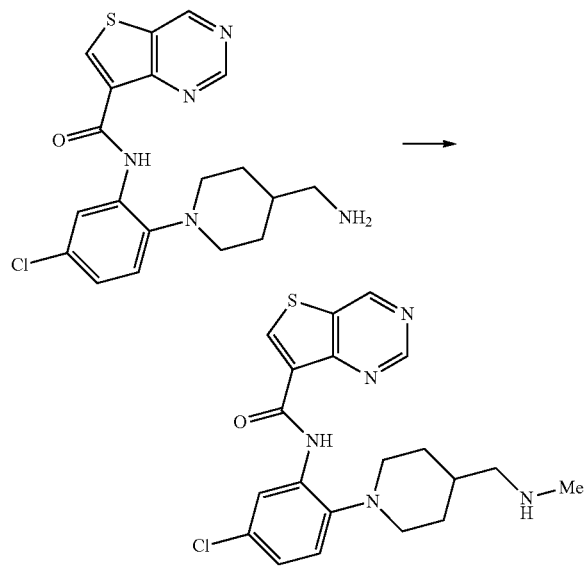

To a suspension of thieno[3,2-d]pyrimidine-7-carboxylic acid [2-(4-aminomethyl-piperidin-1-yl)-5-chloro-phenyl]-amide (70 mg, 0.17 mmol) in water (1 mL) was added formic acid (22 μL, 0.59 mmol) followed by formaldehyde (36% water solution, 0.4 mL) and the resulting mixture was stirred at room temperature overnight. The reaction mixture was basified by addition of an aqueous solution of sodium hydroxide (2 M) until pH 14 and was then extracted with dichloromethane. The organic layer was separated, dried over anhydrous sodium sulfate, filtered and evaporated under reduced pressure. The crude residue was purified several times by preparative TLC (DCM/MeOH+NH₄OH, 93/7+0.5) to give 25 mg of thieno[3,2-d]pyrimidine-7-carboxylic acid [5-chloro-2-(4-methylaminomethyl-piperidin-1-yl)-phenyl]-amide as a light yellow solid; MS=416 [M+H]⁺; MP=190.0-193.3° C.; and 3 mg of thieno[3,2-d]pyrimidine-7-carboxylic acid [5-chloro-2-(4-dimethylaminomethyl-piperidin-1-yl)-phenyl]-amide as a white powder; MS=430 [M+H]⁺.

Utilizing the above described procedure and the appropriate starting materials, the following compounds were prepared:

pyrazolo[1,5-a]pyrimidine-3-carboxylic acid [5-chloro-2-(4-dimethylaminomethyl-piperidin-1-yl)-phenyl]-amide (white powder); MS=413 [M+H]⁺; and pyrazolo[1,5-a]pyrimidine-3-carboxylic acid [5-chloro-2-(4-methylaminomethyl-piperidin-1-yl)-phenyl]-amide (light yellow powder); MS=399 [M+H]⁺; MP=139.0-146.5° C.

Example 9

Synthesis of 7-Methyl-pyrazolo[1,5-a]pyrimidine-3-carboxylic acid [5-chloro-2-(4-hydroxy-cyclohexyloxy)-phenyl]-amide The synthesis of 7-methyl-pyrazolo[1,5-a]pyrimidine-3-carboxylic acid [5-chloro-2-(4-hydroxy-cyclohexyloxy)-phenyl]-amide was carried out according to the process shown in Scheme 61.

SCHEME 61

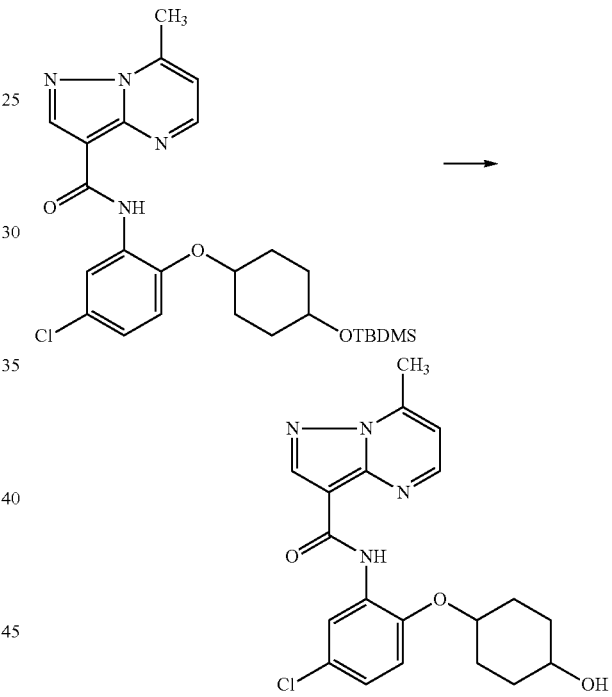

Hydrochloric acid (concentrated, 5 drops) was added to a solution of 7-methyl-pyrazolo[1,5-a]pyrimidine-3-carboxylic acid {2-[4-(tert-butyl-dimethyl-silanyloxy)-cyclohexyloxy]-5-chloro-phenyl}-amide (ca. 0.22 mmol) in methanol (3 mL) and the resulting mixture was heated at 80° C. for 30 minutes. The resulting mixture was cooled, basified by addition of an aqueous solution of sodium hydroxide (4 M, few drops) and evaporated under reduced pressure. The crude residue was purified by flash chromatography to give 28 mg of 7-methyl-pyrazolo[1,5-a]pyrimidine-3-carboxylic acid [5-chloro-2-(4-hydroxy-cyclohexyloxy)-phenyl]-amide (off-white solid). MS=401 [M+H]⁺.

5-Methyl-pyrazolo[1,5-a]pyrimidine-3-carboxylic acid [5-chloro-2-(4-hydroxy-cyclohexyloxy)-phenyl]-amide (white solid) was prepared utilizing the above described procedure and the appropriate starting materials; MS=401 [M+H]⁺; MP=179-182° C.

Example 10

Synthesis of Pyrazolo[1,5-a]pyrimidine-3-carboxylic acid [5-((E)-3-hydroxy-propenyl)-2-methoxy-phenyl]-amide The synthesis of pyrazolo[1,5-a]pyrimidine-3-carboxylic acid [5-((E)-3-hydroxy-propenyl)-2-methoxy-phenyl]-amide was carried out according to the process shown in Scheme 62.

SCHEME 62

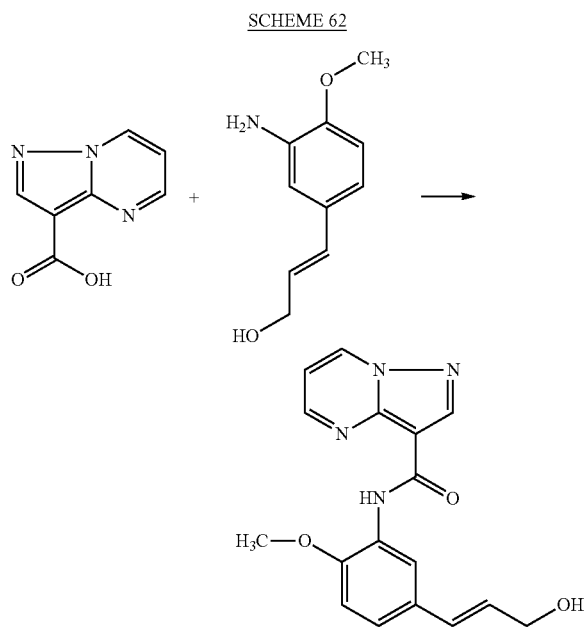

A mixture of diisopropylethylamine (0.25 mL), (E)-3-(3-amino-4-methoxy-phenyl)-prop-2-en-1-ol (90 mg), pyrazolo[1,5-a]pyrimidine-3-carboxylic acid (65 mg), HOBT (85 mg) and HBTU (0.20 g) in anhydrous acetonitrile (5 mL) was heated to 80° C. overnight. The resulting mixture was evaporated under reduced pressure and the residue was partitioned between ethyl acetate and water. The organic layer was separated, washed with brine, dried over anhydrous sodium sulfate, filtered and evaporated under reduced pressure. The crude residue was purified by flash chromatography (MeOH/EtOAc, 3/97) to give an oil. This residue was triturated with ethyl acetate to give, upon standing for 1 hour, 20 mg of (E)-3-(3-amino-4-methoxy-phenyl)-prop-2-en-1-ol as a light brown solid which was collected by filtration. MS=325 [M+H]$^+$.

Example 11

Synthesis of Pyrazolo[1,5-a]pyrimidine-3-carboxylic acid [2-(4-aminomethyl-piperidin-1-yl)-5-chloro-phenyl]-amide The synthesis of pyrazolo[1,5-a]pyrimidine-3-carboxylic acid [2-(4-aminomethyl-piperidin-1-yl)-5-chloro-phenyl]-amide was carried out according to the process shown in Scheme 63.

SCHEME 63

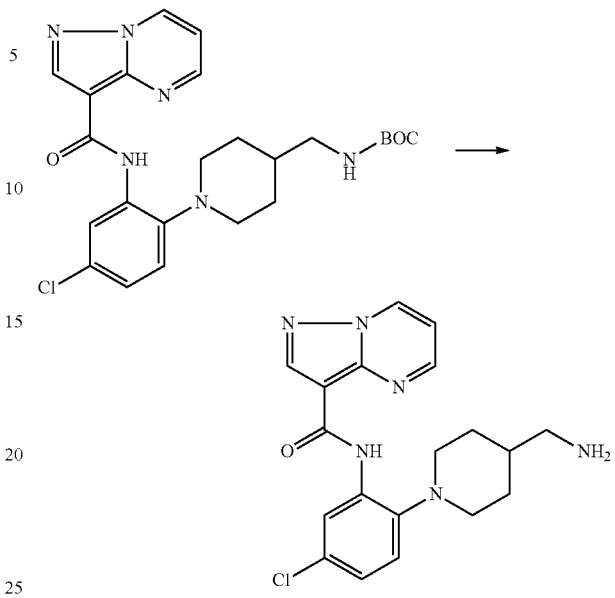

Trifluoroacetic acid (1 mL) was added to a solution of (1-{4-chloro-2-[(pyrazolo[1,5-a]pyrimidine-3-carbonyl)-amino]-phenyl}-piperidin-4-ylmethyl)-carbamic acid tert-butyl ester (80 mg) in dichloromethane (2 mL) and the reaction mixture was stirred at room temperature for 2 hours. The resulting mixture was evaporated under reduced pressure and the residue was dissolved in dichloremethane, carbonate resin (2.8 mmol/g, 200 mg) was added and the mixture was stirred overnight. The solid was filtered off and the filtrate was evaporated under reduced pressure, the residue was purified by flash chromatography (DCM/MeOH/NH$_4$OH) to give 40 mg of a foam. This material was triturated with a mixture of ethyl acetate and hexane (1/1), the solid was collected by filtration, dissolved in a mixture of dichloromethane and methanol and the mixture was evaporated under reduced pressure to give 20 mg of pyrazolo[1,5-a]pyrimidine-3-carboxylic acid [2-(4-aminomethyl-piperidin-1-yl)-5-chloro-phenyl]-amide as a light yellow foam. MS=385 [M+H]$^+$.

The following compounds were prepared utilizing the above described procedure and the appropriate starting materials:

pyrazolo[1,5-a]pyrimidine-3-carboxylic acid [2-(3-aminomethyl-pyrrolidin-1-yl)-5-chloro-phenyl]-amide (light yellow waxy solid) (the trifluorocetate salt was neutralized by treatment with an aqueous solution of sodium hydroxide (2 M)); MS=371 [M+H]$^+$;

thieno[3,2-d]pyrimidine-7-carboxylic acid [2-(4-aminomethyl-piperidin-1-yl)-5-chloro-phenyl]-amide (orange foam); MS=403 [M+H]$^+$;

thieno[3,2-b]pyridine-3-carboxylic acid [2-(4-aminomethyl-piperidin-1-yl)-5-chloro-phenyl]-amide (pink foam); MS=401 [M+H]$^+$;

thieno[3,2-d]pyrimidine-7-carboxylic acid [5-chloro-2-(piperidin-4-yloxy)-phenyl]-amide trifluoroacetate (off-white solid); MS=389 [M+H]$^+$; MP>300° C.;

thieno[3,2-b]pyridine-3-carboxylic acid [7-(4-aminomethyl-piperidin-1-yl)-quinolin-6-yl]-amide (off-white solid); MS=418 [M+H]$^+$;

pyrazolo[1,5-a]pyrimidine-3-carboxylic acid [2-(4-aminomethyl-piperidin-1-yl)-5-chloro-phenyl]-amide trifluoroacetate (white solid); MS=385 [M+H]+; MP=110.0-112.1° C.; and
6-methoxy-pyrazolo[1,5-a]pyrimidine-3-carboxylic acid [2-(4-aminomethyl-piperidin-1-yl)-5-chloro-phenyl]-amide (light yellow solid); MS=415 [M+H]+; MP=210.0-214.4° C.

Example 12

Synthesis of 2-Isopropylamino-thieno[3,2-d]pyrimidine-7-carboxylic acid (7-methoxy-quinolin-6-yl)-amide The synthesis of 2-isopropylamino-thieno[3,2-d]pyrimidine-7-carboxylic acid (7-methoxy-quinolin-6-yl)-amide was carried out according to the process shown in Scheme 64.

A mixture of 2-chloro-thieno[3,2-d]pyrimidine-7-carboxylic acid (7-methoxy-quinolin-6-yl)-amide (200 mg) and isopropylamine (200 μL) in 1,4-dioxane (5 mL) was heated at 100° C. for 20 hours. The reaction mixture was then cooled and the solid which crushed out was collected by filtration, washed with water and ethyl acetate. The filtrate was washed with water and brine, dried over anhydrous sodium sulfate, filtered and evaporated under reduced pressure. The crude residue was purified by flash chromatography (Acetone/DCM) to give combined with the previously obtained solid 137 mg of 2-isopropylamino-thieno[3,2-d]pyrimidine-7-carboxylic acid (7-methoxy-quinolin-6-yl)-amide after drying under vacuum at 60° C. MS=394 [M+H]+; MP=221.4-222.7° C.

Utilizing the above described procedure and the appropriate starting materials, the following compounds were prepared:
5-(2-hydroxy-ethylamino)-thieno[3,2-b]pyridine-3-carboxylic acid (5-chloro-2-methoxy-phenyl)-amide (orange semisolid); MS=378 [M+H]+;
2-(2-hydroxy-ethylamino)-thieno[3,2-d]pyrimidine-7-carboxylic acid (5-chloro-2-methoxy-phenyl)-amide (yellow powder); MS=379 [M+H]+;
2-(3-hydroxy-propylamino)-thieno[3,2-d]pyrimidine-7-carboxylic acid (5-chloro-2-methoxy-phenyl)-amide (light yellow powder); MS=393 [M+H]+; MP=178.0-181.0° C.;
2-(2-hydroxy-ethylamino)-thieno[3,2-d]pyrimidine-7-carboxylic acid quinolin-6-ylamide (light yellow solid); MS=366 [M+H]+; MP>300° C.;
2-[(2-hydroxy-ethyl)-methyl-amino]-thieno[3,2-d]pyrimidine-7-carboxylic acid (5-chloro-2-methoxy-phenyl)-amide (yellow solid); MS=393 [M+H]+; MP=185.0-188.0° C.;
2-(2-hydroxy-ethylamino)-thieno[3,2-d]pyrimidine-7-carboxylic acid (7-methoxy-quinolin-6-yl)-amide (light yellow solid); MS=396 [M+H]+; MP=227.0-229.0° C.;
2-((S)-1-hydroxymethyl-propylamino)-thieno[3,2-d]pyrimidine-7-carboxylic acid (5-chloro-2-methoxy-phenyl)-amide (light yellow solid); MS=407 [M+H]+; MP=195.5-197.0° C.;
2-[(2-hydroxy-ethyl)-methyl-amino]-thieno[3,2-d]pyrimidine-7-carboxylic acid (7-methoxy-quinolin-6-yl)-amide (light yellow powder); MS=410 [M+H]+; MP=205.0-207.0° C.;
2-cyclopropylamino-thieno[3,2-d]pyrimidine-7-carboxylic acid (7-methoxy-quinolin-6-yl)-amide (yellow solid); MS=392 [M+H]+; MP=256.6-260.1° C.;
2-[(2-hydroxy-ethyl)-isopropyl-amino]-thieno[3,2-d]pyrimidine-7-carboxylic acid (7-methoxy-quinolin-6-yl)-amide (light yellow solid); MS=438 [M+H]+;
2-(2,3-dihydroxy-propylamino)-thieno[3,2-d]pyrimidine-7-carboxylic acid (7-methoxy-quinolin-6-yl)-amide (purple solid); MS=426 [M+H]+;
2-isopropylamino-thieno[3,2-d]pyrimidine-7-carboxylic acid (7-methoxy-quinolin-6-yl)-amide (yellow solid); MS=394 [M+H]+;
2-(isopropyl-methyl-amino)-thieno[3,2-d]pyrimidine-7-carboxylic acid (7-methoxy-quinolin-6-yl)-amide (off-white solid); MS=408 [M+H]+;
2-isobutylamino-thieno[3,2-d]pyrimidine-7-carboxylic acid (7-methoxy-quinolin-6-yl)-amide (yellow solid); MS=408 [M+H]+; MP=194.4-198.9° C.;
2-isopropylamino-thieno[3,2-d]pyrimidine-7-carboxylic acid [5-chloro-2-(4-hydroxy-cyclohexyloxy)-phenyl]-amide (off-white solid); MS=460 [M]+; MP=112.9-113.9° C.;
2-((R)-2-hydroxy-1-methyl-ethylamino)-thieno[3,2-d]pyrimidine-7-carboxylic acid (7-methoxy-quinolin-6-yl)-amide (light yellow solid); MS=410 [M+H]+;
2-(2-amino-ethylamino)-thieno[3,2-d]pyrimidine-7-carboxylic acid (5-chloro-2-methoxy-phenyl)-amide (white solid); MS=378 [M+H]+;
2-(2-acetylamino-ethylamino)-thieno[3,2-d]pyrimidine-7-carboxylic acid (5-chloro-2-methoxy-phenyl)-amide (light yellow solid); MS=420 [M+H]+; MP=238.0-240.9° C.;
2-[(2-amino-ethyl)-methyl-amino]-thieno[3,2-d]pyrimidine-7-carboxylic acid (5-chloro-2-methoxy-phenyl)-amide (off-white solid); MS=392 [M+H]+; MP=144.0-147.6° C.;
2-[(2-amino-ethyl)-methyl-amino]-thieno[3,2-d]pyrimidine-7-carboxylic acid (7-methoxy-quinolin-6-yl)-amide (light brown solid); MS=409 [M+H]+; MP=195.0-197.0° C.;
2-(3-amino-propylamino)-thieno[3,2-d]pyrimidine-7-carboxylic acid (7-methoxy-quinolin-6-yl)-amide (off-white solid); MS=409 [M+H]+; and
2-(2-amino-ethylamino)-thieno[3,2-d]pyrimidine-7-carboxylic acid (7-methoxy-quinolin-6-yl)-amide (orange solid); MS=395 [M+H]+.

Example 13

Synthesis of 6-Hydroxymethyl-thieno[3,2-b]pyridine-3-carboxylic acid (7-methoxy-quinolin-6-yl)-amide The synthesis of 6-hydroxymethyl-thieno[3,2-b]pyridine-3-carboxylic acid (7-methoxy-quinolin-6-yl)-amide was carried out according to the process shown in Scheme 65

SCHEME 65

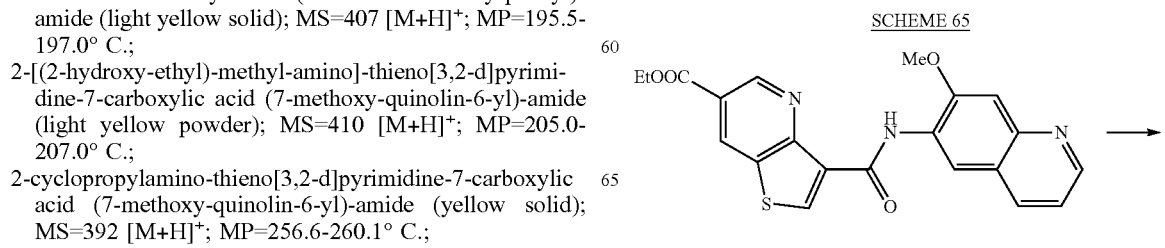

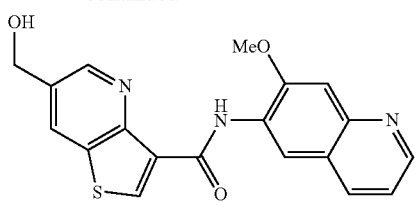

A solution of lithium aluminum hydride (3.5 M in toluene, 0.1 mL) was added to a suspension of 3-(7-methoxy-quinolin-6-ylcarbamoyl)-thieno[3,2-b]pyridine-6-carboxylic acid ethyl ester (30 mg) in tetrahydrofuran (2 mL) and the resulting orange solution was stirred for 10 minutes. The reaction mixture was then quenched by addition of a saturated aqueous solution of ammonium chloride. The resulting mixture was filtered through a CELITE™ pad and the filter cake was washed with ethyl acetate. The filtrate was separated and the organic layer was dried over anhydrous sodium sulfate, filtered and evaporated under reduced pressure. The crude residue was purified by flash chromatography (DCM/MeOH, 97/3) to give 8 mg of 6-hydroxymethyl-thieno[3,2-b]pyridine-3-carboxylic acid (7-methoxy-quinolin-6-yl)-amide as an off-white solid. MS=365 [M+H]+.

Example 14

Synthesis of 6-Hydroxy-pyrazolo[1,5-a]pyrimidine-3-carboxylic acid [7-(4-aminomethyl-piperidin-1-yl)-quinolin-6-yl]-amide hydrochloride The synthesis of 6-hydroxy-pyrazolo[1,5-a]pyrimidine-3-carboxylic acid [7-(4-aminomethyl-piperidin-1-yl)-quinolin-6-yl]-amide hydrochloride was carried out according to the process shown in Scheme 66.

SCHEME 66

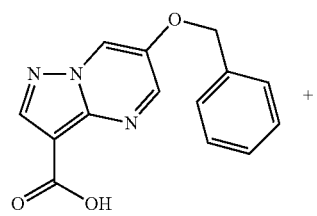

+

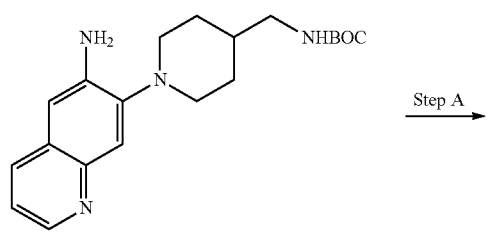

Step A →

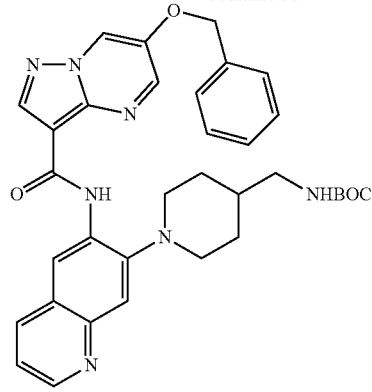

Step B →

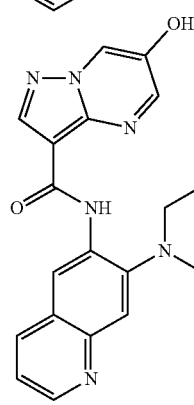

Step C →

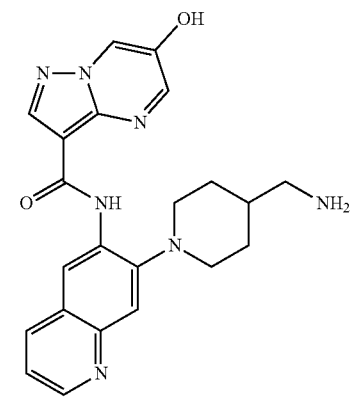

Step A: Synthesis of (1-{6-[(6-benzyloxy-pyrazolo[1,5-a]pyrimidine-3-carbonyl)-amino]-quinolin-7-yl}-piperidin-4-ylmethyl)-carbamic acid tert-butyl ester Thionyl chloride (0.27 mL, 3.7 mmol) was added to 6-benzyloxy-pyrazolo[1,5-a]pyrimidine-3-carboxylic acid (0.25 g, 0.94 mmol) at room temperature and the resulting mixture was stirred until a clear solution was obtained. The reaction mixture was concentrated under reduced pressure, to the residue was added dichloromethane (10 mL) followed by a solution of [1-(6-amino-quinolin-7-yl)-piperidin-4-ylmethyl]-carbamic acid tert-butyl ester (0.33 g, 0.94 mmol) and diisopropylethylamine (0.16 mL, 0.94 mmol) in dichloromethane (2 mL) at 0° C. and the resulting mixture was stirred at room temperature overnight. The reaction mixture was heated at 60° C. for 6 hours and then was partitioned between water and dichloromethane. The organic layer was separated, dried over anhydrous sodium sulfate, filtered and evaporated under reduced pressure. The residue was purified by flash chromatography (EtOAc/hexane, 1/1) to afford 0.420 g of (1-{6-[(6-benzyloxy-pyrazolo[1,5-a]pyrimidine-3-carbonyl)-amino]-quinolin-7-yl}-piperidin-4-ylmethyl)-carbamic acid tert-butyl ester as a solid.

Step B: Synthesis of (1-{6-[(6-hydroxy-pyrazolo[1,5-a]pyrimidine-3-carbonyl)-amino]-quinolin-7-yl}-piperidin-4-ylmethyl)-carbamic acid tert-butyl ester A mixture of (1-{6-[(6-benzyloxy-pyrazolo[1,5-a]pyrimidine-3-carbonyl)-amino]-quinolin-7-yl}-piperidin-4-ylmethyl)-carbamic acid tert-butyl ester (0.4 g) and palladium on carbon (10%, 50 mg) in ethanol (20 mL) was stirred under hydrogen atmosphere (balloon pressure) for 2 days. The resulting mixture was filtered over a CELITE™ pad and the filtrate was evaporated under reduced pressure. The crude residue was purified by flash chromatography to afford 0.220 g of (1-{6-[(6-hydroxy-pyrazolo[1,5-a]pyrimidine-3-carbonyl)-amino]-quinolin-7-yl}-piperidin-4-ylmethyl)-carbamic acid tert-butyl ester as a yellow solid.

Utilizing the above described procedure and the appropriate starting materials, the following compounds were prepared:
6-hydroxy-pyrazolo[1,5-a]pyrimidine-3-carboxylic acid (7-methoxy-quinolin-6-yl)-amide (light yellow powder); MS=336 [M+H]$^+$; MP=265-268° C.; and
6-hydroxy-pyrazolo[1,5-a]pyrimidine-3-carboxylic acid [5-chloro-2-(4-hydroxymethyl-piperidin-1-yl)-phenyl]-amide (off-white powder); MS=402 [M+H]$^+$.

Step C: Synthesis of 6-hydroxy-pyrazolo[1,5-a]pyrimidine-3-carboxylic acid [7-(4-aminomethyl-piperidin-1-yl)-quinolin-6-yl]-amide hydrochloride A solution of hydrochloric acid (1 M in Et$_2$O, 5 mL) was added to a solution of (1-{6-[(6-hydroxy-pyrazolo[1,5-a]pyrimidine-3-carbonyl)-amino]-quinolin-7-yl}-piperidin-4-ylmethyl)-carbamic acid tert-butyl ester (0.22 g) in a mixture of dichloromethane and methanol (1/1, 10 mL) and the resulting mixture was stirred at room temperature overnight. The solid formed was collected by filtration, washed with ethanol and dried under reduced pressure to give 224 mg of 6-hydroxy-pyrazolo[1,5-a]pyrimidine-3-carboxylic acid [7-(4-aminomethyl-piperidin-1-yl)-quinolin-6-yl]-amide hydrochloride as a light yellow powder. MS=418 [M+H]$^+$; MP>300° C.

6-Hydroxy-pyrazolo[1,5-a]pyrimidine-3-carboxylic acid [2-(4-aminomethyl-piperidin-1-yl)-5-chloro-phenyl]-amide bishydrochloride (white powder) was prepared utilizing the above described procedure and the appropriate starting materials; Step A was performed as described in Example 1. MS=401 [M+H]$^+$; MP=285.0-288.0° C.

Example 15

Synthesis of Pyrazolo[1,5-a]pyrimidine-3-carboxylic acid [5-chloro-2-(piperidin-4-yloxy)-phenyl]-amide hydrochloride The synthesis of pyrazolo[1,5-a]pyrimidine-3-carboxylic acid [5-chloro-2-(piperidin-4-yloxy)-phenyl]-amide hydrochloride was carried out according to the process shown in Scheme 67.

SCHEME 67

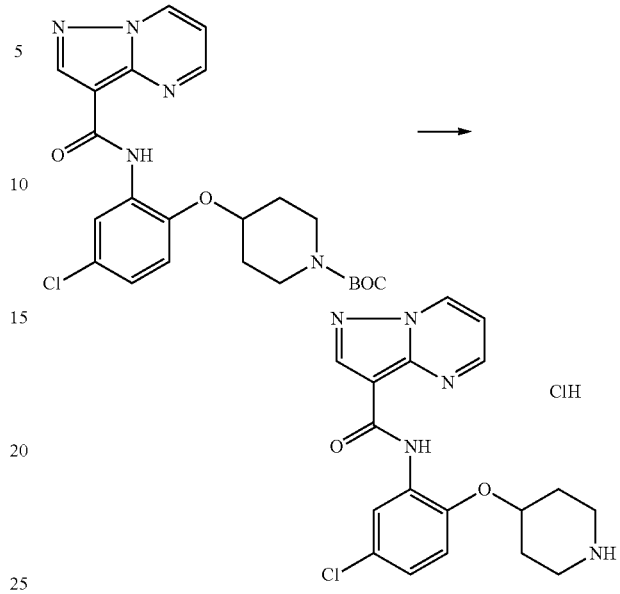

A solution of hydrochloric acid (1 M in E$_2$O, 10 mL) was added, at room temperature, to a solution of 4-{4-chloro-2-[(pyrazolo[1,5-a]pyrimidine-3-carbonyl)-amino]-phenoxy}-piperidine-1-carboxylic acid tert-butyl ester (0.2 g, 0.424 mmol) in dichloromethane (5 mL) and the resulting mixture was stirred at room temperature for 60 hours. The solid formed was collected by filtration and washed once with dichloromethane, 3 times with methanol, once again with dichloromethane and once with hexane, then was dried in a vacuum oven at 60° C. to afford 125 mg (72% yield) of pyrazolo[1,5-a]pyrimidine-3-carboxylic acid [5-chloro-2-(piperidin-4-yloxy)-phenyl]-amide hydrochloride salt as an off-white solid. MS=372 [M+H]$^+$.

Utilizing the above described procedure and the appropriate starting materials, the following compounds were prepared:
pyrazolo[1,5-a]pyrimidine-3-carboxylic acid [2-(4-aminomethyl-piperidin-1-yl)-4-phenylcarbamoyl-phenyl]-amide bishydrochloride (light yellow powder); MS=470 [M+H]$^+$;
pyrazolo[1,5-a]pyrimidine-3-carboxylic acid [3-amino-2-(4-aminomethyl-piperidin-1-yl)-phenyl]-amide trihydrochloride (off-white powder); MS=366 [M+H]$^+$;
pyrazolo[1,5-a]pyrimidine-3-carboxylic acid [2-(4-amino-piperidin-1-yl)-5-chloro-phenyl]-amide (off-white powder); MS=371 [M+H]$^+$; MP=213.5-232.4° C.;
pyrazolo[1,5-a]pyrimidine-3-carboxylic acid (4'-aminomethyl-4-chloro-biphenyl-2-yl)-amide hydrochloride (white powder); MS=378 [M+H]$^+$; MP=286.1-288.7° C.;
pyrazolo[1,5-a]pyrimidine-3-carboxylic acid [7-(4-aminomethyl-piperidin-1-yl)-quinolin-6-yl]-amide bis hydrochloride (light yellow powder); MS=402 [M+H]$^+$; MP=197.0-198.0° C.;
thieno[3,2-d]pyrimidine-7-carboxylic acid [7-(4-aminomethyl-piperidin-1-yl)-quinolin-6-yl]-amide hydrochloride (yellow powder); MS=419 [M+H]$^+$; M=255.9-260.0° C.;
thieno[3,2-d]pyrimidine-7-carboxylic acid [7-(piperidin-4-yloxy)-quinolin-6-yl]-amide hydrochloride (white powder); MS=406 [M+H]$^+$; MP>300° C.;

thieno[3,2-d]pyrimidine-7-carboxylic acid [7-(3-amino-propoxy)-quinolin-6-yl]-amide hydrochloride (white powder); MS=380 [M+H]$^+$; MP=234.0-237.0° C.;

thieno[3,2-d]pyrimidine-7-carboxylic acid [7-(pyrrolidin-3-yloxy)-quinolin-6-yl]-amide hydrochloride (white powder); MS=392 [M+H]$^+$; MP>300° C.;

thieno[3,2-d]pyrimidine-7-carboxylic acid [2-(4-amino-cyclohexyloxy)-5-chloro-phenyl]-amide hydrochloride (off-white powder); MS=403 [M+H]$^+$; M=284.9-288.1° C.;

pyrazolo[1,5-a]pyrimidine-3-carboxylic acid [7-(piperidin-4-yloxy)-quinolin-6-yl]-amide (off-white powder); MS=389 [M+H]$^+$; MP>300° C.;

pyrazolo[1,5-a]pyrimidine-3-carboxylic acid {2-[4-(1-amino-ethyl)-piperidin-1-yl]-5-chloro-phenyl}-amide (white powder); MS=399 [M+H]$^+$; M=178.8-179.7° C.; and pyrazolo[1,5-a]pyrimidine-3-carboxylic acid {2-[3-(1-amino-ethyl)-pyrrolidin-1-yl]-5-chloro-phenyl}-amide (orange solid); MS=385 [M+H]$^+$; M=228.0-229.0° C.

Example 16

Synthesis of Pyrazolo[1,5-a]pyrimidine-3-carboxylic acid [5-chloro-2-(oxazol-5-ylmethoxy)-phenyl]-amide The synthesis of pyrazolo[1,5-a]pyrimidine-3-carboxylic acid [5-chloro-2-(oxazol-5-ylmethoxy)-phenyl]-amide was carried out according to the process shown in Scheme 68.

SCHEME 68

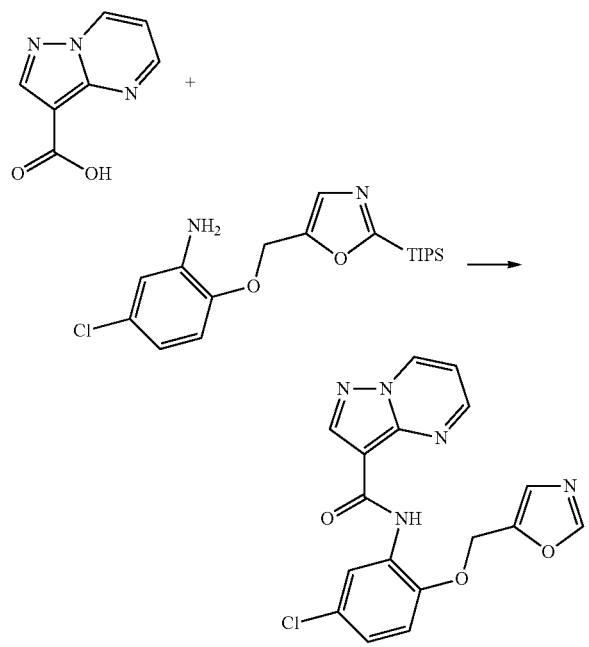

5-Chloro-2-(2-triisopropylsilanyl-oxazol-5-ylmethoxy)-phenylamine was coupled with pyrazolo[1,5-a]pyrimidine-3-carboxylic acid in presence of HBTU as described in Example 1. The product was deprotected by heating with an aqueous solution of sodium hydroxide in methanol for 2 hours. The reaction mixture was cooled; the solid formed was collected by filtration and washed with water. The crude residue was purified by flash chromatography to give 18 mg of pyrazolo[1,5-a]pyrimidine-3-carboxylic acid [5-chloro-2-(oxazol-5-ylmethoxy)-phenyl]-amide as an off-white solid. MS=370 [M+H]$^+$.

Example 17

Synthesis of Thieno[3,2-d]pyrimidine-7-carboxylic acid amide

The synthesis of thieno[3,2-d]pyrimidine-7-carboxylic acid amide was carried out according to the process shown in Scheme 69.

SCHEME 69

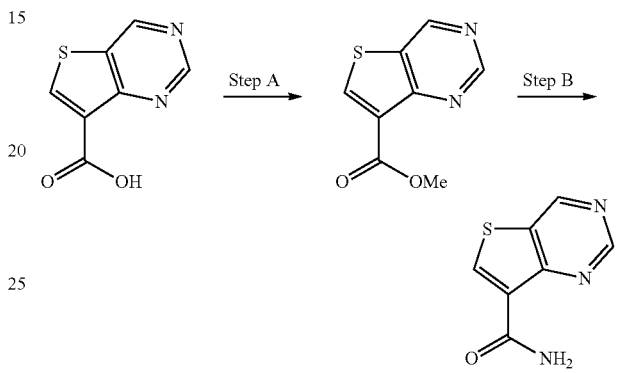

Step A: Synthesis of thieno[3,2-d]pyrimidine-7-carboxylic acid methyl ester

Trimethylsilyldiazomethane (2 M in hexane, 1 mL) was added to a suspension of thieno[3,2-d]pyrimidine-7-carboxylic acid (50 mg) in a mixture of dichloromethane and methanol (95/5, 1 mL) and the resulting mixture was stirred at room temperature for 1 hour. The reaction mixture was then evaporated under reduced pressure and the crude residue was purified by flash chromatography (DCM/MeOH, 97/3) to give 40 mg of thieno[3,2-d]pyrimidine-7-carboxylic acid methyl ester.

Step B: Synthesis of thieno[3,2-d]pyrimidine-7-carboxylic acid amide

Ammonium hydroxide (concentrated, 2 mL) was added to a solution of thieno[3,2-d]pyrimidine-7-carboxylic acid methyl ester (40 mg) in 1,4-dioxane (2 mL) and the resulting mixture was heated in a sealed tube at 100° C. overnight. The reaction mixture was then cooled and extracted with ethyl acetate. The combined organic extracts were dried over anhydrous sodium sulfate, filtered and evaporated under reduced pressure. The crude residue was purified by flash chromatography (DCM/MeOH, 95/5) to give 12 mg of thieno[3,2-d]pyrimidine-7-carboxylic acid amide as a light brown solid. MS=180 [M+H]$^+$.

Example 18

Synthesis of Pyrazolo[1,5-a]pyrimidine-3-carboxylic acid [5-chloro-2-((R)-2,3-dihydroxy-propoxy)-phenyl]-amide The synthesis of pyrazolo[1,5-a]pyrimidine-3-carboxylic acid [5-chloro-2-((R)-2,3-dihydroxy-propoxy)-phenyl]-amide was carried out according to the process shown in Scheme 70.

SCHEME 70

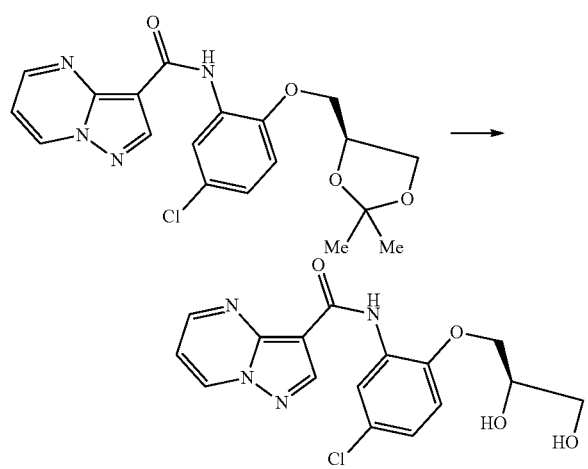

A mixture of pyrazolo[1,5-a]pyrimidine-3-carboxylic acid [5-chloro-2-((S)-2,2-dimethyl-[1,3]dioxolan-4-yl-methoxy)-phenyl]-amide (40 mg) and an aqueous solution of hydrochloric acid (2 M, 5 mL) in tetrahydrofuran (5 mL) was heated at 70° C. for 15 minutes. The resulting mixture was cooled and the solid formed was collected by filtration, washed with a diluted aqueous solution of sodium hydroxide and with water, dried in a vacuum oven to give 30 mg of pyrazolo[1,5-a]pyrimidine-3-carboxylic acid [5-chloro-2-((R)-2,3-dihydroxy-propoxy)-phenyl]-amide as a white solid. MS=362 [M]$^+$.

Utilizing the above described procedure and the appropriate starting materials, the following compounds were prepared:
pyrazolo[1,5-a]pyrimidine-3-carboxylic acid [5-chloro-2-((S)-2,3-dihydroxy-propoxy)-phenyl]-amide (off-white solid); MS=362 [M]$^+$; and
pyrazolo[1,5-a]pyrimidine-3-carboxylic acid [5-chloro-2-(3,4-dihydroxy-butoxy)-phenyl]-amide (white powder); MS=377 [M+H]$^+$; MP=223.0-224.5° C.

Example 19

Synthesis of Pyrazolo[1,5-a]pyrimidine-3-carboxylic acid [2-(3-amino-pyrrolidin-1-yl)-5-chloro-phenyl]-amide The synthesis of pyrazolo[1,5-a]pyrimidine-3-carboxylic acid [2-(3-amino-pyrrolidin-1-yl)-5-chloro-phenyl]-amide was carried out according to the process shown in Scheme 71.

SCHEME 71

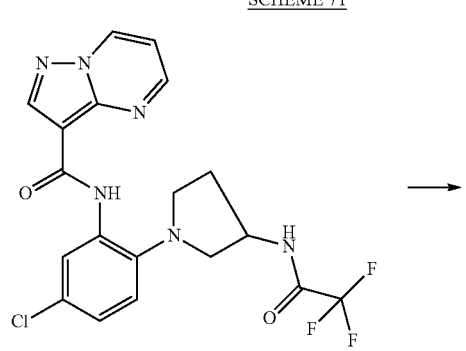

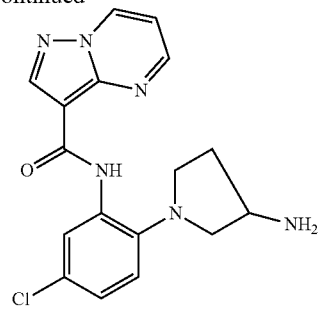

A mixture of pyrazolo[1,5-a]pyrimidine-3-carboxylic acid {5-chloro-2-[3-(2,2,2-trifluoro-acetylamino)-pyrrolidin-1-yl]-phenyl}-amide (50 mg), methanol (2 mL) and an aqueous solution of sodium hydroxide (4 M, 1 mL) was heated at 60° C. for 1 hour. The resulting mixture was cooled, diluted with ethyl acetate, washed with water and brine, dried over anhydrous sodium sulfate, filtered and evaporated under reduced pressure to afford 30 mg of pyrazolo[1,5-a]pyrimidine-3-carboxylic acid [2-(3-amino-pyrrolidin-1-yl)-5-chloro-phenyl]-amide (light yellow foam) without further purifications. MS=356 [M]$^+$.

Example 20

Synthesis of 6-Hydroxy-pyrazolo[1,5-a]pyrimidine-3-carboxylic acid (5-chloro-2-piperidin-1-yl-phenyl)-amide The synthesis of 6-hydroxy-pyrazolo[1,5-a]pyrimidine-3-carboxylic acid (5-chloro-2-piperidin-1-yl-phenyl)-amide was carried out according to the process shown in Scheme 72.

SCHEME 72

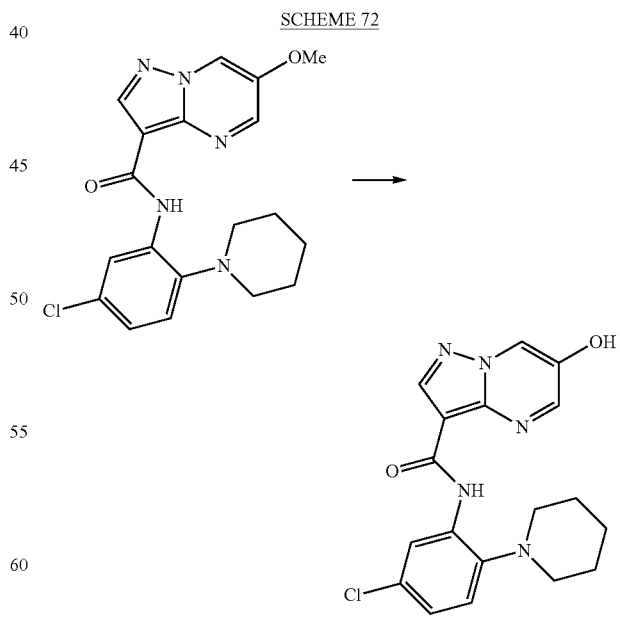

A mixture of 6-methoxy-pyrazolo[1,5-a]pyrimidine-3-carboxylic acid (5-chloro-2-piperidin-1-yl-phenyl)-amide (100 mg) and sodium methanethiolate (45 mg) in N,N-dimethylformamide (ca. 2 mL) was heated in a sealed tube at 160° C. for 48 hours. The resulting mixture was evaporated under reduced pressure and the residue was dissolved in a mixture of chloroform and methanol, absorbed onto silica gel and purified by flash chromatography (DCM/MeOH/AcOH) to give 25.4 mg (26% yield) of 6-hydroxy-pyrazolo[1,5-a]pyrimidine-3-carboxylic acid (5-chloro-2-piperidin-1-yl-phenyl)-amide as a yellow solid. MS=372 [M+H]$^+$; MP>300° C.

6-Hydroxy-pyrazolo[1,5-a]pyrimidine-3-carboxylic acid {2-[4-(tert-butyl-dimethyl-silanyloxy)-cyclohexyloxy]-5-chloro-phenyl}-amide was synthesized utilizing the above described procedure and the appropriate starting materials.

Example 21

Synthesis of 6-hydroxy-pyrazolo[1,5-a]pyrimidine-3-carboxylic acid [5-chloro-2-(4-dimethylaminomethyl-piperidin-1-yl)-phenyl]-amide The synthesis of 6-hydroxy-pyrazolo[1,5-a]pyrimidine-3-carboxylic acid [5-chloro-2-(4-dimethylaminomethyl-piperidin-1-yl)-phenyl]-amide was carried out according to the process shown in Scheme 73.

SCHEME 73

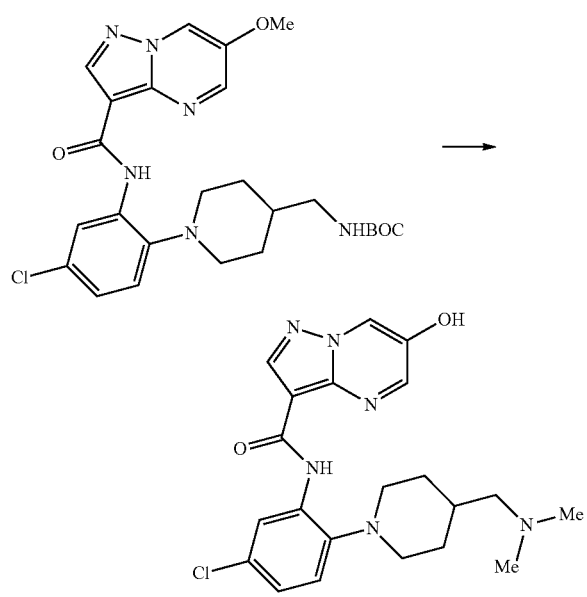

A mixture of 1-{4-chloro-2-[(6-methoxy-pyrazolo[1,5-a]pyrimidine-3-carbonyl)-amino]-phenyl}-piperidin-4-ylmethyl)-carbamic acid tert-butyl ester (120 mg, 0.23 mmol) and sodium methanethiolate (164 mg) in N,N-dimethylformamide (ca. 3 mL) was heated in a sealed tube at 220° C. in a microwave reactor for 20 minutes. The resulting mixture was evaporated under reduced pressure and the residue was dissolved in a mixture of dichloromethane and methanol, absorbed onto silica gel and purified by flash chromatography (DCM/MeOH) to give 32.0 mg of 6-hydroxy-pyrazolo[1,5-a]pyrimidine-3-carboxylic acid [5-chloro-2-(4-dimethylaminomethyl-piperidin-1-yl)-phenyl]-amide as a brown solid. MS=429 [M+H]$^+$.

2-Chloro-thieno[3,2-d]pyrimidine-7-carboxylic acid

Step A

To a solution of 15.0 g (87.6 mmole) of methyl 3-amino-4-methylthiophene-2-carboxylate in 437 mL of acetic acid and 45 mL of water was added 21.6 g (263 mmole) of potassium cyanate in 71 mL of water via additional funnel. The mixture was stirred at room temperature for over night. 75 percent of the solvent was removed. Precipitation was observed and filtered. 450 mL of 6% aqueous sodium hydroxide was added. The mixture was refluxed at 130 degrees for 4 hours, then cooled down and acidified with 60 ml of 12N hydrochloric acid to pH of 6. Precipitation was observed, filtered, washed with water and dried in high vacuum for over night to give 10.55 g of 7-methylthienol[3,2-d]pyrimidine-2,4(1H,3H)-dione as a white solid.

Step B

A mixture of 10.0 g (54.9 mmole) 7-methylthienol[3,2-d]pyrimidine-2,4(1H,3H)-dione and 140 mL of phosphorus oxychloride was refluxed for over night, then concentrated under reduced pressure. The residue was slowly added into ice water, and extracted three times with ethyl acetate. The organic layer was washed with brine, dried over anhydrous sodium sulfate, filtered and concentrated under reduced pressure. The residue was purified by silica gel chromatography, eluting with hexanes-ethyl acetate (gradient 100:0-80:20) to give 9.5 g of 2,4-dichloro-7-methyl-thienol[3,2-d]pyrimidine as a yellow solid.

Step C

To a solution of 4.8 g (21.9 mmole) 2,4-dichloro-7-methyl-thienol[3,2-d]pyrimidine in 80 mL of ethyl acetate and 10 mL of isopropanol was added 3.95 g (48.2 mmole) of sodium acetate and 0.97 g (6.91 mmole) of palladium hydroxide. The mixture was place on Parr Shaker at 45 psi hydrogen for over night. The reaction was filtered through celite cake, washed with dichloromethane and removed under reduced pressure. The residue was purified by silica gel chromatography, eluting with hexanes-ethyl acetate (gradient 100:0-75:25) to give 4.28 g of 2-chloro-7-methyl-thienol[3,2-d]pyrimidine as a white solid.

Step D

To a solution of 2.00 g (10.8 mmole) 2-chloro-7-methyl-2-chloro-thienol[3,2-d]pyrimidine in 72 mL of anhydrous carbon tetrachloride was added 1.99 g (11.2 mmole) of N-bromosuccinimide and 0.142 g (0.867 mmole) of 2,2'-azobis(2-methylpropionitrile) respectively. The mixture was heated to reflux for 8 hours, cooled down, filtered and concentrated under reduced pressure to yield 4.23 g of 7-bromomethyl-2-chloro-thienol[3,2-d]pyrimidine as a yellow oil, which was used for next step.

Step E

To a solution of 2.85 g (10.8 mmole) 7-bromomethyl-2-chloro-thienol[3,2-d]pyrimidine in 72 mL of anhydrous acetonitrile was added 2.83 mL (16.2 mmole) of N,N-diisopropylethylamine and 3.59 g (37.8 mmole) of pyridine-N-oxide respectively. The mixture was heated to 100 degrees for over night. Water and ethyl acetate were added to the reaction mixture. The aqueous layer was washed with ethyl acetate. The organic layer was washed with brine, dried over anhydrous sodium sulfate, filtered and concentrated under reduced pressure. The residue was purified by silica gel chromatography, eluting with hexanes-ethyl acetate (gradient 100:0-60:40) to give 0.640 g of 2-chloro-thieno[3,2-d]pyrimidine-7-carbaldehyde as a yellow solid.

Step F

To a suspension of 0.640 g (3.22 mmole) 2-chloro-thieno[3,2-d]pyrimidine-7-carbaldehyde in 20 mL of tetrahydrofuran, 10 mL of tert-butanol and 10 mL of water was added 1.25 g (12.9 mmole) of sulfamic acid. A solution of 0.729 g (8.06 mmole) sodium chlorite and 3.33 g (24.5 mmole) of potassium dihydrogen phosphate in 24 mL of water was slowly added via additional funnel. The reaction mixture was stirred at room temperature for over night. Water and ethyl acetate were added, separated. Aqueous layer was washed with ethyl acetate. Organic layer was washed with brine, dried over anhydrous sodium sulfate, filtered and concentrated under reduced pressure. The solid residue was dried in high vacuum for over night to give 0.660 g of 2-chloro-thieno[3,2-d]pyrimidine-7-carboxylic acid as a yellow solid. MH+/Z=215

Example 22

2-(cis-2-Amino-cyclohexylamino)-thieno[3,2-d]pyrimidine-7-carboxylic acid quinolin-8-ylamide

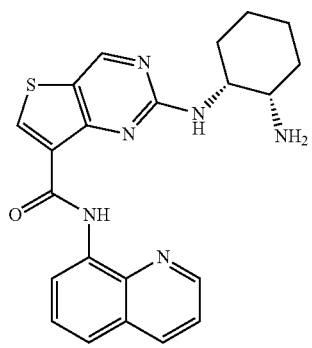 [SMILES: N[C@H]1CCCC[C@H]1Nc1ncc2scc(C(=O)Nc3cccc4cccnc34)c2n1]

Step A

To a solution of 0.050 g (0.235 mmole) of 2-chloro-thieno[3,2-d]pyrimidine-7-carboxylic acid, 0.034 g (0.235 mmole) of 8-aminoquinoline and 0.12 ml (0.7 mmole) of diisopropylethylamine and 2 mL of dimethylformamide was added 0.12 g (0.28 mmole) of O-(benzotriazol-1-yl)-N,N,N',N'-bis(tetramethylene)uronium hexafluorophosphate. The mixture was stirred at room temperature for 3 hours. Aqueous sodium carbonate was added, extracted with $CH_2Cl_2$, organic layer was washed with sodium carbonate, brine, dried over anhydrous $Na_2SO_4$, filtered and concentrated to give 80 mg of a mixture of 2-chloro-thieno[3,2-d]pyrimidine-7-carboxylic acid quinolin-8-ylamide and 2-(benzotriazol-1-yloxy)-thieno[3,2-d]pyrimidine-7-carboxylic acid quinolin-8-ylamide as a slight yellow solid, which was used for the next step without further purification.

Step B

A suspension of the mixture of 80 mg of 2-chloro-thieno[3,2-d]pyrimidine-7-carboxylic acid quinolin-8-ylamide and 2-(benzotriazol-1-yloxy)-thieno[3,2-d]pyrimidine-7-carboxylic acid quinolin-8-ylamide and 0.17 g (1.41 mmole) of cis-1,2-diaminocyclohexane (from step a) in Dioxane (3 mL) was stirred at 60° C. for overnight. The reaction were cooled down and diluted with $CH_2Cl_2$, washed with aqueous $Na_2CO_3$, brine, dried over anhydrous $Na_2SO_4$, concentrated and purified by flash chromatography (silica gel, 40 g, 0% to 30% MeOH (0.7 N) in $CH_2Cl_2$) to 40 mg of 2-(cis-2-aminocyclohexylamino)-thieno[3,2-d]pyrimidine-7-carboxylic acid quinolin-8-ylamide as light yellow solid. MH+/Z=419.

Example 23

2-(cis-2-Amino-cyclohexylamino)-thieno[3,2-d]pyrimidine-7-carboxylic acid benzo[1,3]dioxol-5-ylamide

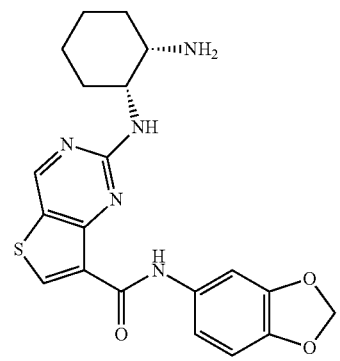 [SMILES: N[C@H]1CCCC[C@H]1Nc1ncc2scc(C(=O)Nc3ccc4c(c3)OCO4)c2n1]

Step A

To a solution of 0.050 g (0.235 mmole) of 2-chloro-thieno[3,2-d]pyrimidine-7-carboxylic acid, 0.032 g (0.235 mmole) of 3,4-(methylenedioxy)aniline and 0.12 ml (0.7 mmole) of diisopropylethylamine and 2 mL of dimethylformamide was added 0.12 g (0.28 mmole) of O-(benzotriazol-1-yl)-N,N,N',N'-bis(tetramethylene)uronium hexafluorophosphate. The mixture was stirred at room temperature for 3 hours. Aqueous sodium carbonate was added, extracted with $CH_2Cl_2$, organic layer was washed with sodium carbonate, brine, dried over anhydrous $Na_2SO_4$, filtered and concentrated to give 80 mg of a mixture of 2-Chloro-thieno[3,2-d]pyrimidine-7-carboxylic acid benzo[1,3]dioxol-5-ylamide and 2-(Benzotriazol-1-yloxy)-thieno[3,2-d]pyrimidine-7-carboxylic acid benzo[1,3]dioxol-5-ylamide as a slight yellow solid, which was used for the next step without further purification.

Step B

A suspension of the mixture of 80 mg of 2-Chloro-thieno[3,2-d]pyrimidine-7-carboxylic acid benzo[1,3]dioxol-5-ylamide and 2-(Benzotriazol-1-yloxy)-thieno[3,2-d]pyrimidine-7-carboxylic acid benzo[1,3]dioxol-5-ylamide (from step a) and 0.17 g (1.41 mmole) of cis-1,2-diaminocyclohexane in Dioxane (3 mL) was stirred at 60° C. for overnight. The reaction were cooled down and diluted with $CH_2Cl_2$, washed with aqueous $Na_2CO_3$, brine, dried over anhydrous $Na_2SO_4$, concentrated and purified by flash chromatography (silica gel, 40 g, 0% to 30% MeOH (0.7 N) in $CH_2Cl_2$) to 40 mg of 2-(cis-2-Amino-cyclohexylamino)-thieno[3,2-d]pyrimidine-7-carboxylic acid benzo[1,3]dioxol-5-ylamide as light yellow solid. MH+/Z=412.

Example 24

2-(cis-2-Amino-cyclohexylamino)-thieno[3,2-d]pyrimidine-7-carboxylic acid (3,4-dimethoxy-phenyl)-amide

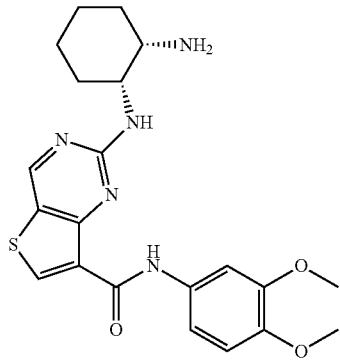 [SMILES: COc1ccc(NC(=O)c2csc3cnc(N[C@@H]4CCCC[C@@H]4N)nc23)cc1OC]

Step A

To a solution of 0.050 g (0.235 mmole) of 2-chloro-thieno[3,2-d]pyrimidine-7-carboxylic acid, 0.032 g (0.235 mmole) of 3,4-dimethoxyaniline and 0.12 ml (0.7 mmole) of diisopropylethylamine and 2 ml of dimethylformamide was added 0.12 g (0.28 mmole) of O-(benzotriazol-1-yl)-N,N,N',N'-bis(tetramethylene)uronium hexafluorophosphate. The mixture was stirred at room temperature for 3 hours. Aqueous sodium carbonate was added, extracted with $CH_2Cl_2$, organic layer was washed with sodium carbonate, brine, dried over anhydrous $Na_2SO_4$, filtered and concentrated to give 85 mg of a mixture of 2-Chloro-thieno[3,2-d]pyrimidine-7-carboxylic acid (3,4-dimethoxy-phenyl)-amide and 2-(Benzotriazol-1-yloxy)-thieno[3,2-d]pyrimidine-7-carboxylic acid (3,4-dimethoxy-phenyl)-amide as a slight yellow solid, which was used for the next step without further purification.

Step B

A suspension of the mixture of 85 mg of 2-Chloro-thieno[3,2-d]pyrimidine-7-carboxylic acid (3,4-dimethoxy-phenyl)-amide and 2-(Benzotriazol-1-yloxy)-thieno[3,2-d]pyrimidine-7-carboxylic acid (3,4-dimethoxy-phenyl)-amide (from step a) and 0.17 g (1.41 mmole) of cis-1,2-diaminocyclohexane in Dioxane (3 mL) was stirred at 60° C. for overnight. The reaction were cooled down and diluted with $CH_2Cl_2$, washed with aqueous $Na_2CO_3$, brine, dried over anhydrous $Na_2SO_4$, concentrated and purified by flash chromatography (silica gel, 40 g, 0% to 30% MeOH (0.7 N) in $CH_2Cl_2$) to 50 mg of 2-(cis-2-Amino-cyclohexylamino)-thieno[3,2-d]pyrimidine-7-carboxylic acid (3,4-dimethoxyphenyl)-amide as light yellow solid. MH+/Z=428.

Example 25

2-(cis-2-amino-cyclohexylamino)-thieno[3,2-d]pyrimidine-7-carboxylic acid (1-methyl-1H-benzoimidazol-4-yl)-amide

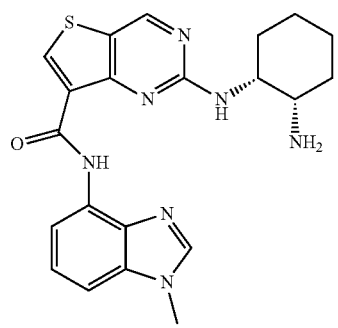 [SMILES: Cn1cnc2c(NC(=O)c3csc4cnc(N[C@@H]5CCCC[C@@H]5N)nc34)cccc21]

Step A

To a solution of 0.050 g (0.233 mmole) 2-chloro-thieno[3,2-d]pyrimidine-7-carboxylic acid, 0.0686 g (0.466 mmole) of 1-methyl-1H-benzol[d]imidazol-4-amine, 0.122 mL (0.699 mmole) of N,N-diisopropylethylamine and 1.55 mL of dimethylformamide was added 0.111 g (0.256 mmole) of O-(benzotriazol-1-yl)-N,N,N',N'-bis(tetramethylene)uronium hexafluorophosphate. The mixture was stirred at room temperature for overnight. Water and dichloromethane were added. The aqueous layer was washed three times with dichloromethane. The combined organic layer was washed with aqueous sodium carbonate, brine, dried over anhydrous sodium sulfate, filtered and concentrated under reduced pressure. Purification by silica gel chromatography, eluting with hexanes-ethyl acetate (gradient 50:50-0:100) gave 0.042 g of 2-chloro-thieno[3,2-d]pyrimidine-7-carboxylic acid (1-methyl-1H-benzoimidazol-4-yl)-amide as a yellow solid.

Step B

To a solution of 0.041 g (0.119 mmole) 2-chloro-thieno[3,2-d]pyrimidine-7-carboxylic acid(1-methyl-1H-benzoimidazol-4-yl)-amide in 1.19 mL of dioxane was added 0.082 g (0.716 mmole) of cis-cyclohexane-1,2-diamine. The mixture was heated at 100 degrees for over night. Water and dichloromethane were added, separated. The aqueous layer was washed with dichloromethane twice. The organic layer was washed with aqueous sodium carbonate, brine, dried over anhydrous sodium sulfate, filtered and concentrated under reduced pressure. Purification by silica gel chromatography, eluting with dichloromethane-0.7 N ammonia solution in methanol (gradient 100:0-90:10) gave 0.019 g of 2-(cis-2-amino-cyclohexylamino)-thieno[3,2-d]pyrimidine-7-carboxylic acid (1-methyl-1H-benzoimidazol-4-yl)-amide as a light yellow solid. MH+/Z=422

Example 26

2-(cis-2-amino-cyclohexylamino)-thieno[3,2-d]pyrimidine-7-carboxylic acid (2,4-dimethoxy-phenyl)-amide

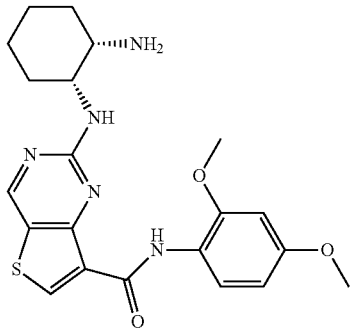 [SMILES: COc1ccc(NC(=O)c2csc3cnc(N[C@@H]4CCCC[C@@H]4N)nc23)c(OC)c1]

Step A

To a solution of 0.050 g (0.233 mmole) 2-chloro-thieno[3,2-d]pyrimidine-7-carboxylic acid, 0.0714 g (0.466 mmole) of 1-methyl-1H-benzol[d]imidazol-4-amine, 0.122 mL (0.699 mmole) of N,N-diisopropylethylamine and 1.55 mL of dimethylformamide was added 0.111 g (0.256 mmole) of O-(benzotriazol-1-yl)-N,N,N',N'-bis(tetramethylene)uronium hexafluorophosphate. The mixture was stirred at room temperature for over night. Water and dichloromethane were added. The aqueous layer was washed three times with dichloromethane. The combined organic layer was washed with aqueous sodium carbonate, brine, dried over anhydrous sodium sulfate, filtered and concentrated under reduced pressure. Purification by silica gel chromatography, eluting with hexanes-ethyl acetate (gradient 100:0-60:40) gave 0.050 g of 2-chloro-thieno[3,2-d]pyrimidine-7-carboxylic acid(2,4-dimethoxy-phenyl)-amide as a yellow solid.

Step B

To a solution of 0.047 g (0.134 mmole) 2-chloro-thieno[3,2-d]pyrimidine-7-carboxylic acid(2,4-dimethoxy-phenyl)-amide in 1.34 mL of dioxane was added 0.0967 mL (0.806 mmole) of (cis-cyclohexane-1,2-diamine. The mixture was heated at 100 degrees for over night. Dichloromethane was added and washed with aqueous sodium bicarbonate. The aqueous layer was washed twice with dichloromethane. The organic layer was washed with brine, dried over anhydrous sodium sulfate, filtered and concentrated under reduced pressure. Purification by silica gel chromatography, eluting with dichloromethane-0.7 N ammonia solution in methanol (gradient 100:0-90:10) gave 0.052 g of 2-(cis-2-amino-cyclohexylamino)-thieno[3,2-d]pyrimidine-7-carboxylic acid (2,4-dimethoxy-phenyl)-amide as a yellow solid. MH+/Z=428

Example 27

2-(cis-2-amino-cyclohexylamino)-thieno[3,2-d]pyrimidine-7-carboxylic acid (5,6-dimethoxy-pyridin-2-yl)-amide

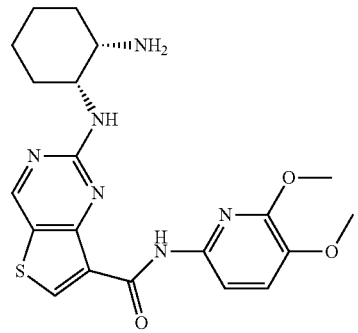 [SMILES: COc1ccc(NC(=O)c2csc3cnc(N[C@@H]4CCCC[C@@H]4N)nc23)nc1OC]

Step A

To a solution of 0.050 g (0.233 mmole) 2-chloro-thieno[3,2-d]pyrimidine-7-carboxylic acid, 0.0718 g (0.466 mmole) of 5,6-dimethoxypyridin-2-amine, 0.122 mL (0.699 mmole) of N,N-diisopropylethylamine and 1.55 ml of dimethylformamide was added 0.111 g (0.256 mmole) of O-(benzotriazol-1-yl)-N,N,N',N'-bis(tetramethylene)uronium hexafluorophosphate. The mixture was stirred at room temperature for over night. Water and dichloromethane were added.

The aqueous layer was washed three times with dichloromethane. The combined organic layer was washed with aqueous sodium carbonate, brine, dried over anhydrous sodium sulfate, filtered and concentrated under reduced pressure. The residue was dried in high vacuum to give 2-chloro-thieno[3,2-d]pyrimidine-7-carboxylic acid (5,6-dimethoxy-pyridin-2-yl)-amide as a black solid.

Step B

To a solution of 0.0817 g (0.233 mmole) 2-chloro-thieno[3,2-d]pyrimidine-7-carboxylic acid (5,6-dimethoxy-pyridin-2-yl)-amide in 2.33 mL of dioxane was added 0.168 mL (1.4 mmole) of cis-cyclohexane-1,2-diamine. The mixture was heated at 100 degrees for over night. Water and dichloromethane were added, separated. The aqueous layer was washed with dichloromethane twice. The organic layer was washed with aqueous sodium carbonate, brine, dried over anhydrous sodium sulfate, filtered and concentrated under reduced pressure. Purification by silica gel chromatography, eluting with dichloromethane-0.7 N ammonia solution in methanol (gradient 100:0-90:10) gave 0.048 g of 2-(cis-2-amino-cyclohexylamino)-thieno[3,2-d]pyrimidine-7-carboxylic acid (5,6-dimethoxy-pyridin-2-yl)-amide as a light yellow solid. MH+/Z=429.

Example 28

2-(cis-2-amino-cyclohexylamino)-thieno[3,2-d]pyrimidine-7-carboxylic acid (3,4,5-trimethoxy-phenyl)-amide

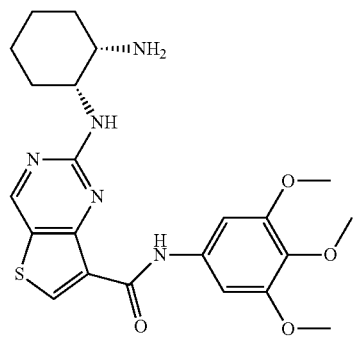 [SMILES: COc1cc(NC(=O)c2csc3cnc(N[C@@H]4CCCC[C@@H]4N)nc23)cc(OC)c1OC]

Step A

To a solution of 0.050 g (0.233 mmole) 2-chloro-thieno[3,2-d]pyrimidine-7-carboxylic acid, 0.0854 g (0.466 mmole) of 3,4,5-trimethoxyaniline, 0.122 mL (0.699 mmole) of N,N-diisopropylethylamine and 1.55 mL of dimethylformamide was added 0.111 g (0.256 mmole) of O-(benzotriazol-1-yl)-N,N,N',N'-bis(tetramethylene)uronium hexafluorophosphate. The mixture was stirred at room temperature for 2 hours. Water and dichloromethane were added. The aqueous layer was washed three times with dichloromethane. The combined organic layer was washed with aqueous sodium carbonate, brine, dried over anhydrous sodium sulfate, filtered and concentrated under reduced pressure. The residue was dried in high vacuum to give 2-chloro-thieno[3,2-d]pyrimidine-7-carboxylic acid (3,4,5-trimethoxy-phenyl)-amide as a yellow solid

Step B

To a solution of 0.0885 g (0.233 mmole) 2-chloro-thieno[3,2-d]pyrimidine-7-carboxylic acid (3,4,5-trimethoxy-phenyl)-amide in 2.33 mL of dioxane was added 0.168 mL (1.4 mmole) of cis-cyclohexane-1,2-diamine. The mixture was heated at 100 degrees for over night. Water and dichloromethane were added, separated. The aqueous layer was washed with dichloromethane twice. The organic layer was washed with aqueous sodium carbonate, brine, dried over anhydrous sodium sulfate, filtered and concentrated under reduced pressure. Purification by silica gel chromatography, eluting with dichloromethane-0.7 N ammonia solution in methanol (gradient 100:0-90:10) gave 0.064 g of 2-(cis-2-amino-cyclohexylamino)-thieno[3,2-d]pyrimidine-7-carboxylic acid (3,4,5-trimethoxy-phenyl)-amide as a light yellow solid. MH+/Z=458.

Example 29

2-(cis-2-amino-cyclohexylamino)-thieno[3,2-d]pyrimidine-7-carboxylic acid quinolin-6-ylamide

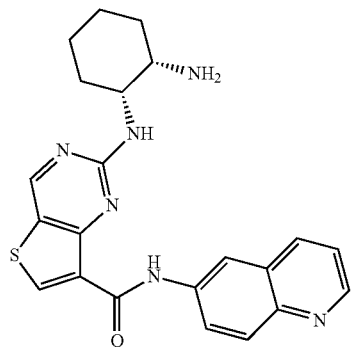 [SMILES: N[C@H]1CCCC[C@H]1Nc1ncc2scc(C(=O)Nc3ccc4ncccc4c3)c2n1]

Step A

To a solution of 0.050 g (0.233 mmole) 2-chloro-thieno[3,2-d]pyrimidine-7-carboxylic acid, 0.0672 g (0.466 mmole) of quinolin-6-amine, 0.122 mL (0.699 mmole) of N,N-diisopropylethylamine and 1.55 mL of dimethylformamide was added 0.111 g (0.256 mmole) of O-(benzotriazol-1-yl)-N,N,N',N'-bis(tetramethylene)uronium hexafluorophosphate. The mixture was stirred at room temperature for 2 hours. Water and dichloromethane were added. The aqueous layer was washed three times with dichloromethane. The combined organic layer was washed with aqueous sodium carbonate, brine, dried over anhydrous sodium sulfate, filtered and concentrated under reduced pressure. The residue was dried in high vacuum to give 2-chloro-thieno[3,2-d]pyrimidine-7-carboxylic acid quinolin-6-ylamide as a yellow-greenish solid

Step B

To a solution of 0.0794 g (0.233 mmole) 2-chloro-thieno[3,2-d]pyrimidine-7-carboxylic acid quinolin-6-ylamide in 2.33 mL of dioxane was added 0.168 mL (1.4 mmole) of cis-cyclohexane-1,2-diamine. The mixture was heated at 100 degrees for 2 hours. Water and dichloromethane were added, separated. The aqueous layer was washed with dichloromethane twice. The organic layer was washed with aqueous sodium carbonate, brine, dried over anhydrous sodium sulfate, filtered and concentrated under reduced pressure. Purification by silica gel chromatography, eluting with dichloromethane-0.7 N ammonia solution in methanol (gradient 100:0-90:10) gave 0.054 g of 2-(cis-2-amino-cyclohexylamino)-thieno[3,2-d]pyrimidine-7-carboxylic acid quinolin-6-ylamide as a light yellow solid. MH+/Z=419.

Example 30

Formulations

Pharmaceutical preparations for delivery by various routes are formulated as shown in the following Tables. "Active ingredient" or "Active compound" as used in the Tables means one or more of the Compounds of Formula I.

Composition for Oral Administration

| Ingredient | % wt./wt. |
|---|---|
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

Composition for Oral Administration

| Ingredient | % wt./wt. |
|---|---|
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

Composition for Oral Administration

| Ingredient | Amount |
|---|---|
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

Parenteral Formulation

| Ingredient | % wt./wt. |
|---|---|
| Active ingredient | 0.25 g |
| Sodium Chloride | qs to make isotonic |
| Water for injection | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

Suppository Formulation

| Ingredient | % wt./wt. |
|---|---|
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

Topical Formulation

| Ingredients | Grams |
|---|---|
| Active compound | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations

Several aqueous suspensions containing from about 0.025-0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50-100 microliters of formulation per actuation. A typical dosing schedule is 2-4 sprays every 4-12 hours.

Example 31

In Vitro IRAK-1 and IRAK-4 Assay

Purified recombinant IRAK-4 protein was incubated with 250 uM synthetic peptide (KKARFSRFAGSSPSQSSM-VAR) in 30 ul of kinase buffer including (20 mM MOPS pH7.2, 25 mM beta glycerol phosphate, 5 mM EGTA, 1 mM sodium orthovanadate, 1 mM DTT, 50 uM ATP, 20 mM MgCl2, 10 uCi $\gamma$-$^{33}$P, 0.1% BSA) for the indicated time. For purified recombinant IRAK-1 protein kinase assay, 50 uM ATP was used. A 25 ul aliquot of the reaction mixture was transferred on to p81 phosphocellulose squares (Upstate Biotechnology, Lake Placid, N.Y.). The assay squares were washed three times with 0.75% phosphoric acid and once with acetone. Enzyme activity was measured by determining the bound radioactivity by liquid scintillation counting.

Example 32

In Vitro SYK Kinase Assay

Spleen tyrosine kinase (SYK) is a tyrosine kinase that plays an important role in B cell signal transduction. SYK activity is measured by phosphorylation of a peptide substrate (Biotin-EPEGDYEEVLE) with [gamma-$^{33}$P]ATP. The enzyme reaction was conducted at 20 uM ATP with 0.05 uCi [gamma-$^{33}$P]ATP (2 uCi for 40 ul assay) and 10 uM peptide substrate at final volume of 40 ul in buffer containing 50 mM Hepes, pH 7.2, 1 mM dithiothreitol, 10 mM MgCl$_2$, 100 uM Na$_3$VO$_4$, 0.1% BSA and 10% DMSO. The enzyme assay was carried out with human full length SYK in the presence or absence of ten compound concentrations. SYK and compound were pre-incubated for 10 minutes. Then, the enzymatic reaction was initiated by addition of ATP and peptide substrate. The reaction mixture was incubated at room temperature for 30 minutes. At the end of incubation, the reaction was terminated by transferring 25 ul of the reaction mixture to 100 ul of 10% streptavidin slurry containing 100 mM EDTA. The reaction product was captured on the affinity resin and sequentially washed on a filtration plate (Millipore, MABVNOB50) with 2M NaCl, 2M M NaCl in 1% phosphoric acid and water to remove free radio nucleotide. Then the incorporation of $^{33}$P into peptide substrate was quantified on a microplate scintillation counter. Compound inhibition potency on SYK was measured by IC$_{50}$ value generated from ten concentration inhibition curve fitted into the 3-parameter model: % inhibition=Maximum/ (1+(IC$_{50}$/[Inhibitor])$^{slope}$). Data were analyzed on Microsoft Excel for parameter estimation.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:

1. A compound of formula II:

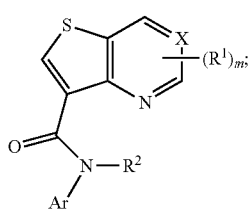

II or a pharmaceutically acceptable salt thereof,
wherein:
  X is N or CH
  m is 1 or 2;
  Ar is:
    optionally substituted aryl; or
    optionally substituted heteroaryl;
  R$^1$ is:
    hydrogen;
    C$_{1-6}$alkyl;
    C$_{1-6}$alkoxy;
    hydroxy;
    hydroxy-C$_{1-6}$alkyl;
    C$_{1-6}$alkyl-amino;
    amino-C$_{1-6}$alkyl;
    amino-C$_{1-6}$alkyl-amino;
    hydroxy-C$_{1-6}$alkylamino;
    amino-C$_{3-6}$cycloalkylamino;
    amino-C$_{3-6}$heterocycloalkylamino;
    aminocarbonyl;
    halo;
    hydroxy-C$_{1-6}$alkyl; or
    hydroxy-C$_{1-6}$alkoxy; and
  R$^2$ is:
    hydrogen; or
    C$_{1-6}$alkyl.

2. The compound of claim 1, wherein R$^2$ is hydrogen.

3. The compound of claim 1, wherein m is 1.

4. The compound of claim 1, wherein Ar is substituted phenyl.

5. The compound of claim 1, wherein Ar is phenyl substituted one, two or three times with a group or groups independently selected from: halo; C$_{1-6}$alkyl; halo-C$_{1-6}$alkyl; C$_{1-6}$alkenyl; C$_{1-6}$alkoxy; halo-C$_{1-6}$alkoxy; hydroxy-C$_{1-6}$alkyl; hydroxy-C$_{1-6}$alkylamino; C$_{1-6}$alkyl-amino; hydroxy; amino; amino-C$_{1-6}$alkyl; aminocarbonyl; hydroxy-C$_{1-6}$alkoxy, hydroxy-C$_{1-6}$alkenyl; C$_{1-6}$alkoxy-C$_{1-6}$alkoxy; C$_{1-6}$alkylsulfonyl; C$_{1-6}$alkylsulfanyl; piperidinyl wherein the piperidinyl moiety is optionally substituted with hydroxy, amino, amino-C$_{1-6}$alkyl, hydroxy-C$_{1-6}$alkyl or aminocarbonyl; phenylaminocarbonyl; hydroxy-C$_{1-6}$alkylamino; cyclohexyloxy wherein the cyclohexyl moiety thereof is optionally substituted with hydroxy, amino, amino-C$_{1-6}$ alkyl or hydroxy-C$_{1-6}$alkyl; cyclopentyloxy wherein the cyclopentyl moiety thereof is optionally substituted with hydroxy, amino, amino-C$_{1-6}$alkyl or hydroxy-C$_{1-6}$alkyl; piperidinyloxy wherein the piperidinyl moiety thereof is optionally substituted with hydroxy, amino, amino-C$_{1-6}$alkyl, hydroxy-C$_{1-6}$alkyl or aminocarbonyl; phenyl wherein the phenyl moiety is optionally substituted with amino, hydroxy, amino-C$_{1-6}$alkyl, hydroxy-C$_{1-6}$alkyl or aminocarbonyl; pyrrolidinyl wherein the pyrrolidinyl moiety is optionally substituted with hydroxy, amino, amino-C$_{1-6}$alkyl, hydroxy-C$_{1-6}$alkyl or aminocarbonyl; pyrrolidinyloxy wherein the pyrrolidinyl moiety is optionally substituted with hydroxy, amino, amino-C$_{1-6}$alkyl, hydroxy-C$_{1-6}$alkyl or aminocarbonyl; piperazinyl wherein the piperazinyl moiety is optionally substituted with C$_{1-6}$alkyl; oxazol-C$_{1-6}$alkoxy wherein the oxazol moiety thereof is optionally substituted with C$_{1-6}$alkyl; morpholinyl; hydroxy-C$_{1-6}$alkylaminocarbonyl; C$_{3-6}$cycloalkyl; azepanyl wherein the azepanyl moiety is optionally substituted with hydroxy, amino, amino-C$_{1-6}$alkyl, hydroxy-C$_{1-6}$ alkyl or aminocarbonyl; benzyl wherein the phenyl moiety thereof is optionally substituted with amino, hydroxy, amino-C$_{1-6}$alkyl, hydroxy-C$_{1-6}$alkyl or aminocarbonyl; C$_{1-6}$alkoxycarbonyl-C$_{1-6}$alkoxy, and C$_{1-6}$alkylcarbonylamino.

6. The compound of claim 1, wherein Ar is phenyl substituted once with halo and once with a group selected from: halo; C$_{1-6}$-alkyl; halo-C$_{1-6}$alkyl; C$_{1-6}$alkenyl; C$_{1-6}$alkoxy; halo-C$_{1-6}$ alkoxy; hydroxy-C$_{1-6}$alkyl; hydroxy-C$_{1-6}$alkylamino; C$_{1-6}$alkyl-amino; hydroxy; amino; amino-C$_{1-6}$alkyl; aminocarbonyl; hydroxy-C$_{1-6}$alkoxy hydroxy-C$_{1-6}$ alkenyl; C$_{1-6}$alkoxy-C$_{1-6}$alkoxy; C$_{1-6}$alkylsulfonyl; C$_{4-6}$alkylsulfanyl; piperidinyl wherein the piperidinyl moiety is optionally substituted with hydroxy, amino, amino-C$_{1-6}$alkyl, hydroxy-C$_{1-6}$alkyl or aminocarbonyl; phenylaminocarbonyl; hydroxy-C$_{1-6}$alkylamino; cyclohexyloxy wherein the cyclohexyl moiety thereof is optionally substituted with hydroxy, amino, amino-C$_{1-6}$alkyl or hydroxy-C$_{1-6}$ alkyl; cyclopentyloxy wherein the cyclopentyl moiety thereof is optionally substituted with hydroxy, amino, amino-C$_{1-6}$alkyl or hydroxy-C$_{1-6}$alkyl; piperidinyloxy wherein the piperidinyl moiety thereof is optionally substituted with hydroxy, amino, amino-$C_{1-6}$alkyl, hydroxy-$C_{1-6}$alkyl or aminocarbonyl; phenyl wherein the phenyl moiety is optionally substituted with amino, hydroxy, amino-$C_{1-6}$alkyl, hydroxy-$C_{1-6}$alkyl or aminocarbonyl; pyrrolidinyl wherein the pyrrolidinyl moiety is optionally substituted with hydroxy, amino, amino-$C_{1-6}$alkyl, hydroxy-$C_{1-6}$alkyl or aminocarbonyl; pyrrolidinyloxy wherein the pyrrolidinyl moiety is optionally substituted with hydroxy, amino, amino-$C_{1-6}$alkyl, hydroxy-$C_{1-6}$alkyl or aminocarbonyl; piperazinyl wherein the piperazinyl moiety is optionally substituted with $C_{1-6}$alkyl; oxazol-$C_{1-6}$alkoxy wherein the oxazol moiety thereof is optionally substituted with $C_{1-6}$alkyl; morpholinyl; hydroxy-$C_{1-6}$ alkylaminocarbonyl; $C_{3-6}$cycloalkyl; azepanyl wherein the azepanyl moiety is optionally substituted with hydroxy, amino, amino-$C_{1-6}$alkyl, hydroxy-$C_{1-6}$alkyl or aminocarbonyl; benzyl wherein the phenyl moiety thereof is optionally substituted with amino, hydroxy, amino-$C_{1-6}$ alkyl, hydroxy-$C_{1-6}$alkyl or aminocarbonyl; $C_{1-6}$alkoxycarbonyl-$C_{1-6}$alkoxy and $C_{1-6}$ alkylcarbonylamino.

7. The compound of claim 1, wherein Ar is substituted aryl selected from: 2-(4-aminomethyl-piperidin-1-yl)-5-chloro-phenyl; 2-(4-aminomethyl-piperidin-1-yl)-4-phenylcarbamoyl-phenyl; 5-chloro-2-[4-(1-hydroxy-ethyl)-piperidin-1-yl]-phenyl; 5-chloro-2-(4-hydroxymethyl-piperidin-1-yl)-phenyl; 5-chloro-2-(4-hydroxy-cyclohexyloxy)-phenyl; 5-chloro-2-piperidin-1-yl-phenyl; 2-(4-aminomethyl-piperidin-1-yl)-5-chloro-phenyl; 2-[4-(1-amino-ethyl)-piperidin-1-yl]-5-chloro-phenyl; 2-(4-carbamoyl-piperidin-1-yl)-5-chloro-phenyl; 5-chloro-2-[3-(1-hydroxy-ethyl)-pyrrolidin-1-yl]-phenyl; 4'-aminomethyl-4-chloro-biphenyl-2-yl; 5-chloro-2-methoxy-phenyl; 3-amino-2-(4-aminomethyl-piperidin-1-yl)-phenyl; 3-amino-2-piperidin-1-yl-phenyl; 5-hydroxymethyl-2-piperidin-1-yl-phenyl; 4-chloro-4'-hydroxymethyl-biphenyl-2-yl; 5-chloro-2-isopropoxy-phenyl; 5-chloro-2-(3-hydroxymethyl-cyclopentyloxy)-phenyl; 5-chloro-2-pyrrolidin-1-yl-phenyl; 5-chloro-2-(3-hydroxy-cyclopentyloxy)-phenyl; 5-chloro-2-(3-hydroxy-propoxy)-phenyl; 5-chloro-2-(4-hydroxy-butoxy; 2-methoxy-4-phenylcarbamoyl-phenyl; 5-chloro-2-(3-hydroxy-piperidin-1-yl)-phenyl; 5-chloro-2-(piperidin-4-yloxy)-phenyl; 4-chloro-4'-hydroxy-biphenyl-2-yl; 5-chloro-2-(3-hydroxy-pyrrolidin-1-yl)-phenyl; 5-chloro-2-(3,4-dihydroxy-butoxy; 5-chloro-2-(4-methyl-piperazin-1-yl)-phenyl; 5-chloro-2-(oxazol-5-ylmethoxy)-phenyl; 5-chloro-2-morpholin-4-yl-phenyl; 4-chloro-biphenyl-2-yl; 2-(3-aminomethyl-pyrrolidin-1-yl)-5-chloro-phenyl; 5-chloro-2-(3-hydroxy-cyclohexyloxy)-phenyl; 4-(3-hydroxy-propylcarbamoyl)-2-methoxy-phenyl; 5-chloro-2-(3-hydroxymethyl-pyrrolidin-1-yl)-phenyl; 5-chloro-2-difluoromethoxy-phenyl; 5-chloro-2-dimethylamino-phenyl; 2-(3-amino-pyrrolidin-1-yl)-5-chloro-phenyl; 5-chloro-2-methylsulfanyl-phenyl; 5-chloro-2-cyclohexyl-phenyl; 3-(2-hydroxy-ethylamino)-2-piperidin-1-yl-phenyl; 5-chloro-2-(4-methyl-oxazol-5-ylmethoxy)-phenyl; biphenyl-2-yl; 5-chloro-2-(3-hydroxy-1,1-dimethyl-propoxy)-phenyl; 2-(4-amino-cyclohexyloxy)-5-chloro-phenyl; 2-azepan-1-yl-5-chloro-phenyl; 4-(2-hydroxy-ethylcarbamoyl)-2-methoxy-phenyl; 4-hydroxy-cyclohexyloxy)-phenyl; 5-chloro-2-(2-methoxy-ethoxy)-phenyl; 4-chloro-3'-hydroxy-biphenyl-2-yl; 5-bromo-2-methoxy-phenyl; 5-chloro-2-[(2-hydroxy-ethyl)-methyl-amino]-phenyl; 5-chloro-2-(4-hydroxy-phenoxy)-phenyl; 4-carbamoyl-2-methoxy-phenyl; 5-chloro-2-isobutoxy-phenyl; 5-chloro-2-(2,3-dihydroxy-propoxy)-phenyl; 5-chloro-2-(3-methoxy-propoxy)-phenyl; 5-chloro-2-(3-hydroxymethyl-piperidin-1-yl)-phenyl; 5-chloro-2-(3-hydroxy-benzyloxy, 5-chloro-2, 4-dimethoxy-phenyl; 2-methoxy-5-vinyl-phenyl; 3-(3-hydroxy-propylamino)-2-piperidin-1-yl-phenyl5-chloro-2-(4-hydroxy-butyl)-phenyl; 2-[3-(1-amino-ethyl)-pyrrolidin-1-yl]-5-chloro-phenyl; 5-chloro-2-[(3-hydroxy-propyl)-methyl-amino]-phenyl; 5-chloro-2-(4-methylaminomethyl-piperidin-1-yl)-phenyl; 5-(3-hydroxy-propenyl)-2-methoxy-phenyl; 5-chloro-2-ethyl-phenyl; 4-methanesulfonyl-2-methoxy-phenyl; 5-chloro-2-(3-hydroxy-phenoxy)-phenyl; 2,4-dimethoxy-phenyl; 5-fluoro-2-methoxy-phenyl; 5-chloro-2-phenoxy-phenyl; 5-(3-hydroxy-propyl)-2-methoxy-phenyl5-chloro-2-(2-hydroxymethyl-piperidin-1-yl)-phenyl; 5-chloro-2-(4-dimethylaminomethyl-piperidin-1-yl)-phenyl; 3-methoxy-biphenyl-4-yl; 5-ethyl-2-methoxy-phenyl; 5-methoxy-2-methyl-biphenyl-4-yl; 2-methoxy-3,5-dimethyl-phenyl; 4-dimethylcarbamoyl-2-methoxy-phenyl; 5-acetylamino-2-methoxy-phenyl; 5-chloro-2-methoxy-4-phenylcarbamoyl-phenyl; and 4-hydroxymethyl-2-methoxy-phenyl; 3-(3-hydroxy-cyclopentyloxy)-naphthalen-2-yl; 3-(3-hydroxy-propoxy)-naphthalen-2-yl; 7-hydroxymethyl-3-methoxy-naphthalen-2-yl; 3-(4-hydroxy-cyclohexyloxy)-naphthalen-2-yl; and 3-methoxy-naphthalen-2-yl.

8. The compound of claim 1, wherein Ar is substituted phenyl selected from: 2-(4-aminomethyl-piperidin-1-yl)-5-chloro-phenyl; 2-(4-aminomethyl-piperidin-1-yl)-4-phenylcarbamoyl-phenyl; 5-chloro-2-[4-(1-hydroxy-ethyl)-piperidin-1-yl]-phenyl; 5-chloro-2-(4-hydroxymethyl-piperidin-1-yl)-phenyl; 5-chloro-2-(4-hydroxy-cyclohexyloxy)-phenyl; 5-chloro-2-piperidin-1-yl-phenyl; 2-(4-aminomethyl-piperidin-1-yl)-5-chloro-phenyl; 2-[4-(1-amino-ethyl)-piperidin-1-yl]-5-chloro-phenyl; 2-(4-carbamoyl-piperidin-1-yl)-5-chloro-phenyl; 5-chloro-2-[3-(1-hydroxy-ethyl)-pyrrolidin-1-yl]-phenyl; 4'-aminomethyl-4-chloro-biphenyl-2-yl; 5-chloro-2-methoxy-phenyl; 3-amino-2-(4-aminomethyl-piperidin-1-yl)-phenyl; 3-amino-2-piperidin-1-yl-phenyl; 5-hydroxymethyl-2-piperidin-1-yl-phenyl; 4-chloro-4'-hydroxymethyl-biphenyl-2-yl; 5-chloro-2-isopropoxy-phenyl; 5-chloro-2-(3-hydroxymethyl-cyclopentyloxy)-phenyl; 5-chloro-2-pyrrolidin-1-yl-phenyl; 5-chloro-2-(3-hydroxy-cyclopentyloxy)-phenyl; 5-chloro-2-(3-hydroxy-propoxy)-phenyl; 5-chloro-2-(4-hydroxy-butoxy, 2-methoxy-4-phenylcarbamoyl-phenyl; 5-chloro-2-(3-hydroxy-piperidin-1-yl)-phenyl; 5-chloro-2-(piperidin-4-yloxy)-phenyl; 4-chloro-4'-hydroxy-biphenyl-2-yl; 5-chloro-2-(3-hydroxy-pyrrolidin-1-yl)-phenyl; 5-chloro-2-(3,4-dihydroxy-butoxy; 5-chloro-2-(4-methyl-piperazin-1-yl)-phenyl; 5-chloro-2-(oxazol-5-ylmethoxy)-phenyl; 5-chloro-2-morpholin-4-yl-phenyl; 4-chloro-biphenyl-2-yl; 2-(3-aminomethyl-pyrrolidin-1-yl)-5-chloro-phenyl; 5-chloro-2-(3-hydroxy-cyclohexyloxy)-phenyl; 4-(3-hydroxy-propylcarbamoyl)-2-methoxy-phenyl; 5-chloro-2-(3-hydroxymethyl-pyrrolidin-1-yl)-phenyl; 5-chloro-2-difluoromethoxy-phenyl; 5-chloro-2-dimethylamino-phenyl; 2-(3-amino-pyrrolidin-1-yl)-5-chloro-phenyl; 5-chloro-2-methylsulfanyl-phenyl; 5-chloro-2-cyclohexyl-phenyl; 3-(2-hydroxy-ethylamino)-2-piperidin-1-yl-phenyl; 5-chloro-2-(4-methyl-oxazol-5-ylmethoxy)-phenyl; biphenyl-2-yl; 5-chloro-2-(3-hydroxy-1, 1-dimethyl-propoxy)-phenyl; 2-(4-amino-cyclohexyloxy)-5-chloro-phenyl; 2-azepan-1-yl-5-chloro-phenyl; 4-(2-hydroxy-ethylcarbamoyl)-2-methoxy-phenyl; 4-hydroxy-cyclohexyloxy)-phenyl; 5-chloro-2-(2-methoxy-ethoxy)-phenyl; 4-chloro-3'-hydroxy-biphenyl-2-yl; 5-bromo-2-methoxy-phenyl; 5-chloro-2-[(2-hydroxy-ethyl)-methyl-amino]-phenyl; 5-chloro-2-(4-hydroxy-phenoxy)-phenyl; 4-carbamoyl-2-methoxy-phenyl; 5-chloro-2-isobutoxy-phenyl; 5-chloro-2-(2,3-dihydroxy-propoxy)-phenyl; 5-chloro-2-(3-methoxypropoxy)-phenyl; 5-chloro-2-(3-hydroxymethyl-piperidin-1-yl)-phenyl; 5-chloro-2-(3-hydroxy-benzyloxy; 5-chloro-2,4-dimiethoxy-phenyl; 2-methoxy-5-vinyl-phenyl; 3-(3-hydroxy-propylamino)-2-piperidin-1-yl-phenyl5-chloro-2-(4-hydroxy-butyl)-phenyl; 2-[3-(1-amino-ethyl)-pyrrolidin-1-yl]-5-chloro-phenyl; 5-chloro-2-[(3-hydroxy-propyl)-methyl-amino]-phenyl; 5-chloro-2-(4-methylaminomethyl-piperidin-1-yl)-phenyl; 5-(3-hydroxy-propenyl)-2-methoxy-phenyl; 5-chloro-2-ethyl-phenyl; 4-methanesulfonyl-2-methoxy-phenyl; 5-chloro-2-(3-hydroxy-phenoxy)-phenyl; 2,4-dimethoxy-phenyl; 5-fluoro-2-methoxy-phenyl; 5-chloro-2-phenoxy-phenyl; 5-(3-hydroxy-propyl)-2-methoxy-phenyl5-chloro-2-(2-hydroxymethyl-piperidin-1-yl)-phenyl; and 5-chloro-2-(4-dimethylaminomethyl-piperidin-1-yl)-phenyl.

9. The compound of claim 1, wherein Ar is optionally substituted heteroaryl.

10. The compound of claim 1, wherein Ar is heteroaryl selected from: pyridinyl; benzo[1,3]dioxolyl; quinolinyl; 2-oxo-2,3-dihydro-indolyl; indolyl: benzimidazolyl; or indazolyl; each optionally substituted once or twice with a group or groups independently selected from: halo; $C_{1-6}$alkyl; halo-$C_{1-6}$alkyl; $C_{1-6}$alkenyl; $C_{1-6}$alkoxy; halo-$C_{1-6}$ alkoxy; hydroxy-$C_{1-6}$alkyl; hydroxy-$C_{1-6}$alkylamino; $C_{1-6}$alkyl-amino: hydroxy; amino: amino-$C_{1-6}$alkyl; aminocarbonyl: hydroxy-$C_{1-6}$alkoxy; hydroxy-$C_{1-6}$alkenyl; $C_{1-6}$alkoxy-$C_{1-6}$alkoxy; $C_{1-6}$alkylsulfonyl; $C_{1-6}$alkylsulfanyl; piperidinyl wherein the piperidinyl moiety is optionally substituted with hydroxy, amino, amino-$C_{1-6}$alkyl, hydroxy-$C_{1-6}$alkyl or aminocarbonyl; phenylaminocarbonyl; hydroxy-$C_{1-6}$alkylamino; cyclohexyloxy wherein the cyclohexyl moiety thereof is optionally substituted with hydroxy, amino, amino-$C_{1-6}$alkyl or hydroxy-$C_{1-6}$alkyl; cyclopentyloxy wherein the cyclopentyl moiety thereof is optionally substituted with hydroxy, amino, amino-$C_{1-6}$alkyl or hydroxy-$C_{1-6}$alkyl; piperidinyloxy wherein the piperidinyl moiety thereof is optionally substituted with hydroxy, amino, amino-$C_{1-6}$alkyl, hydroxy-$C_{1-6}$alkyl or aminocarbonyl; phenyl wherein the phenyl moiety is optionally substituted with amino, hydroxy, amino-$C_{1-6}$alkyl, hydroxy-$C_{1-6}$alkyl or aminocarbonyl; pyrrolidinyl wherein the pyrrolidinyl moiety is optionally substituted with hydroxy, amino, amino-$C_{1-6}$alkyl, hydroxy-$C_{1-6}$alkyl or aminocarbonyl; pyrrolidinyloxy wherein the pyrrolidinyl moiety is optionally substituted with hydroxy, amino, amino-$C_{1-6}$alkyl, hydroxy-$C_{1-6}$alkyl or aminocarbonyl; piperazinyl wherein the piperazinyl moiety is optionally substituted with $C_{1-6}$alkyl; oxazol-$C_{1-6}$alkoxy wherein the oxazol moiety thereof is optionally substituted with $C_{1-6}$alkyl; morpholinyl; hydroxy-$C_{1-66}$alkylaminocarbonyl; $C_{3-6}$cycloalkyl; azepanyl wherein the azepanyl moiety is optionally substituted with hydroxy, amino, amino-$C_{1-6}$alkyl, hydroxy-$C_{1-6}$alkyl or aminocarbonyl; benzyl wherein the phenyl moiety thereof is optionally substituted with amino, hydroxy, amino-$C_{1-6}$alkyl, hydroxy-$C_{1-6}$alkyl or aminocarbonyl; $C_{1-6}$alkoxycarbonyl-$C_{1-6}$alkoxy; and $C_{1-6}$alkylcarbonylamino.

11. The compound of claim 1, wherein Ar is quinolinyl optionally substituted once or twice with a group or groups independently selected from: $C_{1-6}$alkyl; $C_{1-6}$alkoxy; hydroxy-$C_{1-6}$ alkoxy; hydroxy-$C_{1-6}$alkylamino; amino-$C_{1-6}$alkoxy; cyclohexyloxy wherein the cyclohexyl moiety thereof is optionally substituted with hydroxy, amino, amino-$C_{1-6}$alkyl or hydroxy-$C_{1-6}$ alkyl; piperidinyl wherein the piperidinyl moiety is optionally substituted with hydroxy, amino, amino-$C_{1-6}$alkyl, hydroxy-$C_{1-6}$alkyl or aminocarbonyl; piperidinyloxy wherein the piperidinyl moiety thereof is optionally substituted with hydroxy, amino, amino-$C_{1-6}$alkyl, hydroxy-$C_{1-6}$alkyl or aminocarbonyl; cyclopentyloxy wherein the cyclopentyl moiety thereof is optionally substituted with hydroxy, amino, amino-$C_{1-6}$alkyl or hydroxy-$C_{1-6}$alkyl; and pyrrolidinyloxy wherein the pyrrolidinyl moiety is optionally substituted with hydroxy, amino, amino-$C_{1-6}$alkyl, hydroxy-$C_{1-6}$alkyl or aminocarbonyl.

12. The compound of claim 1, wherein Ar is Ar is quinolin-6-yl substituted at the 7-position, and optionally substituted at the 2-position, with a group or groups independently selected from: $C_{1-6}$alkyl; $C_{1-6}$alkoxy; hydroxy-$C_{1-6}$alkoxy, hydroxy-$C_{1-6}$alkylamino; amino-$C_{1-6}$alkoxy; cyclohexyloxy wherein the cyclohexyl moiety thereof is optionally substituted with hydroxy, amino, amino-$C_{1-6}$alkyl or hydroxy-$C_{1-6}$alkyl; piperidinyl wherein the piperidinyl moiety is optionally substituted with hydroxy, amino, amino-$C_{1-6}$alkyl, hydroxy-$C_1$alkyl or aminocarbonyl; piperidinyloxy wherein the piperidinyl moiety thereof is optionally substituted with hydroxy, amino, amino-$C_{1-6}$alkyl, hydroxy-$C_{1-6}$alkyl or aminocarbonyl; cyclopentyloxy wherein the cyclopentyl moiety thereof is optionally substituted with hydroxy, amino, amino-$C_{1-6}$alkyl or hydroxy-$C_{1-6}$alkyl; and pyrrolidinyloxy wherein the pyrrolidinyl moiety is optionally substituted with hydroxy, amino, amino-$C_{1-6}$alkyl, hydroxy-$C_{1-6}$alkyl or aminocarbonyl.

13. The compound of claim 1, wherein Ar is heteroaryl selected from: 7-(4-aminomethyl-piperidin-1-yl)-quinolin-6-yl; 2-(2-hydroxy-ethylamino)-7-methoxy-quinolin-6-yl; 7-(4-hydroxy-cyclohexyloxy)-quinolin-6-yl; 7-methoxy-quinolin-6-yl; 7-piperidin-1-yl-quinolin-6-yl; 7-(3-hydroxy-cyclopentyloxy)-quinolin-6-yl; 7-(3-hydroxy-1-methyl-butoxy)-quinolin-6-yl; 7-(3-hydroxy-butoxy)-quinolin-6-yl; 7-(piperidin-4-yloxy)-quinolin-6-yl; 7-(3-hydroxy-1,1-dimethyl-propoxy)-quinolin-6-yl; 7-(3-amino-propoxy)-quinolin-6-yl; 7-(3-hydroxy-cyclopentyloxy)-quinolin-6-yl; 7-(piperidin-4-yloxy)-quinolin-6-yl; 7-(3-hydroxy-propoxy)-quinolin-6-yl; 7-(pyrrolidin-3-yloxy)-quinolin-6-yl; 7-(4-hydroxymethyl-piperidin-1-yl)-quinolin-6-yl; 7-(4-aminomethyl-piperidin-1-yl)-quinolin-6-yl; quinolin-6-yl; 5-(4-hydroxymethyl-piperidin-1-yl)-2-oxo-2,3-dihydro-1H-indol-6-yl; 5-(4-hydroxymethyl-phenyl)-2-methyl-1H-indol-6-yl; 2-oxo-5-piperidin-1-yl-2,3-dihydro-1H-indol-6-yl; 6-methoxy-1H-indazol-5-yl; 5-methoxy-2-methyl-1H-indol-6-yl; 5-methoxy-1H-indol-6-yl; or 1-(3-hydroxy-propyl)-1H-benzoimidazol-2-yl.

14. The compound of claim 1, wherein each $R^1$ is independently: hydrogen; $C_{1-6}$alkyl; $C_{1-6}$alkoxy; hydroxy; hydroxy-$C_{1-6}$alkyl; $C_{1-6}$alkyl-amino; amino-$C_{1-6}$alkyl; amino-$C_{1-6}$alkyl-amino; hydroxy-$C_{1-6}$alkylamino; halo; or aminocarbonyl.

15. The compound of claim 1, wherein each $R^1$ is independently: hydrogen; hydroxy; 2-amino-ethyl)-methyl-amino; 2-amino-ethylamino; methy; methoxy; 2-hydroxy-ethyl)-methyl-amino; hydroxymethyl; 2-hydroxy-1-methyl-ethylamino; 2-hydroxy-ethylamino; 2,3-dihydroxy-propylamino; 3-amino-propylamino; aminocarbonyl; 2-hydroxy-ethyl)-isopropyl-amino; bromo; isobutylamino; isopropyl-methyl-amino; 3-hydroxy-propylamino; 1-hydroxymethyl-propylamino; 2-hydroxy-ethyl; 2-acetylamino-ethylamino; 3-hydroxy-propyl; or isopropyl-amino.

16. The compound of claim 1, wherein said compound is of formula IIa:

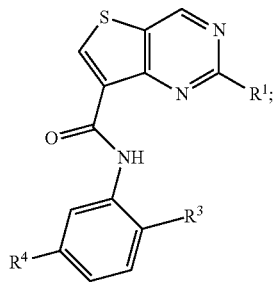

IIa wherein:

$R^3$ and $R^4$ each independently is: halo; $C_{1-6}$alkyl; halo-$C_{1-6}$alkyl; $C_{1-6}$alkenyl; $C_{1-6}$alkoxy; halo-$C_{1-6}$alkoxy; hydroxy-$C_{1-6}$alkyl; hydroxy-$C_{1-6}$alkylamino; $C_{1-6}$alkyl-amino; hydroxy; amino; amino-$C_{1-6}$alkyl; aminocarbonyl; hydroxy-$C_{1-6}$alkoxy; hydroxy-$C_{1-6}$alkenyl; $C_{1-6}$alkoxy-$C_{1-6}$alkoxy; $C_{1-6}$alkylsulfonyl; $C_{1-6}$alkylsulfanyl; piperidinyl wherein the piperidinyl moiety is optionally substituted with hydroxy, amino, amino-$C_{1-6}$alkyl, hydroxy-$C_{1-6}$alkyl or aminocarbonyl; phenylaminocarbonyl; hydroxy-$C_{1-6}$alkylamino; cyclohexyloxy wherein the cyclohexyl moiety thereof is optionally substituted with hydroxy, amino, amino-$C_{1-6}$alkyl or hydroxy-$C_{1-6}$alkyl; cyclopentyloxy wherein the cyclopentyl moiety thereof is optionally substituted with hydroxy, amino, amino-$C_{1-6}$alkyl or hydroxy-$C_{1-6}$alkyl; piperidinyloxy wherein the piperidinyl moiety thereof is optionally substituted with hydroxy, amino, amino-$C_{1-6}$alkyl, hydroxy-$C_{1-6}$alkyl or aminocarbonyl; phenyl wherein the phenyl moiety is optionally substituted with amino, hydroxy, amino-$C_{1-6}$alkyl, hydroxy-$C_{1-6}$alkyl or aminocarbonyl; pyrrolidinyl wherein the pyrrolidinyl moiety is optionally substituted with hydroxy, amino, amino-$C_{1-6}$alkyl, hydroxy-$C_{1-6}$alkyl or aminocarbonyl; pyrrolidinyloxy wherein the pyrrolidinyl moiety is optionally substituted with hydroxy, amino, amino-$C_{1-6}$alkyl, hydroxy-$C_{1-6}$alkyl or aminocarbonyl; piperazinyl wherein the piperazinyl moiety is optionally substituted with $C_{1-6}$alkyl; oxazol-$C_{1-6}$alkoxy wherein the oxazol moiety thereof is optionally substituted with $C_{1-6}$alkyl; morpholinyl; hydroxy-$C_{1-6}$alkylaminocarbonyl; $C_{3-6}$cycloalkyl; azepanyl wherein the azepanyl moiety is optionally substituted with hydroxy, amino, amino-$C_{1-6}$alkyl, hydroxy-$C_{1-6}$ alkyl or aminocarbonyl; benzyl wherein the phenyl moiety thereof is optionally substituted with amino, hydroxy, amino-$C_{1-6}$alkyl, hydroxy-$C_{1-6}$alkyl or aminocarbonyl; $C_{1-6}$alkoxycarbonyl-$C_{1-6}$ alkoxy; or $C_{1-6}$alkylcarbonylamino; and $R^1$ is as recited in claim 1.

17. The compound of claim 16, wherein $R^4$ is halo.

18. The compound of claim 1, wherein said compound is of formula IIb:

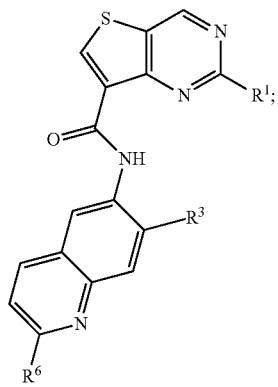

IIb wherein:

$R^5$ and $R^6$ each independently is: hydrogen; halo; $C_{1-6}$alkyl; halo-$C_{1-6}$alkyl; $C_{1-6}$alkenyl; $C_{1-6}$alkoxy; halo-$C_{1-6}$alkoxy; hydroxy-$C_{1-6}$alkyl; hydroxy-$C_{1-6}$ alkylamino; $C_{1-6}$alkyl-amino; hydroxy, amino; amino-$C_{1-6}$alkyl; aminocarbonyl; hydroxy-$C_{1-6}$alkoxy; hydroxy-$C_{1-6}$alkenyl; $C_{1-6}$ alkoxy-$C_{1-6}$alkoxy; $C_{1-6}$alkylsulfonyl; $C_{1-6}$alkylsulfanyl; piperidinyl wherein the piperidinyl moiety is optionally substituted with hydroxy, amino, amino-$C_{1-6}$alkyl, hydroxy-$C_{1-6}$ alkyl or aminocarbonyl; phenylaminocarbonyl; hydroxy-$C_{1-6}$alkylamino; cyclohexyloxy wherein the cyclohexyl moiety thereof is optionally substituted with hydroxy, amino, amino-$C_{1-6}$alkyl or hydroxy-$C_{1-6}$ alkyl; cyclopentyloxy wherein the cyclopentyl moiety thereof is optionally substituted with hydroxy, amino, amino-$C_{1-6}$alkyl or hydroxy-$C_{1-6}$alkyl; piperidinyloxy wherein the piperidinyl moiety thereof is optionally substituted with hydroxy, amino, amino-$C_{1-6}$alkyl, hydroxy-$C_{1-6}$alkyl or aminocarbonyl; phenyl wherein the phenyl moiety is optionally substituted with amino, hydroxy, amino-$C_{1-6}$alkyl, hydroxy-$C_{1-6}$alkyl or aminocarbonyl; pyrrolidinyl wherein the pyrrolidinyl moiety is optionally substituted with hydroxy, amino, amino-$C_{1-6}$alkyl, hydroxy-$C_{1-6}$alkyl or aminocarbonyl; pyrrolidinyloxy wherein the pyrrolidinyl moiety is optionally substituted with hydroxy, amino, amino-$C_{1-6}$ alkyl, hydroxy-$C_{1-6}$alkyl or aminocarbonyl; piperazinyl wherein the piperazinyl moiety is optionally substituted with $C_{1-6}$alkyl; oxazol-$C_{1-6}$alkoxy wherein the oxazol moiety thereof is optionally substituted with $C_{1-6}$alkyl; morpholinyl; hydroxy-$C_{1-6}$alkylaminocarbonyl; $C_{3-6}$cycloalkyl; azepanyl wherein the azepanyl moiety is optionally substituted with hydroxy, amino, amino-$C_{1-6}$alkyl, hydroxy-$C_{1-6}$alkyl or aminocarbonyl; benzyl wherein the phenyl moiety thereof is optionally substituted with amino, hydroxy, amino-$C_{1-6}$alkyl, hydroxy-$C_{1-6}$alkyl or aminocarbonyl; $C_{1-6}$alkoxycarbonyl-$C_{1-6}$alkoxy, or $C_{1-6}$alkylcarbonylamino; and $R^1$ is as recited in claim 1.

19. A composition comprising:
(a) a pharmaceutically acceptable carrier; and
(b) the compound of claim 1.

* * * * *

UNITED STATES PATENT AND TRADEMARK OFFICE
CERTIFICATE OF CORRECTION

PATENT NO.         : 10,023,589 B2
APPLICATION NO.    : 14/975004
DATED              : July 17, 2018
INVENTOR(S)        : Nidhi Arora et al.

It is certified that error appears in the above-identified patent and that said Letters Patent is hereby corrected as shown below:

In the Claims

At Column 218, Line 58, Claim 6 "C4-6alkylsulfanyl" should be replaced with "C1-6alkylsulfanyl."

At Column 221, Line 3, Claim 8 "4-dimiethoxy-phenyl" should be replaced with "4-dimethoxy-phenyl."

At Column 221, Line 50, Claim 10 "hydroxy-C1-66alkylaminocarbonyl" should be replaced with "hydroxy-C1-6alkylaminocarbonyl."

At Column 222, Line 19, Claim 12 "hydroxy-C1alkyl" should be replaced with "hydroxy-C1-6alkyl."

At Column 224, Lines 1-16, Claim 18 the chemical structure

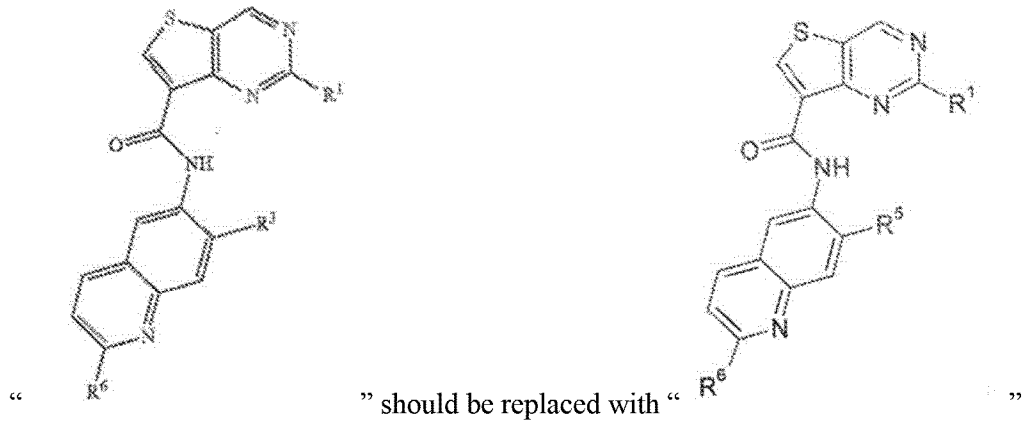

Signed and Sealed this
Twenty-eighth Day of August, 2018

Andrei Iancu
*Director of the United States Patent and Trademark Office*